US011091557B2

(12) United States Patent
Altintas et al.

(10) Patent No.: US 11,091,557 B2
(45) Date of Patent: Aug. 17, 2021

(54) METHODS OF PRODUCING MULTISPECIFIC ANTIBODIES AGAINST CD40 AND CD137

(71) Applicants: GENMAB A/S, Copenhagen V (DK); BioNTech SE, Mainz (DE)

(72) Inventors: Isil Altintas, Utrecht (NL); David Satijn, Utrecht (NL); Rik Rademaker, Utrecht (NL); Paul Parren, Odijk (NL); Friederike Gieseke, Mainz (DE); Ugur Sahin, Mainz (DE)

(73) Assignees: GENMAB A/S, Copenhagen V (DK); BioNTech SE, Mainz (DE)

( * ) Notice: Subject to any disclaimer, the term of this patent is extended or adjusted under 35 U.S.C. 154(b) by 195 days.

(21) Appl. No.: 16/316,534

(22) PCT Filed: Jul. 14, 2017

(86) PCT No.: PCT/EP2017/067924
§ 371 (c)(1),
(2) Date: Jan. 9, 2019

(87) PCT Pub. No.: WO2018/011421
PCT Pub. Date: Jan. 18, 2018

(65) Prior Publication Data
US 2020/0062853 A1 Feb. 27, 2020

(30) Foreign Application Priority Data
Jul. 14, 2016 (WO) ................. PCT/EP2016/066840

(51) Int. Cl.
*A61K 39/395* (2006.01)
*C07K 16/28* (2006.01)
*G01N 33/569* (2006.01)

(52) U.S. Cl.
CPC ...... *C07K 16/2878* (2013.01); *A61K 39/3955* (2013.01); *G01N 33/56972* (2013.01); *C07K 2317/24* (2013.01); *C07K 2317/31* (2013.01); *C07K 2317/524* (2013.01); *C07K 2317/526* (2013.01); *C07K 2317/53* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | |
|---|---|---|
| 2003/0118588 A1 | 6/2003 | Diehl et al. |
| 2003/0223989 A1 | 12/2003 | Pluenneke |
| 2009/0074711 A1 | 3/2009 | Martin |
| 2014/0099254 A1 | 4/2014 | Chang |
| 2016/0256527 A1 | 9/2016 | Gurney |

FOREIGN PATENT DOCUMENTS

| | | |
|---|---|---|
| AU | 2004279877 B2 | 4/2005 |
| EP | 1975182 A1 | 10/2008 |
| WO | WO 2002/028481 A2 | 4/2002 |
| WO | WO 2003/040170 A2 | 5/2003 |
| WO | WO 2005/092927 A1 | 10/2005 |
| WO | WO 2011/104558 A1 | 9/2011 |
| WO | WO 2011/131746 A2 | 10/2011 |
| WO | WO 2015/001085 A1 | 1/2015 |
| WO | WO 2016/110584 A1 | 7/2016 |

OTHER PUBLICATIONS

Christiansen et al., (2011) "Eradication of solid tumors using histone deacetylase inhibitors combined with immune-stimulating antibodies", *Proceedings of the National Academy of Sciences*, 108(10):4141-4146.
Gray et al., (2008) "Optimising anti-tumour CD8 T-cell responses using combinations of immunomodulatory antibodies", *European Journal of Immunology*, 38(9):2499-2511.
Haynes et al., (2008) "Immunogenic anti-cancer chemotherapy as an emerging concept", *Current Opinion in Immunology*, 20(5):545-557.
International Patent Application No. PCT/EP2017/067924, filed Jul. 14, 2017, GENMAB A/S: International Search Report and Written Opinion, dated Dec. 21, 2017 (26 pages).
Westwood et al., (2014) "Combination anti-CD137 and anti-CD40 antibody therapy in murine myc-driven hematological cancers", *Leukemia Research*, 38(8):948-954.
Yonezawa et al., (2015) "Boosting Cancer Immunotherapy with Anti-CD137 Antibody Therapy", *Clinical Cancer Research*, 21(14):3113-3120.
Chen et al., "Enhancement and destruction of antibody function by somatic mutation: unequal occurrence is controlled by V gene combinatorial associations", The EMBO Journal, 1995, 14(12): 2784-2794.
Colman et al., "Effects of amino acid sequence changes on antibody-antigen interactions", Research in Immunology, 1994,145: 33-36.
D'Angelo et al., "Many Routes to an Antibody Heavy-Chain CDR3: Necessary, Yet Insufficient, for Specific Binding," Frontiers in Immunology, vol. 9, Article 395 Mar. 2018; (Year: 2018).

(Continued)

*Primary Examiner* — Phillip Gambel

(74) *Attorney, Agent, or Firm* — Lathrop GPM LLP; James H. Velema, Esq.; James V. DeGiulio, Esq.

(57) ABSTRACT

Multispecific antibodies binding to human CD40 and human CD137, methods for preparing such multispecific antibodies, and methods of using such multispecific antibodies for therapeutic or other purposes.

20 Claims, 33 Drawing Sheets

Specification includes a Sequence Listing.

(56) References Cited

OTHER PUBLICATIONS

Fisher et al., "Targeting of 4-1BB by monoclonal antibody PF-05082566 enhances T-cell function and promotes anti-tumor activity", 2012 61: 1721-17333.
Gray et al., "Optimising anti-tumor CD8 T-cell responses using . . . ". European Journal of Immunology. vol. 38 (9), 2008. p. 2499-2511.
Gros et al., PD-1 identifies the patient-specific CD8+ tumor reactive repertoire infiltrating human tumors J. Clin Invest 2014;124(5):2246-59.
Kussie et al., "A single engineered amino acid substitution changes antibody fine specificity," J. Immunol., 152:146-152, (Year: 1994).
Murillo et al., Therapeutic Antitumor Efficacy of Anti-CD137 Agonistic Monoclonal Antibody in Mouse Models of Myeloma. Clin cancer res. 2008;14(21):6895-906.
Rudikoff et al., "Single amino acid substitution altering antigen-binding specificity", Proc. Natl Acad. Sci. USA, 1982, 79: 1979-1983, Immunology.
Uno et al., (2006) "Eradication of established tumors in mice by a combination antibody-based therapy", Nature Medicine, 12(6):693-698.

Figure 1

```
                                        1                                                    50
      Human  (TNR9_HUMAN)      (1)  ------MGNSCYNIVATLLLVLNFERTRSLQDPCSNCPAGTFCDNNRNQIC
   Elephant  (XP_003413533)    (1)  MQDFIMGNEYYNIVATLLVINFERTGEQDSCRECLAGTICVENESQIC
  Wild Boar  (XP_005665023)    (1)  MQDFIMGNEYYNIVATLLVINFERTRSPDPCSNCAGTFCENIEEC 51                                                   100
      Human  (TNR9_HUMAN)     (46)  SPCPPNSFSSAGGQRTCDICRQCKGVFRTRKECSSTSNAECDCTPGFHCL
   Elephant  (XP_003413533)   (51)  SPCPLNSFSSEGGQMECDECRECEGVFRTEACSETREAECECEGFHCL
  Wild Boar  (XP_005665023)   (51)  MPCPENSFSSEGQEACECRECEGVFRTEKECSSTSNAVCECPGFECL 101                                                  150
      Human  (TNR9_HUMAN)     (96)  GAGCSMCEQDCKQGQELTKKGCKDCCFGTFNDQKRGICRPWTNCSLDGKS
   Elephant  (XP_003413533)  (101)  GAGCEMCEQDCKQGQELTKEGCKDCCEGTFNDQKEGICRPWTNCSLEGKS
  Wild Boar  (XP_005665023)  (101)  GAGCEMCEEYCEQGQELTEEGCKDCEFGTFNDEEEGECRPWTECSLAGKE 151                                                  200
      Human  (TNR9_HUMAN)    (146)  VLVNGTKERDVVCGPSPADLSPGASSVTPPAPAREPGHSPQIISFFLALT
   Elephant  (XP_003413533)  (151)  VLENGTKERDVVCGPEAADSFPEESSVTVPAPEREPEHHPQIIEFFLALI
  Wild Boar  (XP_005665023)  (151)  VLENGTKARDVVCGPRPEDESPGEESETMPEPEGEPGHESEEIIFFLALM 201                                                  250
      Human  (TNR9_HUMAN)    (196)  STALLFLLFFLTLRFSVVKRGRKKLLYIFKQPFMRPVQTTQEEDGCSCRF
   Elephant  (XP_003413533)  (201)  SEALLFLEFFLEERFSVEKWGRKKLLYIFKQPFEEPVQTEQEEDGCSCRF
  Wild Boar  (XP_005665023)  (201)  STAEEVLESELELRFSVVEEGRKKLLYIVKQPFEEPEQTEQEEDECSCRF
                                        251
      Human  (TNR9_HUMAN)    (246)  PEEEEGGCEL
   Elephant  (XP_003413533)  (251)  PEEEEGECEL
  Wild Boar  (XP_005665023)  (251)  PEEEEGECEL
```

A

A

METHODS OF PRODUCING MULTISPECIFIC ANTIBODIES AGAINST CD40 AND CD137

RELATED APPLICATIONS

This application is a national stage application under 35 U.S.C. § 371 of PCT/EP2017/067924, filed Jul. 14, 2017, which designated the U.S. and claims the benefit of PCT/EP2016/066840, filed Jul. 14, 2016. The entire contents of the foregoing applications are incorporated herein by reference.

SEQUENCE LISTING

This application contains a Sequence Listing which has been submitted electronically in ASCII format and is incorporated herein by reference in its entirety. The ASCII copy, created on Aug. 23, 2019, is named "P101_Sequence_Listing_12166-0009.txt" and is 119,412 bytes in size.

FIELD OF THE INVENTION

The present invention relates to multispecific antibodies binding to CD40 and CD137, and to uses of such multispecific antibodies, in particular to the use for treatment of cancer.

BACKGROUND OF THE INVENTION

CD40 is a member of the tumor necrosis factor (TNF) receptor (TNFR) family and is known as a co-stimulatory protein found on a diversity of cell types. CD40 is constitutively expressed by antigen-presenting cells (APCs), including dendritic cells (DCs), B cells and macrophages. It can also be expressed by endothelial cells, platelets, smooth muscle cells, fibroblasts and epithelial cells. Consistent with its widespread expression on normal cells, CD40 is also expressed on a wide range of tumor cells.

The presentation of peptide antigens in the context of MHC class II molecules to antigen-specific CD4$^+$ T cells, together with co-stimulatory signals (from CD80 and/or CD86), results in the activation of CD4$^+$ T cells and the up-regulation of the DC licensing factors CD40 ligand (CD40L) and lymphotoxin-α1β2 (LTα1β2). Expression of CD40L and LTα1β2 on activated antigen-specific CD4$^+$ T cells induces signaling through CD40 and the LTβ receptor (LTβR), and this licenses DCs to induce CD8$^+$ T-cell responses. CD40 signaling results in the production of interleukin-12 (IL-12) and the up-regulation of CD70, CD86, 4-1BB ligand (4-1BBL), OX40 ligand (OX40L) and GITR ligand (GITRL), whereas LTβR signaling leads to the production of type I interferons (IFNs). The signaling system that controls the activity of nuclear factor kappaB (NF-kB) is responsive to virtually all TNFR superfamily members. Pathogen-associated molecular patterns (PAMPs) and damage-associated molecular patterns (DAMPs) also contribute to these events. Priming of CD8$^+$ T cells by MHC class I-restricted peptides results in the up-regulation of CD27, 4-1BB, OX40 and glucocorticoid-induced TNFR-related protein (GITR). Stimulation of these receptors on CD8$^+$ T cells by their cognate TNF superfamily ligands, in combination with IL-12 and type I IFNs, results in robust CD8$^+$ T cell activation, proliferation and effector function, as well as the formation and maintenance of CD8$^+$ T cell memory. CD40 antibodies can exert different actions, CD40-expressing tumor cell kill by induction of antibody-dependent cell-mediated cytotoxicity (ADCC), complement-dependent cytotoxicity (CDC) or antibody-dependent cell-mediated phagocytosis (ADCP), induction of cell signaling to induce direct apoptosis or growth arrest, but also, independent of CD40 expression on the tumor cells, through licensing of APCs to stimulate an anti-cancer immune response. Antibodies binding to CD40 can trigger CD40 on APCs to prime effector cytotoxic T lymphocytes (CTLs) and induce release of IL-2 by these cells, and indirectly activate NK cells. Antibodies stimulating CD40 have been disclosed in the prior art, and include CP-870,893, a human IgG2 antibody (WO 2003/040170); dacetuzumab, a humanized IgG1 antibody (WO 2000/075348) and Chi Lob 7/4, a chimeric IgG1 antibody (US 2009/0074711). Furthermore, an antagonistic CD40 antibody has been disclosed, lucatumumab, a human IgG1 antibody (WO 2002/028481).

CD137 (4-1BB) is also a member of the TNFR family. CD137 is a co-stimulatory molecule on CD8$^+$ and CD4$^+$ T cells, regulatory T cells (Tregs), Natural Killer T cells (NK(T) cells), B cells and neutrophils. On T cells, CD137 is not constitutively expressed, but induced upon T-cell receptor (TCR) activation (for example, on tumor infiltrating lymphocytes (TILs) (Gros et al., J. Clin Invest 2014; 124 (5):2246-59)). Stimulation via its natural ligand 4-1BBL or agonist antibodies leads to signaling using TRAF-2 and TRAF-1 as adaptors. Early signaling by CD137 involves K-63 poly-ubiquitination reactions that ultimately result in activation of the nuclear factor(NF)-kB and mitogen-activated protein(MAP)-kinase pathways. Signaling leads to increased T cell co-stimulation, proliferation, cytokine production, maturation and prolonged CD8$^+$ T-cell survival. Agonistic antibodies against CD137 have been shown to promote anti-tumor control by T cells in various pre-clinical models (Murillo et al., Clin Cancer Res 2008; 14(21):6895-906). Antibodies stimulating CD137 can induce survival and proliferation of T cells, thereby enhancing the anti-tumor immune response. Antibodies stimulating CD137 have been disclosed in the prior art, and include urelumab, a human IgG4 antibody (AU2004279877) and utomilumab, a human IgG2 antibody (Fisher et al. 2012 Cancer Immunol. Immunother. 61: 1721-1733).

Westwood J A, et al., Leukemia Research 38 (2014), 948-954 discloses "Combination anti-CD137 and anti-CD40 antibody therapy in murine myc-driven hematological cancers".

US20090074711 discloses "Human therapies using chimeric agonistic anti-human CD40 antibody".

However, despite these and other advances in the art, there is a need for multispecific antibodies that can bind both CD40 and CD137, simultaneously binding to CD40-expressing APCs and CD137-expressing T cells, thereby bringing these cell types in close contact. This, in turn, can lead to activation of both cell types and efficient induction of anti-tumor immunity.

SUMMARY OF THE INVENTION

The present inventors have identified multispecific antibodies that can bind both CD40 and CD137 and elicit T cell and APC activation.

So, in one aspect, the invention relates to a multispecific antibody comprising
(i) a first antigen-binding region binding to human CD40, and (ii) a second antigen-binding region binding to human CD137.

In some embodiments, the invention relates to such a multispecific antibody wherein the first antigen-binding region comprises heavy and light chain variable region CDR1, CDR2 and CDR3 which comprise specific amino acid sequences, optionally with mutations, or the amino acid sequences of an antibody which competes with or has the specificity of an antibody comprising such specific amino acid sequences. In specific embodiments, the first antigen-binding region comprises heavy and light chain variable sequences comprising the CDR1, CDR2 and CDR3 of anti-CD40 antibody 001, or competes with or has the specificity of such an antibody.

In some embodiments, the invention relates to such a multispecific antibody wherein the second antigen-binding region comprises heavy and light chain variable sequences wherein the CDR1, CDR2 and CDR3 comprise specific amino acid sequences or provide specific amino acid sequences, optionally with mutations, or comprise the amino acid sequences of an antibody which competes with or has the specificity of an antibody comprising such specific amino acid sequences. In specific embodiments, the second antigen-binding region comprises heavy and light chain variable sequences comprising the CDR1, CDR2 and CDR3 of anti-CD137 antibody 001, 002, 003, 004, 005, 006, 007, 008, 009, 010, 011 or 012, or competes with or has the specificity of any such antibody.

These and other aspects and embodiments, including nucleic acids encoding the amino acid sequences of such multispecific antibodies; expression vectors comprising such nucleic acids; host cells comprising such nucleic acids or expression vectors; compositions comprising such multispecific antibodies; such compositions for use in treating cancer or other diseases; methods for producing such multispecific antibodies; and diagnostic methods and kits based on such multispecific antibodies, are described in further detail below.

BRIEF DESCRIPTION OF THE DRAWINGS

FIG. 1: Sequence alignments for human, African elephant and wild boar CD137. Amino acids in African elephant or wild boar CD137 that differ from those in the human sequence are highlighted in black.

TABLE 1

Sequences

Figure 2:
FIG. 2: CD137 shuffle constructs, containing African elephant (shuffle 5) or wild boar (shuffle 1-4, 6) CD137 domains.

| Sequence name | Type of sequence | Sequence | Sequence identifier |
|---|---|---|---|
| CD40-001 antibody (mouse) | VH CDR1 | GYTFTEYI | SEQ ID NO: 1 |
| | VH CDR2 | IIPNNGGT | SEQ ID NO: 2 |
| | VH CDR3 | TRREVYGRNYYALDY | SEQ ID NO: 3 |
| | VL CDR1 | QGINNY | SEQ ID NO: 4 |
| | VL CDR2 | YTS | |
| | VL CDR3 | QQYSNLPYT | SEQ ID NO: 5 |
| | VH | EVQLQQSGPDLVKPGASVKISCKTS GYTFTEYIMHWVKQSHGKSLEWIG GIIPNNGGTSYNQKFKDKATMTVDK SSSTGYMELRSLTSEDSAVYYCTRRE VYGRNYYALDYWGQGTLVTVSS | SEQ ID NO: 6 |
| | VL | DIQMTQTTSSLSASLGDRVTITCSA SQGINNYLNWYQQKPDGTVKLLIYY TSSLHSGVPSRFSGSGSGTDYSLTIS NLEPEDIATYYCQQYSNLPYTFGGGT KLEIK | SEQ ID NO: 7 |
| CD137 antibody clone 001 (rabbit) | VH CDR1 | GFSLSSYA | SEQ ID NO: 8 |
| | VH CDR2 | IWNNGAT | SEQ ID NO: 9 |
| | VH CDR3 | ARSANDAWSTYSDL | SEQ ID NO: 10 |
| | VL CDR1 | QTITNY | SEQ ID NO: 11 |
| | VL CDR2 | KAS | |
| | VL CDR3 | QNYYYGSSSGYGFV | SEQ ID NO: 12 |
| | VH | QSVEESGGRLVTPGTPLTLTCTVSGFS LSSYAVSWVRQAPGKGLEWIGVIWN NGATHYATWAKGRFTISKASTTVDLK VTSPTTEDTATYFCARSANDAWSTYS DLWGQGTLVTVSS | SEQ ID NO: 13 |
| | VL | DIVMTQTPASVEAAVGGTVTIKCQASQ TITNYLSWYQQKPGQPPKLLIYKASTLT SGVSSRFKGSGSGTEFTLTISDLESDDA ATYYCQNYYYGSSSGYGFVFGGGTEVVV K | SEQ ID NO: 14 |
| CD137 antibody clone 002 (rabbit) | VH CDR1 | GFSLTYYA | SEQ ID NO: 15 |
| | VH CDR2 | IYDNGAT | SEQ ID NO: 16 |
| | VH CDR3 | ARSANNAWSTYSNL | SEQ ID NO: 17 |
| | VL CDR1 | EDISSY | SEQ ID NO: 18 |
| | VL CDR2 | KAS | |
| | VL CDR3 | QSYYSGSISGYGFV | SEQ ID NO: 19 |
| | VH | QSVEESGGRLVTPGTPLTLTCTVSGFS LTYYAVTWVRQPPGKGLEWIGVIYDN GATAFATWAKGRFTMSKNSTTVALKV TSPTTEDTATYFCARSANNAWSTYSN LWGQGTLVTVSS | SEQ ID NO: 20 |
| | VL | DIVMTQTPSSVSAAVGGTVTINCQAS EDISSYLSWYQQKLGQPPKLLIYKAST | SEQ ID NO: 21 |

TABLE 1-continued

Sequences

| Sequence name | Type of sequence | Sequence | Sequence identifier |
|---|---|---|---|
| | | LESGVPSRFKGSGSGTEYTLTISDLES DDAATYYCQSYYSGSISGYGFVFGGGT GVVVK | |
| CD137 antibody clone 003 (rabbit) | VH CDR1 | GFTISSYH | SEQ ID NO: 22 |
| | VH CDR2 | IYGGTATT | SEQ ID NO: 23 |
| | VH CDR3 | ARARYSGGSYANYVFNL | SEQ ID NO: 24 |
| | VL CDR1 | QSISSY | SEQ ID NO: 25 |
| | VL CDR2 | RTS | |
| | VL CDR3 | QGYDWSSSNRYDNT | SEQ ID NO: 26 |
| | VH | QSVEESGGRLVTPGTPLTLTCTAS GFTISSYHMIWVRQAPGEGLEWI GDIYGGTATTDYASWAKGRFTIS KTSTTVDLKMTSLTTEDTATYFCA RARYSGGSYANYVFNLWGQGTLV TVSS | SEQ ID NO: 27 |
| | VL | DIVMTQTPASVEAAVGGTVTIKCQ ASQSISSYLAWYQQKPGQPPKLLI YRTSTLESGVPSRFKGSGSGTEFTL TISDLESADAATYYCQGYDWSSSN RYDNTFGGGTEVVVK | SEQ ID NO: 28 |
| CD137 antibody clone 004 (rabbit) | VH CDR1 | GFSLSRYD | SEQ ID NO: 29 |
| | VH CDR2 | ISSSGGT | SEQ ID NO: 30 |
| | VH CDR3 | AREGDYWDFNL | SEQ ID NO: 31 |
| | VL CDR1 | QSISNL | SEQ ID NO: 32 |
| | VL CDR2 | GAS | |
| | VL CDR3 | AGGFPGLDTVAA | SEQ ID NO: 33 |
| | VH | QSLEESGGRLVTPGTPLTLTCTASGF SLSRYDMSWVRQAPGKGLEYIGVIS SSGGTNYANWAKGRFTISKTSTTVD LKITSPTTEDTATYFCAREGDYWDFN LWGPGTLVTVSS | SEQ ID NO: 34 |
| | VL | AQVLTQTPSSVSAAVGGTVTINCQA SQSISNLLAWYQQKPGQPPKLLIYG ASTLASGVPSRFSGSGSGTEFTLTIS DLESDDAATYYCAGGFPGLDTVAAF GGGTEAVVT | SEQ ID NO: 35 |
| CD137 antibody clone 005 (rabbit) | VH CDR1 | GFTISDFH | SEQ ID NO: 36 |
| | VH CDR2 | IITSASTT | SEQ ID NO: 37 |
| | VH CDR3 | ARSTYTDTSGYYFDF | SEQ ID NO: 38 |
| | VL CDR1 | QSIYNGNR | SEQ ID NO: 39 |
| | VL CDR2 | SAS | |
| | VL CDR3 | LGSYDCDSADCFA | SEQ ID NO: 40 |
| | VH | QSVEESGGRLVTPGTPLTLTCTASG FTISDFHVTWVRQAPGKGLEWIGTI ITSASTTAYATWARGRFTISKSSTTV NLKIVSPTTEDTATYFCARSTYTDTS GYYFDFWGQGTLVTVSS | SEQ ID NO: 41 |
| | VL | AQVLTQTASPVSAAVGGTVIINCQSS QSIYNGNRLSWYQQKPGQPPKLLIYS ASTLASGVSSRFKGSGSGTQFTLAISD VQSDDAATYYCLGSYDCDSADCFAFG GGTEVVVE | SEQ ID NO: 42 |
| CD137 antibody clone 006 (rabbit) | VH CDR1 | GFSLSSYA | SEQ ID NO: 43 |
| | VH CDR2 | ISTSGIT | SEQ ID NO: 44 |
| | VH CDR3 | ARLNGFDDYVRYFDF | SEQ ID NO: 45 |
| | VL CDR1 | ESIASN | SEQ ID NO: 46 |
| | VL CDR2 | AAS | |
| | VL CDR3 | QSAFYVSSSDNA | SEQ ID NO: 47 |
| | VH | QSVEESGGRLVTPGTPLTLTCTVSGFS LSSYAMSWVRQAPGKGLEWIGIISTS GITYYASWAKGRFTISKTSTMVDLKIT SPTTEDTATYFCARLNGFDDYVRYFDF WGLGTLVTVSS | SEQ ID NO: 48 |
| | VL | AIELTQTPSSVSAAVGGTVTINCQASE SIASNLAWYQQKPGQPPKLLIYAASYL ASGVPSRFKGSGSGTEYTLTISGVQSA DAATYYCQSAFYVSSSDNAFGGGTEVV VK | SEQ ID NO: 49 |
| CD137 antibody clone 007 (rabbit) | VH CDR1 | GFSLSSYD | SEQ ID NO: 50 |
| | VH CDR2 | IGSDGSA | SEQ ID NO: 51 |

TABLE 1-continued

Sequences

| Sequence name | Type of sequence | Sequence | Sequence identifier |
|---|---|---|---|
| | VH CDR3 | ARDWNDYWAHDL | SEQ ID NO: 52 |
| | VL CDR1 | QIVTSKSA | SEQ ID NO: 53 |
| | VL CDR2 | KAS | |
| | VL CDR3 | AGGYYNSGDLNP | SEQ ID NO: 54 |
| | VH | QSLEESGGRLVTPGTPLTLTCTASGFSLSSYDVSWVRQAPGKGLEYIGFIGSDGSAHYATWVKGRFTISKTSTTVDLKITSPTTEDTATYFCARDWNDYWAHDLWGPGTLVTVSS | SEQ ID NO: 55 |
| | VL | AQVLTQTTSPVSAAVGGTVTINCQASQIVTSKSALSWYQQKPGQPPRLLIYKASTLASGVPSRFSGSGSGTQFTLTISDLESDDAATYYCAGGYYNSGDLNPFGGGTEVVVK | SEQ ID NO: 56 |
| CD137 antibody clone 008 (rabbit) | VH CDR1 | GFSLSSYD | SEQ ID NO: 57 |
| | VH CDR2 | ISSSGNT | SEQ ID NO: 58 |
| | VH CDR3 | AREGDYWDFNL | SEQ ID NO: 59 |
| | VL CDR1 | QSISNL | SEQ ID NO: 60 |
| | VL CDR2 | RAS | |
| | VL CDR3 | AGGFPGLDTGAT | SEQ ID NO: 61 |
| | VH | QSLEESGGRLVTPGTPLTLTCTASGFSLSSYDMSWVRQAPGKGLEYIGYISSSGNTYYASWAKSRFTISKTSTTVDLKITSPTTEDTATYFCAREGDYWDFNLWGPGTLVTVSS | SEQ ID NO: 62 |
| | VL | AQVLTQTPSSVSAAVGGTVTINCQASQSISNLLAWYQQKPGQRPRLLIYRASTLASGVPSRFKGSGSGTEFTLTISDLESEDAATYYCAGGFPGLDTGATFGGGTEAVVT | SEQ ID NO: 63 |
| CD137 antibody clone 009 (rabbit) | VH CDR1 | GFSLNDYW | SEQ ID NO: 64 |
| | VH CDR2 | IDVGGSL | SEQ ID NO: 65 |
| | VH CDR3 | ARGGLTYGFDL | SEQ ID NO: 66 |
| | VL CDR1 | EDISSY | SEQ ID NO: 67 |
| | VL CDR2 | GAS | |
| | VL CDR3 | HYYATISGLGVA | SEQ ID NO: 68 |
| | VH | QSLEESGGRLVTPGTPLTLTCTVSGFSLNDYWMSWVRQAPGKGLEWIGYIDVGGSLYYASWAKGRFTISRTSTTVDLKMTSLTTEDTATYFCARGGLTYGFDLWGPGTLVTVSS | SEQ ID NO: 69 |
| | VL | DIVMTQTPASVSEPVGGTVTINCQASEDISSYLAWYQQKPGQRPKRLIYGASDLASGVPSRFSASGSGTEYALTISDLESADAATYYCHYYATISGLGVAFGGGTEVVVK | SEQ ID NO: 70 |
| CD137 antibody clone 010 (rabbit) | VH CDR1 | GFSLSTYA | SEQ ID NO: 71 |
| | VH CDR2 | VYDNGYI | SEQ ID NO: 72 |
| | VH CDR3 | ARSADGSWSTYFNL | SEQ ID NO: 73 |
| | VL CDR1 | ESISNY | SEQ ID NO: 74 |
| | VL CDR2 | KAS | |
| | VL CDR3 | QTNYCCSSSDNGFA | SEQ ID NO: 75 |
| | VH | QSVEESGGRLVTPGTPLTLTCTVSGFSLSTYAMIWVRQAPGKGLEWIGVVYDNGYISHATWVKGRFTISKTSTTVGLEITSPTTEDTATYFCARSADGSWSTYFNLWGQGTLVTVSS | SEQ ID NO: 76 |
| | VL | DIVMTQTPASVEAAVGGTVTIKCQASESISNYLAWYQQKPGQPPKLLIYKASTLASGVSSRFKGSGSGTEFTLTISDLESADAATYYCQTNYCCSSSDNGFAFGGGTEVVVK | SEQ ID NO: 77 |
| CD137 antibody clone 011 (rabbit) | VH CDR1 | GIDLSSYH | SEQ ID NO: 78 |
| | VH CDR2 | IAYGGNT | SEQ ID NO: 79 |
| | VH CDR3 | ARGYSEDSYWGL | SEQ ID NO: 80 |
| | VL CDR1 | QNIENY | SEQ ID NO: 81 |
| | VL CDR2 | DTS | |
| | VL CDR3 | QQDYGIIFVDNI | SEQ ID NO: 82 |
| | VH | QSLEESGGRLVTPGTPLTLTCTVSGIDLSSYHMCWVRQAPGKGLEYIGYIAYGGNTYYANWAKGRFTISKTSTTVDLRITS | SEQ ID NO: 83 |

TABLE 1-continued

Sequences

| Sequence name | Type of sequence | Sequence | Sequence identifier |
|---|---|---|---|
| | | PTTEDTATYFCARGYSEDSYWGLWGP GTLVTVSS | |
| | VL | AYDMTQTPASVEAAVGGTVTIKCQAS QNIENYLAWYQQKPGQPPKLLIYDTS KLTSGVPSRFSGSGSGTDFTLTISGVQ SDDAATYYCQQDYGIIFVDNIFGGGTE VVVK | SEQ ID NO: 84 |
| CD137 antibody clone 012 (rabbit) | VH CDR1 | GFSLSDYY | SEQ ID NO: 85 |
| | VH CDR2 | MSGSGST | SEQ ID NO: 86 |
| | VH CDR3 | ARDGDYAGWGYATGAFDP | SEQ ID NO: 87 |
| | VL CDR1 | QSVVGNSL | SEQ ID NO: 88 |
| | VL CDR2 | SAS | |
| | VL CDR3 | TGRYNSDTDTFV | SEQ ID NO: 89 |
| | VH | QSVEESGGRLVTPGTPLTLTCTVSGFSL SDYYMTWVRQAPGKGLEYIGIMSGSG STYYASWAKGRFTISKTSSTTLELKITS PTTEDTAIYFCARDGDYAGWGYATGAF DPWGPGTLVTVSS | SEQ ID NO: 90 |
| | VL | AAVLTQTPSPVSAAVGGTVTISCQASQ SVVGNSLLSWFQKKPGQPPKLLIYSAS SLASGVPSRFKGSGSGTQFTLTISDLES DDAATYYCTGRYNSDTDTFVFGGGTEV VVK | SEQ ID NO: 91 |
| Human CD137 (TNR9_Human) | | MGNSCYNIVATLLLVLNFERTRSLQDPCS NCPAGTFCDNNRNQICSPCPPNSFSSAG GQRTCDICRQCKGVFRTRKECSSTSNAE CDCTPGFHCLGAGCSMCEQDCKQGQELT KKGCKDCCFGTFNDQKRGICRPWTNCSL DGKSVLVNGTKERDVVCGPSPADLSPGA SSVTPPAPAREPGHSPQIISFFLALTSTALL FLLFFLTLRFSVVKRGRKKLLYIFKQPFMRP VQTTQEEDGCSCRFPEEEEGGCEL | SEQ ID NO: 92 |
| Human CD137 shuffle 6 (amino acids 24-47 replaced by wild boar CD137) | | MGNSCYNIVATLLLVLNFERTRSVPDPCS NCSAGTFCGKNIQELCMPCPPNSFSSAG GQRTCDICRQCKGVFRTRKECSSTSNAE CDCTPGFHCLGAGCSMCEQDCKQGQELT KKGCKDCCFGTFNDQKRGICRPWTNCSL DGKSVLVNGTKERDVVCGPSPADLSPGA SSVTPPAPAREPGHSPQIISFFLALTSTALL CCCEL | SEQ ID NO: 93 |
| Human CD137 shuffle 5 (amino acids 48-88 replaced by African elephant CD137) | | MGNSCYNIVATLLLVLNFERTRSLQDPCS NCPAGTFCDNNRNQICSPCPLNSFSSTGG QMNCDMCRKCEGVFKTKRACSPTRDAEC ECTPGFHCLGAGCSMCEQDCKQGQELTK KGCKDCCFGTFNDQKRGICRPWTNCSLD GKSVLVNGTKERDVVCGPSPADLSPGAS SVTPPAPAREPGHSPQIISFFLALTSTALLF LLFFLTLRFSVVKRGRKKLLYIFKQPFMRP VQTTQEEDGCSCRFPEEEEGGCEL | SEQ ID NO: 94 |
| Human CD137 shuffle 4 (amino acids 89-114 replaced by wild boar CD137) | | MGNSCYNIVATLLLVLNFERTRSLQDPCS NCPAGTFCDNNRNQICSPCPPNSFSSAG GQRTCDICRQCKGVFRTRKECSSTSNAE CDCVPGFRCLGAGCAMCEEYCQQGQELT QKGCKDCCFGTFNDQKRGICRPWTNCSL DGKSVLVNGTKERDVVCGPSPADLSPGA SSVTPPAPAREPGHSPQIISFFLALTSTALL FLLFFLTLRFSVVKRGRKKLLYIFKQPFMRP VQTTQEEDGCSCRFPEEEEGGCEL | SEQ ID NO: 95 |
| Human CD137 shuffle 3 (amino acids 115-138 replaced by wild boar CD137) | | MGNSCYNIVATLLLVLNFERTRSLQDPCS NCPAGTFCDNNRNQICSPCPPNSFSSAG GQRTCDICRQCKGVFRTRKECSSTSNAE CDCTPGFHCLGAGCSMCEQDCKQGQELT KEGCKDCSFGTFNDEEHGVCRPWTDCSL DGKSVLVNGTKERDVVCGPSPADLSPGA SSVTPPAPAREPGHSPQIISFFLALTSTALL FLLFFLTLRFSVVKRGRKKLLYIFKQPFMRP VQTTQEEDGCSCRFPEEEEGGCEL | SEQ ID NO: 96 |

TABLE 1-continued

Sequences

| Sequence name | Type of sequence | Sequence | Sequence identifier |
|---|---|---|---|
| Human CD137 shuffle 2 (amino acids 139-161 replaced by wild boar CD137) | | MGNSCYNIVATLLLVLNFERTRSLQDPCSNCPA GTFCDNNRNQICSPCPPNSFSSAGGQRTCDICR QCKGVFRTRKECSSTSNAECDCTPGFHCLGAGC SMCEQDCKQGQELTKKGCKDCCFGTFND QKRGICRPWTN<u>CSLAGKPVLMNGTKARD VVCGPR</u>PADLSPGASSVTPPAPAREPGHS PQIISFFLALTSTALLFLLFFLTLRFSVVKRG RKKLLYIFKQPFMRPVQTTQEEDGCSCRF PEEEEGGCEL | SEQ ID NO: 97 |
| Human CD137 shuffle 1 (amino acids 162-186 replaced by wild boar CD137) | | MGNSCYNIVATLLLVLNFERTRSLQDPCSNCPA GTFCDNNRNQICSPCPPNSFSSAGGQRTCDICR QCKGVFRTRKECSSTSNAECDCTPGFHCLGAGC SMCEQDCKQGQELTKKGCKDCCFGTFNDQKR GICRPWTNCSLDGKSVLVNGTKERDVVCGP<u>SPT DFSPGTPSTTMPVPGGEPGHTSH</u>IISFFLALTST ALLFLLFFLTLRFSVVKRGRKKLLYIFKQPFMRPV QTTQEEDGCSCRFPEEEEGGCEL | SEQ ID NO: 98 |
| b12 | VH CDR1 | GYRFSNFV | SEQ ID NO: 99 |
| | VH CDR2 | INPYNGNK | SEQ ID NO: 100 |
| | VH CDR3 | ARVGPYSWDDSPQDNYYMDV | SEQ ID NO: 101 |
| | VL CDR 1 | HSIRSRR | SEQ ID NO: 102 |
| | VL CDR 2 | CVS | |
| | VL CDR 3 | QVYGASSYT | SEQ ID NO: 103 |
| | VH | QVQLVQSGAEVKKPGASVKVSCQASGYR FSNFVIHWVRQAPGQRFEWMGWINPYN GNKEFSAKFQDRVTFTADTSANTAYMELR SLRSADTAVYYCARVGPYSWDDSPQDNY YMDVWGKGTTVIVSS | SEQ ID NO: 104 |
| | VL | EIVLTQSPGTLSLSPGERATFSCRSSHSIR SRRVAWYQHKPGQAPRLVIHGVSNRASG ISDRFSGSGSGTDFTLTITRVEPEDFALW CQVYGASSYTFGQGTKLERK | SEQ ID NO: 105 |
| IgG1m(a) CH3 region | | GQPREPQVYTLPPSRDELTKNQVSLTCLV KGFYPSDIAVEWESNGQPENNYKTTPPVL DSDGSFFLYSKLTVDKSRWQQGNVFSCS VMHEALHNHYTQKSLSLSPGK | SEQ ID NO: 106 |
| IgG1m(f) CH3 region | | GQPREPQVYTLPPSREEMTKNQVSLTCLV KGFYPSDIAVEWESNGQPENNYKTTPPVL DSDGSFFLYSKLTVDKSRWQQGNVFSCS VMHEALHNHYTQKSLSLSPGK | SEQ ID NO: 107 |
| IgG1m(ax) CH3 region | | GQPREPQVYTLPPSRDELTKNQVSLTCLV KGFYPSDIAVEWESNGQPENNYKTTPPVL DSDGSFFLYSKLTVDKSRWQQGNVFSCS VMHEGLHNHYTQKSLSLSPGK | SEQ ID NO: 108 |
| IgG1 heavy chain constant region-WT* | | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKRVEPKSCDKTHTCPPCPAPE LLGGPSVFLFPPKPKDTLMISRTPEVTCVV VDVSHEDPEVKFNWYVDGVEVHNAKTKP REEQYNSTYRVVSVLTVLHQDWLNGKEY KCKVSNKALPAPIEKTISKAKGQPREPQV YTLPPSREEMTKNQVSLTCLVKGFYPSDIA VEWESNGQPENNYKTTPPVLDSDGSFFLY SKLTVDKSRWQQGNVFSCSVMHEALHN HYTQKSLSLSPGK | SEQ ID NO: 109 |
| IgG1 heavy chain constant region-F405L* | | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKRVEPKSCDKTHTCPPCPAPE LLGGPSVFLFPPKPKDTLMISRTPEVTCVV VDVSHEDPEVKFNWYVDGVEVHNAKTKP REEQYNSTYRVVSVLTVLHQDWLNGKEY KCKVSNKALPAPIEKTISKAKGQPREPQV YTLPPSREEMTKNQVSLTCLVKGFYPSDIA | SEQ ID NO: 110 |

TABLE 1-continued

Sequences

| Sequence name | Type of sequence | Sequence | Sequence identifier |
|---|---|---|---|
| | | VEWESNGQPENNYKTTPPVLDSDGSFLL YSKLTVDKSRWQQGNVFSCSVMHEALH NHYTQKSLSLSPGK | |
| IgG1 heavy chain constant region-K409R* | | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKRVEPKSCDKTHTCPPCPAPE LLGGPSVFLFPPKPKDTLMISRTPEVTCVV VDVSHEDPEVKFNWYVDGVEVHNAKTKP REEQYNSTYRVVSVLTVLHQDWLNGKEY KCKVSNKALPAPIEKTISKAKGQPREPQV YTLPPSREEMTKNQVSLTCLVKGFYPSDIA VEWESNGQPENNYKTTPPVLDSDGSFFLY SRLTVDKSRWQQGNVFSCSVMHEALHN HYTQKSLSLSPGK | SEQ ID NO: 111 |
| Human IgG1 heavy chain constant sequence with FEAR* | | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKRVEPKSCDKTHTCPPCPAPE FEGGPSVFLFPPKPKDTLMISRTPEVTCVV VAVSHEDPEVKFNWYVDGVEVHNAKTKP REEQYNSTYRVVSVLTVLHQDWLNGKEY KCKVSNKALPAPIEKTISKAKGQPREPQV YTLPPSREEMTKNQVSLTCLVKGFYPSDIA VEWESNGQPENNYKTTPPVLDSDGSFFLY SRLTVDKSRWQQGNVFSCSVMHEALHN HYTQKSLSLSPGK | SEQ ID NO: 112 |
| Human IgG1 heavy chain constant sequence with FEAL* | | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKRVEPKSCDKTHTCPPCPAPE FEGGPSVFLFPPKPKDTLMISRTPEVTCVV VAVSHEDPEVKFNWYVDGVEVHNAKTKP REEQYNSTYRVVSVLTVLHQDWLNGKEY KCKVSNKALPAPIEKTISKAKGQPREPQV YTLPPSREEMTKNQVSLTCLVKGFYPSDIA VEWESNGQPENNYKTTPPVLDSDGSFLL YSKLTVDKSRWQQGNVFSCSVMHEALH NHYTQKSLSLSPGK | SEQ ID NO: 113 |
| Human Kappa light chain constant sequence | | RTVAAPSVFIFPPSDEQLKSGTASVVCLLN NFYPREAKVQWKVDNALQSGNSQESVTE QDSKDSTYSLSSTLTLSKADYEKHKVYAC EVTHQGLSSPVTKSFNRGEC | SEQ ID NO: 114 |
| Human CD40 | | MVRLPLQCVLWGCLLTAVHPEPPTACREK QYLINSQCCSLCQPGQKLVSDCTEFTETE CLPCGESEFLDTWNRETHCHQHKYCDPN LGLRVQQKGTSETDTICTCEEGWHCTSE ACESCVLHRSCSPGFGVKQIATGVSDTIC EPCPVGFFSNVSSAFEKCHPWTSCETKDL VVQQAGTNKTDVVCGPQDRLRALVVIPII FGILFAILLVLVFIKKVAKKPTNKAPHPKQE PQEINFPDDLPGSNTAAPVQETLHGCQPV TQEDGKESRISVQERQ | SEQ ID NO: 115 |
| Human IgG1 heavy chain constant sequence with FEA* | | ASTKGPSVFPLAPSSKSTSGGTAALGCLV KDYFPEPVTVSWNSGALTSGVHTFPAVLQ SSGLYSLSSVVTVPSSSLGTQTYINVNH KPSNTKVDKRVEPKSCDKTHTCPPCPAPE FEGGPSVFLFPPKPKDTLMISRTPEVTCVV VAVSHEDPEVKFNWYVDGVEVHNAKTKP REEQYNSTYRVVSVLTVLHQDWLNGKEY KCKVSNKALPAPIEKTISKAKGQPREPQV YTLPPSREEMTKNQVSLTCLVKGFYPSDIA VEWESNGQPENNYKTTPPVLDSDGSFFLY SKLTVDKSRWQQGNVFSCSVMHEALHN HYTQKSLSLSPGK | SEQ ID NO: 116 |

TABLE 1-continued

Sequences

| Sequence name | Type of sequence | Sequence | Sequence identifier |
|---|---|---|---|
| CD40-001 humanized antibody (HC6 and LC1): | | | |
| VH-CD40-001-HC6 | VH | EVQLVQSGAEVKKPGASVKVSCKTSGYT FTEYIMHWVRQAPGQGLEWMGGIIPNNG GTSYNQKFQGRVTMTVDKSTSTGYMELS SLRSEDTAVYYCTRREVYGRNYYALDYW GQGTLVTVSS | SEQ ID NO: 117 |
| CD40-001-HC6 | HC, IgG1 | EVQLVQSGAEVKKPGASVKVSCKTSGYT FTEYIMHWVRQAPGQGLEWMGGIIPNNG GTSYNQKFQGRVTMTVDKSTSTGYMELS SLRSEDTAVYYCTRREVYGRNYYALDYW GQGTLVTVSSASTKGPSVFPLAPSSKSTS GGTAALGCLVKDYFPEPVTVSWNSGALTS GVHTFPAVLQSSGLYSLSSVVTVPSSSLG TQTYICNVNHKPSNTKVDKRVEPKSCDKT HTCPPCPAPELLGGPSVFLFPPKPKDTLMI SRTPEVTCVVVDVSHEDPEVKFNWYVDG VEVHNAKTKPREEQYNSTYRVVSVLTVLH QDWLNGKEYKCKVSNKALPAPIEKTISKA KGQPREPQVYTLPPSREEMTKNQVSLTCL VKGFYPSDIAVEWESNGQPENNYKTTPPV LDSDGSFFLYSKLTVDKSRWQQGNVFSC SVMHEALHNHYTQKSLSLSPGK | SEQ ID NO: 118 |
| CD40-001-HC6-FEAL | HC, IgG1 FEAL | EVQLVQSGAEVKKPGASVKVSCKTSGYT FTEYIMHWVRQAPGQGLEWMGGIIPNNG GTSYNQKFQGRVTMTVDKSTSTGYMELS SLRSEDTAVYYCTRREVYGRNYYALDYW GQGTLVTVSSASTKGPSVFPLAPSSKSTS GGTAALGCLVKDYFPEPVTVSWNSGALTS GVHTFPAVLQSSGLYSLSSVVTVPSSSLG TQTYICNVNHKPSNTKVDKRVEPKSCDKT HTCPPCPAPEFEGGPSVFLFPPKPKDTLMI SRTPEVTCVVVAVSHEDPEVKFNWYVDG VEVHNAKTKPREEQYNSTYRVVSVLTVLH QDWLNGKEYKCKVSNKALPAPIEKTISKA KGQPREPQVYTLPPSREEMTKNQVSLTCL VKGFYPSDIAVEWESNGQPENNYKTTPPV LDSDGSFLLYSKLTVDKSRWQQGNVFSC SVMHEALHNHYTQKSLSLSPGK | SEQ ID NO: 119 |
| CD40-001-HC6-FEAR | HC, IgG1 FEAR | EVQLVQSGAEVKKPGASVKVSCKTSGYT FTEYIMHWVRQAPGQGLEWMGGIIPNNG GTSYNQKFQGRVTMTVDKSTSTGYMELS SLRSEDTAVYYCTRREVYGRNYYALDYW GQGTLVTVSSASTKGPSVFPLAPSSKSTS GGTAALGCLVKDYFPEPVTVSWNSGALTS GVHTFPAVLQSSGLYSLSSVVTVPSSSLG TQTYICNVNHKPSNTKVDKRVEPKSCDKT HTCPPCPAPEFEGGPSVFLFPPKPKDTLMI SRTPEVTCVVVAVSHEDPEVKFNWYVDG VEVHNAKTKPREEQYNSTYRVVSVLTVLH QDWLNGKEYKCKVSNKALPAPIEKTISKA KGQPREPQVYTLPPSREEMTKNQVSLTCL VKGFYPSDIAVEWESNGQPENNYKTTPPV LDSDGSFFLYSRLTVDKSRWQQGNVFSC SVMHEALHNHYTQKSLSLSPGK | SEQ ID NO: 120 |
| VL-CD40-001-LC1 | VL | DIQMTQSPSSLSASVGDRVTITCSASQGI NNYLNWYQQKPGKAVKLLIYYTSSLHSGV PSRFSGSGSGTDYTFTISSLQPEDIATYYC QQYSNLPYTFGGGTKVEIK | SEQ ID NO: 121 |
| CD40-001-LC1 | LC, kappa | DIQMTQSPSSLSASVGDRVTITCSASQGI NNYLNWYQQKPGKAVKLLIYYTSSLHSGV PSRFSGSGSGTDYTFTISSLQPEDIATYYC QQYSNLPYTFGGGTKVEIKRTVAAPSVFIF PPSDEQLKSGTASVVCLLNNFYPREAKVQ WKVDNALQSGNSQESVTEQDSKDSTYSL SSTLTLSKADYEKHKVYACEVTHQGLSSP VTKSFNRGEC | SEQ ID NO: 122 |

TABLE 1-continued

Sequences

| Sequence name | Type of sequence | Sequence | Sequence identifier |
|---|---|---|---|
| CD137-009 humanized antibody (HC7 and LC2): | | | |
| VH-CD137-009-HC7 | VH | EVQLVESGGGLVQPGRSLRLSCTASGFSL NDYWMSWVRQAPGKGLEWVGYIDVGGS LYYAASVKGRFTISRDDSKSIAYLQMNSL KTEDTAVYYCARGGLTYGFDLWGQGTLV TVSS | SEQ ID NO: 123 |
| CD137-009-HC7 | HC, IgG1 | EVQLVESGGGLVQPGRSLRLSCTASGFSL NDYWMSWVRQAPGKGLEWVGYIDVGGS LYYAASVKGRFTISRDDSKSIAYLQMNSL KTEDTAVYYCARGGLTYGFDLWGQGTLV TVSSASTKGPSVFPLAPSSKSTSGGTAAL GCLVKDYFPEPVTVSWNSGALTSGVHTFP AVLQSSGLYSLSSVVTVPSSSLGTQTYIC NVNHKPSNTKVDKRVEPKSCDKTHTCPP CPAPELLGGPSVFLFPPKPKDTLMISRTPE VTCVVVDVSHEDPEVKFNWYVDGVEVHN AKTKPREEQYNSTYRVVSVLTVLHQDWL NGKEYKCKVSNKALPAPIEKTISKAKGQP REPQVYTLPPSREEMTKNQVSLTCLVKGF YPSDIAVEWESNGQPENNYKTTPPVLDSD GSFFLYSKLTVDKSRWQQGNVFSCSVMH EALHNHYTQKSLSLSPGK | SEQ ID NO: 124 |
| CD137-009-HC7-FEAR | HC, IgG1 FEAR | EVQLVESGGGLVQPGRSLRLSCTASGFSL NDYWMSWVRQAPGKGLEWVGYIDVGGS LYYAASVKGRFTISRDDSKSIAYLQMNSL KTEDTAVYYCARGGLTYGFDLWGQGTLV TVSSASTKGPSVFPLAPSSKSTSGGTAAL GCLVKDYFPEPVTVSWNSGALTSGVHTFP AVLQSSGLYSLSSVVTVPSSSLGTQTYIC NVNHKPSNTKVDKRVEPKSCDKTHTCPP CPAPEFEGGPSVFLFPPKPKDTLMISRTPE VTCVVVAVSHEDPEVKFNWYVDGVEVHN AKTKPREEQYNSTYRVVSVLTVLHQDWL NGKEYKCKVSNKALPAPIEKTISKAKGQP REPQVYTLPPSREEMTKNQVSLTCLVKGF YPSDIAVEWESNGQPENNYKTTPPVLDSD GSFFLYSRLTVDKSRWQQGNVFSCSVMH EALHNHYTQKSLSLSPGK | SEQ ID NO: 125 |
| CD137-009-HC7-FEAL | HC, IgG1 FEAL | EVQLVESGGGLVQPGRSLRLSCTASGFSL NDYWMSWVRQAPGKGLEWVGYIDVGGS LYYAASVKGRFTISRDDSKSIAYLQMNSL KTEDTAVYYCARGGLTYGFDLWGQGTLV TVSSASTKGPSVFPLAPSSKSTSGGTAAL GCLVKDYFPEPVTVSWNSGALTSGVHTFP AVLQSSGLYSLSSVVTVPSSSLGTQTYIC NVNHKPSNTKVDKRVEPKSCDKTHTCPP CPAPEFEGGPSVFLFPPKPKDTLMISRTPE VTCVVVAVSHEDPEVKFNWYVDGVEVHN AKTKPREEQYNSTYRVVSVLTVLHQDWL NGKEYKCKVSNKALPAPIEKTISKAKGQP REPQVYTLPPSREEMTKNQVSLTCLVKGF YPSDIAVEWESNGQPENNYKTTPPVLDSD GSFLLYSKLTVDKSRWQQGNVFSCSVMH EALHNHYTQKSLSLSPGK | SEQ ID NO: 126 |
| VL-CD137-009-LC2 | VL | DIVMTQSPSSLSASVGDRVTITCQASEDI SSYLAWYQQKPGKAPKRLIYGASDLASG VPSRFSASGSGTDYTFTISSLQPEDIATYY CHYYATISGLGVAFGGGTKVEIK | SEQ ID NO: 127 |
| CD137-009-LC2 | LC, kappa | DIVMTQSPSSLSASVGDRVTITCQASEDI SSYLAWYQQKPGKAPKRLIYGASDLASG VPSRFSASGSGTDYTFTISSLQPEDIATYY CHYYATISGLGVAFGGGTKVEIKRTVAAP SVFIFPPSDEQLKSGTASVVCLLNNFYPRE AKVQWKVDNALQSGNSQESVTEQDSKD STYSLSSTLTLSKADYEKHKVYACEVTHQ GLSSPVTKSFN RGEC | SEQ ID NO: 128 |

TABLE 1-continued

Sequences

| Sequence name | Type of sequence | Sequence | Sequence identifier |
|---|---|---|---|
| Human CD137 (shuffle 6) | Amino acids 24-47 of human CD137 | LQDPCSNCPAGTFCDNNRNQICSP | SEQ ID NO: 129 |
| Human CD137 (shuffle 5) | Amino acids 48-88 of human CD137 | CPPNSFSSAGGQRTCDICRQCKGVFRTR KECSSTSNAECDC | SEQ ID NO: 130 |
| Human CD137 (shuffle 4) | Amino acids 89-114 of human CD137 | TPGFHCLGAGCSMCEQDCKQGQELTK | SEQ ID NO: 131 |
| Human CD137 (shuffle 3) | Amino acids 115-138 of human CD137 | KGCKDCCFGTFNDQKRGICRPWTN | SEQ ID NO: 132 |
| Human CD137 (shuffle 2) | Amino acids 139-161 of human CD137 | CSLDGKSVLVNGTKERDVVCGPS | SEQ ID NO: 133 |
| Human CD137 (shuffle 1) | Amino acids 162-186 of human CD137 | PADLSPGASSVTPPAPAREPGHSPQ | SEQ ID NO: 134 |
| Wild Boar CD137 | | MGNGYYNIVATVLLVMNFERTRSVPDPCS NCSAGTFCGKNIQELCMPCPSNSFSSTSG QKACNVCRKCEGVFRTKKECSSTSNAVC ECVPGFRCLGAGCAMCEEYCQQGQELTQ EGCKDCSFGTFNDEEHGVCRPWTDCSLA GKPVLMNGTKARDVVCGPRPTDFSPGTP STTMPVPGGEPGHTSHVIIFFLALMSTAVF VLVSYLALRFSVVQQGRKKLLYIVKQPFLK PAQTVQEEDACSCRFPEEEEGECEL | SEQ ID NO: 135 |
| African Elephant CD137 | | MGNGYYNMVATVLLVMNFERTGAVQDSC RDCLAGTYCVKNESQICSPCPLNSFSSTG GQMNCDMCRKCEGVFKTKRACSPTRDAE CECVSGFHCLGAGCTMCQQDCKQGQEL TKEGCKDCCLGTFNDQKNGICRPWTNCS LEGKSVLANGTKKRDVVCGPPAADSFPDT SSVTVPAPERKPDHHPQIITFFLALISAALL FLVFFLVVRFSVAKWGRKKLLYIFKQPFIK PVQTAQEEDGCSCRFPEEEEGDCEL | SEQ ID NO: 136 |

*amino acids positions 118-447 according to EU numbering

DETAILED DESCRIPTION OF THE INVENTION

Definitions

The term "CD40" as used herein, refers to CD40, also referred to as tumor necrosis factor receptor superfamily member 5 (TNFRSF5), which is the receptor for the ligand TNFSF5/CD40L. CD40 is known to transduce TRAF6- and MAP3K8-mediated signals that activate ERK in macrophages and B cells, leading to induction of immunoglobulin secretion by the B cells. Other synonyms used for CD40 include, but are not limited to, B-cell surface antigen CD40, Bp50, CD40L receptor and CDw40. In one embodiment, CD40 is human CD40, having UniProt accession number P25942. The sequence of human CD40 is also shown in SEQ ID NO:115. Amino acids 1-20 of SEQ ID NO:115 correspond to the signal peptide of human CD40; while amino acids 21-193 of SEQ ID NO:115 correspond to the extracellular domain of human CD40; and the remainder of the protein; i.e. from amino acids 194-215 and 216-277 of SEQ ID NO:115 is transmembrane and cytoplasmic domain, respectively.

The term "CD137" as used herein, refers to CD137 (4-1BB), also referred to as tumor necrosis factor receptor superfamily member 9 (TNFRSF9), which is the receptor for the ligand TNFSF9/4-1BBL. CD137 (4-1BB) is believed to be involved in T-cell activation. Other synonyms for CD137 include, but are not limited to, 4-1BB ligand receptor, CDw137, T-cell antigen 4-1BB homolog and T-cell antigen ILA. In one embodiment, CD137 (4-1BB) is human CD137 (4-1BB), having UniProt accession number Q07011. The sequence of human CD137 is also shown in SEQ ID NO:92. Amino acids 1-23 of SEQ ID NO:92 correspond to the signal peptide of human CD137; while amino acids 24-186 of SEQ ID NO:92 correspond to the extracellular domain of human CD137; and the remainder of the protein, i.e. from amino acids 187-213 and 214-255 of SEQ ID NO:92 are transmembrane and cytoplasmic domain, respectively.

The term "chimeric antibody" as used herein, refers to an antibody wherein the variable region is derived from a non-human species (e.g. derived from rodents) and the constant region is derived from a different species, such as human. Chimeric antibodies may be generated by antibody engineering. "Antibody engineering" is a term used generically for different kinds of modifications of antibodies, and processes for antibody engineering are well-known for the skilled person. In particular, a chimeric antibody may be generated by using standard DNA techniques as described in Sambrook et al., 1989, Molecular Cloning: A laboratory Manual, New York: Cold Spring Harbor Laboratory Press, Ch. 15. Thus, the chimeric antibody may be a genetically or an enzymatically engineered recombinant antibody. It is within the knowledge of the skilled person to generate a chimeric antibody, and thus, generation of the chimeric antibody may be performed by other methods than those described herein. Chimeric monoclonal antibodies for therapeutic applications in humans are developed to reduce anticipated antibody immunogenicity of non-human antibodies, e.g. rodent antibodies. They may typically contain non-human (e.g. murine or rabbit) variable regions, which are specific for the antigen of interest, and human constant antibody heavy and light chain domains. The terms "variable region" or "variable domain" as used in the context of chimeric antibodies, refer to a region which comprises the CDRs and framework regions of both the heavy and light chains of an immunoglobulin, as described below.

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody CDRs, which together form the antigen-binding site, onto a homologous human acceptor framework region (FR) (see WO92/22653 and EP0629240). In order to fully reconstitute the binding affinity and specificity of the parental antibody, the substitution of framework residues from the parental antibody (i.e. the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties and/or additional amino acid mutations may be introduced in the constant region.

As used herein, a protein which is "derived from" another protein, e.g., a parent protein, means that one or more amino acid sequences of the protein are identical or similar to one or more amino acid sequences in the other or parent protein. For example, in an antibody, binding arm, antigen-binding region, constant region, or the like which is derived from another or a parent antibody, binding arm, antigen-binding region, or constant region, one or more amino acid sequences are identical or similar to those of the other or parent antibody, binding arm, antigen-binding region, or constant region. Examples of such one or more amino acid sequences include, but are not limited to, those of the VH and VL CDRs and/or one or more or all of the framework regions, VH, VL, CL, hinge, or CH regions. For example, a humanized antibody can be described herein as "derived from" a non-human parent antibody, meaning that at least the VL and VH CDR sequences are identical or similar to the VH and VL CDR sequences of said non-human parent antibody. A chimeric antibody can be described herein as being "derived from" a non-human parent antibody, meaning that typically the VH and VL sequences may be identical or similar to those of the non-human parent antibody. Another example is a binding arm or an antigen-binding region which may be described herein as being "derived from" a particular parent antibody, meaning that said binding arm or antigen-binding region typically comprises identical or similar VH and/or VL CDRs, or VH and/or VL sequences to the binding arm or antigen-binding region of said parent antibody. As described elsewhere herein, however, amino acid modifications such as mutations can be made in the CDRs, constant regions or elsewhere in the antibody, binding arm, antigen-binding region or the like, to introduce desired characteristics. When used in the context of one or more sequences derived from a first or parent protein, a "similar" amino acid sequence preferably has a sequence identity of at least about 50%, such as at least about 60%, at least about 70%, at least about 80%, at least about 90%, at least about 95%, or at least about 97%, 98% or 99%.

Non-human antibodies can be generated in a number of different species, such as mouse, rabbit, chicken, guinea pig, llama and goat.

Monoclonal antibodies can be produced by a variety of techniques, including conventional monoclonal antibody methodology, e.g., the standard somatic cell hybridization technique of Kohler and Milstein, Nature 256: 495 (1975). Other techniques for producing monoclonal antibodies can be employed, e.g., viral or oncogenic transformation of B-lymphocytes or phage display techniques using libraries of antibody genes, and such methods are well known to a person skilled in the art.

Hybridoma production in such non-human species is a very well established procedure. Immunization protocols and techniques for isolation of splenocytes of immunized animals/non-human species for fusion are known in the art. Fusion partners (e.g., murine myeloma cells) and fusion procedures are also known.

The term "human antibody" as used herein, refers to antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

Human monoclonal antibodies can be generated using transgenic or transchromosomal mice carrying parts of the human immune system rather than the mouse system.

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain (abbreviated "HC") typically is comprised of a heavy chain variable region (abbreviated herein as $V_H$ or VH) and a heavy chain constant region (abbreviated herein as $C_H$ or CH). The heavy chain constant region typically is comprised of three domains, $C_H1$, $C_H2$, and $C_H3$. The heavy chain may typically further comprise a hinge region. Each light chain (abbreviated "LC") typically is comprised of a light chain variable region (abbreviated herein as $V_L$ or VL) and a light chain constant region (abbreviated herein as $C_L$ or CL). The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk 3. Mol. Biol. 196, 901-917 (1987)). Unless otherwise stated or contradicted by context, CDR sequences herein are identified according to IMGT rules using DomainGapAlign (Program version: 4.9.1; 2013-12-19) (Lefranc M P., Nucleic Acids Research 1999; 27:209-212, and Ehrenmann F., Kaas Q. and Lefranc M.-P. Nucleic Acids Research 2010; 38, D301-307; see also internet http address www.imgt.org/).

Unless otherwise stated or contradicted by context, reference to amino acid positions in the constant regions in the present invention is according to the EU-numbering (Edelman et al., Proc Natl Acad Sci USA. 1969 May; 63(1):78-85; Kabat et al., Sequences of Proteins of Immunological Interest, Fifth Edition. 1991 NIH Publication No. 91-3242).

The term "antibody" (Ab) in the context of the present invention refers to a molecule comprising at least one antibody variable domain such as an immunoglobulin heavy chain variable region, or an immunoglobulin heavy chain variable region and a light chain variable region, or a fragment thereof, or a derivative of either thereof, which has the ability to specifically bind to an antigen, such as under typical physiological conditions with a half-life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). In particular the antibody may be an immunoglobulin molecule, a fragment of an immunoglobulin molecule or a derivative thereof. The variable regions of the heavy and light chains of the immunoglobulin molecule contain a binding domain that interacts with an antigen. The constant regions of the antibodies may mediate the binding of the immunoglobulin to host tissues or factors, including various cells of the immune system (such as effector cells) and components of the complement system such as C1q, the first component in the classical pathway of complement activation. As indicated above, the term antibody herein, unless otherwise stated or clearly contradicted by context, includes fragments of an antibody that are antigen-binding fragments, i.e., retain the ability to specifically bind to the antigen. It has been shown that the antigen-binding function of an antibody may be performed by fragments of a full-length antibody. Examples of antigen-binding fragments encompassed within the term "antibody" include (i) a Fab' or Fab fragment, a monovalent fragment consisting of the $V_L$, $V_H$, $C_L$ and $C_H1$ domains, or a monovalent antibody as described in WO2007059782 (Genmab); (ii) F(ab')$_2$ fragments, bivalent fragments comprising two Fab fragments linked by a disulfide bridge at the hinge region; (iii) an Fd fragment consisting essentially of the $V_H$ and $C_H1$ domains; (iv) an Fv fragment consisting essentially of the $V_L$ and $V_H$ domains of a single arm of an antibody, (v) a dAb fragment (Ward et al., Nature 341, 544-546 (1989)), which consists essentially of a VH domain and also called domain antibodies (Holt et al; Trends Biotechnol. 2003 November; 21(11): 484-90); (vi) camelid or nanobodies (Revets et al; Expert Opin Biol Ther. 2005 January; 5(1):111-24) and (vii) an isolated complementarity determining region (CDR). Furthermore, although the two domains of the Fv fragment, $V_L$ and $V_H$, are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention, as well as bispecific formats of such fragments, are discussed further herein. It also should be understood that the term antibody, unless specified otherwise, also includes polyclonal antibodies, monoclonal antibodies (mAbs), antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype and/or subclass.

Regular antibodies; e.g. antibodies raised in any species are normally monospecific, bivalent antibodies, which means that they comprise two antigen-binding regions which bind to the same epitope.

The term "multispecific antibody" in the context of the present invention refers to an antibody having different antigen-binding regions defined by different antibody sequences. Thus a multispecific antibody may have two, three, four, five or more different antigen-binding regions. Examples of multispecific antibodies include antibodies having two different antigen-binding regions; i.e. a bispecific antibody.

Examples of multispecific antibodies comprising three or more different antigen-binding regions include but are not limited to (i) bispecific antibodies coupled with an additional single chain variable Fragment (scFv) at their Fc part (Weidle et al., Cancer Genomics Proteomics. 2013 January-February; 10(1):1-18), (ii) fusion proteins consisting of three or more scFv (triabody, tetrabody; Chames et al., FEMS Microbiol Lett. 2000 Aug. 1; 189(1):1-8) and (iii) fusion proteins connected to scFv (Kermer et. al. Mol Cancer Ther. 2014 January; 13(1):112-21).

The term "bispecific antibody" in the context of the present invention refers to an antibody having two different antigen-binding regions defined by different antibody sequences.

When used herein, unless contradicted by context, the term "Fab-arm" or "arm" refers to one heavy chain-light chain pair and is used interchangeably with "half molecules" herein.

The term "binding arm comprising an antigen-binding region" means an antibody molecule or fragment that comprises an antigen-binding region. Thus, a binding arm can comprise, e.g., the six VH and VL CDR sequences, the VH and VL sequences, a Fab or Fab' fragment, or a Fab-arm.

When used herein, unless contradicted by context, the term "Fc region" refers to an antibody region comprising at least a hinge region, a CH2 domain, and a CH3 domain.

As used herein, the term "isotype" refers to the specific type of immunoglobulin encoded by the HC (for instance IgG, IgD, IgA, IgE, and IgM) or LC (kappa, K or lambda, λ) genes. Within each isotype, there may be several subclasses, such as IgG1, IgG2, IgG3, IgG4, IgA1, IgA2, etc.

The term "monovalent antibody" means in the context of the present invention that an antibody molecule is capable of binding a single molecule of the antigen, and thus is not capable of antigen cross-linking.

A "CD40 antibody" or "anti-CD40 antibody" is an antibody as described above, which binds specifically to the antigen CD40.

A "CD137 antibody" or "anti-CD137 antibody" is an antibody as described above, which binds specifically to the antigen CD137.

A "CD40xCD137 antibody" or "anti-CD40xCD137 antibody" is a bispecific antibody, which comprises two different antigen-binding regions, one of which binds specifically to the antigen CD40 and one of which binds specifically to the antigen CD137.

The term "specifically binds", "specifically binding", "specific binding" or other similar wording refers to the ability of an antibody to preferentially bind to a particular antigen compared to other antigens, or to a particular part (epitope) of an antigen compared to other parts of the same antigen.

As used herein, the term "binding" in the context of the binding of an antibody to a predetermined antigen or epitope typically is a binding with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antibody as the ligand and the antigen as the analyte (or vice versa), and binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than the $K_D$ for binding to a non-specific antigen (e.g., BSA, casein) other than the predetermined antigen or a closely-related antigen. The amount with which the affinity is higher is dependent on the $K_D$ of the antibody, so that when the $K_D$ of the antibody is very low (that is, the antibody is highly specific), then the amount with which the affinity for the antigen is higher than the affinity for a non-specific antigen may be at least 10,000 fold.

The term "$k_d$" (sec$^{-1}$), as used herein, refers to the dissociation rate constant of a particular antibody-antigen interaction. Said value is also referred to as the $k_{off}$ value.

The term "$K_D$" (M), as used herein, refers to the dissociation equilibrium constant of a particular antibody-antigen interaction.

Two antibodies have the "same specificity" if they bind to the same antigen and to the same epitope. Whether an antibody to be tested recognizes the same epitope as a certain antigen-binding antibody, i.e., the antibodies bind to the same epitope, may be tested by different methods well known to a person skilled in the art.

The competition between the antibodies can be detected by a cross-blocking assay. For example, a competitive ELISA assay may be used as a cross-blocking assay. For example, target antigen may be coated on the wells of a microtiter plate and antigen-binding antibody and candidate competing test antibody may be added. The amount of the antigen-binding antibody bound to the antigen in the well indirectly correlates with the binding ability of the candidate competing test antibody that competes therewith for binding to the same epitope. Specifically, the larger the affinity of the candidate competing test antibody is for the same epitope, the smaller the amount of the antigen-binding antibody bound to the antigen-coated well. The amount of the antigen-binding antibody bound to the well can be measured by labeling the antibody with detectable or measurable labeling substances.

An antibody competing for binding to an antigen with another antibody, e.g., an antibody comprising heavy and light chain variable regions as described herein, or an antibody having the specificity for an antigen of another antibody, e.g., an antibody comprising heavy and light chain variable regions as described herein, may be an antibody comprising variants of said heavy and/or light chain variable regions as described herein, e.g. modifications in the CDRs and/or a certain degree of identity as described herein.

An "isolated multispecific antibody" as used herein is intended to refer to a multispecific antibody which is substantially free of other antibodies having different antigenic specificities (for instance an isolated bispecific antibody that specifically binds to CD40 and CD137 is substantially free of monospecific antibodies that specifically bind to CD40 or CD137).

The term "epitope" means a protein determinant capable of specific binding to an antibody. Epitopes usually consist of surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents. The epitope may comprise amino acid residues directly involved in the binding and other amino acid residues, which are not directly involved in the binding, such as amino acid residues which are effectively blocked or covered by the specifically antigen-binding peptide (in other words, the amino acid residue is within the footprint of the specifically antigen-binding peptide).

The term "monoclonal antibody" as used herein refers to a preparation of antibody molecules of single molecular composition. A monoclonal antibody composition displays a single binding specificity and affinity for a particular epitope.

When used herein the term "heterodimeric interaction between the first and second CH3 regions" refers to the interaction between the first CH3 region and the second CH3 region in a first-CH3/second-CH3 heterodimeric antibody.

When used herein the term "homodimeric interactions of the first and second CH3 regions" refers to the interaction between a first CH3 region and another first CH3 region in a first-CH3/first-CH3 homodimeric antibody and the interaction between a second CH3 region and another second CH3 region in a second-CH3/second-CH3 homodimeric antibody.

When used herein the term "homodimeric antibody" refers to an antibody comprising two first Fab-arms or half-molecules, wherein the amino acid sequence of said Fab-arms or half-molecules is the same.

When used herein the term "heterodimeric antibody" refers to an antibody comprising a first and a second Fab-arm or half-molecule, wherein the amino acid sequence of said first and second Fab-arms or half-molecules are different. In particular, the CH3 region, or the antigen-binding region, or the CH3 region and the antigen-binding region of said first and second Fab-arms/half-molecules are different.

The term "reducing conditions" or "reducing environment" refers to a condition or an environment in which a substrate, such as a cysteine residue in the hinge region of an antibody, is more likely to become reduced than oxidized.

The present invention also provides multispecific antibodies, such as bispecific antibodies, comprising functional variants of the $V_L$ regions, $V_H$ regions, or one or more CDRs of the bispecific antibodies of the examples. A functional variant of a $V_L$, $V_H$, or CDR used in the context of a bispecific antibody still allows each antigen-binding region of the bispecific antibody to retain at least a substantial proportion (at least about 50%, 60%, 70%, 80%, 90%, 95% or more) of the affinity and/or the specificity/selectivity of the parent bispecific antibody and in some cases such a bispecific antibody may be associated with greater affinity, selectivity and/or specificity than the parent bispecific antibody.

Such functional variants typically retain significant sequence identity to the parent bispecific antibody. The percent identity between two sequences is a function of the number of identical positions shared by the sequences (i.e., % homology=#of identical positions/total #of positions× 100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

In the context of the present invention the following notations are, unless otherwise indicated, used to describe a mutation; name of amino acid which is mutated, followed by the position number which is mutated, followed by what the mutation encompass. Thus if the mutation is a substitution, the name of the amino acid which replaces the prior amino acid is included, if the amino acid is deleted it is indicated by a *, if the mutation is an addition the amino acid being added is included after the original amino acid. Amino acid names may be one or three-letter codes. Thus for example; substitution of a Lysine in position 409 with an Arginine is referred to as K409R, substitution of Lysine in position 409 with any amino acid is referred to as K409X, deletion of Lysine in position 409 is referred to as K409* and addition of P after Lysine at position K409 is referred to as K409KP.

Exemplary variants include those which differ from the VH and/or VL and/or CDRs of the parent sequences mainly by conservative substitutions; for instance 12, such as 11, 10, 9, 8, 7, 6, 5, 4, 3, 2 or 1 of the substitutions in the variant are conservative amino acid residue replacements.

In the context of the present invention, conservative substitutions may be defined by substitutions within the classes of amino acids reflected in the following:
Amino acid residue classes for conservative substitutions:
Acidic Residues: Asp (D) and Glu (E)
Basic Residues: Lys (K), Arg (R), and His (H)
Hydrophilic Uncharged Residues: Ser (S), Thr (T), Asn (N), and Gln (Q)
Aliphatic Uncharged Residues: Gly (G), Ala (A), Val (V), Leu (L), and Ile (I)
Non-polar Uncharged Residues: Cys (C), Met (M), and Pro (P)
Aromatic Residues: Phe (F), Tyr (Y), and Trp (W)

The first and/or second antigen-binding region of the present invention may also be a variant of a first and/or second antigen-binding region, respectively, disclosed herein.

It is well known to a person skilled in the art how to introduce modifications and that certain amino acids of the CDR sequences may be modified; e.g. by amino acid substitutions to e.g. increase affinity of an antibody to its target antigen, reduce potential immunogenicity of non-human antibodies to be used in humans and/or to increase the yield of antibodies expressed by a host cell. Such modifications can be introduced without affecting the epitope of the target antigen to which the antibody binds.

The term "recombinant host cell" (or simply "host cell" or "cell"), as used herein, is intended to refer to a cell into which a nucleic acid, such as an expression vector has been introduced, e.g. a nucleic acid, such as an expression vector encoding a multispecific antibody of the invention. Recombinant host cells include, for example, transfectomas, such as CHO, CHO-S, HEK, HEK293, HEK-293F, Expi293F, PER.C6 or NS0 cells, and lymphocytic cells.

The term "treatment" refers to the administration of an effective amount of a therapeutically active multispecific antibody of the present invention with the purpose of easing, ameliorating, arresting or eradicating (curing) symptoms or disease states.

The term "effective amount" or "therapeutically effective amount" refers to an amount effective, at dosages and for periods of time necessary, to achieve a desired therapeutic result. A therapeutically effective amount of a multispecific antibody may vary according to factors such as the disease state, age, sex, and weight of the individual, and the ability of the multispecific antibody to elicit a desired response in the individual. A therapeutically effective amount is also one in which any toxic or detrimental effects of the multispecific antibody or a fragment thereof, are outweighed by the therapeutically beneficial effects.

The term "anti-idiotypic antibody" refers to an antibody which recognizes unique determinants generally associated with the antigen-binding site of an antibody.

In the context of the present invention the term "induce Fc-mediated effector function to a lesser extent" used in relation to an antibody, including a multispecific antibody, means that the antibody induces Fc-mediated effector functions, such function in particular being selected from the list of IgG Fc receptor (FcgammaR, FcγR) binding, C1q binding, ADCC or CDC, to a lesser extent compared to a human IgG1 antibody comprising (i) the same CDR sequences, in particular comprising the same first and second antigen-binding regions, as said antibody and (ii) two heavy chains comprising human IgG1 hinge, CH2 and CH3 regions.

Fc-mediated effector function may be measured by binding to FcγRs, binding to C1q, or induction of Fc-mediated cross-linking via FcγRs.

Further Aspects and Embodiments of the Invention

The present invention relates to a molecule comprising two different antigen-binding regions, one of which has specificity for human CD40 and one of which has specificity for human CD137.

In a particular embodiment, said molecule may be a multispecific antibody.

Thus the present invention relates to a multispecific antibody comprising (i) a first antigen-binding region binding to human CD40; and (ii) a second antigen-binding region binding to human CD137.

As shown by the inventors of the present invention a bispecific antibody according to the present invention may induce intracellular signaling when binding to CD40 expressed on one cell and binding to CD137 expressed on another cell. Thus, a multispecific antibody according to the present invention is able to trans-activate two different cells. In humans, CD40 is expressed on a number of cells including antigen-presenting cells (APCs), such as dendritic cells, whereas CD137 is expressed on T cells and other cells. Thus, multispecific antibodies, such as bispecific antibodies, according to the present invention binding to CD40 and CD137 are able to bind simultaneously to APCs and T cells expressing these receptors. Without being bound by theory, multispecific antibodies, such as bispecific antibodies, according to the present invention may thus (i) mediate cell-to-cell interaction between APCs and T cells by receptor binding and (ii) activate both CD40 and CD137 at once, which is primarily induced by cross-linking and receptor clustering upon cell-to-cell interaction and not necessarily dependent on agonistic activity of the parental monospecific bivalent antibodies. Thus, these trans-activating multispecific antibodies, such as bispecific antibodies, exert co-stimulatory activity in the context of APC:T cell interactions, and can elicit a T cell response against tumor cells. As such, this mechanism of action can reflect natural T-cell activation via antigen-presentation by activated APCs, allowing for the presentation of a variety of tumor-specific antigens by the APCs to T cells. Without being limited to theory, the costimulatory activity may provide for one or more of (i) only specific T cells being activated (i.e., those that are in contact with an APC) as opposed to any T cell and (ii) re-activation of exhausted T cells, by strong co-stimulation via activated APCs and CD137 triggering and (iii) the priming of T cells by inducing antigen presentation by activated APCs and at the same time triggering CD137.

Thus, a multispecific, such as a bispecific, antibody of the present invention may be used for treatment of a disease which would benefit from activation of T cells, such as cancer.

In one embodiment, the multispecific antibody according to the present invention comprises (I) a first antigen-binding region binding to human CD40, wherein said first antigen-binding region comprises heavy and light chain variable region CDR1, CDR2, and CDR3 selected from the group consisting of:
  a) heavy chain variable region CDR3 having the sequence set forth in SEQ ID NO:3 or a sequence wherein up to four amino acids are modified in SEQ ID NO:3, and light chain variable region CDR3 having the sequence set forth in SEQ ID NO:5 or a sequence wherein up to four amino acids are modified in SEQ ID NO:5; and
  b) heavy and light chain variable region CDR3 of an antibody which (i) competes for human CD40 binding with an antibody comprising heavy and light chain variable region CDR3 according to a) and/or (ii) has the specificity for CD40 of an antibody comprising heavy and light chain variable region CDR3 according to a), and
(II) a second antigen-binding region binding to human CD137.

In a further embodiment, the first antigen-binding region may further comprise heavy chain variable region CDR1 having the sequence as set forth in SEQ ID NO:1 or a sequence wherein up to 2 amino acids are modified in SEQ ID NO:1, and/or heavy chain variable region CDR2 having the sequence as set forth in SEQ ID NO:2 or a sequence wherein up to 2 amino acids are modified in SEQ ID NO:2; and/or light chain variable region CDR1 having the sequence as set forth in SEQ ID NO:4 or a sequence wherein up to 2 amino acids are modified in SEQ ID NO:4, and/or light chain variable region CDR2 having the sequence YTS or a sequence wherein up to 2 amino acids are modified in YTS.

Thus, in one embodiment, the present invention relates to a multispecific antibody comprising
(I) a first antigen-binding region binding to human CD40, wherein said first antigen-binding region comprises heavy and light chain variable region CDR1, CDR2, and CDR3 selected from the group consisting of:
  a) heavy chain variable region CDR1, CDR2 and CDR3 having the sequences set forth in SEQ ID NOs:1, 2 and 3, respectively, and light chain variable region CDR1, CDR2 and CDR3 having the sequences set forth in SEQ ID NOs:4, YTS and 5, respectively;
  b) heavy and light chain variable region CDR1, CDR2 and CDR3 according to a) having a total of one to twelve mutations; and
  c) heavy and light chain variable region CDR1, CDR2 and CDR3 of an antibody which (i) competes for human CD40 binding with an antibody comprising heavy and light chain variable region CDR1, CDR2 and CDR3 according to a) or b) and/or (ii) has the specificity for CD40 of an antibody comprising heavy and light chain variable region CDR1, CDR2 and CDR3 according to a) or b), and
(II) a second antigen-binding region binding to human CD137.

In a further embodiment, said first antigen-binding region comprises a first heavy chain variable (VH) sequence, and a first light chain variable (VL) sequence, and said second antigen-binding region comprises a second heavy chain variable (VH) sequence, and a second light chain variable (VL) sequence, wherein said variable sequences each comprises three CDR sequences, CDR1, CDR2 and CDR3, respectively, and four framework sequences, FR1, FR2, FR3 and FR4, respectively.

In a further embodiment, said multispecific antibody comprises (I) a first binding arm comprising said first antigen-binding region, and (II) a second binding arm comprising said second antigen-binding region.

In one embodiment, the first binding arm comprises said first antigen-binding region and a first heavy chain constant sequence, and the second binding arm comprises said second-antigen-binding region and a second heavy chain constant sequence.

In a further embodiment, (i) said first binding arm comprises said first antigen-binding region, wherein the first binding arm comprises a first heavy chain comprising a first heavy chain variable (VH) sequence and a first heavy chain constant (CH) sequence, and a first light chain comprising a first light chain variable (VL) sequence, and (ii) said second binding arm comprises said second antigen-binding region, wherein the second binding arm comprises a second heavy chain comprising a second heavy chain variable (VH) sequence and a second heavy chain constant (CH) sequence, and a second light chain comprising a second light chain variable (VL) sequence.

In a further embodiment, said first light chain further comprises a first light chain constant (CL) sequence, and said second light chain further comprises a second light chain constant (CL) sequence.

In one embodiment, the first binding arm comprises a first Fab-arm comprising said first antigen-binding region, and the second binding arm comprises a second Fab-arm comprising said second antigen-binding region.

In one embodiment, said first and second antigen-binding regions of the multispecific antibody according to the present invention are derived from a humanized antibody. In one embodiment, the first and second binding arm may be derived from a humanized antibody.

In one embodiment, the first and second binding arms of the multispecific antibody according to the present invention are derived from a full-length antibody.

In one embodiment, the first and second binding arm of the multispecific antibody according to the present invention are derived from a full-length IgG1,λ (lambda) or IgG1,κ (kappa) antibody.

In one embodiment, the first and second binding arms are derived from a monoclonal antibody.

In one embodiment, the first and said second heavy chains of the multispecific antibody according to the present invention are of an IgG isotype. The subclass of the first and second heavy chains may, for example, be separately selected from the group consisting of IgG1, IgG2, IgG3, and IgG4. In one embodiment, the first and second heavy chains are of the same IgG subclass, such as IgG1.

In one embodiment, the multispecific antibody according to the present invention is an isolated antibody.

In a further embodiment, each of said first and second heavy chains comprises at least a hinge region, a CH2 and a CH3 region. In a further embodiment, the CH3 regions of said first and second heavy chains comprise asymmetrical mutations.

In one embodiment, the multispecific antibody according to the present invention is a bispecific antibody.

In one embodiment, the multispecific antibody according to the present invention may cross-link one cell expressing human CD40, e.g. a first cell, and another cell expressing human CD137, e.g. a second cell.

In one embodiment, said cross-linking is determined by an assay using a first cell line expressing human CD40 and a second cell line expressing human CD137, and wherein either the first or the second cell line comprises a reporter structure resulting in the production of a measurable reporter upon NF-κB activation.

In one embodiment said first cell may be an antigen-presenting cell and said second cell may be a T-cell, such as a CD4$^+$ or a CD8$^+$ T-cell.

Different methods may be used to determine cross-linking a first cell expressing CD40 and a second cell expressing CD137, and the present invention is not limited to any particular method.

In one embodiment, said cross-linking may be determined by a reporter assay e.g. as described in Example 4. In brief, said assay comprises co-culturing a reporter cell line expressing a first target antigen and transduced with a reporter gene (luciferase for instance) driven by NF-κB response elements with a second cell line expressing a second target antigen, adding a multispecific antibody according to the present invention in concentrations from 100 ng/mL to 10,000 ng/mL to the cell co-culture, and measuring reporter gene expression, e.g. luciferase generation, wherein said first target antigen is human CD40 and said second target antigen is human CD137 or vice versa.

A multispecific antibody capable of inducing cross-linking of the CD40 and CD137 expressed on different cells, will in this assay result in measurable activation of the first target antigen based on the reporter gene expression upon NF-κB pathway activation.

In one embodiment, the multispecific antibody according to the present invention may be able to induce reporter gene expression produced upon NF-κB activation only upon addition of the second cell line expressing the second target antigen without the NF-κB reporter gene.

In one embodiment, the multispecific antibody according to the present invention may be able to induce higher reporter gene expression produced upon NF-κB activation when the second cell line expressing the second target antigen without the NF-κB reporter gene is added compared to addition of a second cell line not expressing the second target antigen.

In one embodiment, the multispecific antibody is a bispecific antibody, and said bispecific antibody may, in one embodiment:
(i) induce reporter gene expression when added to a co-culture of the reporter cell line expressing CD137 and the second cell line expressing CD40, or
(ii) induce a higher amount of the reporter gene expression when added to the co-culture of the reporter cell line expressing CD137 and the second cell line expressing CD40, compared to a reference bispecific antibody comprising the same second antigen-binding region binding to human CD137, but wherein the first antigen-binding region of the reference bispecific antibody binds to an irrelevant target antigen, e.g. wherein the first antigen-binding region comprises heavy chain variable region CDR1, CDR2 and CDR3 having the sequences set forth in SEQ ID NOs:99, 100 and 101, respectively, and light chain variable region CDR1, CDR2 and CDR3 having the sequences set forth in SEQ ID NOs:102, GVS and 103, respectively.

In one embodiment, the multispecific antibody is a bispecific antibody, and said bispecific antibody may, in one embodiment:
(i) induce reporter gene expression when added to a co-culture of the reporter cell line expressing CD40 and the second cell line expressing CD137, or
(ii) induce a higher amount of the reporter gene expression when added to the co-culture of the reporter cell line expressing CD40 and the second cell line expressing CD137, compared to a reference bispecific antibody comprising the same first antigen-binding region binding to human CD40, but wherein the second antigen-binding region of the reference bispecific antibody comprises heavy chain variable region CDR1, CDR2 and CDR3 having the sequences set forth in SEQ ID NOs:99, 100 and 101, respectively, and light chain variable region CDR1, CDR2 and CDR3 having the sequences set forth in SEQ ID NOs:102, GVS and 103, respectively.

In one embodiment, the multispecific antibody according to the present invention induces and/or enhances proliferation of T cells, e.g. wherein said T cells are CD4$^+$ and/or CD8$^+$ T cells.

Different methods for determining or measuring proliferation of T cells may be used and the present invention is not limited to any particular method.

In one embodiment, said induction or enhancement of proliferation of T cells is determined by a non-antigen-specific T-cell proliferation assay, e.g. as described in Example 5. Thus induction and/or enhancement of proliferation of T cells may be determined by sub-optimal activation of T cells in a PBMC pool (peripheral blood mononuclear lymphocyte). The sub-optimal activation may be determined by titrating the concentration of anti-CD3 antibody added to a PBMC pool, measuring T cell proliferation and choosing the anti-CD3 antibody concentration which results in low T cell proliferation but allows for further enhancement of the T cell proliferation. This concentration is PBMC-donor-dependent and is determined for each donor before the assay is performed.

In one embodiment, said induction or enhancement of proliferation of T cells is determined by activating T cells in PBMCs with said sub-optimal concentration of an anti-CD3 antibody, contacting the PBMCs with the multispecific antibody and determining proliferation of the T cells. In a further embodiment, the PBMCs may be labelled with CFSE, contacting the PBMCs with the multispecific antibody may be performed by incubation for 4 days, and proliferation of the T cells may be measured by flow cytometry.

Inducing a certain reaction or effect such as "inducing proliferation of T cells" may mean that there was no such reaction or effect such as proliferation of T cells before induction, but it may also mean that there was a certain level of reaction or effect such as proliferation of T cells before induction and after induction said reaction or effect such as proliferation of T cells is enhanced. Thus, "inducing" also includes "enhancing".

Proliferation of T cells may also be measured by an antigen-specific T cell proliferation assay, e.g., as described in Example 6, using a test antigen of interest. Thus, induction and/or enhancement of T cell proliferation may be measured by co-culturing T cells expressing a TCR specific for a peptide of the test antigen presented in major histocompatibility complex (MHC) and DCs presenting a corresponding peptide in MHC, which is then recognized by the TCR. For example, the T cells may be CD8+ T cells and the MHC may be MHC Class I, or the T cells may be CD4+ T cells and the MHC may be MHC Class II. T cells expressing a specific TCR may be generated by transduction with mRNA encoding the TCR. DCs presenting the corresponding peptide may be generated by transduction of the DCs with mRNA encoding the antigen. Co-culture of the TCR-positive T cells with the antigen-presenting cells induces T-cell proliferation; the extent of the proliferation may depend on the antigen density presented by the DCs and/or on the strength of the costimulatory signal. In one embodiment, proliferation of T cells may be measured by such an antigen-specific T-cell assay using CFSE labeled T-cells, adding antibodies to be tested and after 4 days measuring T cell proliferation by flow cytometry.

In one embodiment, said induction or enhancement of proliferation of T cells is determined using tumor-infiltrating lymphocytes (TILs) in an ex vivo expansion assay, e.g., as described in Example 11. The effect of the multispecific antibody of the invention on the induction or enhancement of proliferation of the TILs may be assessed by incubating a human tumor sample with interleukin-2 (IL-2) and said antibody, and retrieving and counting viable TILs after incubation for a period of about 10 to about 14 days. An induction or enhancement of proliferation of TILs can then be determined by comparison with a suitable control, e.g., a human tumor sample incubated without any multispecific antibody or with a reference (control) multispecific antibody. For example, a sample of human tumor tissue can be isolated, e.g., via a biopsy or from a surgical specimen, washed in serum-free medium, and tumor pieces with a diameter of about 1-2 mm placed into culture dishes or wells, e.g., 1 or 2 tumor pieces in 1 mL suitable medium, and incubated at 37° C. A suitable medium can be, for example, a serum-free medium (e.g. X-VIVO 15) supplemented with 10% Human Serum Albumin, 1% Pen/Strep, 1% Fungizone and IL-2 at a concentration ranging from 10 to 100 U/mL, e.g., 10 U/mL or 100 U/mL. The multispecific antibody can then be added at a suitable concentration in TIL medium. After a total culture period of 10-14 days, optionally splitting the cell culture if needed during this period, TILs can be harvested and counted, e.g., by flow cytometry, using, e.g., anti-CD3, anti-CD4, anti-CD8, anti-CD56 and 7-AAD antibodies to permit detection of viable CD4+ and CD8+ T cells as well as NK cells.

In one embodiment, the multispecific antibody is a bispecific antibody, which induces and/or enhances more proliferation of T cells compared to a reference bispecific antibody comprising a second antigen-binding region according to any aspect or embodiment described herein, but wherein the first antigen-binding region comprises heavy chain variable region CDR1, CDR2 and CDR3 having the sequences set forth in SEQ ID NOs:99, 100 and 101, respectively, and light chain variable region CDR1, CDR2 and CDR3 having the sequences set forth in SEQ ID NOs:102, GVS and 103, respectively.

In one embodiment, the multispecific antibody is a bispecific antibody, which induces and/or enhances more proliferation of T cells compared to a reference bispecific antibody comprising a first antigen-binding region according to any aspect or embodiment described herein, but wherein the second antigen-binding region comprises heavy chain variable region CDR1, CDR2 and CDR3 having the sequences set forth in SEQ ID NOs:99, 100 and 101, respectively, and light chain variable region CDR1, CDR2 and CDR3 having the sequences set forth in SEQ ID NOs:102, GVS and 103, respectively.

Binding to CD40

As described above, the multispecific antibody according to the present invention comprises a first antigen-binding region binding to human CD40.

In one embodiment, the multispecific antibody according to the present invention comprises a first antigen-binding region binding to human CD40, wherein said first antigen-binding region comprises heavy and light chain variable region CDR3 selected from the group consisting of:
  a) heavy chain variable region CDR3 having the sequence set forth in SEQ ID NO:3 or a sequence wherein up to four amino acids are modified in SEQ ID NO:3, and light chain variable region CDR3 having the sequence set forth in SEQ ID NO:5 or a sequence wherein up to four amino acids are modified in SEQ ID NO:5,
  b) heavy and light chain variable region CDR3 of an antibody which (i) competes for human CD40 binding with an antibody comprising heavy and light chain variable region CDR3 according to a) and/or (ii) has the specificity for CD40 of an antibody comprising heavy and light chain variable region CDR3 according to a).

In a further embodiment, the first antigen-binding region may further comprise a heavy chain variable region CDR1 having the sequence as set forth in SEQ ID NO:1 or a sequence wherein up to 2 amino acids are modified in SEQ ID NO:1, and/or heavy chain variable region CDR2 having the sequence as set forth in SEQ ID NO:2 or a sequence wherein up to 2 amino acids are modified in SEQ ID NO:2; and/or light chain variable region CDR1 having the sequence as set forth in SEQ ID NO:4 or a sequence wherein up to 2 amino acids are modified in SEQ ID NO:4, and/or light chain variable region CDR2 having the sequence YTS or a sequence wherein up to 2 amino acids are modified in YTS.

In one embodiment, the multispecific antibody according to the present invention comprises a first antigen-binding region binding to human CD40, wherein said first antigen-binding region comprises heavy and light chain variable region CDR1, CDR2 and CDR3 selected from the group consisting of:
  a) heavy chain variable region CDR1, CDR2 and CDR3 having the sequences set forth in SEQ ID NOs:1, 2 and 3, respectively, and light chain variable region CDR1, CDR2 and CDR3 having the sequences set forth in SEQ ID NOs:4, YTS and 5, respectively,
  b) heavy and light chain variable region CDR1, CDR2 and CDR3 according to a) having a total of one to twelve mutations; and
  c) heavy and light chain variable region CDR1, CDR2 and CDR3 of an antibody which (i) competes for human CD40 binding with an antibody comprising heavy and light chain variable region CDR1, CDR2 and CDR3 according to a) or b) and/or (ii) has the specificity for CD40 of an antibody comprising heavy and light chain variable region CDR1, CDR2 and CDR3 according to a) or b).

In one embodiment said first antigen-binding region comprises a first heavy chain variable (VH) sequence, and a first light chain variable (VL) sequence, wherein said variable sequences each comprises three CDR sequences, CDR1, CDR2 and CDR3, respectively.

In one embodiment, said first antigen-binding region comprises a first heavy chain variable (VH) sequence, and a first light chain variable (VL) sequence, and wherein said variable sequences each comprises three CDR sequences, CDR1, CDR2 and CDR3, respectively, and four framework sequences, FR1, FR2, FR3 and FR4, respectively.

In one embodiment, said first antigen-binding region comprises heavy chain variable region CDR1, CDR2 and CDR3 having the sequences set forth in SEQ ID NOs:1, 2 and 3, respectively, and light chain variable region CDR1, CDR2 and CDR3 having the sequences set forth in SEQ ID NOs:4, YTS and 5, respectively. Thus the first antigen-binding region may comprise heavy and light chain variable region CDR1, CDR2 and CDR3 having the sequences of the CD40 antibody as set forth in Table 1.

An example of an antibody comprising such a first antigen-binding region is the chimeric antibody Chi Lob 7/4 and CD40-001 disclosed herein.

In another embodiment, said first antigen-binding region comprises heavy chain variable region CDR1, CDR2 and CDR3 having the sequences set forth in SEQ ID NOs:1, 2 and 3, respectively, and light chain variable region CDR1, CDR2 and CDR3 having the sequences set forth in SEQ ID NOs:4, YTS and 5, respectively having a total of one to twelve mutations, such as one to eleven mutations, one to ten mutations, one to eight mutations, one to seven mutations, one to six mutations, one to five mutations, one to four mutations, one to three mutations, or one to two mutations.

In one embodiment, said mutation may be an amino acid substitution, such as a conservative amino acid substitution.

In one embodiment, said mutations may be distributed across the VH CDR1, 2 and 3 and VL CDR 1, 2 and 3 so that each of the VH and VL CDR3 comprises at the most three mutations and each of the VH and VL CDR2 and CDR1 comprises at the most two amino acid mutations.

In a further embodiment, the first antigen-binding region comprises heavy and light chain CDR1, CDR2 and CDR3 having the sequences set forth in SEQ ID NOs:1, 2, 3, 4, YTS and 5, respectively, having a total of one to twelve mutations and wherein the VH and VL CDR3 each comprises up to three amino acid mutations, and the VH and VL CDR1 and CDR2 each comprises up to two amino acid mutations.

In a further embodiment, the first antigen-binding region comprises heavy and light chain CDR1, CDR2 and CDR3 having the sequences set forth in SEQ ID NOs:1, 2, 3, 4, YTS and 5, respectively, having a total of one to ten mutations, such as one to eight, and wherein the VH and VL CDR1, CDR2, and CDR3 each comprises up to two amino acid mutations.

In a further embodiment, the first antigen-binding region comprises heavy and light chain CDR1, CDR2 and CDR3 having the sequences set forth in SEQ ID NOs:1, 2, 3, 4, YTS and 5, respectively, having a total of one to six mutations, and wherein the VH and VL CDR1, CDR2, and CDR3 each comprises at the most one amino acid mutation.

It is well known to a person skilled in the art how to introduce mutations and that certain amino acids of the CDR sequences may be mutated; e.g. by amino acid substitutions to e.g. increase affinity of the antibody to its target antigen, reduce potential immunogenicity of non-human antibodies to be used in humans and/or to increase the yield of antibodies expressed by a host cell. Such mutations can be introduced without affecting the epitope of the target to which the antibody binds.

In another embodiment, said first antigen-binding region comprises heavy and light chain variable region CDR1, CDR2 and CDR3 of an antibody which (i) competes for human CD40 binding with an antibody comprising heavy and light chain variable region CDR1, CDR2 and CDR3 according to a) or b) and/or (ii) has the specificity for CD40 of an antibody comprising heavy and light chain variable region CDR1, CDR2 and CDR3 according to a) or b).

In a further embodiment, said first antigen-binding region comprises heavy and light chain variable regions of an antibody which (i) competes for human CD40 binding with an antibody comprising heavy and light chain variable region CDR1, CDR2 and CDR3 according to a) or b) and/or (ii) has the specificity for CD40 of an antibody comprising heavy and light chain variable region CDR1, CDR2 and CDR3 according to a) or b).

The term "competes" refers in this context to the competition between two antibodies for binding to a target antigen. If two antibodies do not block each other for binding to a target antigen, such antibodies are non-competing and this is an indication that said antibodies do not bind to the same part, i.e. epitope of the target antigen. It is well known to a person skilled in the art how to test for competition of antibodies for binding to a target antigen. An example of such a method is a so-called cross-competition assay, which may e.g. be performed as an ELISA or by flow-cytometry.

For example, an ELISA-based assay may be performed by coating ELISA plate wells with each of the antibodies; adding the competing antibody and His-tagged extracellular domain of the target antigen and incubate; detecting whether the added antibody inhibited binding of the His-tagged protein to the coated antibody may be performed by adding biotinylated anti-His antibody, followed by Streptavidin-poly-HRP, and further developing the reaction with ABTS and measuring the absorbance at 405 nm. For example a flow-cytometry assay may be performed by incubating cells expressing the target antigen with an excess of unlabeled antibody, incubating the cells with a sub-optimal concentration of biotin-labelled antibody, followed by incubation with fluorescently labeled streptavidin and analyzing by flow cytometry.

In one embodiment, said VH sequence of the first antigen-binding region comprises an amino acid sequence having at least 70%, at least 75%, at least 80%, at least 85%, at least 90%, at least 95%, at least 97%, at least 99%, or 100% identity to at least one of SEQ ID NO:117 and SEQ ID NO:6, such as SEQ ID NO:117.

In one embodiment, said VL sequence of the first antigen-binding region comprises an amino acid sequence having at least 70%, at least 75%, at least 80%, at least 85%, at least 90%, at least 95%, at least 97%, at least 99% or 100% identity to at least one of SEQ ID NO:121 and SEQ ID NO:7, such as SEQ ID NO:121.

In one embodiment, said VH and VL sequence of the first antigen-binding region each comprises a sequence having at least 70%, at least 75%, at least 80%, at least 85%, at least 90%, at least 95%, at least 97%, at least 99%, or 100% identity to SEQ ID NO:6 and SEQ ID NO:7, respectively.

In one embodiment, said VH and VL sequence of the first antigen-binding region each comprises a sequence having at least 70%, at least 75%, at least 80%, at least 85%, at least 90%, at least 95%, at least 97%, at least 99%, or 100% identity to SEQ ID NO:117 and SEQ ID NO:121, respectively.

In one embodiment, the VH and VL sequences only deviate in the non-CDR sequences as set forth in SEQ ID NO:6 and 7, respectively.

In one embodiment, the VH and VL sequences only deviate in the non-CDR sequences as set forth in SEQ ID NO:117 and 121, respectively.

In one embodiment, the VH and VL sequences only deviate in the framework sequences.

In one embodiment, the respective FR1, FR2, FR3 and FR4 framework sequences of the VH and VL sequences of the first antigen-binding region has at least 70%, at least 75%, at least 80%, at least 85%, at least 90%, at least 95%, at least 97%, at least 99%, or 100% amino acid sequence identity to the respective FR1, FR2, FR3 and FR4 framework sequences of said VH and VL sequences.

In one embodiment, the respective FR1, FR2, FR3 and FR4 framework sequences of the VH and VL sequences of the first antigen-binding region has at least 70%, at least 75%, at least 80%, at least 85%, at least 90%, at least 95%, at least 97%, or at least 99% amino acid sequence identity to the respective FR1, FR2, FR3 and FR4 framework sequences of the VH sequence as set forth in SEQ ID NO:6, and VL sequence as set forth in SEQ ID NO:7.

In one embodiment, the respective FR1, FR2, FR3 and FR4 framework sequences of the VH and VL sequences of the first antigen-binding region has at least 70%, at least 75%, at least 80%, at least 85%, at least 90%, at least 95%, at least 97%, or at least 99% amino acid sequence identity to the respective FR1, FR2, FR3 and FR4 framework sequences of the VH sequence as set forth in SEQ ID NO:6, and VL sequence as set forth in SEQ ID NO:7, and the heavy and light chain variable region CDR1, CDR2 and CDR3 of the first antigen-binding region has a total of one to twelve mutations compared to the heavy and light chain variable region CDR1, CDR2 and CDR3 having the sequences as set forth in SEQ ID NOs:1, 2, 3, 4, YTS and 5, respectively. In a further embodiment, said mutations may be as described above.

In an even further embodiment, the respective FR1, FR2, FR3 and FR4 framework sequences of the VH and VL sequences of the first antigen-binding region has at least 70%, at least 75%, at least 80%, at least 85%, at least 90%, at least 95%, at least 97%, at least 99%, or 100% amino acid sequence identity to the respective FR1, FR2, FR3 and FR4 framework sequences of the VH sequence as set forth in SEQ ID NO:6, and VL sequence as set forth in SEQ ID NO:7, and the first antigen-binding region comprises heavy and light chain variable region CDR1, CDR2 and CDR3 having the sequences as set forth in SEQ ID NOs:1, 2, 3, 4, YTS and 5, respectively.

In one embodiment, the respective FR1, FR2, FR3 and FR4 framework sequences of the VH and VL sequences of the first antigen-binding region has at least 70%, at least 75%, at least 80%, at least 85%, at least 90%, at least 95%, at least 97%, at least 99%, or 100% amino acid sequence identity to the respective FR1, FR2, FR3 and FR4 framework sequences of the VH sequence as set forth in SEQ ID NO:117, and VL sequence as set forth in SEQ ID NO:121, and the heavy and light chain variable region CDR1, CDR2 and CDR3 of the first antigen-binding region has a total of one to twelve mutations compared to the heavy and light chain variable region CDR1, CDR2 and CDR3 having the sequences as set forth in SEQ ID NOs:1, 2, 3, 4, YTS and 5, respectively. In a further embodiment, said mutations may be as described above.

In an even further embodiment, the respective FR1, FR2, FR3 and FR4 framework sequences of the VH and VL sequences of the first antigen-binding region has at least 70%, at least 75%, at least 80%, at least 85%, at least 90%, at least 95%, at least 97%, at least 99%, or 100% amino acid sequence identity to the respective FR1, FR2, FR3 and FR4 framework sequences of the VH sequence as set forth in SEQ ID NO:117, and VL sequence as set forth in SEQ ID NO:121, and the first antigen-binding region comprises heavy and light chain variable region CDR1, CDR2 and CDR3 having the sequences as set forth in SEQ ID NOs:1, 2, 3, 4, YTS and 5, respectively.

In one embodiment, said VH sequence of the first antigen-binding region comprises the amino acid sequence of SEQ ID NO:117.

In one embodiment, said VL sequence of the first antigen-binding region comprises the amino acid sequence of SEQ ID NO:121.

In a further embodiment, said VH and VL sequences of the first antigen-binding region comprise the amino acid sequences of SEQ ID NO:117 and SEQ ID NO:121, respectively.

In one embodiment, said VH sequence of the first antigen-binding region comprises the amino acid sequence of SEQ ID NO:6.

In one embodiment, said VL sequence of the first antigen-binding region comprises the amino acid sequence of SEQ ID NO:7.

In a further embodiment, said VH and VL sequences of the first antigen-binding region comprises the amino acid sequences of SEQ ID NO:6 and SEQ ID NO:7, respectively.

In one embodiment, the multispecific antibody according to the present invention may comprise a first binding arm comprising said first antigen-binding region of any aspect or embodiment herein.

In one embodiment, the multispecific antibody according to the present invention comprises a first binding arm comprising said first antigen-binding region and a first heavy chain constant sequence.

In one embodiment, the multispecific antibody according to the present invention comprises a first binding arm comprising said first antigen-binding region, wherein the first binding arm comprises a first heavy chain comprising a first heavy chain variable (VH) sequence and a first heavy chain constant (CH) sequence, and a first light chain comprising a first light chain variable (VL) sequence.

In one embodiment, said first light chain further comprises a first light chain constant (CL) sequence.

In a further embodiment, said first heavy chain comprises at least a hinge region, a CH2 and a CH3 region.

In a specific embodiment, the multispecific antibody according to the present invention comprises a first Fab-arm comprising said first antigen-binding region.

In one embodiment, the first antigen-binding region may be derived from a mouse antibody.

In one embodiment, the first antigen-binding region may be derived from a chimeric antibody, such as Chi Lob 7/4.

In one embodiment, the first antigen-binding region may be derived from a humanized antibody.

In one embodiment, the first binding arm may be derived from a full-length antibody.

In one embodiment, the first binding arm may be derived from a full-length IgG1,λ (lambda) or IgG1,κ (kappa) antibody.

In one embodiment, the first binding arm may be derived from a monoclonal antibody.

In one embodiment, said first heavy chain may be of an IgG isotype, optionally selected from the group consisting of IgG1, IgG2, IgG3, and IgG4.

In one embodiment, the first binding arm may be derived from an antibody comprising a HC comprising SEQ ID NO:118 and an LC comprising SEQ ID NO:122, optionally with one or more mutations in the constant region of the HC, such as 1 to 10, such as 1 to 5, such as 1, 2, 3, 4 or 5 mutations.

In one embodiment, the first binding arm comprises a HC comprising SEQ ID NO:118, 119 or 120 and an LC comprising SEQ ID NO:122.

Binding to CD137

The multispecific antibody according to the present invention comprises a second antigen-binding region binding to human CD137.

In a further embodiment, the second antigen-binding region also binds to cynomolgus CD137.

In one embodiment, said second antigen-binding region comprises heavy and light chain variable region CDR3 selected from the group consisting of:

a) heavy chain variable region CDR3 having the sequence set forth in SEQ ID NO:10 or a sequence wherein up to four amino acids are modified in SEQ ID NO:10, and light chain variable region CDR3 having the sequence set forth in SEQ ID NO:12 or a sequence wherein up to four amino acids are modified in SEQ ID NO:12 (CD137 clone 001), b) heavy chain variable region CDR3 having the sequence set forth in SEQ ID NO:17 or a sequence wherein up to four amino acids are modified in SEQ ID NO:17, and light chain variable region CDR3 having the sequence set forth in SEQ ID NO:19 or a sequence wherein up to four amino acids are modified in SEQ ID NO:19 (CD137 clone 002), c) heavy chain variable region CDR3 having the sequence set forth in SEQ ID NO:24 or a sequence wherein up to four amino acids are modified in SEQ ID NO:24, and light chain variable region CDR3 having the sequence set forth in SEQ ID NO:26 or a sequence wherein up to four amino acids are modified in SEQ ID NO:26 (CD137 clone 003), d) heavy chain variable region CDR3 having the sequence set forth in SEQ ID NO:31 or a sequence wherein up to four amino acids are modified in SEQ ID NO:31, and light chain variable region CDR3 having the sequence set forth in SEQ ID NO:33 or a sequence wherein up to four amino acids are modified in SEQ ID NO:33 (CD137 clone 004), e) heavy chain variable region CDR3 having the sequence set forth in SEQ ID NO:38 or a sequence wherein up to four amino acids are modified in SEQ ID NO:38, and light chain variable region CDR3 having the sequence set forth in SEQ ID NO:40 or a sequence wherein up to four amino acids are modified in SEQ ID NO:40 (CD137 clone 005), f) heavy chain variable region CDR3 having the sequence set forth in SEQ ID NO:45 or a sequence wherein up to four amino acids are modified in SEQ ID NO:45, and light chain variable region CDR3 having the sequence set forth in SEQ ID NO:47 or a sequence wherein up to four amino acids are modified in SEQ ID NO:47 (CD137 clone 006), g) heavy chain variable region CDR3 having the sequence set forth in SEQ ID NO:52 or a sequence wherein up to four amino acids are modified in SEQ ID NO:52, and light chain variable region CDR3 having the sequence set forth in SEQ ID NO:54 or a sequence wherein up to four amino acids are modified in SEQ ID NO:54 (CD137 clone 007), h) heavy chain variable region CDR3 having the sequence set forth in SEQ ID NO:59 or a sequence wherein up to four amino acids are modified in SEQ ID NO:59, and light chain variable region CDR3 having the sequence set forth in SEQ ID NO:61 or a sequence wherein up to four amino acids are modified in SEQ ID NO:61 (CD137 clone 008), i) heavy chain variable region CDR3 having the sequence set forth in SEQ ID NO:66 or a sequence wherein up to four amino acids are modified in SEQ ID NO:66, and light chain variable region CDR3 having the sequence set forth in SEQ ID NO:68 or a sequence wherein up to four amino acids are modified in SEQ ID NO:68 (CD137 clone 009), j) heavy chain variable region CDR3 having the sequence set forth in SEQ ID NO:73 or a sequence wherein up to four amino acids are modified in SEQ ID NO:73, and light chain variable region CDR3 having the sequence set forth in SEQ ID NO:75 or a sequence wherein up to four amino acids are modified in SEQ ID NO:75 (CD137 clone 010), k) heavy chain variable region CDR3 having the sequence set forth in SEQ ID NO:80 or a sequence wherein up to four amino acids are modified in SEQ ID NO:80, and light chain variable region CDR3 having the sequence set forth in SEQ ID NO:82 or a sequence wherein up to four amino acids are modified in SEQ ID NO:82 (CD137 clone 011), l) heavy chain variable region CDR3 having the sequence set forth in SEQ ID NO:87 or a sequence wherein up to four amino acids are modified in SEQ ID NO:87, and light chain variable region CDR3 having the sequence set forth in SEQ ID NO:89 or a sequence wherein up to four amino acids are modified in SEQ ID NO:89 (CD137 clone 012), and m) heavy and light chain variable region CDR3 of an antibody which (i) competes for human CD137 binding with an antibody comprising heavy and light chain variable region CDR3 according to any of a) to l) and/or (ii) has the specificity for CD137 of an antibody comprising heavy and light chain variable CDR3 according to any of a) to l).

In a further embodiment, said second antigen-binding region further comprises heavy and/or light chain region CDR1 and CDR2 selected from the group consisting of:

a) heavy chain variable region CDR1 having the sequence set forth in SEQ ID NO:8 or a sequence wherein up to two amino acids are modified in SEQ ID NO:8, and/or heavy chain variable region CDR2 having the sequence set forth in SEQ ID NO:9 or a sequence wherein up to two amino acids are modified in SEQ ID NO:9, and/or light chain variable region CDR1 having the sequence set forth in SEQ ID NO:11 or a sequence wherein up to two amino acids are modified in SEQ ID NO:11, and/or light chain variable region CDR2 having the sequence KAS or a sequence wherein up to two amino acids are modified in KAS (CD137 clone 001), b) heavy chain variable region CDR1 having the sequence set forth in SEQ ID NO:15 or a sequence wherein up to two amino acids are modified in SEQ ID NO:15, and/or heavy chain variable region CDR2 having the sequence set forth in SEQ ID NO:16 or a sequence wherein up to two amino acids are modified in SEQ ID NO:16, and/or light chain variable region CDR1 having the sequence set forth in SEQ ID NO:18 or a sequence wherein up to two amino acids are modified in SEQ ID NO:18, and/or light chain variable region CDR2 having the sequence KAS or a sequence wherein up to two amino acids are modified in KAS (CD137 clone 002), c) heavy chain variable region CDR1 having the sequence set forth in SEQ ID NO:22 or a sequence wherein up to two amino acids are modified in SEQ ID NO:22, and/or heavy chain variable region CDR2 having the sequence set forth in SEQ ID NO:23 or a sequence wherein up to two amino acids are modified in SEQ ID NO:23, and/or light chain variable region CDR1 having the sequence set forth in SEQ ID NO:25 or a sequence wherein up to two amino acids are modified in SEQ ID NO:25, and/or light chain variable region CDR2 having the sequence RTS or a sequence wherein up to two amino acids are modified in RTS (CD137 clone 003), d) heavy chain variable region CDR1 having the sequence set forth in SEQ ID NO:29 or a sequence wherein up to two amino acids are modified in SEQ ID NO:29, and/or heavy chain variable region CDR2 having the sequence set forth in SEQ ID NO:30 or a sequence wherein up to two amino acids are modified in SEQ ID NO:30, and/or light chain variable region CDR1 having the sequence set forth in SEQ ID NO:32 or a sequence wherein up to two amino acids are modified in SEQ ID NO:32, and/or light chain variable region CDR2 having the sequence GAS or a sequence wherein up to two amino acids are modified in GAS (CD137 clone 004), e) heavy chain variable region CDR1 having the sequence set forth in SEQ ID NO:36 or a sequence wherein up to two amino acids are modified in SEQ ID NO:36, and/or heavy chain variable region CDR2 having the sequence set forth in SEQ ID NO:37 or a sequence wherein up to two amino acids are modified in SEQ ID NO:37, and/or light chain variable region CDR1 having the sequence set forth in SEQ ID NO:39 or a sequence wherein up to two amino acids are modified in SEQ ID NO:39, and/or light chain variable region CDR2 having the sequence SAS or a sequence wherein up to two amino acids are modified in SAS (CD137 clone 005), f) heavy chain variable region CDR1 having the sequence set forth in SEQ ID NO:43 or a sequence wherein up to two amino acids are modified in SEQ ID NO:43, and/or heavy chain variable region CDR2 having the sequence set forth in SEQ ID NO:44 or a sequence wherein up to two amino acids are modified in SEQ ID NO:44, and/or light chain variable region CDR1 having the sequence set forth in SEQ ID NO:46 or a sequence wherein up to two amino acids are modified in SEQ ID NO:46, and/or light chain variable region CDR2 having the sequence AAS or a sequence wherein up to two amino acids are modified in AAS (CD137 clone 006), g) heavy chain variable region CDR1 having the sequence set forth in SEQ ID NO:50 or a sequence wherein up to two amino acids are modified in SEQ ID NO:50, and/or heavy chain variable region CDR2 having the sequence set forth in SEQ ID NO:51 or a sequence wherein up to two amino acids are modified in SEQ ID NO:51, and/or light chain variable region CDR1 having the sequence set forth in SEQ ID NO:53 or a sequence wherein up to two amino acids are modified in SEQ ID NO:53, and/or light chain variable region CDR2 having the sequence KAS or a sequence wherein up to two amino acids are modified in KAS (CD137 clone 007), h) heavy chain variable region CDR1 having the sequence set forth in SEQ ID NO:57 or a sequence wherein up to two amino acids are modified in SEQ ID NO:57, and/or heavy chain variable region CDR2 having the sequence set forth in SEQ ID NO:58 or a sequence wherein up to two amino acids are modified in SEQ ID NO:58, and/or light chain variable region CDR1 having the sequence set forth in SEQ ID NO:60 or a sequence wherein up to two amino acids are modified in SEQ ID NO:60, and/or light chain variable region CDR2 having the sequence RAS or a sequence wherein up to two amino acids are modified in RAS (CD137 clone 008), i) heavy chain variable region CDR1 having the sequence set forth in SEQ ID NO:64 or a sequence wherein up to two amino acids are modified in SEQ ID NO:64, and/or heavy chain variable region CDR2 having the sequence set forth in SEQ ID NO:65 or a sequence wherein up to two amino acids are modified in SEQ ID NO:65, and/or light chain variable region CDR1 having the sequence set forth in SEQ ID NO:67 or a sequence wherein up to two amino acids are modified in SEQ ID NO:67, and/or light chain variable region CDR2 having the sequence GAS or a sequence wherein up to two amino acids are modified in GAS (CD137 clone 009), j) heavy chain variable region CDR1 having the sequence set forth in SEQ ID NO:71 or a sequence wherein up to two amino acids are modified in SEQ ID NO:71, and/or heavy chain variable region CDR2 having the sequence set forth in SEQ ID NO:72 or a sequence wherein up to two amino acids are modified in SEQ ID NO:72, and/or light chain variable region CDR1 having the sequence set forth in SEQ ID NO:74 or a sequence wherein up to two amino acids are modified in SEQ ID NO:74, and/or light chain variable region CDR2 having the sequence KAS or a sequence wherein up to two amino acids are modified in KAS (CD137 clone 010), k) heavy chain variable region CDR1 having the sequence set forth in SEQ ID NO:78 or a sequence wherein up to two amino acids are modified in SEQ ID NO:78, and/or heavy chain variable region CDR2 having the sequence set forth in SEQ ID NO:79 or a sequence wherein up to two amino acids are modified in SEQ ID NO:79, and/or light chain variable region CDR1 having the sequence set forth in SEQ ID NO:81 or a sequence wherein up to two amino acids are modified in SEQ ID NO:81, and/or light chain variable region CDR2 having the sequence DTS or a sequence wherein up to two amino acids are modified in DTS (CD137 clone 011), and l) heavy chain variable region CDR1 having the sequence set forth in SEQ ID NO:85 or a sequence wherein up to two amino acids are modified in SEQ ID NO:85, and/or heavy chain variable region CDR2 having the sequence set forth in SEQ ID NO:86 or a sequence wherein up to two amino acids are modified in SEQ ID NO:86, and/or light chain variable region CDR1 having the sequence set forth in SEQ ID NO:88 or a sequence wherein up to two amino acids are modified in SEQ ID NO:88, and/or light chain variable region CDR2 having the sequence SAS or a sequence wherein up to two amino acids are modified in SAS (CD137 clone 012).

In one embodiment said second antigen-binding region comprises heavy and light chain variable region CDR1, CDR2 and CDR3 selected from the group consisting of:

a) heavy chain variable region CDR1, CDR2 and CDR3 having the sequences set forth in SEQ ID NOs:8, 9 and 10, respectively, and light chain variable region CDR1, CDR2 and CDR3 having the sequences set forth in SEQ ID NOs:11, KAS and 12, respectively, (CD137 clone 001), b) heavy chain variable region CDR1, CDR2 and CDR3 having the sequences set forth in SEQ ID NOs:15, 16 and 17, respectively, and light chain variable region CDR1, CDR2 and CDR3 having the sequences set forth in SEQ ID NOs:18, KAS and 19, respectively, (CD137 clone 002), c) heavy chain variable region CDR1, CDR2 and CDR3 having the sequences set forth in SEQ ID NOs:22, 23, and 24, respectively, and light chain variable region CDR1, CDR2 and CDR3 having the sequences set forth in SEQ ID NOs:25, RTS and 26, respectively, (CD137 clone 003), d) heavy chain variable region CDR1, CDR2 and CDR3 having the sequences set forth in SEQ ID NOs:29, 30 and 31, respectively, and light chain variable region CDR1, CDR2 and CDR3 having the sequences set forth in SEQ ID NOs:32, GAS and 33, respectively, (CD137 clone 004), e) heavy chain variable region CDR1, CDR2 and CDR3 having the sequences set forth in SEQ ID NOs:36, 37 and 38, respectively, and light chain variable region CDR1, CDR2 and CDR3 having the sequences set forth in SEQ ID NOs:39, SAS and 40, respectively, (CD137 clone 005), f) heavy chain variable region CDR1, CDR2 and CDR3 having the sequences set forth in SEQ ID NOs:43, 44 and 45, respectively, and light chain variable region CDR1, CDR2 and CDR3 having the sequences set forth in SEQ ID NOs:46, AAS, and 47, respectively, (CD137 clone 006), g) heavy chain variable region CDR1, CDR2 and CDR3 having the sequences set forth in SEQ ID NOs:50, 51 and 52, respectively, and light chain variable region CDR1, CDR2 and CDR3 having the sequences set forth in SEQ ID NOs:53, KAS and 54, respectively, (CD137 clone 007), h) heavy chain variable region CDR1, CDR2 and CDR3 having the sequences set forth in SEQ ID NOs:57, 58 and 59, respectively, and light chain variable region CDR1, CDR2 and CDR3 having the sequences set forth in SEQ ID NOs:60, RAS and 61, respectively, (CD137 clone 008), i) heavy chain variable region CDR1, CDR2 and CDR3 having the sequences set forth in SEQ ID NOs:64, 65 and 66, respectively, and light chain variable region CDR1, CDR2 and CDR3 having the sequences set forth in SEQ ID NOs:67, GAS and 68, respectively, (CD137 clone 009), j) heavy chain variable region CDR1, CDR2 and CDR3 having the sequences set forth in SEQ ID NOs:71, 72 and 73, respectively, and light chain variable region CDR1, CDR2 and CDR3 having the sequences set forth in SEQ ID NOs:74, KAS and 75, respectively, (CD137 clone 010), k) heavy chain variable region CDR1, CDR2 and CDR3 having the sequences set forth in SEQ ID NOs:78, 79 and 80, respectively, and light chain variable region CDR1, CDR2 and CDR3 having the sequences set forth in SEQ ID NOs:81, DTS and 82, respectively, (CD137 clone 011), l) heavy chain variable region CDR1, CDR2 and CDR3 having the sequences set forth in SEQ ID NOs:85, 86 and 87, respectively, and light chain variable region CDR1, CDR2 and CDR3 having the sequences set forth in SEQ ID NOs:88, SAS and 89, respectively, (CD137 clone 012), m) heavy and light chain variable region CDR1, CDR2 and CDR3 according to any of a) to l) having a total of one to twelve mutations, and n) heavy and light chain variable region CDR1, CDR2 and CDR3 of an antibody which (i) competes for human CD137 binding with an antibody comprising heavy and light chain variable region CDR1, CDR2 and CDR3 according to any of a) to m) and/or (ii) has the specificity for CD137 of an antibody comprising heavy and light chain variable region CDR1, CDR2 and CDR3 according to any of a) to m).

Thus, the second antigen-binding region may comprise the heavy and light chain variable region CDR1, CDR2 and CDR3 sequences of a CD137 antibody as set forth in Table 1; i.e. CD137 clone 001, CD137 clone 002, CD137 clone 003, CD137 clone 004, CD137 clone 005, CD137 clone 006, CD137 clone 007, CD137 clone 008, CD137 clone 009, CD137 clone 010, CD137 clone 011 or CD137 clone 012. In particular, the second antigen-binding region may comprise the heavy and light chain variable region CDR1, CDR2 and CDR3 sequences from the same CD137 antibody clone, optionally wherein the framework regions are primarily human framework regions, optionally comprising one or more amino acid back-mutations to the non-human amino acid sequence.

In a further embodiment, the second antigen-binding region comprises heavy and light chain variable regions of an antibody which (i) competes for human CD137 binding with an antibody comprising heavy and light chain variable region CDR1, CDR2 and CDR3 according to any of a) to m) and/or (ii) has the specificity for CD137 of an antibody comprising heavy and light chain variable region CDR1, CDR2 and CDR3 according to any of a) to m).

In one embodiment, said second antigen-binding region binds to human CD137 (SEQ ID NO:92) to a higher degree than it binds to a mutant human CD137 (SEQ ID NO:93). The mutant human CD137 of SEQ ID NO:93 is also referred to as shuffle 6 herein.

In another embodiment, said second antigen-binding region binds to human CD137 (SEQ ID NO:92) to a higher degree than it binds to a mutant human CD137 (SEQ ID NO:94). The mutant human CD137 of SEQ ID NO:94 is also referred to as shuffle 5 herein.

In a further embodiment, said second antigen-binding region binds to human CD137 (SEQ ID NO:92) to the same degree that it binds to a mutant human CD137 (SEQ ID NO:95). The mutant human CD137 of SEQ ID NO:95 is also referred to as shuffle 4 herein.

In the context of the present invention "to a higher degree" means that the affinity of the second antigen-binding region is higher for human CD137 (SEQ ID NO:92) than for a mutant human CD137 (SEQ ID NO:93 and 94, shuffle 6 and 5 respectively). If there is no binding to the mutant CD137, the affinity for human CD137 will be infinitely higher than for said mutant CD137. However, in case of binding to said mutant CD137 the affinity may be 2-fold, such as 3-fold, or 4-fold, or 5-fold, or 6-fold higher for human CD137 than for the respective mutant CD137.

In the context of the present invention "to the same degree" means that the affinity of the second antigen-binding region is similar for human CD137 (SEQ ID NO:92) and for a mutant human CD137 (SEQ ID NO:95, shuffle 4). In particular, "similar" in this context may mean that the affinity for human CD137 and for said mutant CD137 differs at the most by 2.5-fold, such as 2.2-fold, or 2.0-fold, or 1.8-fold, or 1.75-fold or 1.5-fold.

The mutant human CD137 in SEQ ID NO:93 corresponds to the amino acid sequence of human CD137 wherein amino acids 24-47 (shuffle 6) were replaced by the corresponding amino acids from wild boar CD137.

Thus, in one embodiment, the second antigen-binding region binds to an epitope of human CD137 which comprises or requires one or more of the amino acids L, Q, D, P, C, S, N, C, P, A, G, T, F, C, D, N, N, R, N, Q, I, C, S and P at positions 24-47 of SEQ ID NO:92 (corresponding to SEQ ID NO:129).

The mutant human CD137 in SEQ ID NO:94 corresponds to the amino acid sequence of human CD137 wherein amino acids 48-88 (shuffle 5) were replaced by the corresponding amino acids from African elephant CD137.

Thus, in one embodiment, the second antigen-binding region binds to an epitope of human CD137 which comprises or requires one or more of the amino acids C, P, P, N, S, F, S, S, A, G, G, Q, R, T, C, D, I, C, R, Q, C, K, G, V, F, R, T, R, K, E, C, S, S, T, S, N, A, E, C, D and C at positions 48-88 of SEQ ID NO:92 (corresponding to SEQ ID NO:130).

The mutant human CD137 in SEQ ID NO:95 corresponds to the amino acid sequence of human CD137 wherein amino acids 59-114 (shuffle 4) were replaced by the corresponding amino acids from African elephant CD137.

Thus, in one embodiment, the second antigen-binding region does not bind to an epitope of human CD137 which comprises or requires one or more of the amino acids T, P, G, F, H, C, L, G, A, G, C, S, M, C, E, Q, D, C, K, Q, G, Q, E, L, T and K 89-114 at positions of SEQ ID NO:92 (corresponding to SEQ ID NO:131).

In one embodiment, binding to the mutant and human CD137 may be performed as the shuffle assay described in Example 2. Thus, binding to human CD137 (SEQ ID NO:92) and mutant human CD137 (SEQ ID NOs:93, 94 and 95) may be determined by preparing shuffle constructs derived from human CD137 in which protein domains of the human CD137 are replaced by the corresponding domain of CD137 from different species, using human CD137 and the different species of CD137 as reference constructs; transducing cells with plasmids encoding the reference construct or the shuffle constructs, respectively, and measuring binding of the antibody to each these CD137 constructs by flow cytometry, such as FACS.

Loss of binding to certain shuffle constructs indicates that the corresponding region is likely to be involved in the antibody epitope. Thus, protein domains of human CD137 contributing to the epitope of the anti-human CD137 antibodies may thereby be determined by the shuffle assay. The different species of CD137 used to create the shuffle constructs should be chosen so that the monoclonal anti-human CD137 antibodies do not bind to the whole CD137 protein from these different species (reference construct).

Determination of binding to human CD137 and mutants thereof may in particular be performed with a monoclonal antibody comprising two second antigen-binding regions according to the present invention.

In one embodiment, said second antigen-binding region comprises heavy and light chain variable region CDR1, CDR2 and CDR3 selected from the group consisting of:

a) heavy chain variable region CDR1, CDR2 and CDR3 having the sequences set forth in SEQ ID NOs:8, 9 and 10, respectively, and light chain variable region CDR1, CDR2 and CDR3 having the sequences set forth in SEQ ID NOs:11, KAS and 12, respectively, (CD137 clone 001), b) heavy chain variable region CDR1, CDR2 and CDR3 having the sequences set forth in SEQ ID NOs:15, 16 and 17, respectively, and light chain variable region CDR1, CDR2 and CDR3 having the sequences set forth in SEQ ID NOs:18, KAS and 19, respectively, (CD137 clone 002), c) heavy chain variable region CDR1, CDR2 and CDR3 having the sequences set forth in SEQ ID NOs:36, 37 and 38, respectively, and light chain variable region CDR1, CDR2 and CDR3 having the sequences set forth in SEQ ID NOs:39, SAS and 40, respectively, (CD137 clone 005), d) heavy chain variable region CDR1, CDR2 and CDR3 having the sequences set forth in SEQ ID NOs:43, 44 and 45, respectively, and light chain variable region CDR1, CDR2 and CDR3 having the sequences set forth in SEQ ID NOs:46, AAS and 47, respectively, (CD137 clone 006), e) heavy chain variable region CDR1, CDR2 and CDR3 having the sequences set forth in SEQ ID NOs:64, 65 and 66, respectively, and light chain variable region CDR1, CDR2 and CDR3 having the sequences set forth in SEQ ID NOs:67, GAS and 68, respectively, (CD137 clone 009), f) heavy chain variable region CDR1, CDR2 and CDR3 having the sequences set forth in SEQ ID NOs:71, 72 and 73, respectively, and light chain variable region CDR1, CDR2 and CDR3 having the sequences set forth in SEQ ID NOs:74, KAS and 75, respectively, (CD137 clone 010), g) heavy chain variable region CDR1, CDR2 and CDR3 having the sequences set forth in SEQ ID NOs:85, 86 and 87, respectively, and light chain variable region CDR1, CDR2 and CDR3 having the sequences set forth in SEQ ID NOs:88, SAS and 89, respectively, (CD137 clone 012), h) heavy and light chain variable region CDR1, CDR2 and CDR3 according to any of a) to g) having a total of one to twelve mutations, and i) heavy and light chain variable region CDR1, CDR2 and CDR3 of an antibody which (i) competes for human CD137 binding with an antibody comprising heavy and light chain variable region CDR1, CDR2 and CDR3 according to any of a) to h) and/or (ii) has the specificity for CD137 of an antibody comprising heavy and light chain variable region CDR1, CDR2 and CDR3 according to any of a) to h).

Hence, in one embodiment, said second antigen-binding region comprises heavy and light chain variable region CDR1, CDR2 and CDR3 selected from the group consisting of:
a) heavy chain variable region CDR1, CDR2 and CDR3 having the sequences set forth in SEQ ID NOs:64, 65 and 66, respectively, and light chain variable region CDR1, CDR2 and CDR3 having the sequences set forth in SEQ ID NOs:67, GAS and 68, respectively, (CD137 clone 009),
b) heavy and light chain variable region CDR1, CDR2 and CDR3 according to a) having a total of one to twelve mutations;
c) heavy and light chain variable region CDR1, CDR2 and CDR3 of an antibody which (i) competes for human CD137 binding with an antibody comprising heavy and light chain variable region CDR1, CDR2 and CDR3 according to a) or b) and/or (ii) has the specificity for CD137 of an antibody comprising heavy and light chain variable region CDR1, CDR2 and CDR3 according to a) or b).

In another embodiment, said second antigen-binding region comprises heavy and light chain variable region CDR1, CDR2 and CDR3 selected from the group consisting of:
a) heavy chain variable region CDR1, CDR2 and CDR3 having the sequences set forth in SEQ ID NOs:36, 37 and 38, respectively, and light chain variable region CDR1, CDR2 and CDR3 having the sequences set forth in SEQ ID NOs:39, SAS and 40, respectively, (CD137 clone 005),
b) heavy and light chain variable region CDR1, CDR2 and CDR3 according to a) having a total of one to twelve mutations, and
c) heavy and light chain variable region CDR1, CDR2 and CDR3 of an antibody which (i) competes for human CD137 binding with an antibody comprising heavy and light chain variable region CDR1, CDR2 and CDR3 according to a) or b) and/or (ii) has the specificity for CD137 of an antibody comprising heavy and light chain variable region CDR1, CDR2 and CDR3 according to a) or b).

In a particular embodiment, said second antigen-binding region comprises heavy chain variable region CDR1, CDR2 and CDR3 having the sequences set forth in SEQ ID NOs:64, 65 and 66, respectively, and light chain variable region CDR1, CDR2 and CDR3 having the sequences set forth in SEQ ID NOs:67, GAS and 68, respectively. An example of such an antibody includes, but is not limited to, the antibody referred to herein as CD137 clone 009.

In another embodiment, said second antigen-binding region comprises heavy chain variable region CDR1, CDR2 and CDR3 having the sequences set forth in SEQ ID NOs:36, 37 and 38, respectively, and light chain variable region CDR1, CDR2 and CDR3 having the sequences set forth in SEQ ID NOs:39, SAS and 40, respectively. An example of such an antibody includes, but is not limited to, the antibody referred to herein as CD137 clone 005.

In another embodiment, said second antigen-binding region comprises heavy chain variable region CDR1, CDR2 and CDR3 having the sequences set forth in SEQ ID NOs:64, 65 and 66, respectively, and light chain variable region CDR1, CDR2 and CDR3 having the sequences set forth in SEQ ID NOs:67, GAS and 68, respectively, (CD137 clone 009), having a total of one to twelve mutations, such as one to ten mutations, or one to eight mutations, or one to six mutations, or one to four mutations, or to two mutations.

In another embodiment, said second antigen-binding region comprises heavy chain variable region CDR1, CDR2 and CDR3 having the sequences set forth in SEQ ID NOs:36, 37 and 38, respectively, and light chain variable region CDR1, CDR2 and CDR3 having the sequences set forth in SEQ ID NOs:39, SAS and 40, respectively, (CD137 clone 005), having a total of one to twelve mutations, such as one to ten mutations, or one to eight mutations, or one to six mutations, or one to four mutations, or one to two mutations.

In one embodiment, said mutation may be an amino acid substitution, such as a conservative amino acid substitution.

In one embodiment, said mutations may be distributed across the VH CDR1, 2 and 3 and VL CDR 1, 2 and 3 so that each of the VH and VL CDR3 comprises at the most three mutations and each of the VH and VL CDR2 and CDR1 comprises at the most two amino acid modifications.

Hence, in a further embodiment, the second antigen-binding region comprises heavy and light chain CDR1, CDR2 and CDR3 having the sequences set forth in SEQ ID NOs:64, 65, 66, 67, GAS and 68, respectively, (CD137 clone 009), having a total of one to twelve mutations and wherein the VH and VL CDR3 each comprises up to three amino acid modifications, and the VH and VL CDR1 and CDR2 each comprises up to two amino acid modifications.

In a further embodiment, the second antigen-binding region comprises heavy and light chain CDR1, CDR2 and CDR3 having the sequences set forth in SEQ ID NOs:64, 65, 66, 67, GAS and 68, respectively, (CD137 clone 009), having a total of one to ten mutations, such as one to eight, and wherein the VH and VL CDR1, CDR2, and CDR3 each comprises up to two amino acid modifications.

In a further embodiment, the second antigen-binding region comprises heavy and light chain CDR1, CDR2 and CDR3 having the sequences set forth in SEQ ID NOs:64, 65, 66, 67, GAS and 68, respectively, (CD137 clone 009), having a total of one to six mutations, and wherein the VH and VL CDR1, CDR2, and CDR3 each comprises at most one amino acid modification.

In another embodiment, the second antigen-binding region comprises heavy and light chain CDR1, CDR2 and CDR3 having the sequences set forth in SEQ ID NOs:36, 37, 38, 39, SAS and 40, respectively, (CD137 clone 005), having a total of one to twelve mutations and wherein the VH and VL CDR3 each comprises up to three amino acid modifications, and the VH and VL CDR1 and CDR2 each comprises up to two amino acid modifications.

In a further embodiment, the second antigen-binding region comprises heavy and light chain CDR1, CDR2 and CDR3 having the sequences set forth in SEQ ID NOs:36, 37, 38, 39, SAS and 40, respectively, (CD137 clone 005), having a total of one to ten mutations, such as one to eight, and wherein the VH and VL CDR1, CDR2, and CDR3 each comprises up to two amino acid modifications.

In a further embodiment, the second antigen-binding region comprises heavy and light chain CDR1, CDR2 and CDR3 having the sequences set forth in SEQ ID NOs:36, 37, 38, 39, SAS and 40, respectively, (CD137 clone 005), having a total of one to six mutations, and wherein the VH and VL CDR1, CDR2, and CDR3 each comprises at most one amino acid modification.

In a further embodiment, there may be a total of one to twelve mutations; such as one to ten mutations, or one to eight mutations, or one to six mutations, or one to four mutations, or one to two mutations; and each CDR sequence comprises at the most two amino acid substitutions.

It is well known to a person skilled in the art how to introduce mutations and that certain amino acids of the CDR sequences may be mutated; e.g., by amino acid substitutions to, e.g., increase affinity of the antibody to its target antigen or reducing immunogenicity for non-human antibodies to be used for treatment of humans. Such mutations can be introduced without affecting the epitope of the target antigen to which the antibody binds.

In one embodiment said second antigen-binding region comprises a second heavy chain variable (VH) sequence, and a second light chain variable (VL) sequence and wherein said variable sequences each comprises three CDR sequences, CDR1, CDR2 and CDR3, respectively.

In one embodiment, said second antigen-binding region comprises a second heavy chain variable (VH) sequence, and a second light chain variable (VL) sequence and wherein said variable sequences each comprises three CDR sequences, CDR1, CDR2 and CDR3, respectively, and four framework sequences, FR1, FR2, FR3 and FR4, respectively.

In one embodiment, said VH sequence of the second antigen-binding region comprises an amino acid sequence having at least 70%, at least 75%, at least 80%, at least 85%, at least 90%, at least 95%, at least 97%, at least 99%, or 100% identity to an amino acid sequence selected from the group consisting of:
  a) a VH sequence as set forth in SEQ ID NO:123 (humanized CD137 clone 009)
  b) a VH sequence as set forth in SEQ ID NO:13 (CD137 clone 001)
  c) a VH sequence as set forth in SEQ ID NO:20 (CD137 clone 002)
  d) a VH sequence as set forth in SEQ ID NO:27 (CD137 clone 003)
  e) a VH sequence as set forth in SEQ ID NO:34 (CD137 clone 004)
  f) a VH sequence as set forth in SEQ ID NO:41 (CD137 clone 005)
  g) a VH sequence as set forth in SEQ ID NO:48 (CD137 clone 006)
  h) a VH sequence as set forth in SEQ ID NO:55 (CD137 clone 007)
  i) a VH sequence as set forth in SEQ ID NO:62 (CD137 clone 008)
  j) a VH sequence as set forth in SEQ ID NO:69 (CD137 clone 009)
  k) a VH sequence as set forth in SEQ ID NO:76 (CD137 clone 010)
  l) a VH sequence as set forth in SEQ ID NO:83 (CD137 clone 011)
  m) a VH sequence as set forth in SEQ ID NO:90 (CD137 clone 012)

In one embodiment, said VL sequence of the second antigen-binding region comprises an amino acid sequence having at least 70%, at least 75%, at least 80%, at least 85%, at least 90%, at least 95%, at least 97%, at least 99% or 100% identity to an amino acid sequence selected from the group consisting of:
  a) a VL sequence as set forth in SEQ ID NO:127 (humanized CD137 clone 009)
  b) a VL sequence as set forth in SEQ ID NO:14 (CD137 clone 001)
  c) a VL sequence as set forth in SEQ ID NO:21 (CD137 clone 002)
  d) a VL sequence as set forth in SEQ ID NO:28 (CD137 clone 003)
  e) a VL sequence as set forth in SEQ ID NO:35 (CD137 clone 004)
  f) a VL sequence as set forth in SEQ ID NO:42 (CD137 clone 005)
  g) a VL sequence as set forth in SEQ ID NO:49 (CD137 clone 006)
  h) a VL sequence as set forth in SEQ ID NO:56 (CD137 clone 007)
  i) a VL sequence as set forth in SEQ ID NO:63 (CD137 clone 008)
  j) a VL sequence as set forth in SEQ ID NO:70 (CD137 clone 009)
  k) a VL sequence as set forth in SEQ ID NO:77 (CD137 clone 010)
  l) a VL sequence as set forth in SEQ ID NO:84 (CD137 clone 011)
  m) a VL sequence as set forth in SEQ ID NO:91 (CD137 clone 012)

In one embodiment, said VH and VL sequences of the second antigen-binding region each comprise an amino acid sequence having at least 70%, at least 75%, at least 80%, at least 85%, at least 90%, at least 95%, at least 97%, at least 99% or 100% identity to an amino acid sequence selected from the group consisting of:
  a) a VH sequence as set forth in SEQ ID NO:123 and a VL sequence as set forth in SEQ ID NO:127 (humanized CD137 clone 009)
  b) a VH sequence as set forth in SEQ ID NO:13 and a VL sequence as set forth in SEQ ID NO:14 (CD137 clone 001)
  c) a VH sequence as set forth in SEQ ID NO:20 and a VL sequence as set forth in SEQ ID NO:21 (CD137 clone 002)
  d) a VH sequence as set forth in SEQ ID NO:27 and a VL sequence as set forth in SEQ ID NO:28 (CD137 clone 003)
  e) a VH sequence as set forth in SEQ ID NO:34 and a VL sequence as set forth in SEQ ID NO:35 (CD137 clone 004)
  f) a VH sequence as set forth in SEQ ID NO:41 and a VL sequence as set forth in SEQ ID NO:42 (CD137 clone 005)
  g) a VH sequence as set forth in SEQ ID NO:48 and a VL sequence as set forth in SEQ ID NO:49 (CD137 clone 006)
  h) a VH sequence as set forth in SEQ ID NO:55 and a VL sequence as set forth in SEQ ID NO:56 (CD137 clone 007)
  i) a VH sequence as set forth in SEQ ID NO:62 and a VL sequence as set forth in SEQ ID NO:63 (CD137 clone 008)
  j) a VH sequence as set forth in SEQ ID NO:69 and a VL sequence as set forth in SEQ ID NO:70 (CD137 clone 009)
  k) a VH sequence as set forth in SEQ ID NO:76 and a VL sequence as set forth in SEQ ID NO:77 (CD137 clone 010)
  l) a VH sequence as set forth in SEQ ID NO:83 and a VL sequence as set forth in SEQ ID NO:84 (CD137 clone 011)
  m) a VH sequence as set forth in SEQ ID NO:90 and a VL sequence as set forth in SEQ ID NO:91 (CD137 clone 012).

In one embodiment, said VH sequence of the second antigen-binding region comprises an amino acid sequence having at least 70%, at least 75%, at least 80%, at least 85%, at least 90%, at least 95%, at least 97%, at least 99% or 100% identity to an amino acid sequence selected from the group consisting of:
- a) a VH sequence as set forth in SEQ ID NO:123 (humanized CD137 clone 009)
- b) a VH sequence as set forth in SEQ ID NO:41 (CD137 clone 005)
- c) a VH sequence as set forth in SEQ ID NO:69 (CD137 clone 009)

In one embodiment, said VL sequence of the second antigen-binding region comprises an amino acid sequence having at least 70%, at least 75%, at least 80%, at least 85%, at least 90%, at least 95%, at least 97%, at least 99% or 100% identity to an amino acid sequence selected from the group consisting of:
- a) a VL sequence as set forth in SEQ ID NO:127 (humanized CD137 clone 009)
- b) a VL sequence as set forth in SEQ ID NO:42 (CD137 clone 005)
- c) a VL sequence as set forth in SEQ ID NO:70 (CD137 clone 009)

In one embodiment, said VH and VL sequences of the second antigen-binding region each comprise an amino acid sequence having at least 70%, at least 75%, at least 80%, at least 85%, at least 90%, at least 95%, at least 97%, at least 99% or 100% identity to an amino acid sequence selected from the group consisting of:
- a) a VH sequence as set forth in SEQ ID NO:123 and a VL sequence as set forth in SEQ ID NO:127 (humanized CD137 clone 009)
- b) a VH sequence as set forth in SEQ ID NO:41 and a VL sequence as set forth in SEQ ID NO:42 (CD137 clone 005)
- c) a VH sequence as set forth in SEQ ID NO:69 and a VL sequence as set forth in SEQ ID NO:70 (CD137 clone 009)

In one embodiment, said VH sequence of the second antigen-binding region comprises an amino acid sequence having at least 70%, at least 75%, at least 80%, at least 85%, at least 90%, at least 95%, at least 97% or at least 99% identity to SEQ ID NO:41 (CD137 clone 005).

In one embodiment, said VH sequence of the second antigen-binding region comprises an amino acid sequence having at least 70%, at least 75%, at least 80%, at least 85%, at least 90%, at least 95%, at least 97% or at least 99% identity to SEQ ID NO:69 (CD137 clone 009).

In one embodiment, said VH sequence of the second antigen-binding region comprises an amino acid sequence having at least 70%, at least 75%, at least 80%, at least 85%, at least 90%, at least 95%, at least 97%, at least 99% or 100% identity to SEQ ID NO:123 (humanized CD137 clone 009).

In one embodiment, said VL sequence of the second antigen-binding region comprises an amino acid sequence having at least 70%, at least 75%, at least 80%, at least 85%, at least 90%, at least 95%, at least 97% or at least 99% identity to SEQ ID NO:42 (CD137 clone 005).

In one embodiment, said VL sequence of the second antigen-binding region comprises an amino acid sequence having at least 70%, at least 75%, at least 80%, at least 85%, at least 90%, at least 95%, at least 97% or at least 99% identity to SEQ ID NO:70 (CD137 clone 009).

In one embodiment said VL sequence of the second antigen-binding region comprises an amino acid sequence having at least 70%, at least 75%, at least 80%, at least 85%, at least 90%, at least 95%, at least 97%, at least 99% or 100% identity to SEQ ID NO:127 (humanized CD137 clone 009).

In one embodiment, said VH and said VL sequence of the second antigen-binding region each comprise an amino acid sequence having at least 70%, at least 75%, at least 80%, at least 85%, at least 90%, at least 95%, at least 97% or at least 99% identity to SEQ ID NO:41; and SEQ ID NO:42 (CD137 clone 005), respectively.

In one embodiment, said VH and VL sequence of the second antigen-binding region each comprise an amino acid sequence having at least 70%, at least 75%, at least 80%, at least 85%, at least 90%, at least 95%, at least 97% or at least 99% identity to SEQ ID NO:69 and SEQ ID NO:70 (CD137 clone 009), respectively.

In one embodiment, said VH and VL sequence of the second antigen-binding region each comprise an amino acid sequence having at least 70%, at least 75%, at least 80%, at least 85%, at least 90%, at least 95%, at least 97%, at least 99% or 100% identity to SEQ ID NO:123 and SEQ ID NO:127, respectively (humanized CD137 clone 009).

In one embodiment, said VH and VL sequences only deviate in the framework sequences.

In one embodiment, the respective FR1, FR2, FR3 and FR4 framework sequences of the VH and VL sequences of the first and/or second antigen-binding region have at least 70%, at least 75%, at least 80%, at least 85%, at least 90%, at least 95%, at least 97%, at least 99%, or 100% amino acid sequence identity to the respective FR1, FR2, FR3 and FR4 framework sequences of said VH and VL sequences.

In one embodiment, the VH and VL sequences only deviate in the non-CDR sequences as set forth in SEQ ID NO:41 and 42, respectively, (CD137 clone 005).

In one embodiment the VH and VL sequences only deviate in the non-CDR sequences as set forth in SEQ ID NO:69 and 70, respectively, (CD137 clone 009).

In one embodiment the VH and VL sequences only deviate in the non-CDR sequences as set forth in SEQ ID NO:123 and 127, respectively, (humanized CD137 clone 009).

In one embodiment, the VH and VL sequences only deviate in the framework sequences.

In one embodiment, the respective FR1, FR2, FR3 and FR4 framework sequences of the VH and VL sequences of the first and/or second antigen-binding region have at least 70%, at least 75%, at least 80%, at least 85%, at least 90%, at least 95%, at least 97%, at least 99%, or 100% amino acid sequence identity to the respective FR1, FR2, FR3 and FR4 framework sequences of said VH and VL sequences.

In one embodiment, the respective FR1, FR2, FR3 and FR4 framework sequences of the VH and VL sequences of the second antigen-binding region have at least 70%, at least 75%, at least 80%, at least 85%, at least 90%, at least 95%, at least 97%, or at least 99% amino acid sequence identity to the respective FR1, FR2, FR3 and FR4 framework sequences of the VH sequence as set forth in SEQ ID NO:41, and VL sequence as set forth in SEQ ID NO:42.

In one embodiment, the respective FR1, FR2, FR3 and FR4 framework sequences of the VH and VL sequences of the second antigen-binding region have at least 70%, at least 75%, at least 80%, at least 85%, at least 90%, at least 95%, at least 97%, or at least 99% amino acid sequence identity to the respective FR1, FR2, FR3 and FR4 framework sequences of the VH sequence as set forth in SEQ ID NO:41, and VL sequence as set forth in SEQ ID NO:42, and the heavy and light chain variable region CDR1, CDR2 and CDR3 of the second antigen-binding region have a total of one to twelve mutations compared to the heavy and light chain variable region CDR1, CDR2 and CDR3 having the sequences as set forth in SEQ ID NOs:36, 37, 38, 39, SAS and 40, respectively. In a further embodiment said mutations may be as described above.

In an even further embodiment, the respective FR1, FR2, FR3 and FR4 framework sequences of the VH and VL sequences of the second antigen-binding region have at least 70%, at least 75%, at least 80%, at least 85%, at least 90%, at least 95%, at least 97%, or at least 99% amino acid sequence identity to the respective FR1, FR2, FR3 and FR4 framework sequences of the VH sequence as set forth in SEQ ID NO:41, and VL sequence as set forth in SEQ ID NO:42, and the second antigen-binding region comprises heavy and light chain variable region CDR1, CDR2 and CDR3 having the sequences as set forth in SEQ ID NOs:36, 37, 38, 39, SAS and 40, respectively.

In one embodiment the respective FR1, FR2, FR3 and FR4 framework sequences of the VH and VL sequences of the second antigen-binding region have at least 70%, at least 75%, at least 80%, at least 85%, at least 90%, at least 95%, at least 97%, or at least 99% amino acid sequence identity to the respective FR1, FR2, FR3 and FR4 framework sequences of the VH sequence as set forth in SEQ ID NO:69, and VL sequence as set forth in SEQ ID NO:70.

In one embodiment the respective FR1, FR2, FR3 and FR4 framework sequences of the VH and VL sequences of the second antigen-binding region have at least 70%, at least 75%, at least 80%, at least 85%, at least 90%, at least 95%, at least 97%, or at least 99% amino acid sequence identity to the respective FR1, FR2, FR3 and FR4 framework sequences of the VH sequence as set forth in SEQ ID NO:69, and VL sequence as set forth in SEQ ID NO:70, and the heavy and light chain variable region CDR1, CDR2 and CDR3 of the second antigen-binding region have a total of one to twelve mutations compared to the heavy and light chain variable region CDR1, CDR2 and CDR3 having the sequences as set forth in SEQ ID NOs:64, 65, 66, 67, GAS and 68, respectively. In a further embodiment said mutations may be as described above.

In an even further embodiment the respective FR1, FR2, FR3 and FR4 framework sequences of the VH and VL sequences of the second antigen-binding region have at least 70%, at least 75%, at least 80%, at least 85%, at least 90%, at least 95%, at least 97%, or at least 99% amino acid sequence identity to the respective FR1, FR2, FR3 and FR4 framework sequences of the VH sequence as set forth in SEQ ID NO:69, and VL sequence as set forth in SEQ ID NO:70, and the second antigen-binding region comprises heavy and light chain variable region CDR1, CDR2 and CDR3 having the sequences as set forth in SEQ ID NOs:64, 65, 66, 67, GAS and 68, respectively.

In one embodiment, the respective FR1, FR2, FR3 and FR4 framework sequences of the VH and VL sequences of the second antigen-binding region have at least 70%, at least 75%, at least 80%, at least 85%, at least 90%, at least 95%, at least 97%, at least 99% or 100% amino acid sequence identity to the respective FR1, FR2, FR3 and FR4 framework sequences of the VH sequence as set forth in SEQ ID NO:123, and VL sequence as set forth in SEQ ID NO:127.

In one embodiment the respective FR1, FR2, FR3 and FR4 framework sequences of the VH and VL sequences of the second antigen-binding region have at least 70%, at least 75%, at least 80%, at least 85%, at least 90%, at least 95%, at least 97%, at least 99% or 100% amino acid sequence identity to the respective FR1, FR2, FR3 and FR4 framework sequences of the VH sequence as set forth in SEQ ID NO:123, and VL sequence as set forth in SEQ ID NO:127, and the heavy and light chain variable region CDR1, CDR2 and CDR3 of the second antigen-binding region have a total of one to twelve mutations compared to the heavy and light chain variable region CDR1, CDR2 and CDR3 having the sequences as set forth in SEQ ID NOs:64, 65, 66, 67, GAS and 68, respectively. In a further embodiment said mutations may be as described above.

In an even further embodiment the respective FR1, FR2, FR3 and FR4 framework sequences of the VH and VL sequences of the second antigen-binding region have at least 70%, at least 75%, at least 80%, at least 85%, at least 90%, at least 95%, at least 97%, at least 99% or 100% amino acid sequence identity to the respective FR1, FR2, FR3 and FR4 framework sequences of the VH sequence as set forth in SEQ ID NO:123, and VL sequence as set forth in SEQ ID NO:127, and the second antigen-binding region comprises heavy and light chain variable region CDR1, CDR2 and CDR3 having the sequences as set forth in SEQ ID NOs:64, 65, 66, 67, GAS and 68, respectively.

In one embodiment, said VH sequence of the second antigen-binding region comprises SEQ ID NO:123 (humanized CD137 clone 009).

In one embodiment, said VL sequence of the second antigen-binding region comprises SEQ ID NO:127 (humanized CD137 clone 009).

In one embodiment, said VH and VL sequences of the second antigen-binding region comprise SEQ ID NO:123 and SEQ ID NO:127, respectively.

In one embodiment, said VH sequence of the second antigen-binding region comprises a VH sequence selected from the group consisting of:
  a) SEQ ID NO:41 (CD137 clone 005)
  b) SEQ ID NO:69 (CD137 clone 009)

In one embodiment, said VL sequence of the second antigen-binding region comprises a VL sequence selected from the group consisting of:
  a) SEQ ID NO:42 (CD137 clone 005)
  b) SEQ ID NO:70 (CD137 clone 009)

In one embodiment, said VH and VL sequences of the second antigen-binding are selected from the group consisting of:
  a) a VH sequence as set forth in SEQ ID NO:41 and a VL sequence as set forth in SEQ ID NO:42 (CD137 clone 005),
  b) a VH sequence as set forth in SEQ ID NO:69 and a VL sequence as set forth in SEQ ID NO:70 (CD137 clone 009).

In one embodiment, the multispecific antibody according to the present invention comprises a second binding arm comprising said second antigen-binding region.

In one embodiment, the multispecific antibody according to the present invention comprises a second binding arm comprising said second-antigen-binding region and a second heavy chain constant sequence.

In one embodiment, the multispecific antibody according to the present invention comprises a second binding arm comprising said second antigen-binding region, wherein the second binding arm comprises a second heavy chain comprising a second heavy chain variable (VH) sequence and a second heavy chain constant (CH) sequence, and a second light chain comprising a second light chain variable (VL) sequence.

In one embodiment said second light chain further comprises a second light chain constant sequence.

In a further embodiment, said second heavy chain comprises at least a hinge region, a CH2 and a CH3 region.

In a specific embodiment, the multispecific antibody according to the present invention comprises a second Fab-arm comprising said second antigen-binding region.

In one embodiment, the second antigen-binding region is derived from a rabbit antibody, such as any of anti-CD137 clones 1, 2, 3, 4, 5, 6, 7, 8, 9, 10, 11 and 12, in particular any of clones 5 and 9, disclosed herein.

In one embodiment, the second antigen-binding region is derived from a chimeric antibody, such as an antibody comprising a variable region from any of the anti-CD137 clones 1, 2, 3, 4, 5, 6, 7, 8, 9, 10, 11 and 12, in particular any of clones 5 and 9, disclosed herein.

In one embodiment, the second antigen-binding region is derived from a humanized antibody.

In one embodiment, the second binding arm is derived from a full-length antibody.

In one embodiment the second binding arm is derived from a full-length IgG1,λ (lambda) or IgG1,κ (kappa) antibody.

In one embodiment, the second binding arm is derived from a monoclonal antibody.

In one embodiment, said second heavy chain is of an IgG isotype, optionally having a subclass selected from the group consisting of IgG1, IgG2, IgG3, and IgG4.

In one embodiment, the first binding arm may be derived from an antibody comprising a HC comprising SEQ ID NO:124 and an LC comprising SEQ ID NO:128, optionally with one or more mutations in the constant region of the HC, such as 1 to 10, such as 1 to 5, such as 1, 2, 3, 4 or 5 mutations.

In one embodiment, the first binding arm comprises a HC comprising SEQ ID NO:124, 125 or 126 and an LC comprising SEQ ID NO:128.

Binding to CD40 and CD137

In some embodiments, the present invention relates to a multispecific antibody comprising:
(I) a first antigen-binding region binding to human CD40, wherein said first antigen-binding region comprises heavy and light chain variable regions selected from the group consisting of:
 a) heavy chain variable region CDR1, CDR2 and CDR3 having the sequences set forth in SEQ ID NOs:1, 2 and 3, respectively, and light chain variable region CDR1, CDR2 and CDR3 having the sequences set forth in SEQ ID NOs:4, YTS and 5, respectively,
 b) heavy and light chain variable region CDR1, CDR2 and CDR3 according to a) having a total of one to twelve mutations; and
 c) heavy and light chain variable region CDR1, CDR2 and CDR3 of an antibody which (i) competes for human CD40 binding with an antibody comprising heavy and light chain variable region CDR1, CDR2 and CDR3 according to a) or b) and/or (ii) has the specificity for CD40 of an antibody comprising heavy and light chain variable region CDR1, CDR2 and CDR3 according to a) or b), and
(II) a second antigen-binding region binding to human CD137, wherein said second antigen-binding region comprises heavy and light chain variable regions selected from the group consisting of:
 x) heavy chain variable region CDR1, CDR2 and CDR3 having the sequences set forth in SEQ ID NOs:64, 65 and 66, respectively, and light chain variable region CDR1, CDR2 and CDR3 having the sequences set forth in SEQ ID NOs:67, GAS and 68, respectively, (CD137 clone 009),
 y) heavy and light chain variable region CDR1, CDR2 and CDR3 according to x) having a total of one to twelve mutations; and
 z) heavy and light chain variable region CDR1, CDR2 and CDR3 of an antibody which (i) competes for human CD137 binding with an antibody comprising heavy and light chain variable region CDR1, CDR2 and CDR3 according to x) or y) and/or (ii) has the specificity for CD137 of an antibody comprising heavy and light chain variable region CDR1, CDR2 and CDR3 according to x) or y).

In another embodiment, the present invention relates to a multispecific antibody comprising:
(I) a first antigen-binding region binding to human CD40, wherein said first antigen-binding region comprises heavy and light chain variable regions selected from the group consisting of:
 a) heavy chain variable region CDR1, CDR2 and CDR3 having the sequences set forth in SEQ ID NOs:1, 2 and 3, respectively, and light chain variable region CDR1, CDR2 and CDR3 having the sequences set forth in SEQ ID NOs:4, YTS and 5, respectively,
 b) heavy and light chain variable region CDR1, CDR2 and CDR3 according to a) having a total of one to twelve mutations; and
 c) heavy and light chain variable region CDR1, CDR2 and CDR3 of an antibody which (i) competes for human CD40 binding with an antibody comprising heavy and light chain variable region CDR1, CDR2 and CDR3 according to a) or b) and/or (ii) has the specificity for CD40 of an antibody comprising heavy and light chain variable region CDR1, CDR2 and CDR3 according to a) or b), and
(II) a second antigen-binding region binding to human CD137, wherein said second antigen-binding region comprises heavy and light chain variable regions selected from the group consisting of:
 x) heavy chain variable region CDR1, CDR2 and CDR3 having the sequences set forth in SEQ ID NOs:36, 37 and 38, respectively, and light chain variable region CDR1, CDR2 and CDR3 having the sequences set forth in SEQ ID NOs:39, SAS and 40, respectively, (CD137 clone 005),
 y) heavy and light chain variable region CDR1, CDR2 and CDR3 according to x) having a total of one to twelve mutations; and
 z) heavy and light chain variable region CDR1, CDR2 and CDR3 of an antibody which (i) competes for human CD137 binding with an antibody comprising heavy and light chain variable region CDR1, CDR2 and CDR3 according to x) or y) and/or (ii) has the specificity for CD137 of an antibody comprising heavy and light chain variable region CDR1, CDR2 and CDR3 according to x) or y).

Hence, in one embodiment, said first antigen-binding region comprises heavy chain variable region CDR1, CDR2 and CDR3 having the amino acid sequences set forth in SEQ ID NOs:1, 2 and 3, respectively, and light chain variable region CDR1, CDR2 and CDR3 having the amino acid sequences set forth in SEQ ID NOs:4, YTS and 5, respectively; and said second antigen-binding region comprises
 a) heavy chain variable region CDR1, CDR2 and CDR3 having the sequences set forth in SEQ ID NOs:64, 65 and 66, respectively, and light chain variable region CDR1, CDR2 and CDR3 having the sequences set forth in SEQ ID NOs:67, GAS and 68, respectively, (CD136 clone 009), or b) heavy chain variable region CDR1, CDR2 and CDR3 having the sequences set forth in SEQ ID NOs:36, 37 and 38, respectively, and light chain variable region CDR1, CDR2 and CDR3 having the sequences set forth in SEQ ID NOs:39, SAS and 40 (CD137 clone 005), respectively.

In another embodiment, said first antigen-binding region comprises heavy chain variable region CDR1, CDR2 and CDR3 having the sequences set forth in SEQ ID NOs:1, 2 and 3, respectively, and light chain variable region CDR1, CDR2 and CDR3 having the sequences set forth in SEQ ID NOs:4, YTS and 5, respectively; and said second antigen-binding region comprises heavy chain variable region CDR1, CDR2 and CDR3 having the sequences set forth in SEQ ID NOs:64, 65 and 66, respectively, and light chain variable region CDR1, CDR2 and CDR3 having the sequences set forth in SEQ ID NOs:67, GAS and 68, respectively, (CD137 clone 009).

In another embodiment said first antigen-binding region comprises heavy chain variable region CDR1, CDR2 and CDR3 having the sequences set forth in SEQ ID NOs:1, 2 and 3, respectively, and light chain variable region CDR1, CDR2 and CDR3 having the sequences set forth in SEQ ID NOs:4, YTS and 5, respectively; and said second antigen-binding region comprises heavy chain variable region CDR1, CDR2 and CDR3 having the sequences set forth in SEQ ID NOs:36, 37 and 38, respectively, and light chain variable region CDR1, CDR2 and CDR3 having the sequences set forth in SEQ ID NOs:39, SAS and 40, respectively, (CD137 clone 005).

In a further embodiment, said first antigen-binding region of the multispecific antibody according to the present invention comprises a first heavy chain variable (VH) sequence, and a first light chain variable (VL) sequence, and said second antigen-binding region of the multispecific antibody according to the present invention comprises a second heavy chain variable (VH) sequence, and a second light chain variable (VL) sequence and wherein said variable sequences each comprise three CDR sequences, CDR1, CDR2 and CDR3, respectively, and four framework sequences, FR1, FR2, FR3 and FR4, respectively.

In a further embodiment said VH and VL sequence of the first antigen-binding region each comprises a sequence having at least 70%, at least 75%, at least 80%, at least 85%, at least 90%, at least 95%, at least 97% or at least 99% identity to the amino acid sequence of the VH sequence as set forth in SEQ ID NO:6 and the VL sequence as set forth in SEQ ID NO:7, respectively, and said VH and said VL sequence of the second antigen-binding region each comprises a sequence having at least 70%, at least 75%, at least 80%, at least 85%, at least 90%, at least 95%, at least 97% or at least 99% identity to the amino acid sequence of the VH sequence as set forth in SEQ ID NO:41 and the VL sequence as set forth in SEQ ID NO:42, respectively, (CD137 clone 005).

In another further embodiment, said VH and VL sequence of the first antigen-binding region each comprises a sequence having at least 70%, at least 75%, at least 80%, at least 85%, at least 90%, at least 95%, at least 97% or at least 99% identity to the amino acid sequence of the VH sequence as set forth in SEQ ID NO:6 and the VL sequence as set forth in SEQ ID NO:7, respectively, and said VH and said VL sequence of the second antigen-binding region each comprises a sequence having at least 70%, at least 75%, at least 80%, at least 85%, at least 90%, at least 95%, at least 97% or at least 99% identity to the amino acid sequence of the VH sequence as set forth in SEQ ID NO:69 and the VL sequence as set forth in SEQ ID NO:70, respectively, (CD137 clone 009).

In another further embodiment, said VH and VL sequence of the first antigen-binding region each comprises a sequence having at least 70%, at least 75%, at least 80%, at least 85%, at least 90%, at least 95%, at least 97%, at least 99% or 100% identity to the amino acid sequence of the VH sequence as set forth in SEQ ID NO:117 and the VL sequence as set forth in SEQ ID NO:121, respectively, and said VH and said VL sequence of the second antigen-binding region each comprise a sequence having at least 70%, at least 75%, at least 80%, at least 85%, at least 90%, at least 95%, at least 97%, at least 99% or 100% identity to the amino acid sequence of the VH sequence as set forth in SEQ ID NO:123 and the VL sequence as set forth in SEQ ID NO:127, respectively, (humanized CD137 clone 009).

In a particular embodiment, the present invention relates to a bispecific antibody comprising (I) a first binding arm comprising a first heavy chain comprising a first heavy chain variable (VH) sequence and a first heavy chain constant (CH) sequence, and a first light chain comprising a first light chain variable (VL) sequence and a first light chain constant (CL) sequence, and wherein said heavy first chain variable sequence comprises CDR1, CDR2 and CDR3 having the sequences set forth in SEQ ID NOs:1, 2 and 3, respectively, and said first light chain sequence comprises CDR1, CDR2 and CDR3 having the sequences set forth in SEQ ID NOs:4, YTS and 5, respectively, and (II) a second binding arm comprising a second heavy chain comprising a second heavy chain variable (VH) sequence and a second heavy chain constant (CH) sequence, and a second light chain further comprises a second light chain constant (CL) sequence, and a second light chain variable (VL) sequence, wherein said second heavy chain variable sequence comprises CDR1, CDR2 and CDR3 having the sequences set forth in SEQ ID NOs:64, 65 and 66, respectively, and said second light chain sequence comprises CDR1, CDR2 and CDR3 having the sequences set forth in SEQ ID NOs:67, GAS and 68, respectively, (CD137 clone 009); wherein the first and second heavy chain are of a human IgG1 isotype and wherein the first and second light chain is of IgG1,κ, and wherein the positions corresponding to positions L234, L235, and D265 in a human IgG1 heavy chain according to EU numbering of both the first and second constant heavy chain are F, E, and A, respectively, and wherein (a) the position corresponding to F405 in a human IgG1 heavy chain according to EU numbering of the first constant heavy chain is L, and the position corresponding to K409 in a human IgG1 heavy chain according to EU numbering of the second constant heavy chain is R; or (b) the position corresponding to K409 in a human IgG1 heavy chain according to EU numbering of the first constant heavy chain is R, and the position corresponding to F405 in a human IgG1 heavy chain according to EU numbering of the second constant heavy chain is L.

In a further particular embodiment, the present invention relates to a bispecific antibody comprising (I) a first binding arm comprising a first heavy chain comprising a first heavy chain variable (VH) sequence and a first heavy chain constant (CH) sequence, and a first light chain comprising a first light chain variable (VL) sequence and a first light chain constant (CL) sequence, and wherein said heavy first chain variable sequence comprises CDR1, CDR2 and CDR3 having the sequences set forth in SEQ ID NOs:1, 2 and 3, respectively, and said first light chain sequence comprises CDR1, CDR2 and CDR3 having the sequences set forth in SEQ ID NOs:4, YTS and 5, respectively, and (II) a second binding arm comprising a second heavy chain comprising a second heavy chain variable (VH) sequence and a second heavy chain constant (CH) sequence, and a second light chain further comprises a second light chain constant (CL) sequence, and a second light chain variable (VL) sequence, wherein said second heavy chain variable sequence comprises CDR1, CDR2 and CDR3 having the sequences set forth in SEQ ID NOs:36, 37 and 38, respectively, and said second light chain sequence comprises CDR1, CDR2 and CDR3 having the sequences set forth in SEQ ID NOs:39, SAS and 40, respectively, (CD137 clone 005); and wherein the first and second heavy chain are of a human IgG1 isotype and wherein the first and second light chain is of IgG1,κ, and wherein the positions corresponding to positions L234, L235, and D265 in a human IgG1 heavy chain according to EU numbering of both the first and second constant heavy chain are F, E, and A, respectively, and wherein (a) the position corresponding to F405 in a human IgG1 heavy chain according to EU numbering of the first constant heavy chain is L, and the position corresponding to K409 in a human IgG1 heavy chain according to EU numbering of the second constant heavy chain is R; or (b) the position corresponding to K409 in a human IgG1 heavy chain according to EU numbering of the first constant heavy chain is R, and the position corresponding to F405 in a human IgG1 heavy chain according to EU numbering of the second constant heavy chain is L.

In a specific embodiment, the present invention relates to a bispecific antibody comprising (I) a first binding arm comprising a first heavy chain comprising a first heavy chain variable (VH) sequence and a first heavy chain constant (CH) sequence, and a first light chain comprising a first light chain variable (VL) sequence and a first light chain constant (CL) sequence, and wherein said first VH and VL sequences each comprises a sequence having at least 70%, at least 75%, at least 80%, at least 85%, at least 90%, at least 95%, at least 97%, at least 99% or 100% identity to the amino acid sequence of the VH sequence as set forth in SEQ ID NO:117 and the VL sequence as set forth in SEQ ID NO:121, respectively, and (II) a second binding arm comprising a second heavy chain comprising a second heavy chain variable (VH) sequence and a second heavy chain constant (CH) sequence, and a second light chain further comprises a second light chain constant (CL) sequence, and a second light chain variable (VL) sequence, wherein said second VH and VL sequences comprise a sequence having at least 70%, at least 75%, at least 80%, at least at least at least 95%, at least 97%, at least 99% or 100% identity to 85%,90%, the amino acid sequence of the VH sequence as set forth in SEQ ID NO:123 and the VL sequence as set forth in SEQ ID NO:127, respectively, (humanized CD137 clone 009).

In a further specific embodiment, the present invention relates to a bispecific antibody comprising (I) a first binding arm comprising a first heavy chain comprising a first heavy chain variable (VH) sequence and a first heavy chain constant (CH) sequence, and a first light chain comprising a first light chain variable (VL) sequence and a first light chain constant (CL) sequence, and wherein said first VH sequence comprises SEQ ID NO:117 and said first VL sequence comprises SEQ ID NO:121, and (II) a second binding arm comprising a second heavy chain comprising a second heavy chain variable (VH) sequence and a second heavy chain constant (CH) sequence, and a second light chain further comprises a second light chain constant (CL) sequence, and a second light chain variable (VL) sequence, wherein said second VH sequence comprises SEQ ID NO:123 and said second VL sequence comprises SEQ ID NO:127, (humanized CD137 clone 009).

In a specific embodiment, the present invention relates to a bispecific antibody comprising (I) a first binding arm comprising a first heavy chain comprising a first heavy chain variable (VH) sequence and a first heavy chain constant (CH) sequence, and a first light chain comprising a first light chain variable (VL) sequence and a first light chain constant (CL) sequence, and wherein said first VH and VL sequences comprise a sequence having at least 70%, at least 75%, at least 80%, at least 85%, at least 90%, at least 95%, at least 97%, at least 99% or 100% identity to the amino acid sequence of the VH sequence as set forth in SEQ ID NO:117 and the VL sequence as set forth in SEQ ID NO:121, respectively, and (II) a second binding arm comprising a second heavy chain comprising a second heavy chain variable (VH) sequence and a second heavy chain constant (CH) sequence, and a second light chain further comprises a second light chain constant (CL) sequence, and a second light chain variable (VL) sequence, wherein said second VH and VL sequences comprise a sequence having at least 70%, at least 75%, at least 80%, at least 85%, at least 90%, at least 95%, at least 97%, at least 99% or 100% identity to the amino acid sequence of the VH sequence as set forth in SEQ ID NO:123 and the VL sequence as set forth in SEQ ID NO:127, respectively, (humanized CD137 clone 009), wherein the first and second heavy chain are of a human IgG1 isotype and wherein the first and second light chain is of IgG1,κ, and wherein the positions corresponding to positions L234, L235, and D265 in a human IgG1 heavy chain according to EU numbering of both the first and second constant heavy chain are F, E, and A, respectively, and wherein (a) the position corresponding to F405 in a human IgG1 heavy chain according to EU numbering of the first constant heavy chain is L, and the position corresponding to K409 in a human IgG1 heavy chain according to EU numbering of the second constant heavy chain is R; or (b) the position corresponding to K409 in a human IgG1 heavy chain according to EU numbering of the first constant heavy chain is R, and the position corresponding to F405 in a human IgG1 heavy chain according to EU numbering of the second constant heavy chain is L.

In a further specific embodiment, the present invention relates to a bispecific antibody comprising (I) a first binding arm comprising a first heavy chain comprising a first heavy chain variable (VH) sequence and a first heavy chain constant (CH) sequence, and a first light chain comprising a first light chain variable (VL) sequence and a first light chain constant (CL) sequence, and wherein said first VH sequence comprises SEQ ID NO:117 and said first VL sequence comprises SEQ ID NO:121, and (II) a second binding arm comprising a second heavy chain comprising a second heavy chain variable (VH) sequence and a second heavy chain constant (CH) sequence, and a second light chain further comprises a second light chain constant (CL) sequence, and a second light chain variable (VL) sequence, wherein said second VH sequence comprises SEQ ID NO:123 and said second VL sequence comprises SEQ ID NO:127, (humanized CD137 clone 009), wherein the first and second heavy chain are of a human IgG1 isotype and wherein the first and second light chain is of IgG1,κ, and wherein the positions corresponding to positions L234, L235, and D265 in a human IgG1 heavy chain according to EU numbering of both the first and second constant heavy chain are F, E, and A, respectively, and wherein (a) the position corresponding to F405 in a human IgG1 heavy chain according to EU numbering of the first constant heavy chain is L, and the position corresponding to K409 in a human IgG1 heavy chain according to EU numbering of the second constant heavy chain is R; or (b) the position corresponding to K409 in a human IgG1 heavy chain according to EU numbering of the first constant heavy chain is R, and the position corresponding to F405 in a human IgG1 heavy chain according to EU numbering of the second constant heavy chain is L.

In another aspect, the present invention relates to a bispecific antibody comprising a first binding arm binding to human CD40 and a second binding arm binding to human CD137, wherein (i) said first binding arm comprises a heavy chain (HC) amino acid sequence comprising or consisting of SEQ ID NO:118 and a light chain (LC) amino acid sequence comprising or consisting of SEQ ID NO:122, and (ii) said second binding arm comprises a HC amino acid sequence comprising or consisting of SEQ ID NO:124 and a LC amino acid sequence comprising or consisting of SEQ ID NO:128, optionally wherein SEQ ID NOS:118, SEQ ID NO:124 or both comprise one or more mutations in the constant region of the HC, such as 1 to 10, such as 1 to 5, such as 1, 2, 3, 4 or 5 mutations.

In another aspect, the present invention relates to a bispecific antibody comprising a first binding arm binding to human CD40 and a second binding arm binding to human CD137, wherein (i) said first binding arm comprises a HC amino acid sequence comprising or consisting of SEQ ID NO:119 and a LC amino acid sequence comprising or consisting of SEQ ID NO:122, and (ii) said second binding arm comprises a HC amino acid sequence comprising or consisting of SEQ ID NO:125 and a LC amino acid sequence comprising or consisting of SEQ ID NO:128.

In another aspect, the present invention relates to a bispecific antibody comprising a first binding arm binding to human CD40 and a second binding arm binding to human CD137, wherein (i) said first binding arm comprises a HC amino acid sequence comprising or consisting of SEQ ID NO:120 and a LC amino acid sequence comprising or consisting of SEQ ID NO:122, and (ii) said second binding arm comprises a HC amino acid sequence comprising or consisting of SEQ ID NO:126 and a LC amino acid sequence comprising or consisting of SEQ ID NO:128.

Bispecific Formats

In a particular embodiment the multispecific antibody according to the present invention is a bispecific antibody.

The present invention provides bispecific CD40xCD137 antibodies which are able of cross-linking cells expressing CD40 and cells expressing CD137; such as antigen-presenting cells and T cells, respectively. Depending on the desired functional properties for a particular use, particular antigen-binding regions can be selected from the set of antibodies or antigen-binding regions provided by the present invention. Many different formats and uses of bispecific antibodies are known in the art, and were reviewed by Kontermann; Drug Discov Today, 2015 July; 20(7):838-47 and; MAbs, 2012 March-April; 4(2):182-97.

A bispecific antibody according to the present invention is not limited to any particular bispecific format or method of producing it.

Examples of bispecific antibody molecules which may be used in the present invention comprise (i) a single antibody that has two binding arms comprising different antigen-binding regions; (ii) a single chain antibody that has specificity to two different epitopes, e.g., via two scFvs linked in tandem by an extra peptide linker; (iii) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (iv) a chemically-linked bispecific (Fab')2 fragment; (v) a Tandab, which is a fusion of two single chain diabodies resulting in a tetravalent bispecific antibody that has two binding sites for each of the target antigens; (vi) a flexibody, which is a combination of scFvs with a diabody resulting in a multivalent molecule; (vii) a so-called "dock and lock" molecule, based on the "dimerization and docking domain" in Protein Kinase A, which, when applied to Fabs, can yield a trivalent bispecific binding protein consisting of two identical Fab fragments linked to a different Fab fragment; (viii) a so-called Scorpion molecule, comprising, e.g., two scFvs fused to both termini of a human Fab-arm; and (ix) a diabody.

In one embodiment, the bispecific antibody of the present invention is a diabody, a cross-body, or a bispecific antibody obtained via a controlled Fab-arm exchange (such as described in WO2011131746 (Genmab)).

Examples of different classes of bispecific antibodies include, but are not limited to, (i) IgG-like molecules with complementary CH3 domains to force heterodimerization; (ii) recombinant IgG-like dual targeting molecules, wherein the two sides of the molecule each contain the Fab fragment or part of the Fab fragment of at least two different antibodies; (iii) IgG fusion molecules, wherein full length IgG antibodies are fused to extra Fab fragment or parts of Fab fragment; (iv) Fc fusion molecules, wherein single chain Fv molecules or stabilized diabodies are fused to heavy-chain constant-domains, Fc-regions or parts thereof; (v) Fab fusion molecules, wherein different Fab-fragments are fused together, fused to heavy-chain constant-domains, Fc-regions or parts thereof; and (vi) ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule fused to heavy-chain constant-domains, Fc-regions or parts thereof.

Examples of IgG-like molecules with complementary CH3 domain molecules include, but are not limited to, the Triomab/Quadroma molecules (Trion Pharma/Fresenius Biotech; Roche, WO2011069104), the so-called Knobs-into-Holes molecules (Genentech, WO9850431), CrossMAbs (Roche, WO2011117329) and the electrostatically-matched molecules (Amgen, EP1870459 and WO2009089004; Chugai, US201000155133; Oncomed, WO2010129304), the LUZ-Y molecules (Genentech, Wranik et al. 3. Biol. Chem. 2012, 287(52): 43331-9, doi: 10.1074/jbc.M112.397869. Epub 2012 Nov. 1), DIG-body and PIG-body molecules (Pharmabcine, WO2010134666, WO2014081202), the Strand Exchange Engineered Domain body (SEEDbody) molecules (EMD Serono, WO2007110205), the Biclonics molecules (Merus, WO2013157953), FcΔAdp molecules (Regeneron, WO201015792), bispecific IgG1 and IgG2 molecules (Pfizer/Rinat, WO11143545), Azymetric scaffold molecules (Zymeworks/Merck, WO2012058768), mAb-Fv molecules (Xencor, WO2011028952), bivalent bispecific antibodies (WO2009080254) and the DuoBody® molecules (Genmab A/S, WO2011131746).

Examples of recombinant IgG-like dual targeting molecules include, but are not limited to, Dual Targeting (DT)-Ig molecules (WO2009058383), Two-in-one Antibody (Genentech; Bostrom, et al 2009. Science 323, 1610-1614.), Cross-linked Mabs (Karmanos Cancer Center), mAb2 (F-Star, WO2008003116), Zybody molecules (Zyngenia; LaFleur et al. MAbs. 2013 March-April; 5(2):208-18), approaches with common light chain (Crucell/Merus, U.S. Pat. No. 7,262,028), KABodies (NovImmune, WO2012023053) and CovX-body (CovX/Pfizer; Doppalapudi, V. R., et al 2007. Bioorg. Med. Chem. Lett. 17,501-506.).

Examples of IgG fusion molecules include, but are not limited to, Dual Variable Domain (DVD)-Ig molecules (Abbott, U.S. Pat. No. 7,612,181), Dual domain double head antibodies (Unilever; Sanofi Aventis, WO20100226923), IgG-like Bispecific molecules (ImClone/Eli Lilly, Lewis et al. Nat Biotechnol. 2014 February; 32(2):191-8), Ts2Ab (MedImmune/AZ; Dimasi et al. J Mol Biol. 2009 Oct. 30; 393(3):672-92) and BsAb molecules (Zymogenetics, WO2010111625), HERCULES molecules (Biogen Idec, US007951918), scFv fusion molecules (Novartis), scFv fusion molecules (Changzhou Adam Biotech Inc, CN 102250246) and TvAb molecules (Roche, WO2012025525, WO2012025530).

Examples of Fc fusion molecules include, but are not limited to, ScFv/Fc Fusions (Pearce et al., Biochem Mol Biol Int. 1997 September; 42(6):1179-88), SCORPION molecules (Emergent BioSolutions/Trubion, Blankenship J W, et al. AACR 100th Annual meeting 2009 (Abstract #5465); Zymogenetics/BMS, WO2010111625), Dual Affinity Retargeting Technology (Fc-DART) molecules (MacroGenics, WO2008157379, WO2010080538) and Dual(ScFv)2-Fab molecules (National Research Center for Antibody Medicine—China).

Examples of Fab fusion bispecific antibodies include, but are not limited to, F(ab)2 molecules (Medarex/AMGEN; Deo et al 3 Immunol. 1998 Feb. 15; 160(4):1677-86.), Dual-Action or Bis-Fab molecules (Genentech, Bostrom, et al 2009. Science 323, 1610-1614.), Dock-and-Lock (DNL) molecules (ImmunoMedics, WO2003074569, WO2005004809), Bivalent Bispecific molecules (Biotecnol, Schoonjans, 3 Immunol. 2000 Dec. 15; 165(12):7050-7.) and Fab-Fv molecules (UCB-Celltech, WO 2009040562 A1).

Examples of ScFv-, diabody-based and domain antibodies include, but are not limited to, Bispecific T Cell Engager (BITE) molecules (Micromet, WO2005061547), Tandem Diabody molecules (TandAb) (Affimed) Le Gall et al., Protein Eng Des Sel. 2004 April; 17(4):357-66.), Dual Affinity Retargeting Technology (DART) molecules (MacroGenics, WO2008157379, WO2010080538), Single-chain Diabody molecules (Lawrence, FEBS Lett. 1998 Apr. 3; 425(3):479-84), TCR-like Antibodies (AIT, ReceptorLogics), Human Serum Albumin ScFv Fusion (Merrimack, WO2010059315) and COMBODY molecules (Epigen Biotech, Zhu et al. Immunol Cell Biol. 2010 August; 88(6): 667-75.), dual targeting nanobodies (Ablynx, Hmila et al., FASEB J. 2010) and dual targeting heavy chain only domain antibodies.

In one embodiment, each of said first and second heavy chains comprises at least a hinge region, a CH2 and a CH3 region.

In a further embodiment, the CH3 regions of the first and second heavy chains comprise asymmetrical mutations, such as asymmetrical mutations (also referred to as modifications herein) yielding a stable heterodimeric antibody.

In one embodiment, the bispecific antibody of the invention comprises a first heavy chain comprising a first CH3 region, and a second heavy chain comprising a second CH3 region, wherein the sequences of the first and second CH3 regions are different and are such that the heterodimeric interaction between said first and second CH3 regions is stronger than each of the homodimeric interactions of said first and second CH3 regions. More details on these interactions and how they can be achieved are provided in, e.g., WO 2011/131746 and WO 2013/060867 (Genmab), which are hereby incorporated by reference.

As described further herein, a stable bispecific CD40xCD137 antibody can be obtained at high yield using a particular method on the basis of one homodimeric parental CD40 antibody and one homodimeric parental CD137 antibody containing only a few, fairly conservative, asymmetrical mutations in the CH3 regions. Asymmetrical mutations mean that the sequences of said first and second CH3 regions contain amino acid substitutions at non-identical positions.

Accordingly, in one embodiment of the bispecific antibody as defined in any of the embodiments disclosed herein, the sequences of said first and second heavy chain CH3 regions contain asymmetrical mutations, e.g., a mutation at the position corresponding to position 405 in a human IgG1 heavy chain according to EU numbering in one of the CH3 regions, and a mutation at the position corresponding to position 409 in a human IgG1 heavy chain according to EU numbering in the other CH3 region.

In one aspect, the bispecific antibody as defined in any of the embodiments disclosed herein comprises first and second heavy chains, wherein in said first heavy chain at least one of the amino acids in the positions corresponding to a position selected from the group consisting of T366, L368, K370, D399, F405, Y407, and K409 in a human IgG1 heavy chain according to EU numbering has been substituted, and in said second heavy chain at least one of the amino acids in the positions corresponding to a position selected from the group consisting of T366, L368, K370, D399, F405, Y407, and K409 in a human IgG1 heavy chain according to EU numbering has been substituted, and wherein said first and said second heavy chains are not substituted in the same positions.

In one embodiment of the bispecific antibody as defined in any of the embodiments disclosed herein, the first heavy chain has an amino acid substitution at a position selected from the group consisting of: 366, 368, 370, 399, 405, 407 and 409 in a human IgG1 heavy chain according to EU numbering, and the second heavy chain has an amino acid substitution at a position selected from the group consisting of: 366, 368, 370, 399, 405, 407 and 409 in a human IgG1 heavy chain according to EU numbering, and wherein the first and second heavy chains are not substituted in the same positions.

In one embodiment of the bispecific antibody as defined in any of the embodiments disclosed herein, the first heavy chain has an amino acid substitution at position 366, and said second heavy chain has an amino acid substitution at a position selected from the group consisting of: 368, 370, 399, 405, 407 and 409. In one embodiment the amino acid at position 366 is selected from Ala, Asp, Glu, His, Asn, Val, or Gln.

In one embodiment of the bispecific antibody as defined in any of the embodiments disclosed herein, the first heavy chain has an amino acid substitution at position 368, and said second heavy chain has an amino acid substitution at a position selected from the group consisting of: 366, 370, 399, 405, 407 and 409.

In one embodiment of the bispecific antibody as defined in any of the embodiments disclosed herein, the first heavy chain has an amino acid substitution at position 370, and said second heavy chain has an amino acid substitution at a position selected from the group consisting of: 366, 368, 399, 405, 407 and 409.

In one embodiment of the bispecific antibody as defined in any of the embodiments disclosed herein, the first heavy chain has an amino acid substitution at position 399, and said second heavy chain has an amino acid substitution at a position selected from the group consisting of: 366, 368, 370, 405, 407 and 409.

In one embodiment of the bispecific antibody as defined in any of the embodiments disclosed herein, the first heavy chain has an amino acid substitution at position 405, and said second heavy chain has an amino acid substitution at a position selected from the group consisting of: 366, 368, 370, 399, 407 and 409.

In one embodiment of the bispecific antibody as defined in any of the embodiments disclosed herein, the first heavy chain has an amino acid substitution at position 407, and said second heavy chain has an amino acid substitution at a position selected from the group consisting of: 366, 368, 370, 399, 405, and 409.

In one embodiment of the bispecific antibody as defined in any of the embodiments disclosed herein, the first heavy chain has an amino acid substitution at position 409, and said second heavy chain has an amino acid substitution at a position selected from the group consisting of: 366, 368, 370, 399, 405, and 407.

Accordingly, in one embodiment of the bispecific antibody as defined in any of the embodiments disclosed herein, the sequences of said first and second CH3 regions contain asymmetrical mutations, i.e. mutations at different positions in the two CH3 regions, e.g. a mutation at position 405 in one of the CH3 regions and a mutation at position 409 in the other CH3 region.

In one embodiment of the bispecific antibody as defined in any of the embodiments disclosed herein, the first heavy chain has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second heavy chain has an amino-acid substitution at a position selected from the group consisting of: 366, 368, 370, 399, 405 and 407. In one such embodiment, said first heavy chain has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second heavy chain has an amino acid other than Phe, e.g. Gly, Ala, Val, Ile, Ser, Thr, Lys, Arg, His, Asp, Asn, Glu, Gln, Pro, Trp, Tyr, Cys, Lys, or Leu, at position 405. In a further embodiment hereof, said first heavy chain has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second heavy chain has an amino acid other than Phe, Arg or Gly, e.g. Leu, Ala, Val, Ile, Ser, Thr, Met, Lys, His, Asp, Asn, Glu, Gln, Pro, Trp, Tyr, or Cys, at position 405.

In another embodiment of the bispecific antibody as defined in any of the embodiments disclosed herein, said first heavy chain comprises a Phe at position 405 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second heavy chain comprises an amino acid other than Phe, e.g. Gly, Ala, Val, Ile, Ser, Thr, Lys, Arg, His, Asp, Asn, Glu, Gln, Pro, Trp, Tyr, Leu, Met, or Cys, at position 405 and a Lys at position 409. In a further embodiment hereof, said first heavy chain comprises a Phe at position 405 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second heavy chain comprises an amino acid other than Phe, Arg or Gly, e.g. Leu, Ala, Val, Ile, Ser, Thr, Met, Lys, His, Asp, Asn, Glu, Gln, Pro, Trp, Tyr, or Cys, at position 405 and a Lys at position 409.

In another embodiment of the bispecific antibody as defined in any of the embodiments disclosed herein, said first heavy chain comprises a Phe at position 405 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second heavy chain comprises a Leu at position 405 and a Lys at position 409. In a further embodiment hereof, said first heavy chain comprises a Phe at position 405 and an Arg at position 409 and said second heavy chain comprises an amino acid other than Phe, Arg or Gly, e.g. Leu, Ala, Val, Ile, Ser, Thr, Lys, Met, His, Asp, Asn, Glu, Gln, Pro, Trp, Tyr, or Cys, at position 405 and a Lys at position 409. In another embodiment, said first heavy chain comprises Phe at position 405 and an Arg at position 409 and said second heavy chain comprises a Leu at position 405 and a Lys at position 409.

In a further embodiment of the bispecific antibody as defined in any of the embodiments disclosed herein, said first heavy chain comprises an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second heavy chain comprises a Lys at position 409, a Thr at position 370 and a Leu at position 405. In a further embodiment, said first heavy chain comprises an Arg at position 409 and said second heavy chain comprises a Lys at position 409, a Thr at position 370 and a Leu at position 405.

In an even further embodiment of the bispecific antibody as defined in any of the embodiments disclosed herein, said first heavy chain comprises a Lys at position 370, a Phe at position 405 and an Arg at position 409 and said second heavy chain comprises a Lys at position 409, a Thr at position 370 and a Leu at position 405.

In another embodiment of the bispecific antibody as defined in any of the embodiments disclosed herein, said first heavy chain comprises an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second heavy chain comprises a Lys at position 409 and: a) an Ile at position 350 and a Leu at position 405, or b) a Thr at position 370 and a Leu at position 405.

In another embodiment of the bispecific antibody as defined in any of the embodiments disclosed herein, said first heavy chain comprises an Arg at position 409 and said second heavy chain comprises a Lys at position 409 and: a) an Ile at position 350 and a Leu at position 405, or b) a Thr at position 370 and a Leu at position 405.

In another embodiment of the bispecific antibody as defined in any of the embodiments disclosed herein, said first heavy chain comprises a Thr at position 350, a Lys at position 370, a Phe at position 405 and an Arg at position 409 and said second heavy chain comprises a Lys at position 409 and: a) an Ile at position 350 and a Leu at position 405, or b) a Thr at position 370 and a Leu at position 405.

In another embodiment of the bispecific antibody as defined in any of the embodiments disclosed herein, said first heavy chain comprises a Thr at position 350, a Lys at position 370, a Phe at position 405 and an Arg at position 409 and said second heavy chain comprises an Ile at position 350, a Thr at position 370, a Leu at position 405 and a Lys at position 409.

In one embodiment of the bispecific antibody as defined in any of the embodiments disclosed herein, said first heavy chain has an amino acid other than Lys, Leu or Met at position 409 and said second heavy chain has an amino acid other than Phe at position 405, such as other than Phe, Arg or Gly at position 405; or said first CH3 region has an amino acid other than Lys, Leu or Met at position 409 and said second CH3 region has an amino acid other than Tyr, Asp, Glu, Phe, Lys, Gln, Arg, Ser or Thr at position 407.

In one embodiment, the bispecific antibody as defined in any of the embodiments disclosed herein comprises a first heavy chain having an amino acid other than Lys, Leu or Met at position 409 and a second heavy chain having an amino acid other than Tyr, Asp, Glu, Phe, Lys, Gln, Arg, Ser or Thr at position 407.

In one embodiment, the bispecific antibody as defined in any of the embodiments disclosed herein comprises a first heavy chain having a Tyr at position 407 and an amino acid other than Lys, Leu or Met at position 409 and a second heavy chain having an amino acid other than Tyr, Asp, Glu, Phe, Lys, Gln, Arg, Ser or Thr at position 407 and a Lys at position 409.

In one embodiment, the bispecific antibody as defined in any of the embodiments disclosed herein comprises a first heavy chain having a Tyr at position 407 and an Arg at position 409 and a second heavy chain having an amino acid other than Tyr, Asp, Glu, Phe, Lys, Gln, Arg, Ser or Thr at position 407 and a Lys at position 409.

In another embodiment, said first heavy chain has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second heavy chain has an amino acid other than Tyr, Asp, Glu, Phe, Lys, Gln, Arg, Ser or Thr, e.g. Leu, Met, Gly, Ala, Val, Ile, His, Asn, Pro, Trp, or Cys, at position 407. In another embodiment, said first heavy chain has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second heavy chain has an Ala, Gly, His, Ile, Leu, Met, Asn, Val or Trp at position 407.

In another embodiment of the bispecific antibody as defined in any of the embodiments disclosed herein, said first heavy chain has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second heavy chain has a Gly, Leu, Met, Asn or Trp at position 407.

In another embodiment of the bispecific antibody as defined in any of the embodiments disclosed herein, said first heavy chain has a Tyr at position 407 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second heavy chain has an amino acid other than Tyr, Asp, Glu, Phe, Lys, Gln, Arg, Ser or Thr, e.g. Leu, Met, Gly, Ala, Val, Ile, His, Asn, Pro, Trp, or Cys, at position 407 and a Lys at position 409.

In another embodiment of the bispecific antibody as defined in any of the embodiments disclosed herein, said first heavy chain has a Tyr at position 407 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second heavy chain has an Ala, Gly, His, Ile, Leu, Met, Asn, Val or Trp at position 407 and a Lys at position 409.

In another embodiment of the bispecific antibody as defined in any of the embodiments disclosed herein, said first heavy chain has a Tyr at position 407 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second heavy chain has a Gly, Leu, Met, Asn or Trp at position 407 and a Lys at position 409.

In another embodiment of the bispecific antibody as defined in any of the embodiments disclosed herein, said first heavy chain has a Tyr at position 407 and an Arg at position 409 and said second heavy chain has an amino acid other than Tyr, Asp, Glu, Phe, Lys, Gln, Arg, Ser or Thr, e.g. Leu, Met, Gly, Ala, Val, Ile, His, Asn, Pro, Trp, or Cys, at position 407 and a Lys at position 409.

In another embodiment of the bispecific antibody as defined in any of the embodiments disclosed herein, said first heavy chain has a Tyr at position 407 and an Arg at position 409 and said second heavy chain has an Ala, Gly, His, Ile, Leu, Met, Asn, Val or Trp at position 407 and a Lys at position 409.

In another embodiment of the bispecific antibody as defined in any of the embodiments disclosed herein, said first heavy chain has a Tyr at position 407 and an Arg at position 409 and said second heavy chain has a Gly, Leu, Met, Asn or Trp at position 407 and a Lys at position 409.

In another embodiment of the bispecific antibody as defined in any of the embodiments disclosed herein, the first heavy chain has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409, and the second heavy chain has (i) an amino acid other than Phe, Leu and Met, e.g. Gly, Ala, Val, Ile, Ser, Thr, Lys, Arg, His, Asp, Asn, Glu, Gln, Pro, Trp, Tyr, or Cys, at position 368, or (ii) a Trp at position 370, or (iii) an amino acid other than Asp, Cys, Pro, Glu or Gln, e.g. Phe, Leu, Met, Gly, Ala, Val, Ile, Ser, Thr, Lys, Arg, His, Asn, Trp, Tyr, or Cys, at position 399 or (iv) an amino acid other than Lys, Arg, Ser, Thr, or Trp, e.g. Phe, Leu, Met, Ala, Val, Gly, Ile, Asn, His, Asp, Glu, Gln, Pro, Tyr, or Cys, at position 366.

In one embodiment, the first heavy chain has an Arg, Ala, His or Gly at position 409, and the second heavy chain has (i) a Lys, Gln, Ala, Asp, Glu, Gly, His, Ile, Asn, Arg, Ser, Thr, Val, or Trp at position 368, or (ii) a Trp at position 370, or (iii) an Ala, Gly, Ile, Leu, Met, Asn, Ser, Thr, Trp, Phe, His, Lys, Arg or Tyr at position 399, or (iv) an Ala, Asp, Glu, His, Asn, Val, Gln, Phe, Gly, Ile, Leu, Met, or Tyr at position 366.

In one embodiment, the first heavy chain has an Arg at position 409, and the second heavy chain has (i) an Asp, Glu, Gly, Asn, Arg, Ser, Thr, Val, or Trp at position 368, or (ii) a Trp at position 370, or (iii) a Phe, His, Lys, Arg or Tyr at position 399, or (iv) an Ala, Asp, Glu, His, Asn, Val, Gln at position 366.

In one embodiment, the bispecific antibody as defined in any of the embodiments disclosed herein comprises first and second heavy chains, wherein (i) the amino acid in the position corresponding to F405 in a human IgG1 heavy chain according to EU numbering is L in said first heavy chain, and the amino acid in the position corresponding to K409 in a human IgG1 heavy chain according to EU numbering is R in said second heavy chain, or (ii) the amino acid in the position corresponding to K409 in a human IgG1 heavy chain according to EU numbering is R in said first heavy chain, and the amino acid in the position corresponding to F405 in a human IgG1 heavy chain according to EU numbering is L in said second heavy chain.

In a further embodiment said first and second heavy chain are of a human IgG1 isotype.

In another further embodiment said first and second heavy chain are of a human IgG2 isotype.

In another further embodiment said first and second heavy chain are of a human IgG3 isotype.

In another embodiment, the bispecific antibody as defined in any of the embodiments disclosed herein comprises first and second heavy chains of the human IgG4 isotype, wherein (i) the amino acid in the position corresponding to S228 in a human IgG4 heavy chain according to EU numbering is P in said first heavy chain, and the amino acid in the position corresponding to S228, F405 and R409 in a human IgG4 heavy chain according to EU numbering is P, L and K, respectively, in said second heavy chain, or (ii) the amino acid in the position corresponding to S228, F405 and R409 in a human IgG4 heavy chain according to EU numbering is P, L and K, respectively, in said first heavy chain, and the amino acid in the position corresponding to S228 in a human IgG4 heavy chain according to EU numbering is P in said second heavy chain.

If reference is made herein to amino acids at certain positions of the first heavy chain and/or amino acids at certain positions of the second heavy chain, such reference is to be understood to include embodiments wherein the amino acids at certain positions of the first heavy chain are present at the corresponding positions of the second heavy chain rather than the first heavy chain and/or the amino acids at certain positions of the second heavy chain are present at the corresponding positions of the first heavy chain rather than the second heavy chain.

In addition to the above-specified amino-acid substitutions, said first and second heavy chains may contain further amino-acid substitutions, deletion or insertions relative to wild-type heavy chain sequences.

In a further embodiment, said first and second Fab-arms (or heavy chain constant domains) comprising the first and second heavy chains comprise, except for the specified mutations, a CH3 sequence independently selected from the following:

(IgG1m(a)) (SEQ ID NO:106), (IgG1m(f)) (SEQ ID NO:107), and (IgG1m(ax)) (SEQ ID NO:108).

In one embodiment, neither said first nor said second heavy chain comprises a Cys-Pro-Ser-Cys sequence in the (core) hinge region.

In a further embodiment, both said first and said second heavy chain comprise a Cys-Pro-Pro-Cys sequence in the (core) hinge region.

In separate and specific embodiments, one or both Fab-arms comprise a heavy-chain constant region sequence independently selected from SEQ ID NO:109, 110, 111, 112, 113 and 116 (see Table 1).

Methods of Preparing Bispecific Antibodies

Traditional methods such as the hybrid hybridoma and chemical conjugation methods (Marvin and Zhu (2005) Acta Pharmacol Sin 26:649) can be used in the preparation of the bispecific antibodies of the invention. Co-expression in a host cell of two antibodies, consisting of different heavy and light chains, leads to a mixture of possible antibody products in addition to the desired bispecific antibody, which can then be isolated by, e.g., affinity chromatography or similar methods.

Strategies favoring the formation of a functional bispecific product upon co-expression of different antibody constructs can also be used, e.g., by the method described by Lindhofer et al. (1995 J Immunol 155:219). Fusion of rat and mouse hybridomas producing different antibodies leads to a limited number of heterodimeric proteins because of preferential species-restricted heavy/light chain pairing. Another strategy to promote formation of heterodimers over homodimers is a "knob-into-hole" strategy in which a protuberance is introduced on a first heavy-chain polypeptide and a corresponding cavity in a second heavy-chain polypeptide, such that the protuberance can be positioned in the cavity at the interface of these two heavy chains so as to promote heterodimer formation and hinder homodimer formation. "Protuberances" are constructed by replacing small amino-acid side-chains from the interface of the first polypeptide with larger side chains. Compensatory "cavities" of identical or similar size to the protuberances are created in the interface of the second polypeptide by replacing large amino-acid side-chains with smaller ones (U.S. Pat. No. 5,731,168). EP1870459 (Chugai) and WO 2009/089004 (Amgen) describe other strategies for favoring heterodimer formation upon co-expression of different antibody domains in a host cell. In these methods, one or more residues that make up the CH3-CH3 interface in both CH3 domains are replaced with a charged amino acid such that homodimer formation is electrostatically unfavorable and heterodimerization is electrostatically favorable. WO2007110205 (Merck) describe yet another strategy, wherein differences between IgA and IgG CH3 domains are exploited to promote heterodimerization.

A preferred method for preparing the bispecific CD40xCD137 antibodies of the present invention includes the methods described in WO 2011/131746 and WO 2013/060867 (Genmab) comprising the following steps:

a) providing a first antibody comprising an Fc region, said Fc region comprising a first CH3 region;

b) providing a second antibody comprising a second Fc region, said Fc region comprising a second CH3 region, wherein the first antibody is a CD40 antibody comprising two first antigen-binding regions as described herein and the second antibody is a CD137 antibody comprising two second antigen-binding regions as described herein, or vice versa; and wherein the sequences of said first and second CH3 regions are different and are such that the heterodimeric interaction between said first and second CH3 regions is stronger than each of the homodimeric interactions of said first and second CH3 regions;

c) incubating said first antibody together with said second antibody under reducing conditions; and d) obtaining said bispecific CD40xCD137 antibody.

In one embodiment, said first antibody is incubated together with said second antibody under reducing conditions sufficient to allow the cysteines in the hinge region to undergo disulfide-bond isomerization, wherein the heterodimeric interaction between said first and second antibodies in the resulting heterodimeric antibody is such that no Fab-arm exchange occurs at 0.5 mM GSH after 24 hours at 37° C.

Without being limited to theory, in step c), the heavy-chain disulfide bonds in the hinge regions of the parent antibodies (first and second antibody in step a) and b)) are reduced and the resulting cysteines are then able to form inter heavy-chain disulfide bond with cysteine residues of another parent antibody molecule (originally with a different specificity). In one embodiment of this method, the reducing conditions in step c) comprise the addition of a reducing agent, e.g. a reducing agent selected from the group consisting of: 2-mercaptoethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris (2-carboxyethyl)phosphine. In a further embodiment, step c) comprises restoring the conditions to become non-reducing or less reducing, for example by removal of a reducing agent, e.g. by desalting. In one particular embodiment, bispecific antibodies are generated as follows: the two parental complementary antibodies, both in the same amount, are incubated with 75 mM 2-mercaptoethylamine-HCl (2-MEA) in buffer (e.g., PBS or Tris-EDTA) at 31° C. for 5 hours; the reduction reaction is stopped by removing the reducing agent 2-MEA using spin columns (e.g., Microcon centrifugal filters, 30 k, Millipore) (Labrijn et al. Nature Protocols, Vol 9 No 10, p 2450-2463; 2014). In another particular embodiment, the method is that of Example 3.

For this method, any of the CD40 and CD137 antibodies disclosed herein may be used. In a particular embodiment the first and second antibodies, binding to human CD40 and CD137, respectively, may be chosen so as to obtain a bispecific antibody as described herein.

In one embodiment of this method, said first and/or second antibodies are full-length antibodies.

The Fc regions of the first and second antibodies may be of any isotype, including, but not limited to, an IgG isotype having a subclass selected from the group consisting of IgG1, IgG2, IgG3 and IgG4. In one embodiment of this method, the Fc regions of both said first and said second antibodies are of the IgG1 isotype. In another embodiment, one of the Fc regions of said antibodies is of the IgG1 isotype and the other of the IgG4 isotype. In the latter embodiment, the resulting bispecific antibody comprises an Fc region of an IgG1 and an Fc region of IgG4.

In a further embodiment, one of the parental antibodies has been engineered to not bind Protein A, thus allowing separation of the heterodimeric antibody from said parental homodimeric antibodies by passing the product over a protein A column.

As described above, the sequences of the first and second CH3 regions of the homodimeric parental antibodies are different and are such that the heterodimeric interaction between said first and second CH3 regions is stronger than each of the homodimeric interactions of said first and second CH3 regions. More details on these interactions and how they can be achieved are provided in WO 2011/131746 and WO 2013/060867 (Genmab), which are hereby incorporated by reference in their entirety.

In particular, a stable bispecific CD40xCD137 antibody can be obtained at high yield using the above method of the invention on the basis of two homodimeric antibodies which bind CD40 and CD137, respectively, and contain only a few, fairly conservative, asymmetrical mutations in the CH3 regions. Asymmetrical mutations mean that the sequences of said first and second CH3 regions contain amino acid substitutions at non-identical positions.

The bispecific antibodies of the invention may also be obtained by co-expression of constructs encoding the first and second polypeptides in a single cell. Thus, in a further aspect, the invention relates to a method for producing a bispecific antibody, said method comprising the following steps:

a) providing a first nucleic-acid construct encoding a first polypeptide comprising a first Fc region and a first antigen-binding region binding to human CD40 according to any aspect or embodiment herein, said first Fc region comprising a first CH3 region, b) providing a second nucleic-acid construct encoding a second polypeptide comprising a second Fc region and a second antigen-binding region binding to human CD137 according to any aspect or embodiment herein, said second Fc region comprising a second CH3 region, wherein the sequences of said first and second CH3 regions are different and are such that the heterodimeric interaction between said first and second CH3 regions is stronger than each of the homodimeric interactions of said first and second CH3 regions, and wherein in said first CH3 region at least one of the amino acids in the positions corresponding to a position selected from the group consisting of T366, L368, K370, D399, F405, Y407, and K409 in a human IgG1 heavy chain according to EU numbering has been substituted, and in said second CH3 region at least one of the amino acids in the positions corresponding to a position selected from the group consisting of T366, L368, K370, D399, F405, Y407, and K409 in a human IgG1 heavy chain according to EU numbering has been substituted, and wherein said first and said second heavy chains are not substituted in the same positions, optionally wherein said first and second nucleic acid constructs encode light chain sequences of said first and second antibodies, c) co-expressing said first and second nucleic-acid constructs in a host cell, and d) obtaining said heterodimeric protein from the cell culture.

Thus, the present invention also relates to a recombinant eukaryotic or prokaryotic host cell which produces a bispecific antibody of the present invention.

In one embodiment of the present invention, the bispecific antibody is obtained by any of the methods according to the present invention.

Suitable expression vectors, including promoters, enhancers, etc., and suitable host cells for the production of antibodies are well-known in the art. Examples of host cells include yeast, bacterial and mammalian cells, such as CHO or HEK cells.

In one embodiment, the bispecific antibody as defined in any of the embodiments disclosed herein comprises first and second CH3 regions, except for the specified mutations, comprising the sequence of SEQ ID NO:107 (IgG1m(f)).

In one embodiment, the bispecific antibody as defined in any of the embodiments disclosed herein comprises a first Fc-region and a second Fc-region, wherein neither said first nor said second Fc-region comprises a Cys-Pro-Ser-Cys sequence in the hinge region.

In one embodiment, the bispecific antibody as defined in any of the embodiments disclosed herein comprises a first Fc-region and a second Fc-region, wherein both of said first and said second Fc-region comprise a Cys-Pro-Pro-Cys sequence in the hinge region.

In one embodiment, the bispecific antibody as defined in any of the embodiments disclosed herein comprises a first Fc-region and a second Fc-region, wherein the first and second Fc-regions are human antibody Fc-regions.

In one embodiment, the bispecific antibody as defined in any of the embodiments disclosed herein comprises a first Fc-region and a second Fc-region, wherein said first and second Fc region, except for the specified mutations, comprise a sequence independently selected from the group consisting of SEQ ID NOS:109, 110, 111, 112, 113 and 116.

In one embodiment, the bispecific antibody as defined in any of the embodiments disclosed herein comprises a first Fc-region and a second Fc-region, wherein the first and second antigen-binding regions are from heavy-chain antibodies.

In one embodiment, the bispecific antibody as defined in any of the embodiments disclosed herein comprises a first Fc-region and a second Fc-region, wherein the first and second antigen-binding regions comprise a first and second light chain.

In further embodiments, the co-expression method according to the invention comprises any of the further features described under the in vitro method above.

Inert Format

The effector functions mediated by the Fc region of an antibody allow for the destruction of foreign entities, such as the killing of pathogens and the clearance and degradation of antigens. Antibody-dependent cell-mediated cytotoxicity (ADCC) and antibody-dependent cell-mediated phagocytosis (ADCP) are initiated by binding of the Fc region to Fc receptor (FcR)-bearing cells, whereas complement-dependent cytotoxicity (CDC) and complement-dependent cell-mediated cytotoxicity (CDCC) are initiated by binding of the Fc region to C1q, which initiates the classical route of complement activation.

Fc-mediated effector function, such as ADCC and complement activation, have been suggested to contribute to the therapeutic efficacy of monoclonal antibodies used for the treatment of cancer (Weiner et al. Cell 2012, 148:1081-1084).

The multispecific antibody, such as a bispecific antibody, according to the present invention binds to CD137 which is expressed on T-cells, e.g. CD4$^+$ and/or CD8$^+$ T-cells. By concomitant binding of the antibody to CD40, which is expressed on e.g. antigen-presenting cells (APCs), provides stimulation to both APCs expressing CD40 and T-cells expressing CD137 and thereby e.g. T-cell proliferation can be increased.

In general, binding of an antibody to a target antigen expressed by a cell may lead to interactions with effector molecules such as Fc receptors or complement proteins which may induce Fc-mediated effector functions, such as ADCC or complement activation, which may result in killing of the cell expressing said target antigen. The use of the multispecific antibody, such as a bispecific antibody, according to the present invention is based on its ability to provide co-stimulation to APCs and T cells.

It is, in a particular embodiment, preferred that the multispecific antibody does not bind to FcRs, e.g. FcγRs, and therefore does not induce FcR-mediated cross-linking.

It is, in a further embodiment, preferred that the multispecific antibody does not engage effector functions so as to avoid killing of the CD40 and/or CD137 expressing cells.

In one aspect of the present invention, the multispecific CD40xCD137 antibody according to the present invention comprises (i) a first binding arm comprising a first heavy chain and a first antigen-binding region and (ii) a second binding arm comprising a second heavy chain and a second antigen-binding region, according to any aspect or embodiment described herein.

In one embodiment the multispecific antibody according to present invention comprises a first and a second heavy chain, wherein said antibody induces and/or enhances Fc-mediated effector function to a lesser extent compared to a multispecific antibody comprising the same first and second antigen-binding regions as said antibody, and comprising two heavy chains comprising a human IgG1 hinge, CH2 and CH3 regions.

In one embodiment, the multispecific antibody according to present invention comprises a first and a second antigen-binding region and a first and a second heavy chain, each of the first and second heavy chains comprising a human IgG1 hinge, CH2 and CH3 regions, wherein at least one of the first and second heavy chain comprises a modification so as to induce and/or enhance Fc-mediated effector function to a lesser extent compared to a reference multispecific antibody comprising the same first and second antigen-binding regions as said antibody, and comprising two heavy chains comprising a human IgG1 hinge, CH2 and CH3 regions without said modification.

In one embodiment, said first and second heavy chains are modified so that the multispecific antibody induces and/or enhances Fc-mediated effector function to a lesser extent compared to a multispecific antibody which is identical except for comprising non-modified first and second heavy chains.

In one embodiment, said Fc-mediated effector function may be measured by binding to Fcγ-receptors, binding to C1q, or induction of Fc-mediated cross-linking of FcRs.

In one embodiment, said Fc-mediated effector function is measured by binding to C1q.

In one embodiment, said first and second heavy and light chain constant sequences have been modified so that binding of C1q to said multispecific antibody is reduced compared to a wild-type multispecific antibody by at least 70%, at least 80%, at least 90%, at least 95%, at least 97%, or 100%, wherein C1q binding is determined by ELISA.

Human IgG1 is known for its ability to induce Fc-mediated effector functions, while other human isotypes, such as IgG4, are less able to induce Fc-mediated effector functions.

The first and second heavy chains may each be of any isotype, including, but not limited to, an IgG1 isotype selected from the groups consisting of IgG1, IgG2, IgG3 and IgG4, and may optionally comprise one or more mutations or modifications. In one embodiment, each of the first and second heavy chains is of the IgG4 isotype or derived therefrom, optionally with one or more mutations or modifications. In one embodiment, each of the first and second heavy chains is of the IgG1 isotype or derived therefrom, optionally with one or more mutations or modifications. In another embodiment, one of the heavy chains is of the IgG1 isotype and the other of the IgG4 isotype, or is derived from such respective isotypes, optionally with one or more mutations or modifications.

In one embodiment, one or both of the first and heavy chains are such that an antibody comprising two first or two second heavy chains would be effector-function-deficient. For example, the first and second heavy chains may be of an IgG4 isotype, or a non-IgG4 type, e.g. IgG1, IgG2 or IgG3, which has been mutated such that the ability to mediate effector functions, such as ADCC, has been reduced or even eliminated compared to non-mutated heavy chains. Such mutations have e.g. been described in Dall'Acqua W F et al., J Immunol. 177(2):1129-1138 (2006) and Hezareh M, J Virol.; 75(24):12161-12168 (2001). The multispecific antibody according to the present invention may comprise modifications in the first and second heavy chains compared to a wild type human IgG1 sequence. A multispecific antibody comprising such modifications in the Fc region of the antibody may become an inert, or non-activating, multispecific antibody. The term "inertness", "inert" or "non-activating" as used herein, refers to an Fc region which is at least not able to bind any Fcγ(gamma) receptors, bind to C1q, or induce Fc-mediated cross-linking of FcRs. The inertness of an Fc region, or the first and/or second heavy chain of a multispecific antibody of the present invention may be tested with a bivalent, monospecific antibody comprising said Fc region, or two first heavy chains or two second heavy chains. It may also be tested with a multispecific antibody comprising a first and a second heavy chain.

Several variants can be constructed to make the Fc region of an antibody inactive for interactions with Fcγ receptors and C1q for therapeutic antibody development. The present invention is not limited to any specific mutation relevant for reducing Fc-mediated effector functions. Examples of such variants are described herein.

Thus, amino acids in the Fc region that play a dominant role in the interactions with C1q and the Fcγ receptors may be modified. Examples of amino acid positions that may be modified include positions L234, L235 and P331.

Hence, in one embodiment, in at least one of said first and second heavy chains the amino acid in at least one position corresponding to L234, L235 and P331 in a human IgG1 heavy chain according to EU numbering, may be A, A and S, respectively. (Xu et al., 2000, Cell Immunol. 200(1):16-26; Oganesyan et al., 2008, Acta Cryst. (D64):700-4). Also, L234F and L235E amino acid substitutions can result in Fc regions with abrogated interactions with Fcγ receptors and C1q (Canfield et al., 1991, J. Exp. Med. (173):1483-91; Duncan et al., 1988, Nature (332):738-40). Hence, in one embodiment, in at least one of said first and second heavy chains the amino acids in the positions corresponding to L234 and L235 in a human IgG1 heavy chain according to EU numbering, may be F and E, respectively. A D265A amino acid substitution can decrease binding to all Fc gamma receptors and prevent ADCC (Shields et al., 2001, 3. Biol. Chem. (276):6591-604). Hence, in one embodiment, in at least one of said first and second heavy chains the amino acid in the position corresponding to D265 in a human IgG1 heavy chain according to EU numbering, may be A. Binding to C1q can be abrogated by mutating positions D270, K322, P329, and P331. Mutating these positions to either D270A or K322A or P329A or P331A can make the antibody deficient in CDC activity Idusogie E E, et al., 2000, J Immunol. 164: 4178-84). Hence, in one embodiment, in at least one of said first and second heavy chain, the amino acids in at least one position corresponding to D270, K322, P329 and P331 in a human IgG1 heavy chain according to EU numbering, may be A, A, A, and A, respectively.

An alternative approach to minimize the interaction of the Fc region with Fcγ receptors and C1q is by removal of the glycosylation site of an antibody. Mutating position N297 to e.g. Q, A, or E removes a glycosylation site which is critical for IgG-Fcγ receptor interactions. Hence, in one embodiment, in at least one of said first and second heavy chains, the amino acid in a position corresponding to N297, may be G, Q, A or E in a human IgG1 heavy chain according to EU numbering (Leabman et al., 2013, MAbs; 5(6):896-903). Another alternative approach to minimize interaction of the Fc region with Fcγ receptors may be obtained by the following mutations; P238A, A327Q, P329A or E233P/L234V/L235A/G236del (Shields et al., 2001, J. Biol. Chem. (276):6591-604).

Alternatively, human IgG2 and IgG4 subclasses are considered naturally compromised in their interactions with C1q and Fc gamma Receptors although interactions with Fcγ receptors were reported (Parren et al., 1992, J. Clin Invest. 90: 1537-1546; Bruhns et al., 2009, Blood 113: 3716-3725). Mutations abrogating these residual interactions can be made in both isotypes, resulting in reduction of unwanted side-effects associated with FcR binding. For IgG2, these include V234A and G237A, and for IgG4, L235E. Hence, in one embodiment, in at least one of said first and second heavy chains, such as in both said first and second heavy chains, the amino acid in a position corresponding to V234 and G237 in a human IgG2 heavy chain according to EU numbering, may be A and A, respectively. In one embodiment, the amino acid in a position corresponding to L235 in a human IgG4 heavy chain according to EU numbering, may be E.

Other approaches to further minimize the interaction with Fcγ receptors and C1q in IgG2 antibodies include those described in WO2011066501 and Lightle, S., et al., 2010, Protein Science (19):753-62.

The hinge region of the antibody can also be of importance with respect to interactions with Fcγ receptors and complement (Brekke et al., 2006, 3 Immunol 177:1129-1138; Dall'Acqua W F, et al., 2006, J Immunol 177:1129-1138). Accordingly, mutations in or deletion of the hinge region can influence effector functions of an antibody.

In one embodiment, the multispecific antibody comprises a first and a second heavy chain, wherein in at least one of said first and second immunoglobulin heavy chains one or more amino acids in the positions corresponding to positions L234, L235, D265, N297, and P331 in a human IgG1 heavy chain according to EU numbering, are not L, L, D, N, and P, respectively.

In one embodiment, in both the first and second heavy chains one or more amino acids in the position corresponding to positions L234, L235, D265, N297, and P331 in a human IgG1 heavy chain according to EU numbering, are not L, L, D, N, and P, respectively.

In another embodiment, in at least one of the first and second heavy chains one or more amino acids in the positions corresponding to positions L234, L235 and D265 in a human IgG1 heavy chain according to EU numbering, are not L, L and D, respectively, and the amino acids in the positions corresponding to N297 and P331 in a human IgG1 heavy chain according to EU numbering, are N and P, respectively.

In one embodiment, one or both of the heavy chains comprise a mutation removing the acceptor site for Asn-linked glycosylation or is otherwise manipulated to change the glycosylation properties. For example, in an IgG1 Fc-region, an N297Q mutation can be used to remove an Asn-linked glycosylation site. Accordingly, in a specific embodiment, one or both heavy chains comprise an IgG1 wildtype sequence with an N297Q mutation.

The term "amino acid corresponding to position" as used herein refers to an amino acid position number in a human IgG1 heavy chain. Corresponding amino acid positions in other immunoglobulins may be found by alignment with human IgG1. Unless otherwise stated or contradicted by context, the amino acids of the constant region sequences are herein numbered according to the EU-index of numbering (described in Kabat, E. A. et al., 1991, Sequences of proteins of immunological interest. 5th Edition—US Department of Health and Human Services, NIH publication No. 91-3242, pp 662, 680, 689). Thus, an amino acid or segment in one sequence that "corresponds to" an amino acid or segment in another sequence is one that aligns with the other amino acid or segment using a standard sequence alignment program such as ALIGN, ClustalW or similar, typically at default settings and has at least 50%, at least 80%, at least 90%, or at least 95% identity to a human IgG1 heavy chain. It is considered well-known in the art how to align a sequence or segment in a sequence and thereby determine the corresponding position in a sequence to an amino acid position according to the present invention.

In the context of the present invention, the amino acid position may be defined as described above.

The term "the amino acid is not" or similar wording when referring to amino acids in a heavy chain is to be understood to mean that the amino acid is any other amino acid than the specific amino acid mentioned. For example, the amino acid in the position corresponding to L234 in a human IgG1 heavy chain is not L, means that the amino acid may be any of the other naturally or non-naturally occurring amino acids than L.

In one embodiment, in said first and second heavy chains the amino acid in the position corresponding to position D265 in a human IgG1 heavy chain according to EU numbering, is not D.

In one embodiment, in said first and second heavy chains the amino acid in the position corresponding to D265 in a human IgG1 heavy chain according to EU numbering, is not D, and the amino acids in the positions corresponding to positions N297 and P331 in a human IgG1 heavy chain according to EU numbering, are N and P, respectively.

In one embodiment, in said first and second heavy chains the amino acids in the positions corresponding to position D265 in a human IgG1 heavy chain according to EU numbering is hydrophobic or polar amino acids.

The term "hydrophobic" as used herein in relation to an amino acid residue, refers to an amino acid residue selected from the group consisting of: A, C, F, G, H, I, L, M, R, T, V, W, and Y.

Thus, in one embodiment, in said first and second heavy chains the amino acid in the position corresponding to position D265 in a human IgG1 heavy chain according to EU numbering is selected from the group of amino acids consisting of: A, C, F, G, H, I, L, M, R, T, V, W and Y.

The term "polar" as used herein in relation to amino acid residues, refers to any amino acid residue selected from the group consisting of: C, D, E, H, K, N, Q, R, S, and T. Thus, in one embodiment, in said first and second heavy chains the amino acid in the position corresponding to position D265 in a human IgG1 heavy chain according to EU numbering is selected from the group consisting of: C, E, H, K, N, Q, R, S, and T.

In another embodiment, in said first and second heavy chains the amino acid in the position corresponding to position D265 in a human IgG1 heavy chain according to EU numbering is an aliphatic uncharged, aromatic or acidic amino acid.

The term "aliphatic uncharged" as used herein in relation to amino acid residues, refers to any amino acid residue selected from the group consisting of: A, G, I, L, and V.

Thus, in one embodiment, in said first and second heavy chains the amino acid in the position corresponding to position D265 in a human IgG1 heavy chain according to EU numbering is selected from the group consisting of: A, G, I, L, and V.

The term "aromatic" as used herein in relation to amino acid residues, refers to any amino acid residue selected from the group consisting of: F, T, and W.

Thus, in one embodiment, in said first and second heavy chains the amino acid in the position corresponding to position D265 in a human IgG1 heavy chain according to EU numbering is selected from the group consisting of: F, T, and W.

The term "acidic" as used herein in relation to amino acid residues, refers to any amino acid residue chosen from the group consisting of: D and E.

Thus, in one embodiment, in at least one of said first and second heavy chains the amino acid in the position corresponding to position D265 in a human IgG1 heavy chain according to EU numbering is selected from the group consisting of: D and E.

Thus, in one embodiment, in both said first and second heavy chains the amino acid in the position corresponding to position D265 in a human IgG1 heavy chain according to EU numbering is selected from the group consisting of: D and E.

In a particular embodiment, in at least one of said first and second heavy chains the amino acid in the position corresponding to position D265 in a human IgG1 heavy chain according to EU numbering is selected from the group consisting of: A, E, F, G, I, L, T, V, and W.

In a particular embodiment, in both said first and second heavy chains the amino acid in the position corresponding to position D265 in a human IgG1 heavy chain according to EU numbering is selected from the group consisting of: A, E, F, G, I, L, T, V, and W.

In one embodiment, in at least one of said first and second heavy chains the amino acid in the position corresponding to position D265 in a human IgG1 heavy chain according to EU numbering, is not D.

In one embodiment, in both said first and second heavy chains the amino acid in the position corresponding to position D265 in a human IgG1 heavy chain according to EU numbering, is not D.

In one embodiment, in at least one of said first and second heavy chains the amino acid in the position corresponding to D265 in a human IgG1 heavy chain according to EU numbering, is not D, and the amino acids in the positions corresponding to positions N297 and P331 in a human IgG1 heavy chain according to EU numbering, are N and P, respectively.

In one embodiment, in both said first and second heavy chains the amino acid in the position corresponding to D265 in a human IgG1 heavy chain according to EU numbering, is not D, and the amino acids in the positions corresponding to positions N297 and P331 in a human IgG1 heavy chain according to EU numbering, are N and P, respectively.

In one embodiment, in at least one of said first and second heavy chains the amino acid in the position corresponding to position D265 in a human IgG1 heavy chain according to EU numbering is hydrophobic or polar amino acid.

In one embodiment, in both said first and second heavy chains the amino acid in the position corresponding to position D265 in a human IgG1 heavy chain according to EU numbering is hydrophobic or polar amino acid.

Thus, in one embodiment, in at least one of said first and second heavy chains the amino acid in the position corresponding to position D265 in a human IgG1 heavy chain according to EU numbering is selected from the group of amino acids consisting of: A, C, F, G, H, I, L, M, R, T, V, W and Y.

Thus, in one embodiment, in at least one of said first and second heavy chains the amino acid in the position corresponding to position D265 in a human heavy chain according to EU numbering is selected from the group consisting of: C, E, H, K, N, Q, R, S, and T. In one embodiment, in both said first and second heavy chains the amino acid in the position corresponding to position D265 in a human IgG1 heavy chain according to EU numbering is selected from the group of amino acids consisting of: A, C, F, G, H, I, L, M, R, T, V, W and Y.

In one embodiment, in both said first and second heavy chains the amino acids in the positions corresponding to position D265 in a human heavy chain according to EU numbering is selected from the group consisting of: C, E, H, K, N, Q, R, S, and T.

In another embodiment, in at least one of said first and second heavy chains the amino acid in the position corresponding to position D265 in a human IgG1 heavy chain according to EU numbering is aliphatic uncharged, aromatic or acidic amino acids.

Thus, in one embodiment, in least one of said first and second heavy chains the amino acid in the position corresponding to position D265 in a human IgG1 heavy chain according to EU numbering is selected from the group consisting of: A, G, I, L, and V.

Thus, in one embodiment, in least one of said first and second heavy chains the amino acid in the position corresponding to position D265 in a human IgG1 heavy chain according to EU numbering is selected from the group consisting of: F, T, and W.

Thus, in one embodiment, in least one of said first and second heavy chains the amino acid in the position corresponding to position D265 in a human IgG1 heavy chain according to EU numbering are selected from the group consisting of: D and E.

In a particular embodiment, in least one of said first and second heavy chains the amino acid in the position corresponding to position D265 in a human IgG1 heavy chain according to EU numbering is selected from the group consisting of: A, E, F, G, I, L, T, V, and W.

In another embodiment, in both said first and second heavy chains the amino acid in the position corresponding to position D265 in a human IgG1 heavy chain according to EU numbering is aliphatic uncharged, aromatic or acidic amino acids.

Thus, in one embodiment, in both said first and second heavy chains the amino acid in the position corresponding to position D265 in a human IgG1 heavy chain according to EU numbering is selected from the group consisting of: A, G, I, L, and V.

Thus, in one embodiment, in both said first and second heavy chains the amino acid in the position corresponding to position D265 in a human IgG1 heavy chain according to EU numbering is selected from the group consisting of: F, T, and W.

Thus, in one embodiment, in both said first and second heavy chains the amino acid in the position corresponding to position D265 in a human IgG1 heavy chain according to EU numbering are selected from the group consisting of: D and E.

In a particular embodiment, in both said first and second heavy chains the amino acid in the position corresponding to position D265 in a human IgG1 heavy chain according to EU numbering is selected from the group consisting of: A, E, F, G, I, L, T, V, and W.

In further embodiment, in at least one of said first and second heavy chains the amino acid in the position corresponding to position N297 in a human IgG1 heavy chain according to EU numbering, is not N.

In one embodiment, in at least one of the first and second heavy chains the amino acid in the position corresponding to N297 in a human IgG1 heavy chain according to EU numbering, is not N, and the amino acid in the position corresponding to position P331 in a human IgG1 heavy chain according to EU numbering, is P.

In one embodiment, in said first and second heavy chains the amino acid in the position corresponding to positions N297 in a human IgG1 heavy chain according to EU numbering, is not N.

In one embodiment, in both the first and second heavy chains the amino acid in the position corresponding to N297 in a human IgG1 heavy chain according to EU numbering, is not N, and the amino acid in the position corresponding to position P331 in a human IgG1 heavy chain according to EU numbering, is P.

In further embodiment, in at least one of said first and second heavy chains the amino acids in the positions corresponding to positions L234 and L235 in a human IgG1 heavy chain according to EU numbering, are not L and L, respectively.

In one embodiment, in at least one of the first and second heavy chains the amino acids in the positions corresponding to L234 and L235 in a human IgG1 heavy chain according to EU numbering, are not L and L, respectively, and the amino acids in the positions corresponding to positions N297 and P331 in a human IgG1 heavy chain according to EU numbering, are N and P, respectively.

In one embodiment, in at least one of said first and second heavy chains the amino acids corresponding to positions L234 and L235 in a human IgG1 heavy chain according to EU numbering are selected from the group consisting of: A, C, D, E, F, G, H, I, K, M, N, P, Q, R, S, T, Y, V.

In one embodiment, in at least one of said first and second heavy chains the amino acids in the positions corresponding to positions L234 and L235 in a human IgG1 heavy according to EU numbering chain are hydrophobic or polar amino acids.

Thus, in one embodiment, in at least one of said first and second heavy chains the amino acids in the positions corresponding to positions L234 and L235 in a human IgG1 heavy chain according to EU numbering are each selected from the group consisting of: A, C, F, G, H, I, M, R, T, V, W, and Y.

Thus, in one embodiment, in at least one of said first and second heavy chains the amino acids in the positions corresponding to positions L234 and L235 in a human IgG1 heavy chain according to EU numbering are each selected from the group of amino acids consisting of: C, D, E, H, K, N, Q, R, S, and T.

In a particular embodiment, in at least one of said first and second heavy chains the amino acids in the positions corresponding to positions L234 and L235 in a human IgG1 heavy chain according to EU numbering are each selected from the group consisting of: A, C, D, E, F, G, H, I, K, M, N, Q, R, S, T, V, W, and Y.

In one embodiment, in both said first and second heavy chains the amino acids in the positions corresponding to positions L234 and L235 in a human IgG1 heavy chain according to EU numbering, are not L and L, respectively.

In one embodiment, in both the first and second heavy chains the amino acids in the positions corresponding to L234 and L235 in a human IgG1 heavy chain according to EU numbering, are not L and L, respectively, and the amino acids in the positions corresponding to positions N297 and P331 in a human IgG1 heavy chain according to EU numbering, are N and P, respectively.

In one embodiment, in both said first and second heavy chains the amino acids in the positions corresponding to L234 and L235 in a human IgG1 heavy chain according to EU numbering are hydrophobic or polar amino acids.

In one embodiment, in both said first and second heavy chains the amino acids in the positions corresponding to positions L234 and L235 in a human IgG1 heavy chain according to EU numbering are each selected from the group consisting of: A, C, F, G, H, I, M, R, T, V, W, and Y.

In one embodiment, in both said first and second heavy chains the amino acids in the positions corresponding to positions L234 and L235 in a human IgG1 heavy chain according to EU numbering are each selected from the group of amino acids consisting of: C, D, E, H, K, N, Q, R, S, and T.

In a particular embodiment, in both said first and second heavy chains the amino acids in the positions corresponding to positions L234 and L235 in a human IgG1 heavy chain according to EU numbering are each selected from the group consisting of: A, C, D, E, F, G, H, I, K, M, N, Q, R, S, T, V, W, and Y.

In another embodiment, in at least one of said first and second heavy chains the amino acids in the positions corresponding to positions L234 and L235 in a human IgG1 heavy according to EU numbering chain are aliphatic uncharged, aromatic or acidic amino acids.

Thus, in one embodiment, in at least one of said first and second heavy chains the amino acids in the positions corresponding to positions L234 and L235 in a human IgG1 heavy chain according to EU numbering are each selected from the group consisting of: A, G, I, and V.

Thus, in one embodiment, in at least one of said first and second heavy chains the amino acids in the positions corresponding to positions L234 and L235 in a human IgG1 heavy chain according to EU numbering are each selected from the group consisting of: F, T, and W.

Thus, in one embodiment, in at least one of said first and second heavy chains the amino acids in the positions corresponding to positions L234 and L235 in a human IgG1 heavy chain according to EU numbering are each selected from the group consisting of; D and E.

In a particular embodiment, in at least one of said first and second heavy chains the amino acids in the positions corresponding to L234 and L235 are each selected from the group consisting of: A, D, E, F, G, I, T, V, and W.

In one embodiment, in at least one of said first and second heavy chains the amino acids in the positions corresponding to positions L234 and L235 in a human IgG1 heavy chain according to EU numbering, are F and E; or A and A, respectively.

In one embodiment, in at least one of the first and second heavy chains the amino acids in the positions corresponding to L234 and L235 in a human IgG1 heavy chain according to EU numbering, are F and E; or A and A, respectively, and the amino acids in the positions corresponding to positions N297 and P331 in a human IgG1 heavy chain according to EU numbering, are N and P, respectively.

In one embodiment, in both said first and second heavy chains the amino acids in the positions corresponding to positions L234 and L235 in a human IgG1 heavy chain according to EU numbering, are F and E; or A and A, respectively.

In one embodiment, in both the first and second heavy chains the amino acids in the positions corresponding to L234 and L235 in a human IgG1 heavy chain according to EU numbering, are F and E; or A and A, respectively, and the amino acids in the positions corresponding to positions N297 and P331 in a human IgG1 heavy chain according to EU numbering, are N and P, respectively.

In a particular embodiment, in at least one of said first and second heavy chains the amino acids in the positions corresponding to positions L234 and L235 in a human IgG1 heavy chain according to EU numbering, are F and E, respectively.

In one embodiment, in both said first and second heavy chains the amino acids in the positions corresponding to positions L234 and L235 in a human IgG1 heavy chain according to EU numbering, are F and E, respectively.

In one embodiment, in at least one of said first and second heavy chains at least the amino acids in the positions corresponding to positions L234 and L235 in a human IgG1 heavy chain according to EU numbering, are A and A, respectively.

In one embodiment, in both said first and second heavy chains at least the amino acids in the positions corresponding to positions L234 and L235 in a human IgG1 heavy chain according to EU numbering, are A and A, respectively.

In one embodiment, in at least one of said first and second heavy chains the amino acids in the positions corresponding to positions L234, L235, and D265 in a human IgG1 heavy chain according to EU numbering, are not L, L, and D, respectively.

In one embodiment, in at least one of the first and second heavy chains the amino acids in the positions corresponding to L234, L235, and D265 in a human IgG1 heavy chain according to EU numbering, are not L, L and D, respectively, and the amino acids in the positions corresponding to positions N297 and P331 in a human IgG1 heavy chain according to EU numbering, are N and P, respectively.

In one embodiment, in at least one of said first and second heavy chains the amino acids corresponding to positions L234 and L235 in a human IgG1 heavy chain according to EU numbering are selected from the group consisting of: A, C, D, E, F, G, H, I, K, M, N, P, Q, R, S, T, Y, V, and W, and the amino acid corresponding to position D265 is selected from the group consisting of: A, C, E, F, G, H, I, K, L, M, N, P, Q, R, S, T, Y, V, and W.

In one embodiment, in at least one of said first and second heavy chains the amino acids in the positions corresponding to positions L234, L235 and D265 in a human IgG1 heavy chain according to EU numbering are hydrophobic or polar amino acids.

Thus, in one embodiment, in at least one of said first and second heavy chains the amino acid in the position corresponding to position D265 in a human IgG1 heavy chain according to EU numbering is selected from the group of amino acids consisting of: A, C, F, G, H, I, L, M, R, T, V, W and Y, and the amino acids in the positions corresponding to positions L234 and L235 in a human IgG1 heavy chain according to EU numbering are each selected from the group consisting of: A, C, F, G, H, I, M, R, T, V, W, and Y.

Thus, in one embodiment, in at least one of said first and second heavy chains the amino acids in the positions corresponding to positions L234 and L235 in a human IgG1 heavy chain according to EU numbering are each selected from the group of amino acids consisting of: C, D, E, H, K, N, Q, R, S, and T, the amino acid in the position corresponding to position D265 in a human heavy chain according to EU numbering is selected from the group consisting of: C, E, H, K, N, Q, R, S, and T.

In a particular embodiment, in at least one of said first and second heavy chains the amino acids in the positions corresponding to positions L234 and L235 in a human IgG1 heavy chain according to EU numbering are each selected from the group consisting of: A, C, D, E, F, G, H, I, K, M, N, Q, R, S, T, V, W, and Y, and the amino acid in the position corresponding to position D265 in a human IgG1 heavy chain according to EU numbering is selected from the group consisting of: A, C, E, F, G, H, I, K, L, M, N, Q, R, S, T, V, W, and Y.

In one embodiment, in both said first and second heavy chains the amino acids in the positions corresponding to L234, L235, and D265 in a human IgG1 heavy chain according to EU numbering are hydrophobic or polar amino acids.

In one embodiment, in both said first and second heavy chains the amino acid in the position corresponding to position D265 in a human IgG1 heavy chain according to EU numbering is selected from the group of amino acids consisting of: A, C, F, G, H, I, L, M, R, T, V, W and Y, and the amino acids in the positions corresponding to positions L234 and L235 in a human IgG1 heavy chain according to EU numbering are each selected from the group consisting of: A, C, F, G, H, I, M, R, T, V, W, and Y.

In one embodiment, in both said first and second heavy chains the amino acids in the positions corresponding to positions L234 and L235 in a human IgG1 heavy chain according to EU numbering are each selected from the group of amino acids consisting of: C, D, E, H, K, N, Q, R, S, and T, the amino acid in the position corresponding to position D265 in a human heavy chain according to EU numbering is selected from the group consisting of: C, E, H, K, N, Q, R, S, and T.

In a particular embodiment, in both said first and second heavy chains the amino acids in the positions corresponding to positions L234 and L235 in a human IgG1 heavy chain according to EU numbering are each selected from the group consisting of: A, C, D, E, F, G, H, I, K, M, N, Q, R, S, T, V, W, and Y, and the amino acid in the position corresponding to position D265 in a human IgG1 heavy chain according to EU numbering is selected from the group consisting of: A, C, E, F, G, H, I, K, L, M, N, Q, R, S, T, V, W, and Y.

In another embodiment, in at least one of said first and second heavy chains the amino acids in the positions corresponding to positions L234, L235 and D265 in a human IgG1 heavy chain according to EU numbering are aliphatic uncharged, aromatic or acidic amino acids.

Thus, in one embodiment, in at least one of said first and second heavy chains the amino acid in the position corresponding to position D265 in a human IgG1 heavy chain according to EU numbering is selected from the group consisting of: A, G, I, L, and V, and the amino acids in the positions corresponding to positions L234 and L235 in a human IgG1 heavy chain according to EU numbering are each selected from the group consisting of: A, G, I, and V.

Thus, in one embodiment, in at least one of said first and second heavy chains the amino acids in the positions corresponding to positions L234, L235 and D265 in a human IgG1 heavy chain according to EU numbering are each selected from the group consisting of: F, T, and W.

Thus, in one embodiment, in at least one of said first and second heavy chains the amino acids in the positions corresponding to positions L234, L235, and D265 in a human IgG1 heavy chain according to EU numbering are each selected from the group consisting of: D and E.

In a particular embodiment, in at least one of said first and second heavy chains the amino acid in the position corresponding to position D265 in a human IgG1 heavy chain according to EU numbering is selected from the group consisting of: A, E, F, G, I, L, T, V, and W, and the amino acids in the positions corresponding to L234 and L235 are each selected from the group consisting of: A, D, E, F, G, I, T, V, and W.

In one embodiment, in both said first and second heavy chains the amino acids in the positions corresponding to positions L234, L235 and D265 in a human IgG1 heavy chain according to EU numbering, are not L, L, and D, respectively.

In one embodiment, in both the first and second heavy chains the amino acids in the positions corresponding to L234, L235, and D265 in a human IgG1 heavy chain according to EU numbering, are not L, L, and D, respectively, and the amino acids in the positions corresponding to positions N297 and P331 in a human IgG1 heavy chain according to EU numbering, are N and P, respectively.

In one embodiment, in both said first and second heavy chains the amino acids in the positions corresponding to L234, L235, and D265 in a human IgG1 heavy chain according to EU numbering are aliphatic uncharged, aromatic or acidic amino acids.

In one embodiment, in both said first and second heavy chains the amino acid in the position corresponding to position D265 in a human IgG1 heavy chain according to EU numbering is selected from the group consisting of; A, G, I, L, and V, and the amino acids in the positions corresponding to positions L234 and L235 in a human IgG1 heavy chain according to EU numbering are each selected from the group consisting of; A, G, I, and V.

In one embodiment, in both said first and second heavy chains the amino acids in the positions corresponding to positions L234, L235, and D265 in a human IgG1 heavy chain according to EU numbering are each selected from the group consisting of; D and E.

In a particular embodiment, in both said first and second heavy chains the amino acid in the position corresponding to position D265 in a human IgG1 heavy chain according to EU numbering is selected from the group consisting of: A, E, F, G, I, L, T, V, and W, and the amino acids in the positions corresponding to L234 and L235 are each selected from the group consisting of: A, D, E, F, G, I, T, V, and W.

In one embodiment, in at least one of said first and second heavy chains the amino acids in the positions corresponding to positions L234, L235, and D265 in a human IgG1 heavy chain according to EU numbering, are F, E, and A; or A, A, and A, respectively.

In one embodiment, in at least one of the first and second heavy chains the amino acids in the positions corresponding to L234, L235, and D265 in a human IgG1 heavy chain according to EU numbering, are F, E, and A; or A, A, and A, respectively, and the amino acids in the positions corresponding to positions N297 and P331 in a human IgG1 heavy chain according to EU numbering, are N and P, respectively.

In one embodiment, in both said first and second heavy chains the amino acids in the positions corresponding to positions L234, L235, and D265 in a human IgG1 heavy chain according to EU numbering, are F, E, and A; or A, A, and A, respectively.

In one embodiment, in both the first and second heavy chains the amino acids in the positions corresponding to L234, L235, and D265 in a human IgG1 heavy chain according to EU numbering, are F, E, and A; or A, A, and A, respectively, and the amino acids in the positions corresponding to positions N297 and P331 in a human IgG1 heavy chain according to EU numbering, are N and P, respectively.

In a particular embodiment, in at least one of said first and second heavy chains the amino acids in the positions corresponding to positions L234, L235, and D265 in a human IgG1 heavy chain according to EU numbering, are F, E, and A, respectively.

In a particularly preferred embodiment, in both said first and second heavy chains the amino acids in the positions corresponding to positions L234, L235, and D265 in a human IgG1 heavy chain according to EU numbering, are F, E, and A, respectively.

In one embodiment, in at least one of said first and second heavy chains the amino acids in the positions corresponding to positions L234, L235, and D265 in a human IgG1 heavy chain according to EU numbering, are A, A, and A, respectively.

In one embodiment, in both said first and second heavy chains the amino acids in the positions corresponding to positions L234, L235, and D265 in a human IgG1 heavy chain according to EU numbering, are A, A, and A, respectively.

In another embodiment, in at least one of said first and second heavy chains the amino acids in the positions corresponding to positions L234, L235, D265, N297, and P331 in a human IgG1 heavy chain according to EU numbering, are F, E, A, Q, and S, respectively.

In one embodiment, in both said first and second heavy chains the amino acids in the positions corresponding to positions L234, L235, D265, N297, and P331 in a human IgG1 heavy chain according to EU numbering, are F, E, A, Q, and S, respectively.

In a particular embodiment said first antigen-binding region comprises heavy chain variable region CDR1, CDR2 and CDR3 having the sequences set forth in SEQ ID NOs:1, 2 and 3, respectively, and light chain variable region CDR1, CDR2 and CDR3 having the sequences set forth in SEQ ID NOs:4, YTS and 5, respectively; and said second antigen-binding region comprises heavy chain variable region CDR1, CDR2 and CDR3 having the sequences set forth in SEQ ID NOs:64, 65 and 66, respectively, and light chain variable region CDR1, CDR2 and CDR3 having the sequences set forth in SEQ ID NOs:67, GAS and 68, respectively, (CD137 clone 009), and in at least one of the first and second heavy chains, such as both said first and second heavy chain, the amino acids in positions corresponding to positions L234, L235, and D265 in a human IgG1 heavy chain, are F, E, and A, respectively.

In another embodiment said first antigen-binding region comprises heavy chain variable region CDR1, CDR2 and CDR3 having the sequences set forth in SEQ ID NOs:1, 2 and 3, respectively, and light chain variable region CDR1, CDR2 and CDR3 having the sequences set forth in SEQ ID NOs:4, YTS and 5, respectively; and said second antigen-binding region comprises heavy chain variable region CDR1, CDR2 and CDR3 having the sequences set forth in SEQ ID NOs:36, 37 and 38, respectively, and light chain variable region CDR1, CDR2 and CDR3 having the sequences set forth in SEQ ID NOs:39, SAS and 40, respectively, (CD137 clone 005), and in at least one of the first and second heavy chains, such as both said first and second heavy chain, the amino acids in positions corresponding to positions L234, L235, and D265 in a human IgG1 heavy chain, are F, E, and A, respectively.

A non-activating Fc region prevents the antibody from interacting with Fc-receptors present on blood cells, such as monocytes, or with C1q to activate the classical complement pathway. Reduction of the Fc activity was tested in antibody variants that contain different combinations of amino acid substitutions in the Fc region. Three amino acid substitutions were introduced in the parental antibodies of the present invention, which include the mutations L234F, L235E, and D265A. Substitutions in these three amino acid positions were introduced in the K409R and/or F405L IgG1 backbone. The resulting non-activating antibody variant is termed with the suffix "FEAR" or "FEAL", respectively. Said parental antibodies were used in to generate bispecific antibodies of the present invention as described in the examples.

In one aspect, the multispecific antibodies according to the invention may be modified in the light chain and/or heavy chain to increase the expression level and/or production yield. In one embodiment, the antibodies according to the invention may be modified in the light chain. Such modifications are known in the art and may be performed according to the methods described in e.g. Zheng, L., Goddard, J.-P., Baumann, U., & Reymond, J.-L. (2004). Expression improvement and mechanistic study of the retro-Diels-Alderase catalytic antibody 10F11 by site-directed mutagenesis. Journal of Molecular Biology, 341(3), 807-14.

In a further embodiment of the invention, one or both of the antibodies forming part of the multispecific antibody of the invention have been engineered to reduce or increase the binding to the neonatal Fc receptor (FcRn) in order to manipulate the serum half-life of the multispecific antibody. Techniques for increasing or reducing the serum half-life are well-known in the art. See for example Dall'Acqua et al. 2006, J. Biol. Chem., 281:23514-24; Hinton et al. 2006, J. Immunol., 176:346-56; and Zalevsky et al. 2010 Nat. Biotechnol., 28:157-9.

In one aspect, the multispecific antibody as defined in any of the embodiments disclosed herein comprises a first constant heavy chain (HC) and a first constant light chain (LC), wherein the positions corresponding to positions L234, L235, and D265 in the human IgG1 heavy chain of SEQ ID NO:109 of both the first heavy chain and the second heavy chain are F, E, and A, respectively.

In one embodiment, the multispecific antibody as defined in any of the embodiments disclosed herein comprises a first and second constant heavy chain (HC) and a first and second constant light chain (LC), wherein the positions corresponding to positions L234 and L235 in the human IgG1 heavy chain of SEQ ID NO:109 of both the first heavy chain and the second heavy chain are F and E, respectively.

In one embodiment, the multispecific antibody comprises a first and a second heavy chain, wherein the positions corresponding to positions L234 and L235 in a human IgG1 heavy chain according to EU numbering of both the first heavy chain and the second heavy chain are F and E, respectively, and wherein (i) the position corresponding to F405 in a human IgG1 heavy chain according to EU numbering of the first heavy chain is L, and the position corresponding to K409 in a human IgG1 heavy chain according to EU numbering of the second heavy chain is R, or (ii) the position corresponding to K409 in a human IgG1 heavy chain according to EU numbering of the first heavy chain is R, and the position corresponding to F405 in a human IgG1 heavy chain according to EU numbering of the second heavy chain is L.

In one embodiment, the multispecific antibody comprises a first and a second heavy chain, wherein the positions corresponding to positions L234, L235, and D265 in a human IgG1 heavy chain according to EU numbering of both the first and the second heavy chain are F, E, and A, respectively, and wherein the position corresponding to F405 in a human IgG1 heavy chain according to EU numbering of the first heavy chain is L, and the position corresponding to K409 in a human IgG1 heavy chain according to EU numbering of the second heavy chain is R. Thus in a further embodiment, said first heavy chain comprises the constant heavy chain sequence as set forth in SEQ ID NO:113; and the second heavy chain comprises the constant heavy chain sequence as set forth in SEQ ID NO:112.

In one embodiment, the multispecific antibody comprises a first and a second heavy chain, wherein the positions corresponding to positions L234, L235, and D265 in a human IgG1 heavy chain according to EU numbering of both the first and second heavy chain are F, E, and A, respectively, and wherein the position corresponding to K409 in a human IgG1 heavy chain according to EU numbering of the first heavy chain is R, and the position corresponding to F405 in a human IgG1 heavy chain according to EU numbering of the second heavy chain is L. Thus in a further embodiment, said first heavy chain comprises the constant heavy chain sequence as set forth in SEQ ID NO:112; and the second heavy chain comprises the constant heavy chain sequence as set forth in SEQ ID NO:113.

Nucleic Acids

The present invention also relates to a nucleic acid encoding one or more amino acid sequences according to any aspect or embodiment disclosed herein.

The present invention also relates to a nucleic acid encoding a multispecific antibody as defined in any aspect or embodiment disclosed herein.

The present invention also relates to an expression vector comprising a nucleic acid of the present invention.

The present invention also relates to a host cell comprising a nucleic acid or an expression vector according to the present invention.

In one embodiment said host cell is a recombinant eukaryotic, recombinant prokaryotic, or recombinant microbial host cell.

In a further embodiment, the expression vector further comprises a nucleotide sequence encoding the constant region of a light chain, a heavy chain or both light and heavy chains of an antibody, e.g. a human antibody.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors obtained from combinations of plasmids and phage DNA, and viral nucleic acid (RNA or DNA) vectors. In one embodiment, a nucleic acid is comprised in a naked DNA or RNA vector, including, for example, a linear expression element (as described in for instance Sykes and Johnston, Nat Biotech 17, 355 59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793 800 (2001)), or as a precipitated nucleic acid vector construct, such as a CaPO4-precipitated construct (as described in for instance WO200046147, Benvenisty and Reshef, PNAS USA 83, 9551 55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. Nos. 5,589,466 and 5,973,972).

In one embodiment, the vector is suitable for expression of the CD40 antibody and/or the CD137 antibody in a bacterial cell. Examples of such vectors include expression vectors such as BlueScript (Stratagene), pIN vectors (Van Heeke & Schuster, J Biol Chem 264, 5503 5509 (1989), pET vectors (Novagen, Madison Wis.) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516 544 (1987)).

An expression vector may also or alternatively be a vector suitable for expression in mammalian cells, e.g. a vector comprising glutamine synthetase as a selectable marker, such as the vectors described in Bebbington (1992) Biotechnology (NY) 10:169-175.

A nucleic acid and/or vector may also comprises a nucleic acid sequence encoding a secretion/localization sequence, which can target a polypeptide, such as a nascent polypeptide chain, to the periplasmic space or into cell culture media. Such sequences are known in the art, and include secretion leader or signal peptides.

The expression vector may comprise or be associated with any suitable promoter, enhancer, and other expression-facilitating elements. Examples of such elements include strong expression promoters (e. g., human CMV IE promoter/enhancer as well as RSV, SV40, SL3 3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE.

In one embodiment, the CD40 and/or CD137 antibody-encoding expression vector may be positioned in and/or delivered to the host cell or host animal via a viral vector.

In an even further aspect, the invention relates to a host cell comprising the first and second nucleic-acid constructs specified herein above.

Thus the present invention also relates to a recombinant eukaryotic or prokaryotic host cell which produces a multispecific antibody of the present invention, such as a transfectoma.

The first, CD40-specific, antibody may be expressed in a recombinant eukaryotic or prokaryotic host cell, such as a transfectoma, which produces an antibody as defined herein. The second, CD137-specific, antibody may likewise be expressed in a recombinant eukaryotic or prokaryotic host cell, such as a transfectoma, which produces an antibody. Such antibodies may be used to prepare a multispecific antibody according to the present invention. A multispecific antibody according to the present invention may also be expressed in a recombinant eukaryotic or prokaryotic host cell, such as a transfectoma.

Examples of host cells include yeast, bacterial, plant and mammalian cells, such as CHO, CHO-S, HEK, HEK293, HEK-293F, Expi293F, PER.C6 or NS0 cells or lymphocytic cells. For example, in one embodiment, the host cell may comprise a first and second nucleic acid construct stably integrated into the cellular genome. In another embodiment, the present invention provides a cell comprising a non-integrated nucleic acid, such as a plasmid, cosmid, phagemid, or linear expression element, which comprises a first and second nucleic acid construct as specified above.

In an even further aspect, the invention relates to a transgenic non-human animal or plant comprising nucleic acids encoding one or two sets of a human heavy chain and a human light chain, wherein the animal or plant produces a multispecific antibody of the invention.

The first, CD40-specific, antibody and/or second, CD137-specific, antibody may also be produced by a hybridoma, a transgenic non-human animal or plant comprising nucleic acids encoding one or two sets of a human heavy chain and a human light chain, wherein the animal or plant produces an antibody for use in a multispecific antibody or a multispecific antibody of the invention.

In one aspect, the invention relates to a nucleic acid encoding one or more amino acid sequences set out in Table 1.

In one aspect, the invention relates to an expression vector comprising (i) a nucleic acid sequence encoding a heavy chain sequence of a first binding arm according to any one of the embodiments disclosed herein;

(ii) a nucleic acid sequence encoding a light chain sequence of a first binding arm according to any one of the embodiments disclosed herein;

(iii) a nucleic acid sequence encoding a heavy chain sequence of a second binding arm according to any one of the embodiments disclosed herein;

(iv) a nucleic acid sequence encoding a light chain sequence of a second binding arm according to any one of the of the embodiments disclosed herein;

(v) the nucleic acid set forth in (i) and the nucleic acid set forth in (ii);

(vi) the nucleic acid set forth in (iii) and the nucleic acid set forth in (iv).

(vii) the nucleic acid set forth in (i), (ii), (iii) and (iv).

In a particular embodiment, the nucleic acid may encode a heavy chain variable region comprising the VH CDR1, CDR2 and CDR3 of the CD40 antibody listed in Table 1 and encoding a human IgG1 heavy chain having a sequence selected from the group consisting of SEQ ID NO:110, 111, 112, 113 and 116.

In another embodiment, the nucleic acid may encode a heavy chain variable region comprising the VH CDR1, CDR2 and CDR3 of one the CD137 antibodies listed in Table 1, i.e. any one of clones 001-012, and encoding a human IgG1 heavy chain having a sequence selected from the group consisting of SEQ ID NO:110, 111, 112, 113 and 116.

In separate and specific embodiments, a nucleic acid, nucleic acid construct, a combination of a first and a second nucleic acid construct, an expression vector, or a combination of a first and a second expression vector according to the present invention may encode (a) a HC comprising (i) a VH comprising the VH CDR1, CDR2 and CDR3 of the CD40 antibody in Table 1, and primarily human framework regions, optionally comprising one or more amino acid back-mutations to the non-human amino acid sequence, and (ii) a human IgG1 heavy chain having a sequence selected from the group consisting of SEQ ID NO:110, 111, 112, 113 and 116;

(b) a HC comprising (i) a VH comprising the VH CDR1, CDR2 and CDR3 of one the CD137 antibodies listed in Table 1, i.e. any one of clones 001-012, and primarily human framework regions, optionally comprising one or more amino acid back-mutations to the non-human amino acid sequence, and (ii) a human IgG1 heavy chain having a sequence selected from the group consisting of SEQ ID NO:110, 111, 112, 113 and 116;

(c) an LC comprising (i) a VL comprising the VL CDR1, CDR2 and CDR3 of the CD40 antibody in Table 1, and primarily human framework regions, optionally comprising one or more amino acid back-mutations to the non-human amino acid sequence, and (ii) a light chain constant region having the sequence of SEQ ID NO:114;

(d) an LC comprising (i) a VL comprising the VL CDR1, CDR2 and CDR3 of one the CD137 antibodies listed in Table 1, i.e. any of clones 001-012, and primarily human framework regions, optionally comprising one or more amino acid back-mutations to the non-human amino acid sequence, and (ii) a light chain constant region having the sequence of SEQ ID NO:114;

(e) both (a) and (b);

(f) both (a) and (c);

(g) both (b) and (d);

(h) both (c) and (d); or (i) both (a), (b), (c) and (d).

In other separate and specific embodiments, a nucleic acid, nucleic acid construct, a combination of a first and a second nucleic acid construct, an expression vector, or a combination of a first and a second expression vector according to the present invention may encode (a) a HC comprising (i) a VH comprising the VH CDR1, CDR2 and CDR3 of SEQ ID NOS:1, 2 and 3, and primarily human framework regions, optionally comprising one or more amino acid back-mutations to the non-human amino acid sequence, and (ii) a human IgG1 heavy chain having a sequence selected from the group consisting of SEQ ID NO:110, 111, 112, 113 and 116;

(b) a HC comprising (i) a VH comprising the VH CDR1, CDR2 and CDR3 of SEQ ID NO: 64, 65 and 66, and primarily human framework regions, optionally comprising one or more amino acid back-mutations to the non-human amino acid sequence, and (ii) a human IgG1 heavy chain having a sequence selected from the group consisting of SEQ ID NO:110, 111, 112, 113 and 116;

(c) an LC comprising (i) a VL comprising the VL CDR1, CDR2 and CDR3 of SEQ ID NO:4, YTS and SEQ ID NO:5, and primarily human framework regions, optionally comprising one or more amino acid back-mutations to the non-human amino acid sequence, and (ii) a light chain constant region having the sequence of SEQ ID NO:114;

(d) an LC comprising (i) a VL comprising the VL CDR1, CDR2 and CDR3 of SEQ ID NO: 67, GAS and SEQ ID NO:68, and primarily human framework regions, optionally comprising one or more amino acid back-mutations to the non-human amino acid sequence, and (ii) a light chain constant region having the sequence of SEQ ID NO:114;

(e) both (a) and (b);

(f) both (a) and (c);

(g) both (b) and (d);

(h) both (c) and (d); or (i) both (a), (b), (c) and (d).

In other separate and specific embodiments, a nucleic acid, nucleic acid construct, a combination of a first and a second nucleic acid construct, an expression vector, or a combination of a first and a second expression vector according to the present invention may encode (a) a HC comprising a VH comprising SEQ ID NO:117 and a human IgG1 heavy chain having a sequence selected from the group consisting of SEQ ID NO:110, 111, 112, 113 and 116;

(b) a HC comprising a VH comprising SEQ ID NO:123 and a human IgG1 heavy chain having a sequence selected from the group consisting of SEQ ID NO:110, 111, 112, 113 and 116;

(c) an LC comprising a VL comprising SEQ ID NO:121 and a light chain constant region having the sequence of SEQ ID NO:114;

(d) an LC comprising a VL comprising SEQ ID NO:127 and a light chain constant region having the sequence of SEQ ID NO:114;

(e) both (a) and (b);
(f) both (a) and (c);
(g) both (b) and (d);
(h) both (c) and (d); or
(i) both (a), (b), (c) and (d).

In other separate and specific embodiments, a nucleic acid, a nucleic acid construct, a combination of a first and a second nucleic acid construct, an expression vector, or a combination of a first and a second expression vector according to the present invention may encode (a) a HC comprising SEQ ID NO:118 (CD40-001-HC6, IgG1);
(b) a HC comprising SEQ ID NO:119 (CD40-001-HC6-FEAL);
(c) a HC comprising SEQ ID NO:120 (CD40-001-HC6-FEAR);
(d) a HC comprising SEQ ID NO:124 (CD137-009-HC7);
(e) a HC comprising SEQ ID NO:125 (CD137-009-HC7-FEAR);
(f) a HC comprising SEQ ID NO:126 (CD137-009-HC7-FEAL);
(g) an LC comprising SEQ ID NO:122 (CD40-001-LC1);
(h) an LC comprising SEQ ID NO:128 (CD137-009-LC2);
(i) both (a) and (g);
(j) both (b) and (g);
(k) both (c) and (g);
(l) both (d) and (h);
(m) both (e) and (h);
(n) both (f) and (h);
(o) both (b) and (e);
(p) both (c) and (f);
(q) both (g) and (h);
(r) both (b), (e), (g) and (h);
(s) both (c), (f), (g) and (h).

In one aspect, the invention relates to a method for producing a bispecific antibody according to any one of the embodiments as disclosed herein, comprising the steps of a) culturing a host cell as disclosed herein comprising an expression vector as disclosed herein expressing the first antibody as disclosed herein and purifying said antibody from the culture media;

b) culturing a host cell as disclosed herein comprising an expression vector as disclosed herein expressing the second antibody as disclosed herein and purifying said antibody from the culture media;

c) incubating said first antibody together with said second antibody under reducing conditions sufficient to allow the cysteines in the hinge region to undergo disulfide-bond isomerization, and d) obtaining said bispecific antibody.

In one aspect, the invention relates to a host cell comprising an expression vector as defined above. In one embodiment, the host cell is a recombinant eukaryotic, recombinant prokaryotic, or recombinant microbial host cell.

Compositions

The present invention also relates to a composition comprising a multispecific antibody according to the present invention, a nucleic acid according to the present invention, an expression vector to the present invention or a host cell according to the present invention.

In a further embodiment the composition according to the present invention is a pharmaceutical composition.

In an even further embodiment, the pharmaceutical composition according to the present invention further comprises a pharmaceutically acceptable carrier.

In a further aspect, the invention relates to a pharmaceutical composition comprising:
a multispecific CD40xCD137 antibody as defined in any of the embodiments disclosed herein, and
a pharmaceutically acceptable carrier.

The pharmaceutical composition of the present invention may contain one multispecific antibody of the present invention or a combination of different multispecific antibodies of the present invention.

The pharmaceutical compositions may be formulated in accordance with conventional techniques such as those disclosed in Remington: The Science and Practice of Pharmacy, 19th Edition, Gennaro, Ed., Mack Publishing Co., Easton, Pa., 1995. A pharmaceutical composition of the present invention may e.g. include diluents, fillers, salts, buffers, detergents (e.g., a nonionic detergent, such as Tween-20 or Tween-80), stabilizers (e. g., sugars or protein-free amino acids), preservatives, tissue fixatives, solubilizers, and/or other materials suitable for inclusion in a pharmaceutical composition.

Pharmaceutically acceptable carriers include any and all suitable solvents, dispersion media, coatings, antibacterial and antifungal agents, isotonicity agents, antioxidants and absorption delaying agents, and the like that are physiologically compatible with a multispecific antibody of the present invention. Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, carboxymethyl cellulose colloidal solutions, tragacanth gum and injectable organic esters, such as ethyl oleate, and/or various buffers. Pharmaceutically acceptable carriers include sterile aqueous solutions or dispersions and sterile powders for the extemporaneous preparation of sterile injectable solutions or dispersion. Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole, butylated hydroxytoluene, lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The pharmaceutical composition of the present invention may be prepared with carriers that will protect the multispecific antibody against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art.

Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

The actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. In one embodiment, a pharmaceutical composition of the present invention is administered parenterally. "Administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

In one embodiment the pharmaceutical composition is administered by intravenous or subcutaneous injection or infusion.

Uses

The present invention also relates to the multispecific antibody according to the present invention, the nucleic acid according to the present invention, the expression vector according to the present invention, the host cell according to the present invention, the composition according to the present invention, or the pharmaceutical composition according to the present invention for use as a medicament.

The present invention also relates to the multispecific antibody according to the present invention, the nucleic acid according to the present invention, the expression vector according to the present invention, the host cell according to the present invention, the composition according to the present invention, or the pharmaceutical composition according to the present invention for use in the treatment of a disease, such as cancer or an infectious disease.

According to the invention, the term "disease" refers to any pathological state, in particular cancer, infectious diseases, inflammatory diseases, metabolic diseases, autoimmune disorders, degenerative diseases, apoptosis-associated diseases and transplant rejections.

As used herein, the term "cancer" includes a disease characterized by aberrantly regulated cellular growth, proliferation, differentiation, adhesion, and/or migration. By "cancer cell" is meant an abnormal cell that grows by a rapid, uncontrolled cellular proliferation and continues to grow after the stimuli that initiated the new growth cease.

The term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above.

The term "cancer" according to the invention also comprises cancer metastases. By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The term "infectious disease" refers to any disease which can be transmitted from individual to individual or from organism to organism, and is caused by a microbial agent (e.g. common cold).

Examples of infectious diseases include viral infectious diseases, such as AIDS (HIV), hepatitis A, B or C, herpes, herpes zoster (chicken-pox), German measles (rubella virus), yellow fever, dengue etc. flaviviruses, influenza viruses, hemorrhagic infectious diseases (Marburg or Ebola viruses), and severe acute respiratory syndrome (SARS), bacterial infectious diseases, such as Legionnaire's disease (Legionella), sexually transmitted diseases (e.g. chlamydia or gonorrhea), gastric ulcer (Helicobacter), cholera (Vibrio), tuberculosis, diphtheria, infections by *E. coli, Staphylococci, Salmonella* or *Streptococci* (tetanus); infections by protozoan pathogens such as malaria, sleeping sickness, leishmaniasis; toxoplasmosis, i.e. infections by *Plasmodium, Trypanosoma, Leishmania* and *Toxoplasma*; or fungal infections, which are caused, e.g., by *Cryptococcus neofor-*

*mans, Histoplasma capsulatum, Coccidioides immitis, Blastomyces dermatitidis* or *Candida albicans*.

The term "inflammatory disease" refers to any disease, which is characterized by or associated with high levels of inflammation in tissues, in particular connective tissues, or degeneration of these tissues. A chronic inflammatory disease is a medical condition which is characterized by persistent inflammation. Examples of (chronic) inflammatory diseases include celiac disease, vasculitis, lupus, chronic obstructive pulmonary disease (COPD), irritable bowel disease, atherosclerosis, arthritis, ankylosing spondylitis, Crohn's disease, colitis, chronic active hepatitis, dermatitis and psoriasis.

The term "metabolic disease" refers to any disease or disorder that disrupts normal metabolism. Examples include cystinosis, diabetes, dyslipidemia, hyperthyroidism, hypothyroidism, hyperlipidemia, hypolipidemia, galactosemia, Gaucher's disease, obesity and phenylketonuria.

The term "autoimmune disorder" refers to any disease/disorder in which the body produces an immunogenic (i.e. immune system) response to some constituent of its own tissue. In other words, the immune system loses its ability to recognize some tissue or system within the body as self and targets and attacks it as if it were foreign. Autoimmune diseases can be classified into those in which predominantly one organ is affected (e.g. hemolytic anemia and anti-immune thyroiditis), and those in which the autoimmune disease process is diffused through many tissues (e.g. systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

The term "degenerative disease" refers to any disease in which the function or structure of the affected tissues or organs will increasingly deteriorate over time. Examples include Alzheimer's disease, Parkinson's disease, amyotrophic lateral sclerosis (ALS), Huntington's disease, macular degeneration, multiple sclerosis, muscular dystrophy, Niemann Pick disease, osteoporosis and rheumatoid arthritis.

The term "apoptosis-associated diseases" refers to any disease in which alterations of apoptosis are involved. Examples include cancer, neurological disorders, such as Alzheimer's disease, Parkinson's disease, Huntington's disease, amyotrophic lateral sclerosis (ALS) and stroke, heart diseases, such as ischemia reperfusion and chronic heart failure, infectious diseases and autoimmune diseases.

The term "transplant rejection" refers to the rejection of a transplanted tissue or organ by the recipient's immune system, which may, ultimately, destroy the transplanted tissue or organ.

In one embodiment, the use of the multispecific antibody, nucleic acid, expression vector, host cell or composition for use according to the present invention may be for treating cancer.

In one embodiment, the use of the multispecific antibody, nucleic acid, expression vector, host cell or composition for use according to the present invention may be for treating an infectious disease.

The present invention also relates to a method of treatment of a disease, such as cancer or an infectious disease, comprising administering the multispecific antibody according to the present invention, the nucleic acid according to the present invention, the expression vector according to the present invention, the host cell according to claim the present invention, the composition according to the present invention, or the pharmaceutical composition according to the present invention to a subject in need thereof.

The present invention also relates to use of a multispecific antibody according to the present invention, the nucleic acid according to the present invention, the expression vector according to the present invention, the host cell according to the present invention, the composition according to the present invention, or the pharmaceutical composition according to the present invention for the manufacture of a medicament.

In one embodiment the method or use according to the present invention is for use in combination with one or more further therapeutic agent, such as a chemotherapeutic agent.

In one aspect, the invention relates to the multispecific antibody, such as a bispecific antibody, according to any one of the embodiments disclosed herein, the composition as disclosed herein, or the pharmaceutical composition as disclosed herein for use as a medicament.

In another aspect, the present invention relates to the use of a multispecific antibody according to the present invention in the manufacture of a medicament for the treatment of a disease, such as cancer or an infectious disease.

In one aspect, the invention relates to the multispecific antibody according to any one of the embodiments disclosed herein, the composition as disclosed herein, or the pharmaceutical composition as disclosed herein for use in the treatment of a disease, such as cancer or an infectious disease.

In one aspect, the invention relates to a method of treatment of a disease comprising administering the multispecific antibody according to any one of the embodiments disclosed herein, the composition as disclosed herein, or the pharmaceutical composition as disclosed herein to a subject in need thereof.

The multispecific antibodies of the invention may be used for a number of purposes. In particular, the multispecific antibodies of the invention may be used for the treatment of various forms of cancer, including metastatic cancer and refractory cancer.

In one embodiment the use according to the present invention is in combination with one or more further therapeutic agent, such as a chemotherapeutic agent.

In particular, the multispecific antibodies according to the invention may be useful in therapeutic settings in which increasing proliferation of T cells is relevant. An example of such a therapeutic setting includes but is not limited to cancer or tumors, such as hematological and solid tumors, e.g., melanoma, lung cancer, breast cancer, non-small cell lung cancer (NSCLC), colon cancer, renal cancer, cervical cancer and prostate cancer, such as melanoma or NSCLC. Examples thereof are lung carcinomas, mamma carcinomas, prostate carcinomas, colon carcinomas, renal cell carcinomas, cervical carcinomas, or metastases of such cancer types or tumors.

The present invention also relates to a method for treating cancer, comprising
  a) selecting a subject suffering from a cancer, and
  b) administering to the subject the multispecific antibody of the present invention or a pharmaceutical composition of the present invention.

Also, the invention relates to the use of a multispecific antibody that binds to human CD40 and human CD137 for the preparation of a medicament for the treatment of cancer, such as one of the specific cancer indications mentioned herein.

The invention further relates to a multispecific antibody for use in the treatment of cancer, such as one of the cancer indications mentioned above.

In one embodiment the method or use according to the present invention is for use in combination with one or more further therapeutic agent, such as a chemotherapeutic agent.

For the above mentioned uses any multispecific antibody, such as a bispecific antibody, of the present invention may be used.

In one aspect, the invention relates to a diagnostic composition comprising a multispecific antibody according to any one of the embodiments as disclosed herein.

In one embodiment, the diagnostic composition is a companion diagnostic which is used to screen and select those patients who will benefit from treatment with the multispecific antibody.

In a further embodiment of the methods of treatment of the present invention, the efficacy of the treatment is being monitored during the therapy, e.g. at predefined points in time, by determining tumor burden.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage.

The efficient dosages and the dosage regimens for the multispecific antibodies depend on the disease or condition to be treated and may be determined by the persons skilled in the art. An exemplary, non-limiting range for a therapeutically effective amount of a multispecific antibody of the present invention is about 0.001-30 mg/kg.

A physician or veterinarian having ordinary skill in the art may readily determine and prescribe the effective amount of the pharmaceutical composition required. For example, the physician or veterinarian could start doses of the multispecific antibody employed in the pharmaceutical composition at levels lower than that required in order to achieve the desired therapeutic effect and gradually increase the dosage until the desired effect is achieved. In general, a suitable daily dose of a multispecific antibody of the present invention will be that amount of the compound which is the lowest dose effective to produce a therapeutic effect. Administration may e.g. be parenteral, such as intravenous, intramuscular or subcutaneous. In one embodiment, the multispecific antibodies may be administered by infusion in a weekly dosage of calculated by mg/m². Such dosages can, for example, be based on the mg/kg dosages provided above according to the following: dose (mg/kg)×70: 1.8. Such administration may be repeated, e.g., 1 to 8 times, such as 3 to 5 times. The administration may be performed by continuous infusion over a period of from 2 to 24 hours, such as from 2 to 12 hours. In one embodiment, the multispecific antibodies may be administered by slow continuous infusion over a long period, such as more than 24 hours, in order to reduce toxic side effects.

In one embodiment the multispecific antibodies may be administered in a weekly dosage of calculated as a fixed dose for up to 8 times, such as from 4 to 6 times when given once a week. Such regimen may be repeated one or more times as necessary, for example, after 6 months or 12 months. Such fixed dosages can, for example, be based on the mg/kg dosages provided above, with a body weight estimate of 70 kg. The dosage may be determined or adjusted by measuring the amount of multispecific antibody of the present invention in the blood upon administration by for instance taking out a biological sample and using anti-idiotypic antibodies which target the CD137 antigen antigen-binding region of the multispecific antibodies of the present invention.

In one embodiment, the multispecific antibodies may be administered as maintenance therapy, such as, e.g., once a week for a period of 6 months or more.

A multispecific antibody may also be administered prophylactically in order to reduce the risk of developing cancer, delay the onset of the occurrence of an event in cancer progression, and/or reduce the risk of recurrence when a cancer is in remission.

The multispecific antibodies of the invention may also be administered in combination therapy, i.e., combined with other therapeutic agents relevant for the disease or condition to be treated. Accordingly, in one embodiment, the multispecific antibody-containing medicament is for combination with one or more further therapeutic agents, such as a cytotoxic, chemotherapeutic or anti-angiogenic agent.

Such combined administration may be simultaneous, separate or sequential. For simultaneous administration the agents may be administered as one composition or as separate compositions, as appropriate. The present invention thus also provides methods for treating a disorder, which methods comprise administration of a multispecific antibody of the present invention combined with one or more additional therapeutic agents as described below.

In one embodiment, the present invention provides a method for treating a disorder, which method comprises administration of a therapeutically effective amount of a multispecific antibody of the present invention, and optionally at least one additional therapeutic agent, to a subject in need thereof.

In one embodiment, the present invention provides a method for treating or preventing cancer, which method comprises administration of a therapeutically effective amount of a multispecific antibody of the present invention and at least one additional therapeutic agent to a subject in need thereof.

Pharmaceutical compositions of the invention can also be administered in combination therapy, i.e., combined with other agents, or combined with other treatment regimen. For example the multispecific antibodies may be combined with radiotherapy and/or surgery and/or autologous or allogeneic peripheral stem cell or bone marrow transplantation.

Biomarkers

Thus, in one aspect, the present invention also relates to use of the multispecific antibody as a biomarker.

In another aspect, the invention relates to a kit for detecting cross-linking between CD40- and CD137-expressing cells, in a sample obtained from a patient, such as a blood sample, lymph node sample or bone marrow sample, comprising i) a multispecific antibody according to any one of the embodiments as disclosed herein; and ii) instructions for use of said kit.

In a further aspect, the invention relates to a method for detecting whether cross-linking between CD40- and CD137-expressing cells occurs in a sample obtained from a patient, such as a blood sample, lymph node sample or bone marrow sample, upon administration of a bispecific antibody according to any one of the embodiments as disclosed herein, comprising the steps of:

(i) contacting the sample with a multispecific antibody according to any one of the embodiments as disclosed herein under conditions that allow for formation of a complex between said multispecific antibody and the CD40- and CD137-expressing cells; and (ii) analyzing whether a complex has been formed.

Detection of the complex can be done by methods known in the art, such as performed in Example 4, 5, 6, 10, 11 or 12.

Anti-Idiotypic Antibodies

In another aspect, the invention relates to an anti-idiotypic antibody which binds to the first and/or second antigen-binding region as defined in any one of the embodiments disclosed herein.

In a particular embodiment, the anti-idiotypic antibody binds to the first and/or second antigen-binding region of a multispecific antibody, wherein the first antigen-binding region comprises a VH sequence as set forth in SEQ ID NO:117 and a VL sequence as set forth in SEQ ID NO:121, and the second antigen-binding region comprises a VH sequence comprising SEQ ID NO:123 and a VL sequence comprising SEQ ID NO:127.

In one embodiment, the anti-idiotypic antibody binds to the first antigen-binding region defined in any one of the embodiments disclosed herein. In a specific embodiment, the first antigen-binding region comprises a VH sequence comprising SEQ ID NO:117 and a VL sequence comprising SEQ ID NO:121.

In another embodiment, the anti-idiotypic antibody binds to the second antigen-binding region defined in any one of the embodiments disclosed herein. In a specific embodiment, the second antigen-binding region comprises a VH sequence comprising SEQ ID NO:123 and a VL sequence comprising SEQ ID NO:127.

The present invention is further illustrated by the following examples, which should not be construed as limiting the scope of the invention.

EXAMPLES

Example 1: Generation of Antibodies

The CD40 and each of the CD137 antibodies (i.e. clones 1-12) mentioned in Table 1 above were produced with the VH and VL sequences described in Table 1 and with a human K light chain, and with a human IgG1 heavy chain. The CD40 antibody was produced with two different human IgG1 heavy chains; 1) a human IgG1 heavy chain containing the following amino acid mutations: L234F, L235E, D265A and F405L (FEAL) wherein the amino acid position number is according to EU numbering (corresponding to SEQ ID NO:113); and 2) a human IgG1 heavy chain containing the following amino acid mutations: L234F, L235E, D265A and K409R (FEAR) wherein the amino acid position number is according to EU numbering (corresponding to SEQ ID NO:112).

The CD137 antibodies were all produced with a human IgG1 heavy chain containing the following amino acid mutations: L234F, L235E, D265A and K409R (FEAR) wherein the amino acid position number is according to EU numbering (correspond to SEQ ID NO:112).

Similarly, a b12 antibody was produced comprising VH and VL sequences mentioned in Table 1, and with a human IgG1 light chain and a human IgG heavy chain containing the following amino acid mutations: L234F, L235E, D265A and F405L (FEAL) wherein the amino acid position number is according to EU numbering (correspond to SEQ ID NO:113).

Antibodies were produced under serum-free conditions by co-transfecting relevant heavy and light chain expression vectors in Expi293F™ cells (ThermoFisher catalogue number A14527), using ExpiFectamine™ 293 (ThermoFisher catalogue number A14525), according to the manufacturer's instructions. Antibodies were purified by protein A affinity chromatography and buffer exchanged into 12.6 mM NaH2PO4, 140 mM NaCl, pH 7.4 buffer (B.Braun or Thermo Fisher). After buffer exchange, samples were sterile filtered over 0.2 µm dead-end filters. Purified proteins were analyzed by CE-SDS and HP-SEC. Concentration was measured by absorbance at 280 nm. Purified antibodies were stored at 2-8° C.

Example 2: DNA Shuffling Between Wild Boar or Elephant and Human CD137 to Determine Domains Important for Binding of Anti CD137 Antibodies To determine domains important for binding of anti CD137 antibodies to human CD137, DNA shuffling was performed between human and wild boar CD137 (*Sus scrofa*; XP_005665023) or between human and African elephant CD137 (loxodonta africana; XP_003413533). Shuffle constructs were prepared from DNA encoding human CD137, by replacing human domains with wild boar (shuffle construct 1-4, 6) or elephant (shuffle construct 5) domains. If a domain in human CD137 is important for binding of an anti CD137 antibody, binding will be lost upon replacement of that domain with the wild boar or African elephant domain. Requirement is that the antibody does not bind to the whole CD137 elephant or wild boar sequence Homology between human and wild boar and between human and African elephant CD137 is 70.2 and 74.5%, respectively. FIG. 1 shows sequence alignments of human, wild boar and African elephant CD137. FIG. 2 shows the constructs for human CD137 containing wild boar CD137 or African elephant domains, as indicated.

$3\times10^6$ HEK293T-17 cells were seeded in T75 culture flasks (Greiner Bio-One, cat. no. 658175) in 20 mL RPMI 1640 GlutaMAX medium containing 10% FCS (Biochrom, cat. no. S 0115). After 0/N incubation, cells were transiently transduced with expression vectors encoding the shuffle constructs or the wild boar, African elephant or human CD137 downstream of a constitutively active human elongation factor-1 alpha (EF-1 alpha) promotor using TransIT®-LT1 Transfection Reagent, Mirus Bio (VWR International, cat. no. 731-0029), according to the manufacturer's instructions. The next day, cells were harvested using 1.5 mL Accutase (Sigma Aldrich, cat. no. A6964) (incubation at 37° C. for 5 min.) and flow cytometry was performed, essentially as described in Example 4, to measure surface expression of the shuffle constructs and the human, African elephant and wild boar CD137 and to measure binding of the antibody clones to the different shuffle constructs. To measure cell surface expression of the constructs, transduced cells were incubated with 1 µg/mL goat polyclonal anti-human CD137 (R&D Systems, cat. no. AF838) in FACS buffer (D-PBS supplemented with 5 mM EDTA [Sigma Aldrich, cat. no. 03690] and 5% (v/v) fetal bovine serum [FBS, Biochrom, cat. no. S 0115]) (4° C., 20 min.), followed by incubation with APC-labeled anti-goat IgG (H+L) (R&D Systems, cat. no. F0108) (4° C., 20 min.). Binding of the different CD137 antibody clones to cells expressing the shuffle constructs was measured by incubation of the transduced cells with 1 µg/mL of the antibody clones, followed by APC-labeled AffiniPure F(ab')2 Fragment (1:50 final dilution; Jackson, cat. no. 109-136-127).

Figure 3:
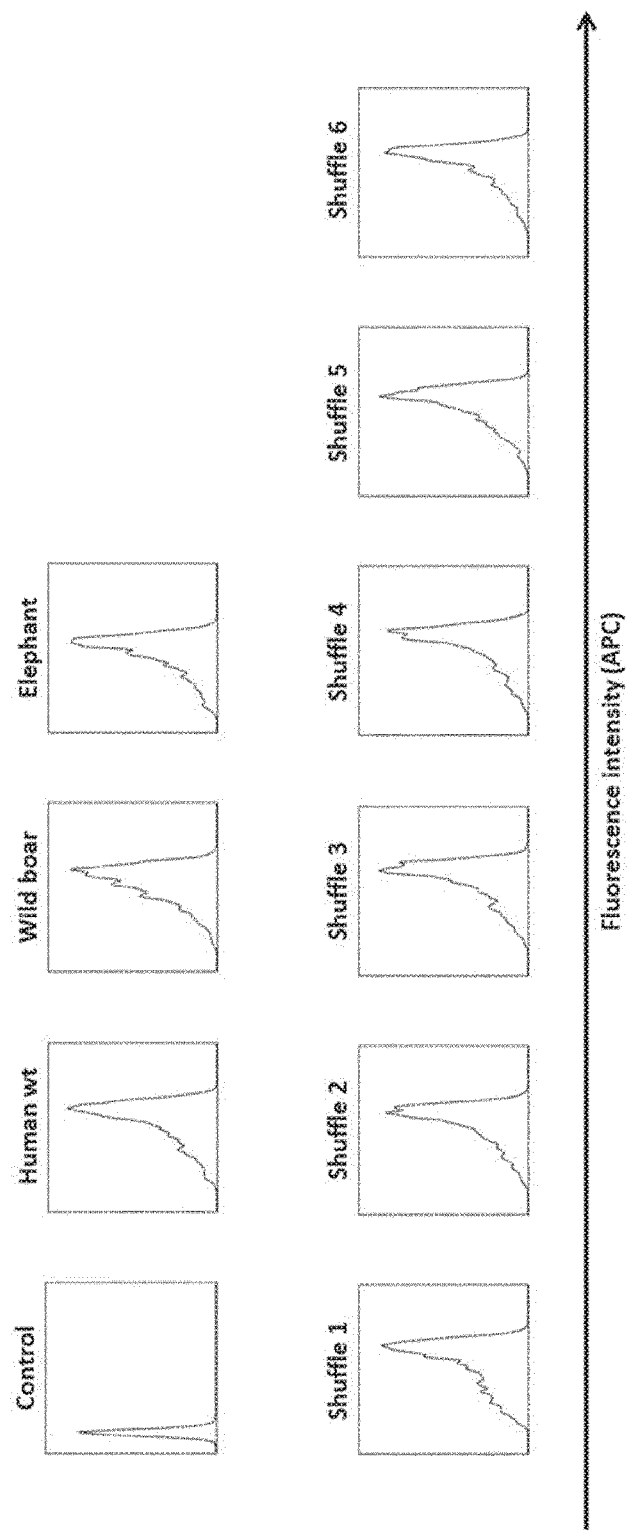
FIG. 3: Expression of CD137 shuffle constructs on HEK293-T17 cells. HEK293-T17 cells were transfected with the CD137 shuffle constructs. Cell surface expression of the constructs was measured by flow cytometry, using a polyclonal anti-CD137 antibody that recognizes human, wild boar and African elephant CD137.

All CD137 shuffle constructs, as well as human, African elephant and wild boar CD137, were expressed on the cell surface with similar expression levels (FIG. 3).

Figure 4:
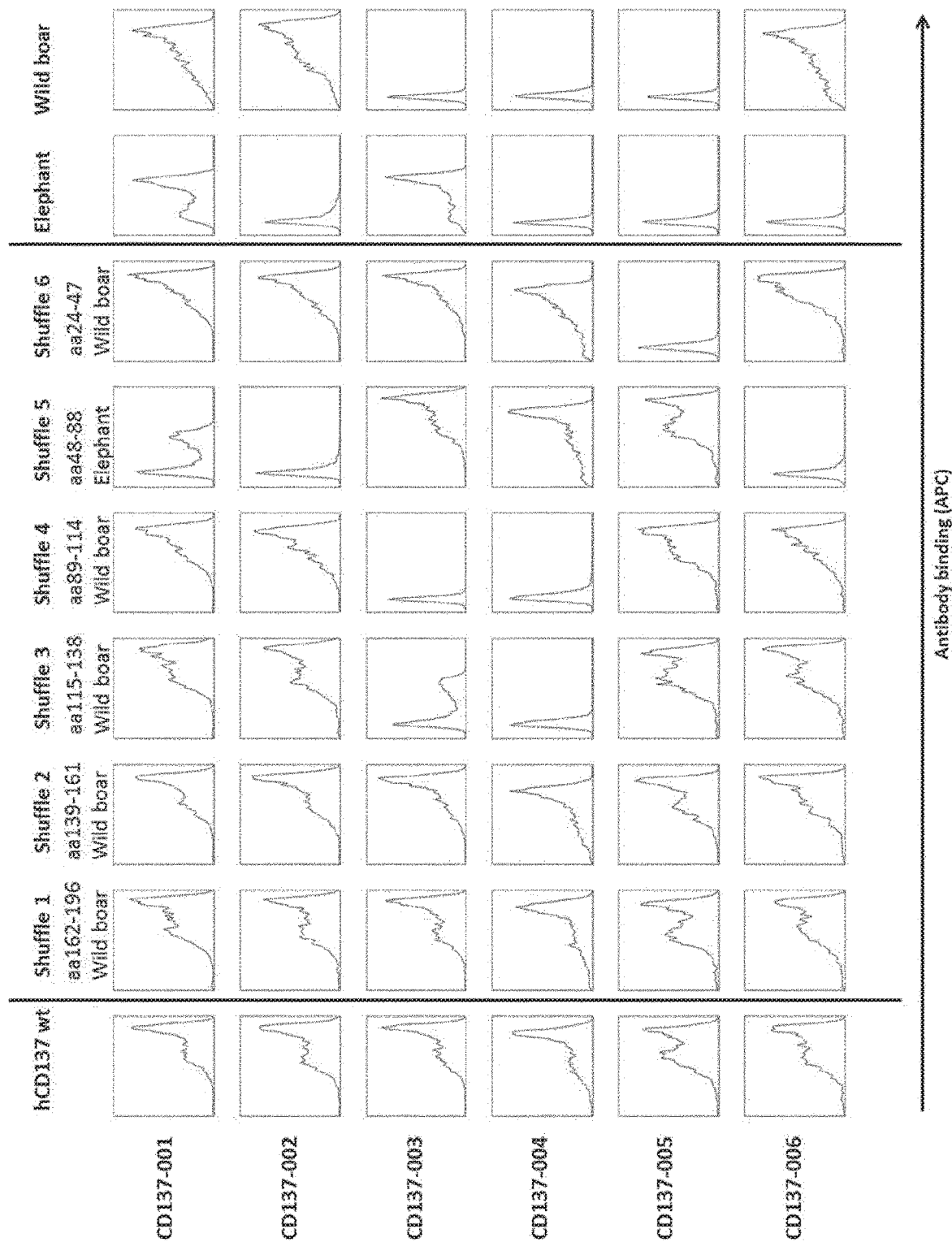
FIG. 4: Binding of CD137 antibody clones to CD137 shuffle constructs expressed on HEK293-T17 cells. HEK293-T17 cells were transfected with the CD137 shuffle constructs, and with human CD137 (hCD137 wt), African elephant of wild boar CD137, as indicated. Binding of the different CD137 antibody clones to these constructs expressed on HEK293-T17 cells was measured by flow cytometry. Staining with polyclonal anti-CD137 antibody is shown as a control.
Figure 4:
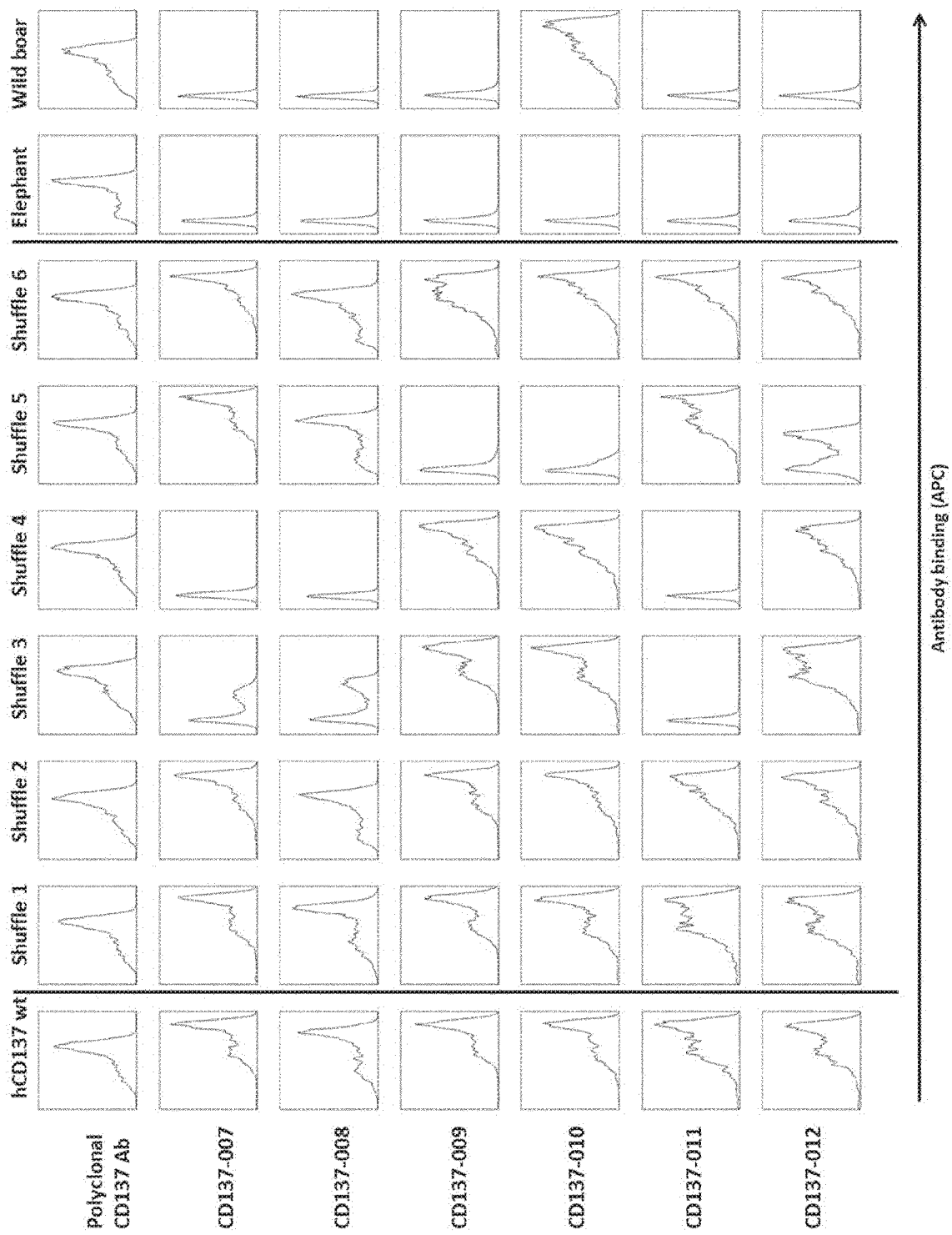

Table 2 and FIG. 4 show that all clones, except for clone 1, showed loss of binding to at least African elephant or wild boar CD137. Clones 2, 3, 4, 5, 6, 7, 8, 9, 10 and 11 showed loss of binding to at least one of the shuffle constructs. Clone 1 showed reduced binding to African elephant and shuffle construct 5, as compared to binding to human CD137. Clone 12 did not show loss of binding to any of the shuffle constructs, but showed reduced binding to shuffle construct 5. None of the clones showed loss of binding or reduced binding to shuffle constructs 1 and 2.

TABLE 2

Summary of binding of the CD137 antibodies to the shuffle constructs

| | Binding similar to human CD137 binding | Binding decreased compared to human CD137 binding | No binding |
|---|---|---|---|
| Wild boar CD137 | Clone 1, 2, 6, 10 | None | Clone 3, 4, 5, 7, 8, 9, 11, 12 |
| African elephant CD137 | None | Clone 1, 3 | Clone 2, 4, 5, 6, 7-12 |
| Shuffle 1 (aa 162-196) | Clone 1-12 | None | None |
| Shuffle 2 (139-161) | Clone 1-12 | None | None |
| Shuffle 3 (115-138) | Clone 1, 2, 5, 6, 9, 10, 12 | Clone 3, 7, 8 | Clone 4, 11 |
| Shuffle 4 (89-114) | Clone 1, 2, 5, 6, 9, 10, 12 | None | Clone 3, 4, 7, 8, 11 |
| Shuffle 5 (48-88) | Clone 3, 4, 5, 7, 8, 11 | Clone 1, 12 | Clone 2, 6, 9, 10 |
| Shuffle 6 (aa 24-47) | Clone 1, 2, 3, 4, 6, 7-12 | None | Clone 5 |

Example 3: Generation of Bispecific Antibodies by 2-MEA-Induced Fab-Arm Exchange A method to produce stable IgG1-based bispecific antibodies is described in WO2011131746 (Genmab). The bispecific antibody product generated by this method described below will no longer participate in Fab-arm exchange. The basis for this method was the use of complimentary CH3 domains, which promote the formation of heterodimers under specific assay conditions. To enable the production of bispecific antibodies by this method, IgG1 molecules carrying certain mutations in the CH3 domain were generated: in one parental IgG1 antibody T350I, K370T and F405L mutations (or minimally F405L), in the other parental IgG1 antibody a K409R mutation.

The concentrations of parental IgG1 antibodies that minimally contained either an F405L or a K409R point mutation were measured using their absorption at 280 nm. Specific extinction coefficients based upon the amino acid sequence were used to infer the protein concentration.

The Cube system is Genmab's flexible robotic work cell. The system was designed and built in collaboration with Peak Analysis and Automation (PAA), Farnborough UK.

Bispecific antibodies were generated by combining the following antibodies from Example 1:
CD40-FEAL antibody combined with each of the CD137-FEAR antibodies,
CD40-FEAR antibody combined with the b12-FEAL antibody, and
Each of the CD137-FEAR antibodies combined with the b12-FEAL antibody The bispecific antibody discovery process is performed in an automated fashion on the Cube system, as shown in FIG. 5 and described below.

Figure 5:
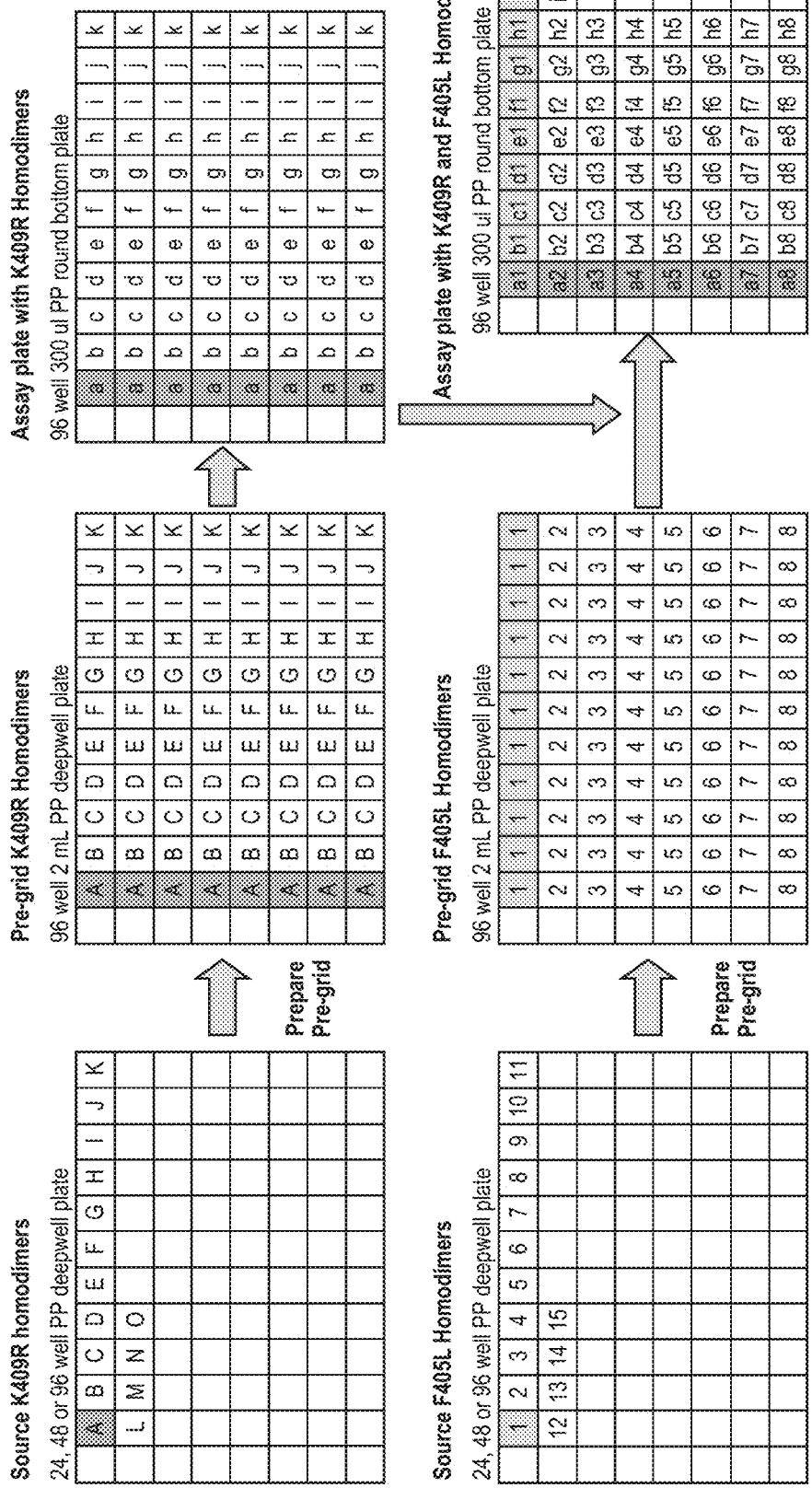
FIG. 5: Matrix-like mixing grids used for automated bispecific antibody discovery. Parental antibodies can be plated as indicated. Parental antibodies can then be combined to obtain bispecific antibodies using a simple matrix-like mixing grid. Controlled Fab-arm exchange can then be performed to obtain bispecific antibodies.

To generate bispecific antibodies, the following (automated) steps are performed:

Depending on the volume required, deep well source plates (96 well clear V-bottom 2 mL polypropylene deep well plate, Corning, cat. no. 3960; 48 well Riplate® SW 5 mL, Ritter, cat. no. 43001-1062; 24 well Riplate SW 10 mL, Ritter, cat. no. 43001-1066) are filled with parental antibodies (F405L- and K409R-containing antibodies in different plates) at a concentration of 1.0 mg/mL (in 1×PBS, B.Braun) (FIG. 5, left plates).

From these source plates, the pre-grid plates (96 well V-bottom, Corning) are prepared by the Cube, according to FIG. 5, middle plates. For each combination with a parental antibody in the exchange grid, 67.5 µL parental antibody is added to the appropriate pre-grid plate.

After the pre-grid, the exchange is performed. Here, two parental antibodies (67.5 µL, 1.0 mg/mL each), each from a different pre-grid plate are added to an exchange plate (96 well round-bottom polypropylene plate, Greiner, cat. no. 650293), each antibody at a final concentration of 0.5 mg/mL (equimolar concentration) (FIG. 5, right plates).

The exchange reaction is started by adding 15 µL 75 mM 2-mercaptoethylamine-HCl (2-MEA) (in 1×PBS, B.Braun) to the exchange plate. The total volume in the exchange plate is now 150 µL (final concentration 2-MEA 7.5 mM)

The exchange plates are incubated at 31° C. for 5 hours in the Cytomat 6000 automated incubator (Thermo Scientific).

The reducing agent 2-MEA is removed by using desalting columns (PhyTip desalting columns, 600 µL resin, PhyNexus, cat. no. PDR 91-60-06), for which flow is based on gravity.

The columns are conditioned by placing an adapter with 96 columns on a waste position, adding two times 450 µL 1×PBS (B.Braun) and allowing the solutions to flow through the columns into the waste.

After conditioning, 100 µL sample from the exchange plate is added, thereby pushing the remaining PBS out of the columns.

After allowing the solutions to flow through the columns into the waste, the adapter with columns is placed on a desalting (or destination) plate (96 well round-bottom, Greiner).

The remaining sample from the exchange plate is added to the columns.

After allowing the samples to flow through the columns into the desalting plate, 225 µL 1×PBS (B.Braun) is added to the columns and the sample is eluted into the desalting plate.

The 2-MEA remains inside the columns. Where appropriate, the columns can be regenerated by washing with 1×PBS (B. Braun).

The desalting plates are stored in the Cytomat 6001 automated incubator (Thermo Scientific) at 8° C. These plates now contain the bispecific antibodies.

The final bispecific antibody samples were filtered over 0.2 μm dead-end filters and the absorbance at 280 nm (A280) of bispecific products was measured to determine the final concentration. Samples were stored at 2-8° C. for at least 24 hours before further use.

The bispecific antibody exchange efficiency was quantified using High Pressure Liquid Chromatography (HPLC)—hydrophobic interaction chromatography (HIC) using a Butyl-NPR, 2.5 μm, 4.6×35 mm HIC-HPLC column (Tosoh Bioscience) with a flow rate of 1 mL/min. Parental antibodies and analysis samples were normalized in concentration and diluted two-fold with HIC eluent A (15.4 mM $K_2HPO_4$, 9.6 mM KH2PO4, 1.5 M (NH4)2SO4; pH 7.0). 50 μL of sample was injected and elution was performed with a 12-min gradient of HIC eluent A to HIC eluent B (15.4 mM $K_2HPO_4$, 9.6 mM $KH_2PO_4$; pH 7.0) with detection at 280 nm. Alternatively, HPLC—analytical cation exchange chromatography (CIEX) was used to quantify the bispecific antibody exchange efficiency. Parental antibodies and analysis samples at 1 mg/mL in mobile Phase A (10 mM $NaPO_4$, pH 7.0) were injected onto the HPLC. The differently charged IgG molecules were separated by using a ProPac WCX-10, 4 mm×250 mm, analytical column with a flow rate of 1 mL/min. 50 μL of sample was injected and elution was performed with a gradient of Mobile Phase A (10 mM $NaPO_4$, pH 7.0; prepared from a 0.1 M stock of sodium phosphate buffer, that was obtained by adding 10.3 g $Na_2HPO_4 \cdot 2H_2O$ and 5.07 g $NaH_2PO_4$ per liter Milli-Q) to Mobile Phase B (10 mM NaPO4, pH 7.0, 0.25 M NaCl) with detection at 280 nm. Empower 3 software (Waters) was used to assign peaks as parental antibodies or bispecific reaction products, and to integrate peak areas to quantify extent of the bispecific antibody exchange reaction. Bispecific antibody reaction products were further analyzed using analytical size exclusion chromatography, using a TSK HP-SEC column (G3000SWxI; Tosoh Biosciences, via Omnilabo, Breda, The Netherlands) and Capillary Electrophoresis—Sodium Dodecyl Sulfate (CE-SDS) using a LabChip GXII (Caliper Life Sciences, Mass.) on a HT Protein Express LabChip (Caliper Life Sciences, Mass.) under reducing and non-reducing conditions according to manufacturer's instructions.

Example 4: Reporter Assay Measuring Trans-Activation by Bispecific Antibodies Binding to CD40 and CD137

CD40 is predominantly expressed on antigen-presenting cells (APCs), such as dendritic cells, whereas CD137 is predominantly expressed on activated T cells. Thus, bispecific antibodies binding to CD40 and CD137 can bind simultaneously to APCs and T cells expressing these receptors. Thereby, these bispecific antibodies can mediate cell-cell contact between APCs and T cells by receptor binding and activate both receptors. This receptor activation can be induced by cross-linking and receptor clustering upon cell-cell interaction and is not necessarily dependent on agonistic activity of the parental monospecific bivalent antibodies. Thus, these trans-activating bispecific antibodies can exert co-stimulatory activity in the context of interactions between APCs and T cells.

Figure 6:
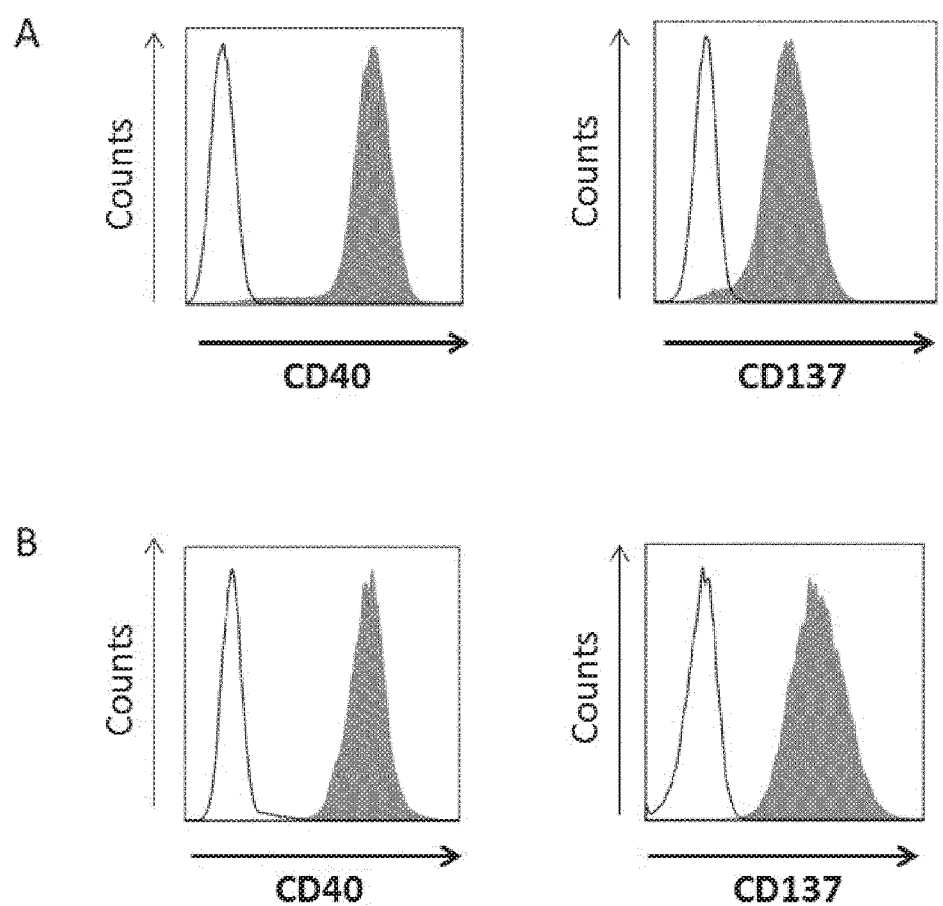
FIG. 6: Expression of CD40 and CD137 on the cell surface of stably transduced HEK293-NFK-gfp-luc and K562 cells. NF-κB/293/GFP-Luc (A) and K562 (B) cells were stably transduced with CD40 or CD137. Surface expression of CD40 (left panels) and CD137 (right panels) was determined by flow cytometry (white curves: control without antibody; grey curves: antibody staining).
Figure 7A:
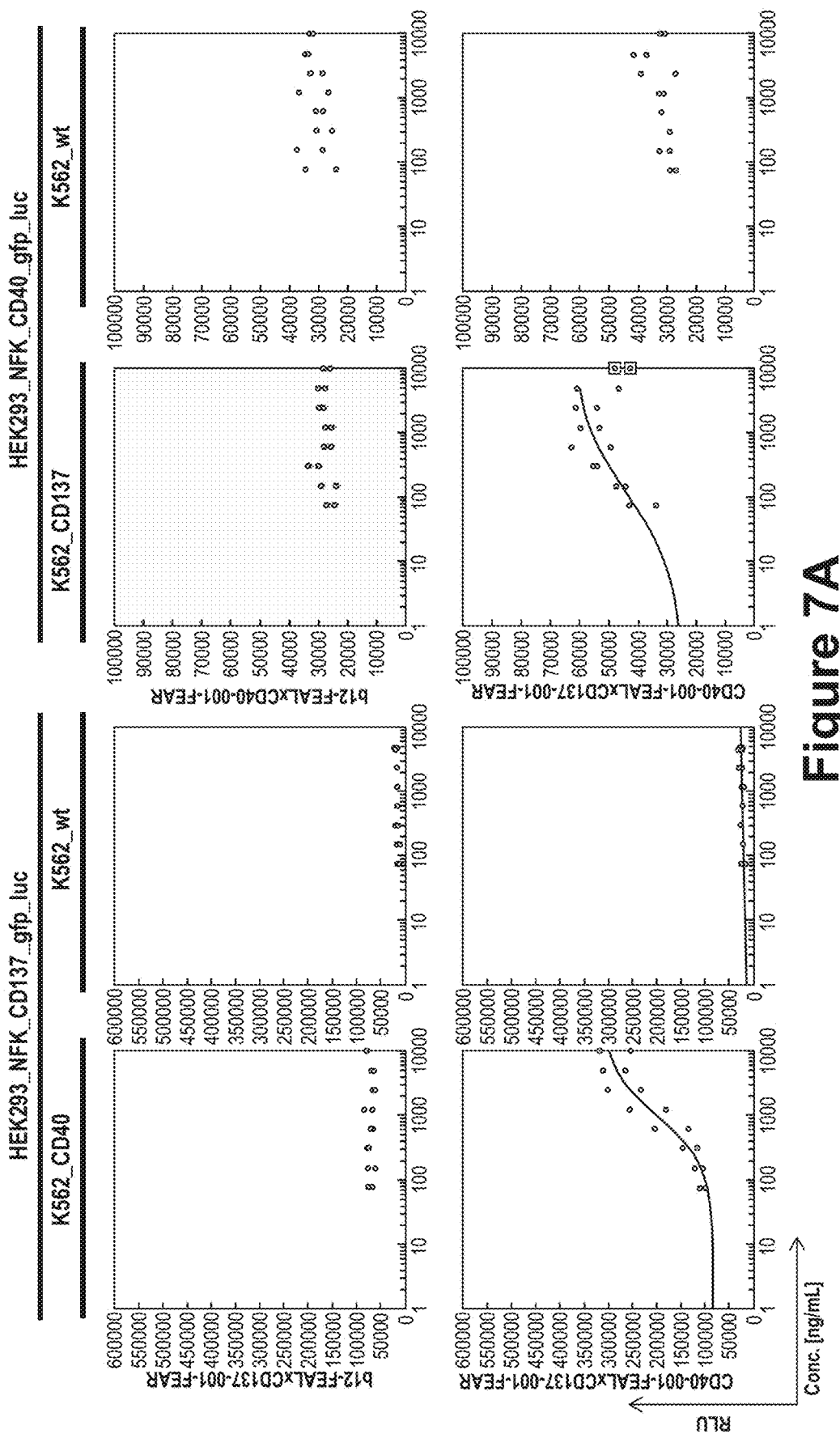
FIG. 7: Analysis of bispecific antibodies simultaneously targeting CD40 and CD137 (CD40xCD137). Bispecific antibodies targeting CD40 and CD137 (CD40-FEALxCD137-FEAR) were tested in the reporter assay in duplicate (A-L: CD40-001xCD137-001 until CD40-001xCD137-012). Activation of CD137 was measured by luciferase activity (relative luminescence units, RLU) of NF-κB/293/GFP-Luc transduced with CD137 (HEK293_NFK_CD137_gfp_luc) upon incubation with the indicated bispecific antibodies and K562 cells transduced with CD40 (K562_CD40) for trans-activation or wildtype K562 cells (K562_wt) as a control. Activation of CD40 was measured by luciferase activity (RLU) of NF-κB/293/GFP-Luc transfected with CD40 (HEK293_NFK_CD40_gfp_luc) upon incubation with the indicated bispecific antibodies and K562 transduced with CD137 (K562_CD137) for trans-activation or wildtype K562 cells (K562_wt) as a control. The two monospecific, monovalent antibodies with one irrelevant arm (b12-FEALxCD137-FEAR, b12-FEALxCD40-FEAR) were used as control for the bispecific CD40xCD137 antibodies.
Figure 7B:
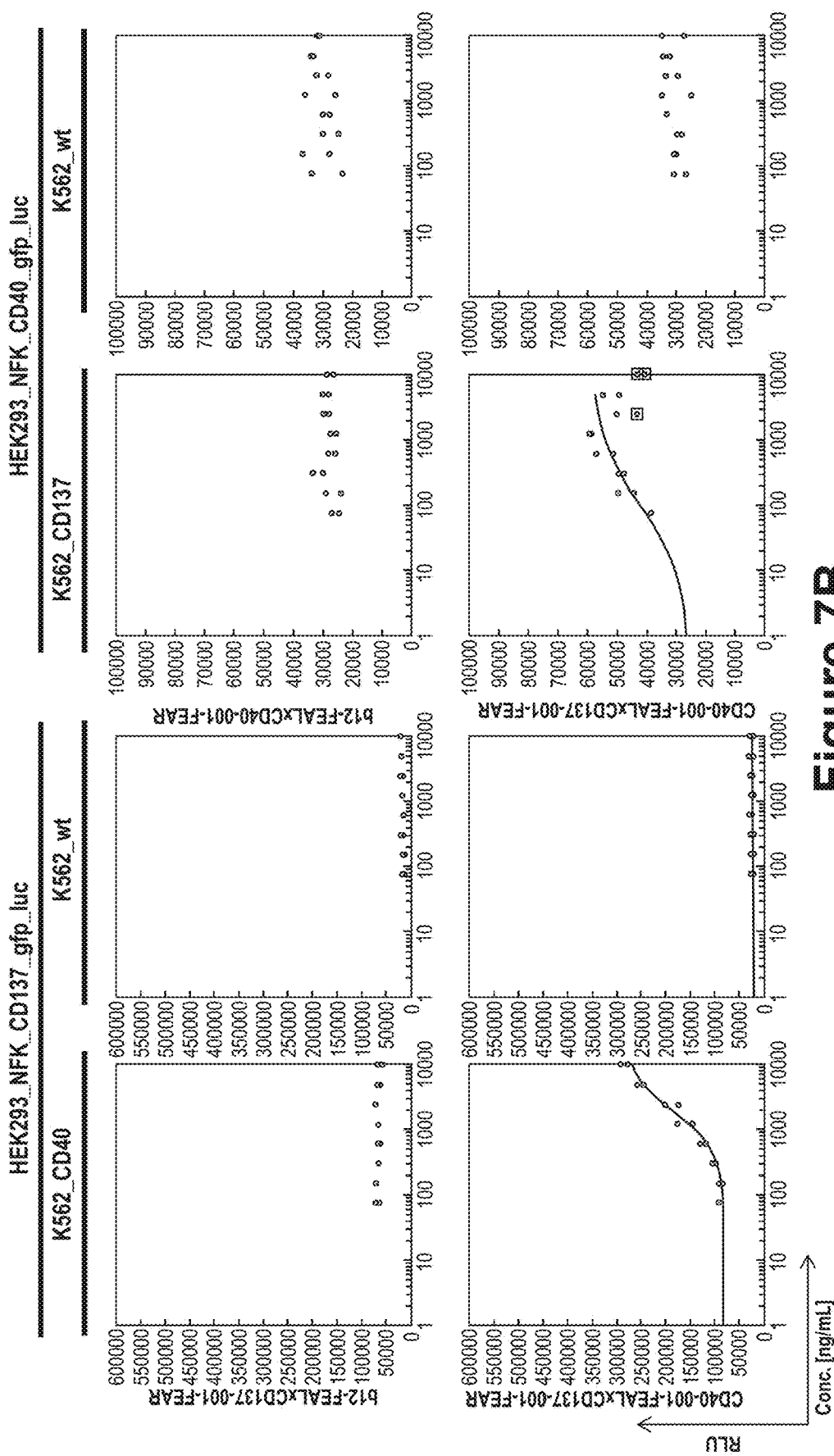
Figure 7C:
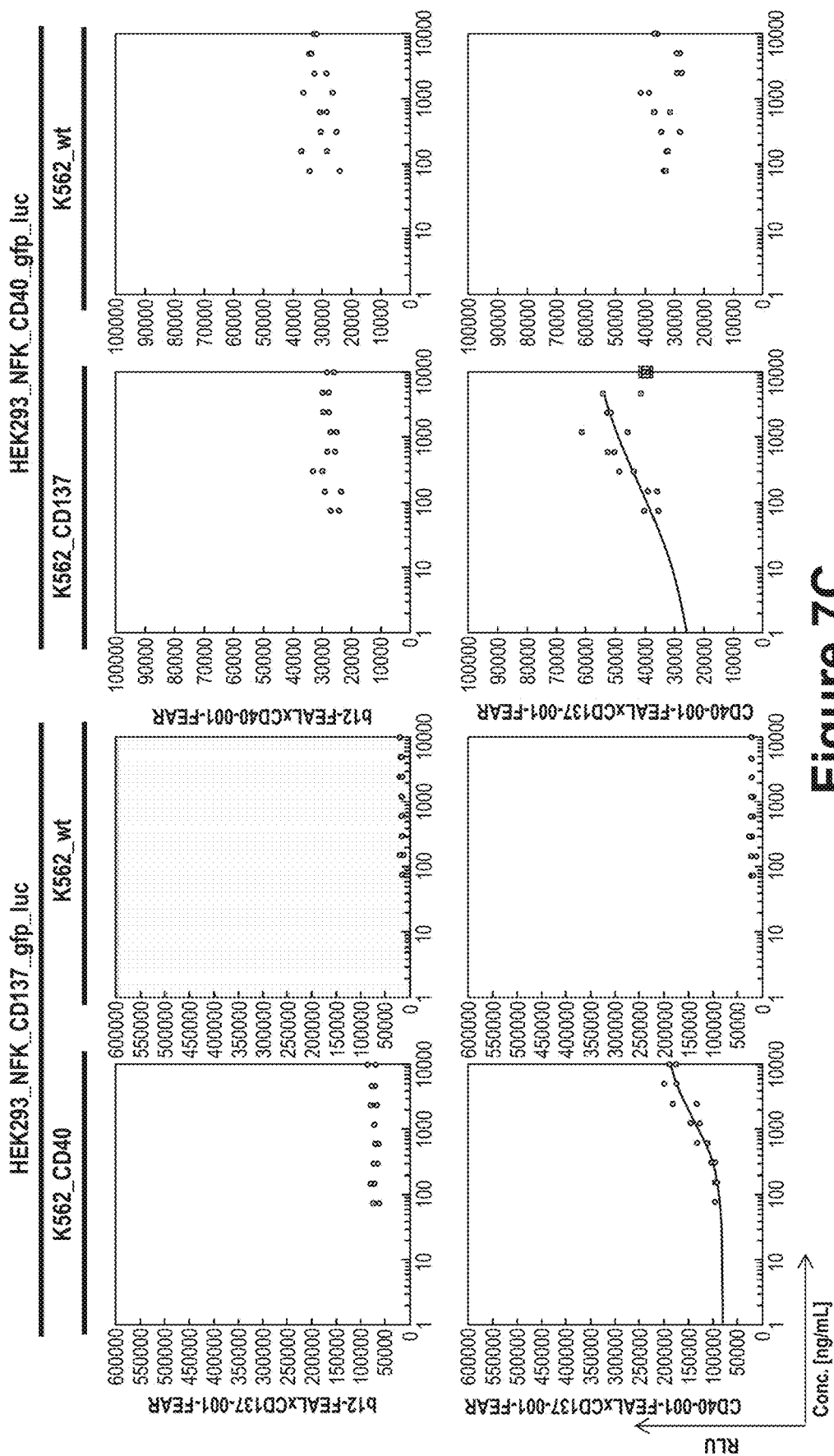
Figure 7D:
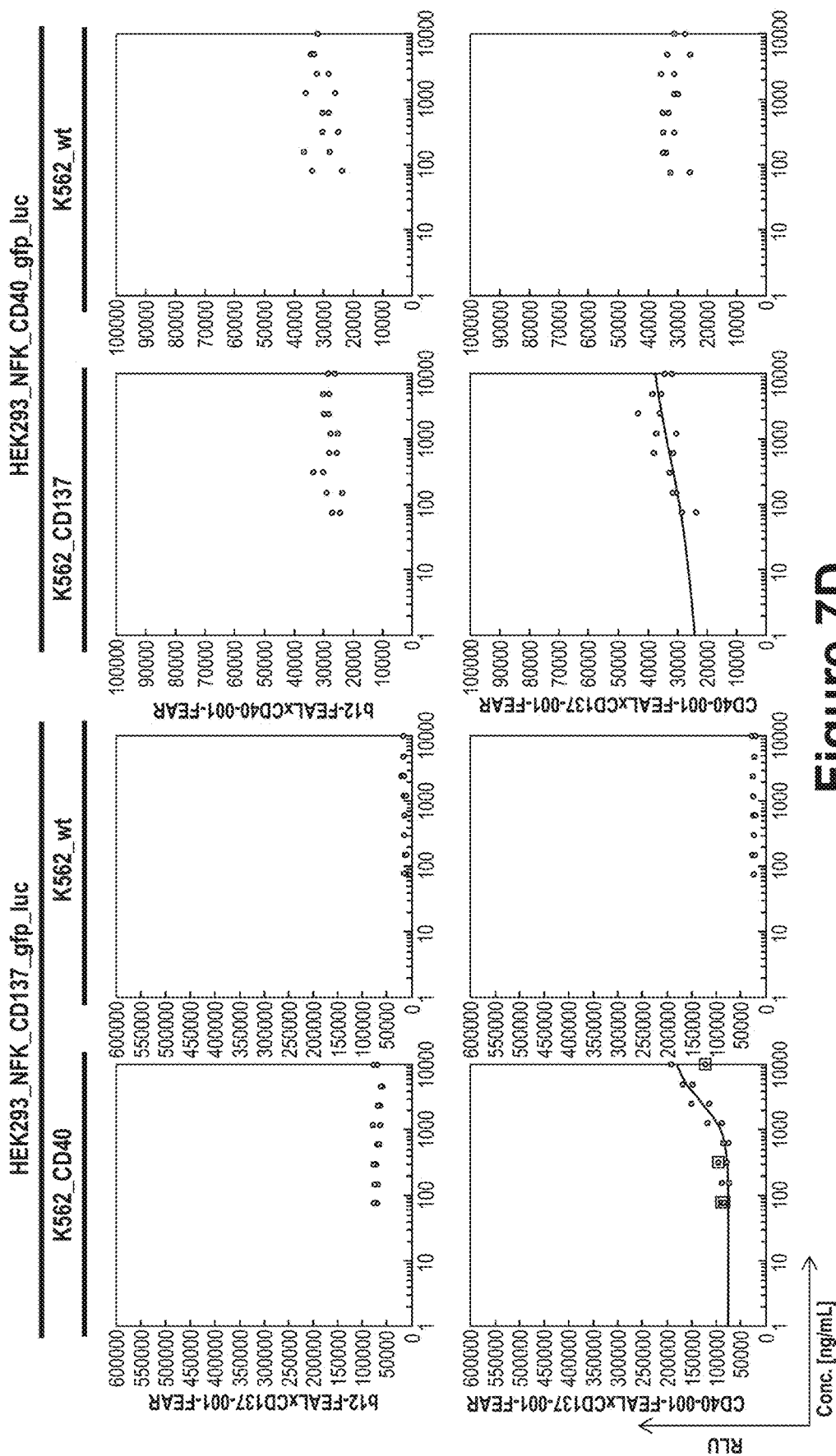
Figure 7E:
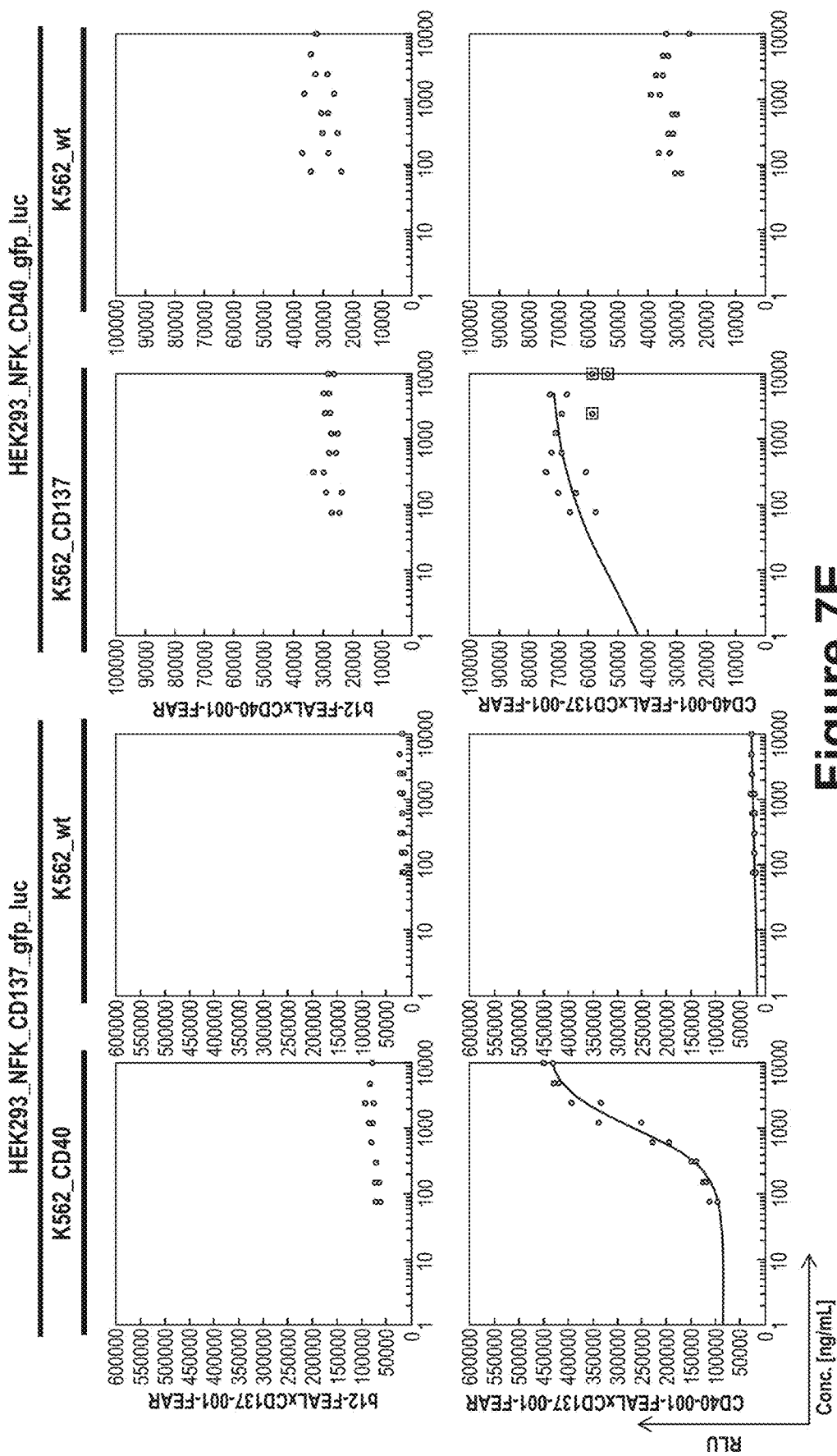
Figure 7F:
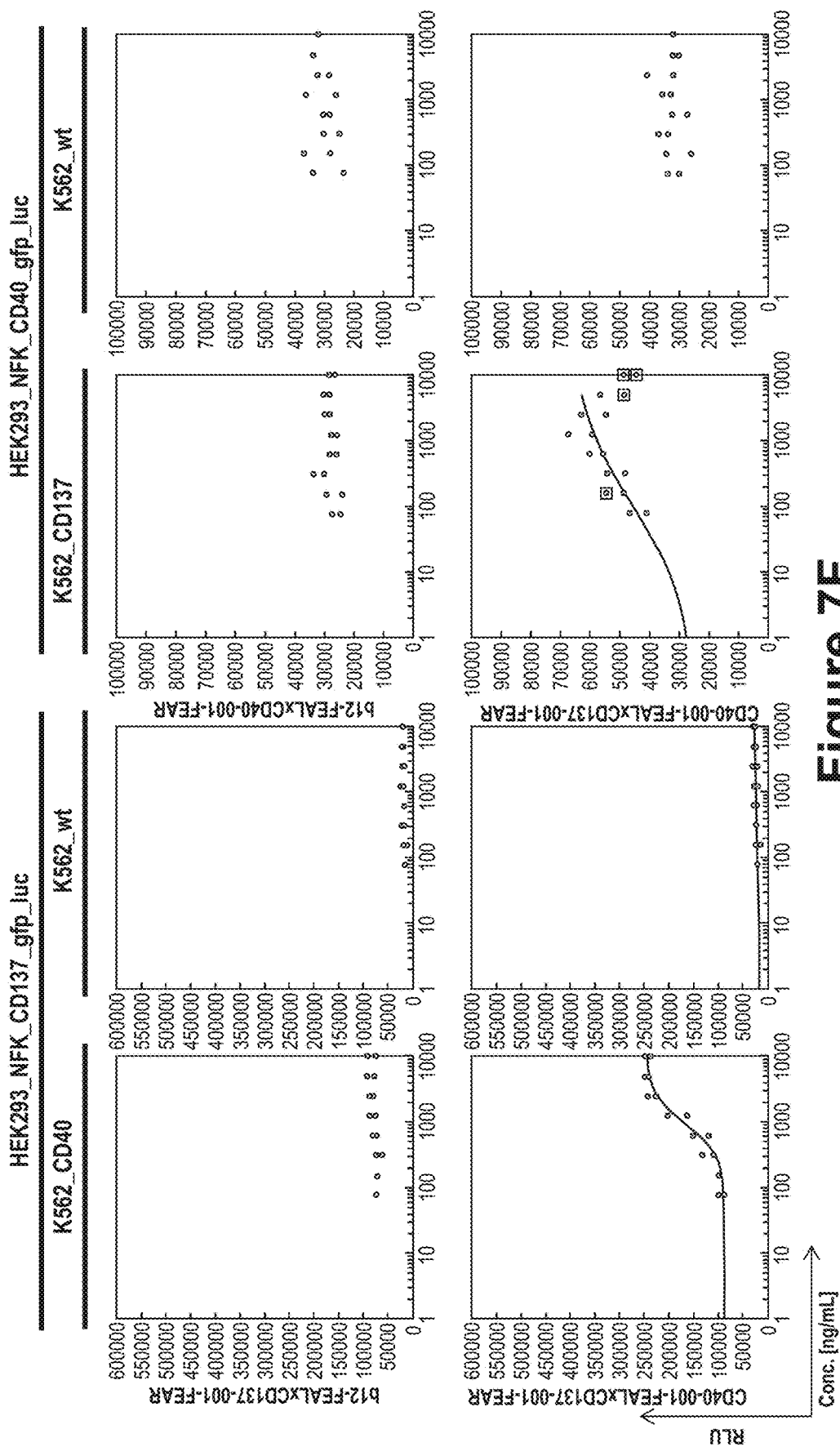
Figure 7G:
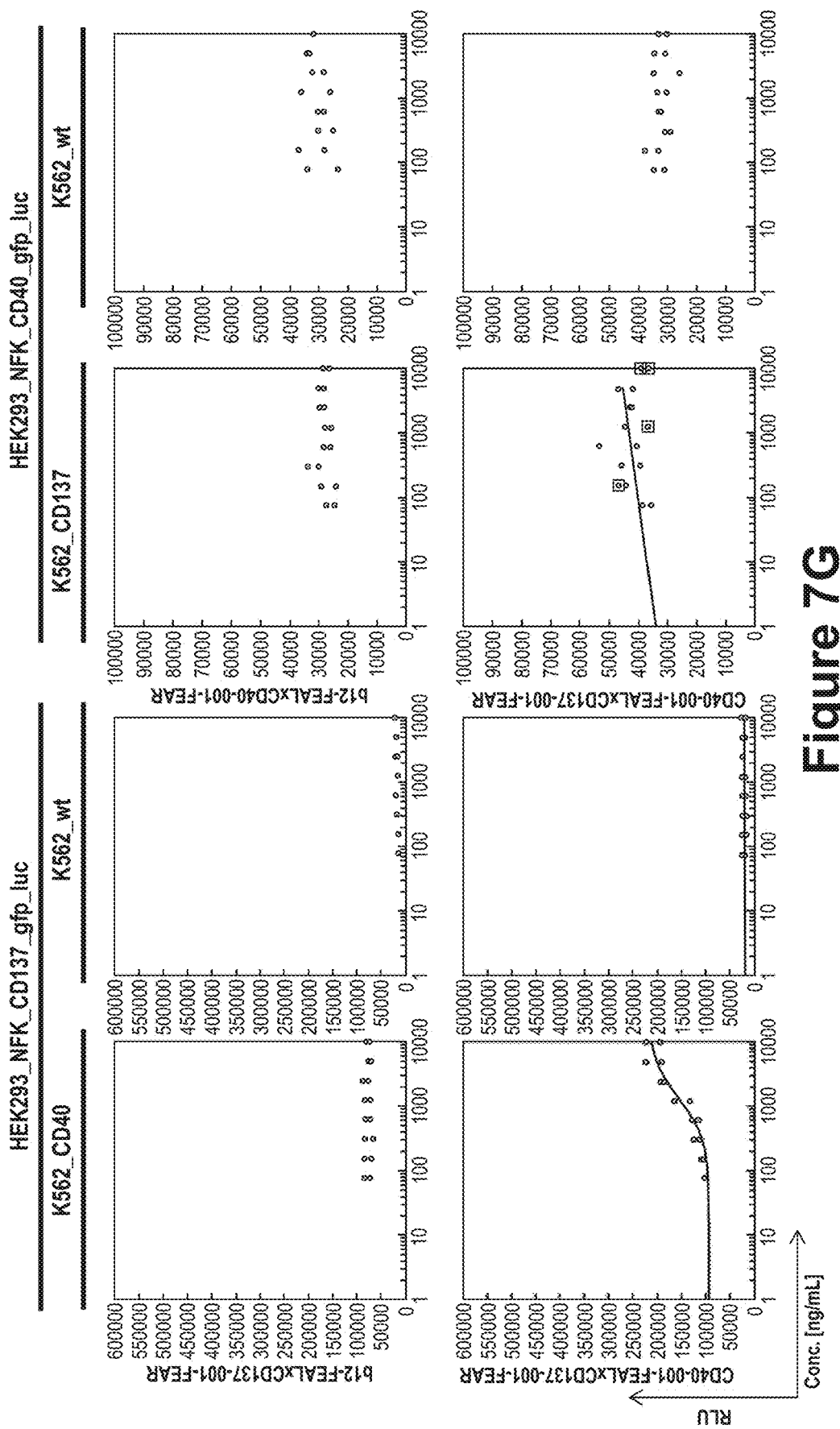
Figure 7H:
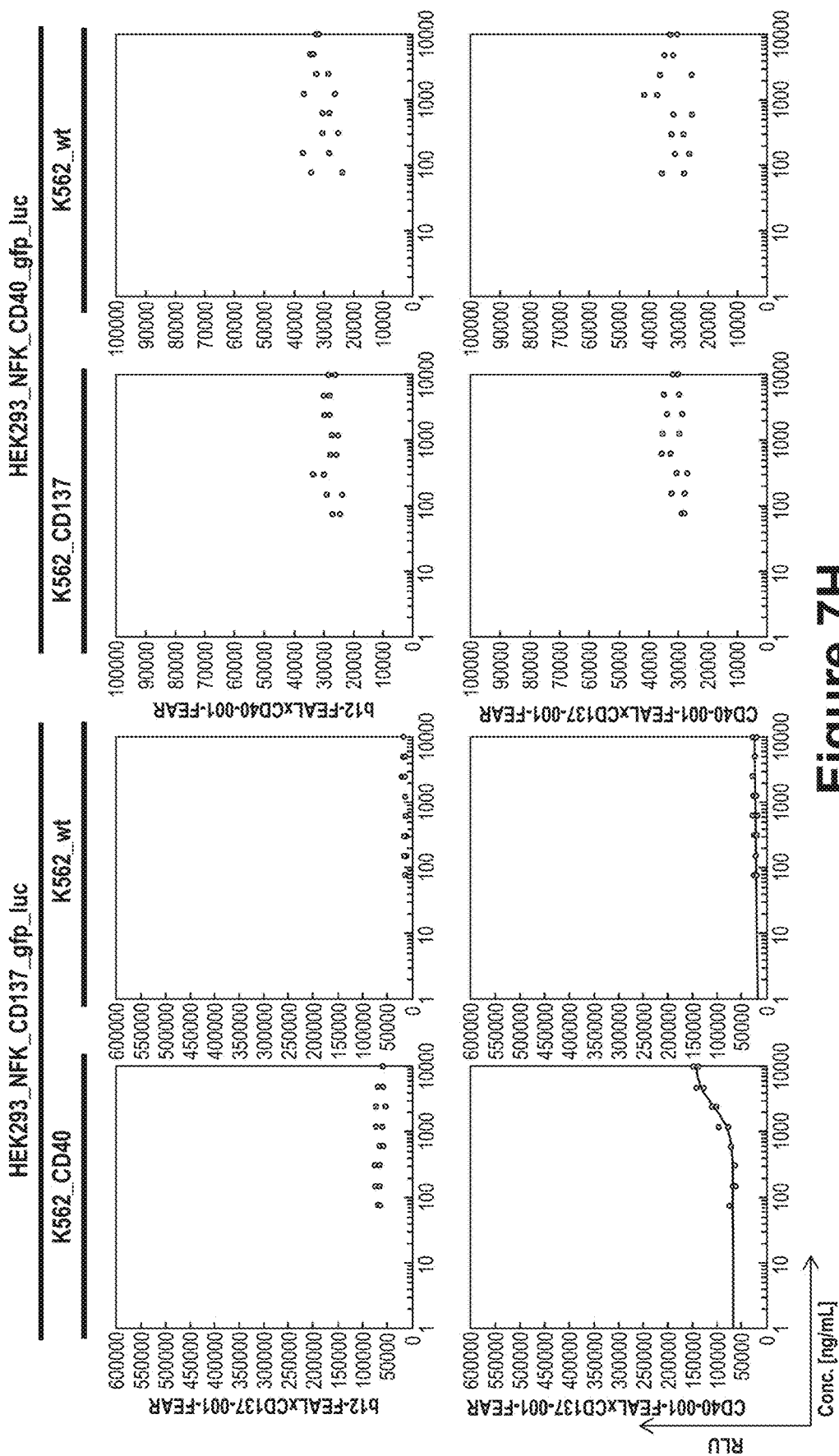
Figure 7I:
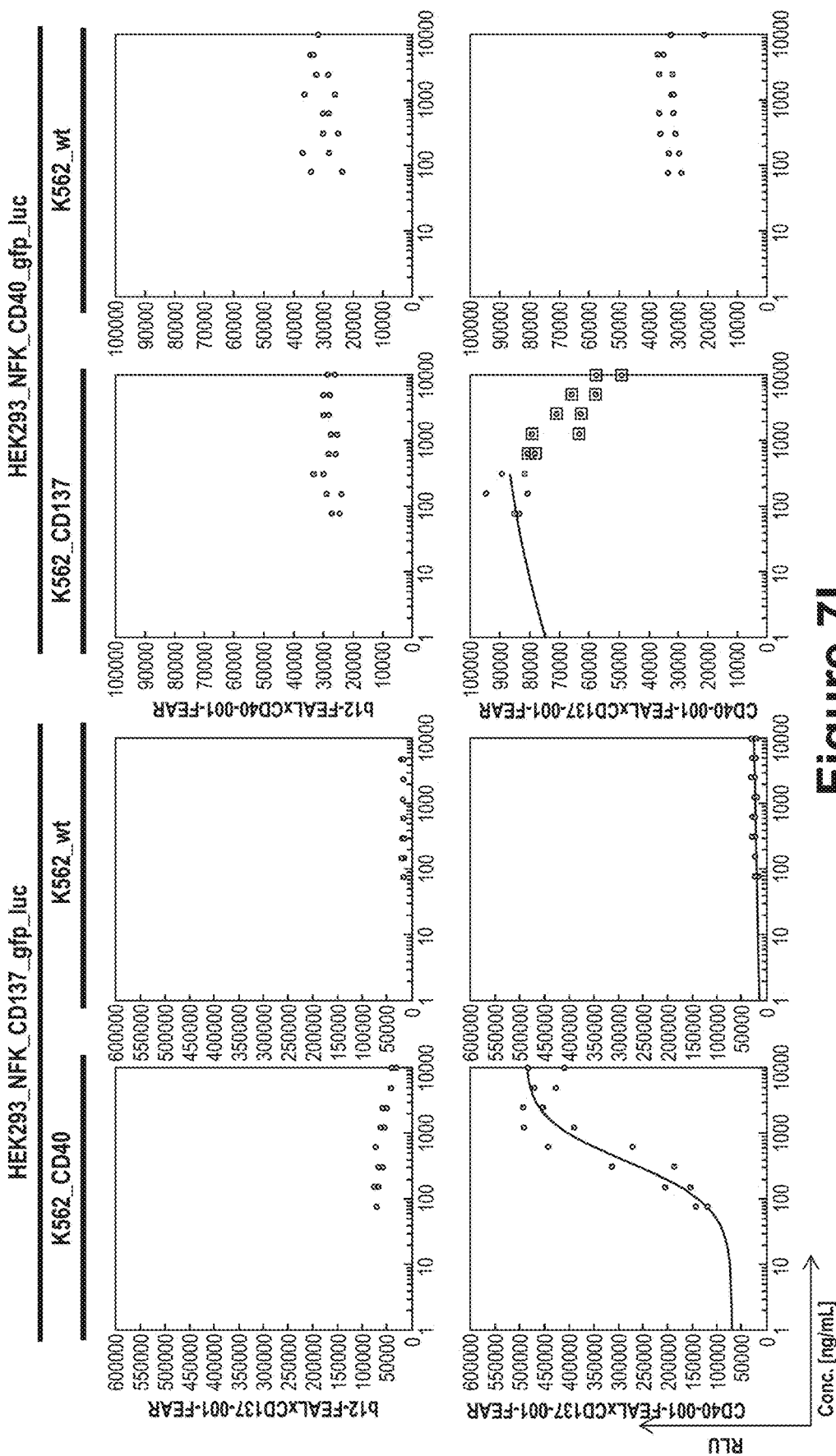
Figure 7J:
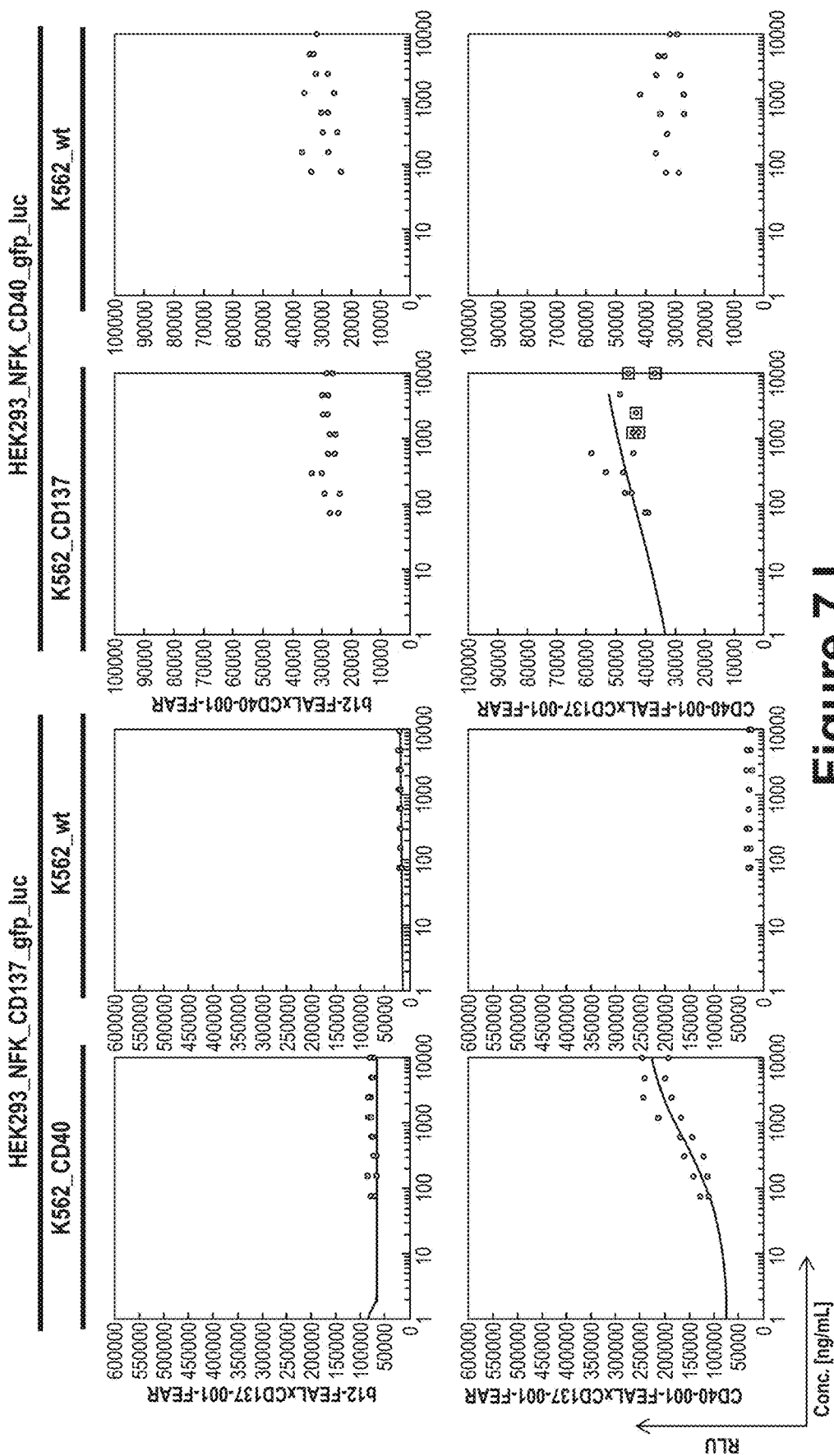
Figure 7K:
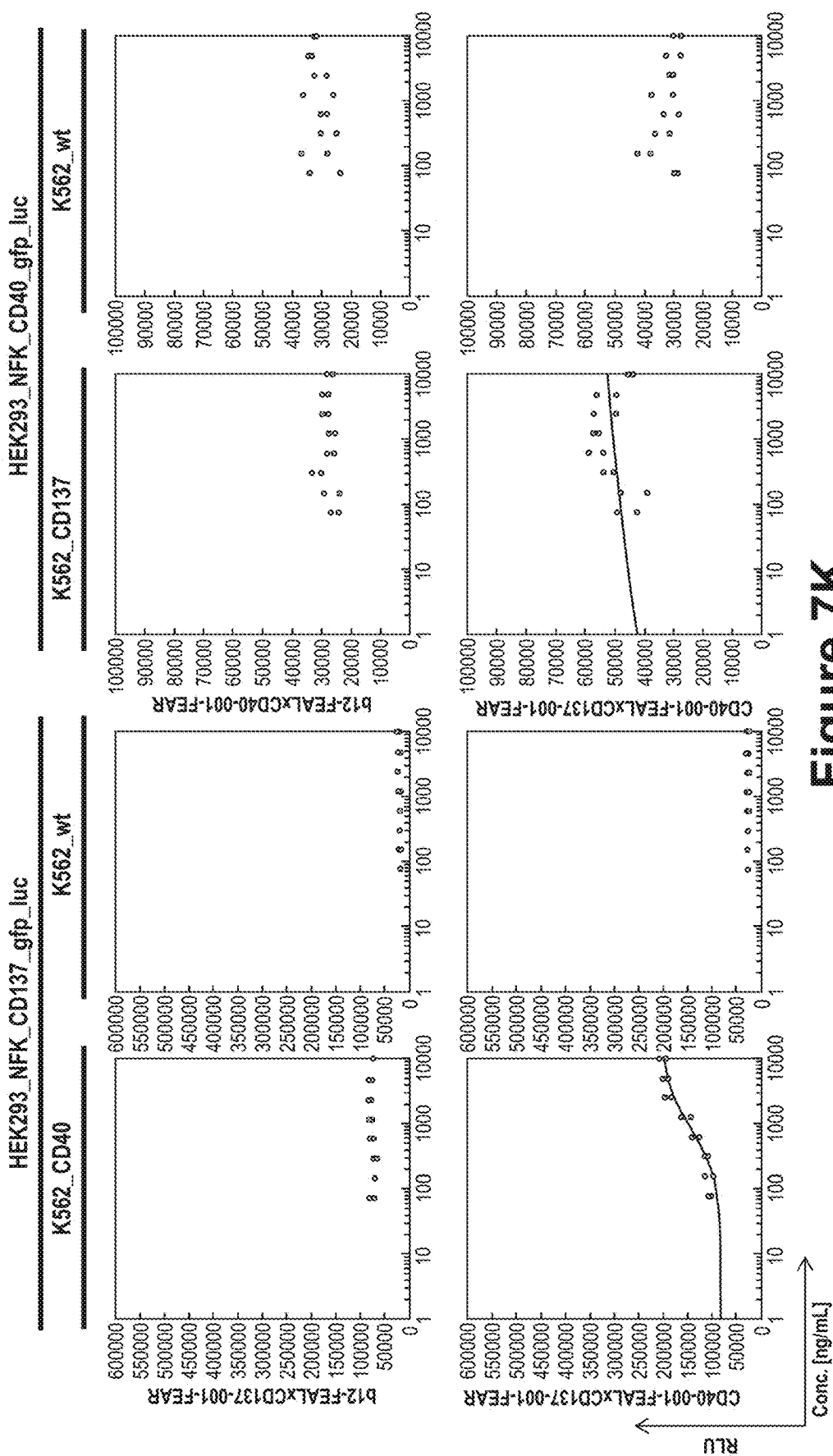
Figure 7L:
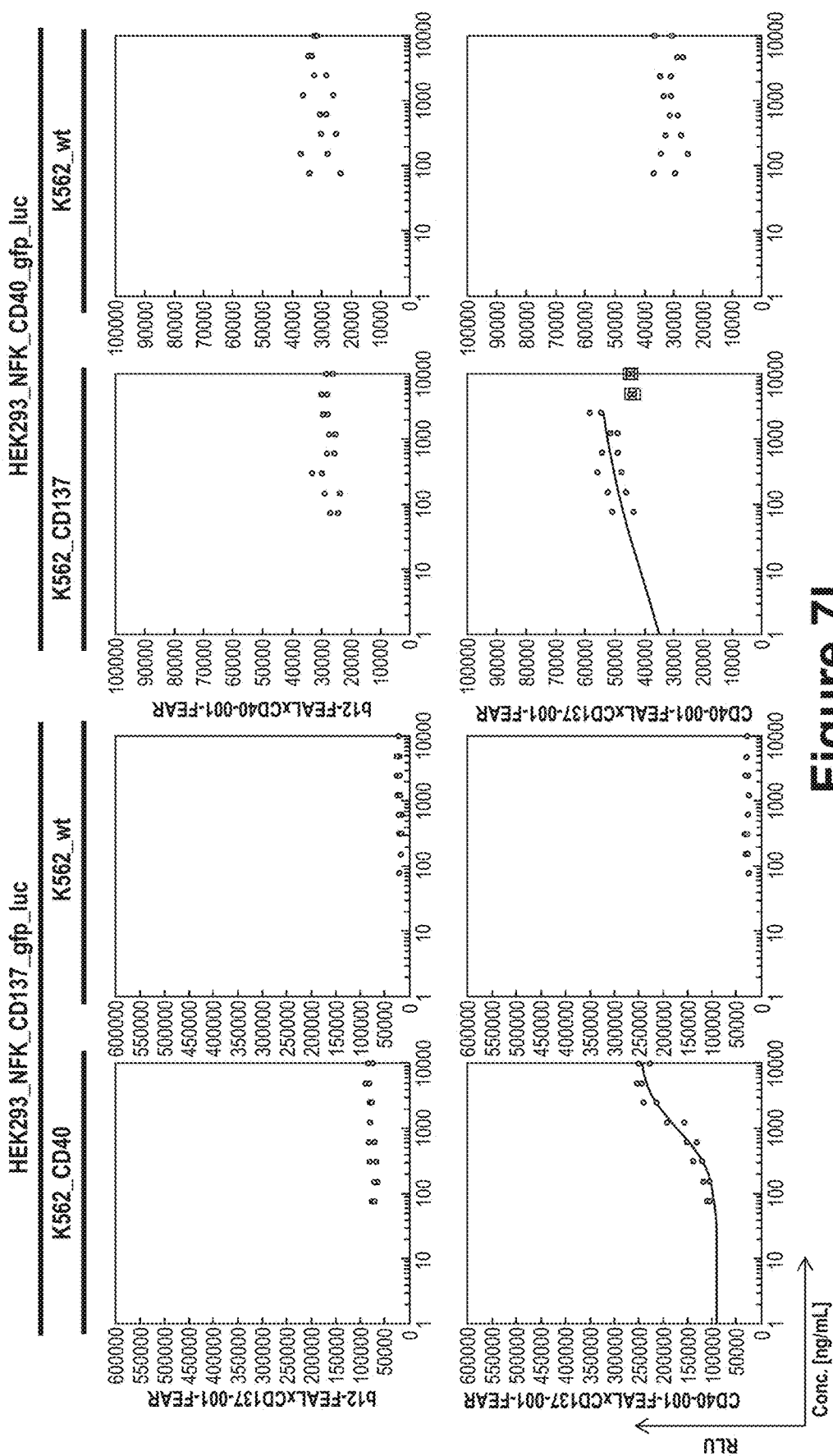

A reporter assay system was established to measure activation of each receptor by the bispecific antibodies. NF-κB/293/GFP-Luc™ Transcriptional Reporter Cell Line (System Biosciences; cat. no. TR860A-1) is a reporter cell line designed for monitoring the NF-κB signal transduction pathway in vitro. Activation of the NF-κB pathway can be monitored by the detection of green fluorescent protein (GFP) fluorescence as well as luciferase activity for quantitative transcription activation reporter assays. NF-κB/293/GFP-Luc cells were stably transduced with expression vectors encoding full length human CD40 or CD137 downstream of a constitutively active human elongation factor-1 alpha (EF-1 alpha) promotor, using TransIT®-LT1 Transfection Reagent, Mirus Bio (VWR International, cat. no. 731-0029), according to the manufacturer's instructions. Stable clones were selected using 10 mg/mL blasticidin (Invivogen, cat. no. ant-bl-1). In addition, K562 cells were stably transduced, as described supra, with human CD40 and CD137 to generate cell lines that can provide the corresponding target antigen for the other arm of the bispecific antibody. Cell surface expression of the receptors was measured by flow cytometry. $0.3×10^6$ cells were spun down (460×g, 5 min.) and washed in FACS buffer (D-PBS supplemented with 5 mM EDTA [Sigma Aldrich, cat. no. 03690] and 5% (v/v) fetal bovine serum [FBS, Biochrom, cat. no. S 0115]) (460×g, 5 min.). 50 μL of 1:50 diluted allophycocyanin (APC)-labeled anti-human CD40 (BD Biosciences, clone 5C3, cat. no. 555591) or phycoerythrin (PE)-labeled anti-human CD137 (BD Biosciences, clone 4B4-1, cat. no. 555956) was added to the cell pellet and incubated at 4° C. in the dark for 20 minutes. After washing three times with FACS buffer, cells were resuspended in 100 μL FACS buffer and binding of the antibodies was detected by flow cytometry on a FACSCanto II (BD Biosciences). Cell surface expression of CD40 and CD137 on transduced NF-κB/293/GFP-Luc cells (FIG. 6A) and K562 cells (FIG. 6B) was nicely shown.

The reporter assay measuring trans-activation was set up as follows: NF-κB/293/GFP-Luc cells expressing one of the two indicated TNF receptors were seeded at 10,000 cells/well in 30 μL RPMI 1640 medium with GlutaMAX supplement (Life Technologies, cat. no. 61870) in white opaque 384-well cell culture plates (PerkinElmer, cat. no. 6007680). Bispecific antibodies binding with one arm to CD40 and with the other arm to CD137 and the corresponding monospecific, monovalent (containing one irrelevant control arm [b12]) control antibodies were added in 10 μL/well to the reporter cells in serial dilutions (in medium), ranging from 0.078 μg/mL to 10 μg/mL final concentration, including a buffer control. 17,000 K562 cells expressing the second TNF receptor or wildtype K562 (K562_wt) cells were added in 10 μL medium to each well and incubated at 37° C. and 5% $CO_2$ for 18 hours. Thus, the bispecific antibodies are able to bind to the first TNF receptor on the NF-κB/293/GFP-Luc cell line and, at the same time, to the second TNF receptor on the K562 cell line. Only receptor activation of the first TNF receptor on NF-κB/293/GFP-Luc cells is measured by luciferase activity induced upon NF-κB signaling. Thus, bispecific antibodies targeting CD40 and CD137 were analyzed by two reporter assays: the first assay measuring CD137 activation induced by simultaneous binding of CD137 on the reporter cell line and CD40 on the K562 cells (HEK293_NFK_CD137_gfp_luc+K562_CD40) and the second assay measuring CD40 activation induced by simultaneous binding of CD40 on the reporter cell line and CD137 on the K562 cells (HEK293_NFK_CD40_gfp_luc+ K562_CD137). Luciferase activity was measured as relative luminescence units on an Envision plate reader (PerkinElmer) after addition of 50 μL/well Steady-Glo® reagent (Promega; cat. no. E2520) reconstituted in Glo Lysis Buffer (Promega; cat. no. E266A) and incubation at room temperature for 30 min.

Only the bispecific CD40xCD137 antibodies (FIG. 7A-L, lower panels, first and third graph) induced luciferase activity (at concentrations of about 100 ng/mL and higher) in NF-κB/293/GFP-Luc cells transduced either with CD137 or with CD40, under trans-activation conditions (incubation with K562-CD40 or K562-CD137, respectively). None of the monospecific, monovalent (containing one irrelevant control arm [b12]) control antibodies induced luciferase activity in the transduced NF-κB/293/GFP-Luc cells (upper panels). Furthermore, in the absence of trans-activation conditions (using wildtype K562 cells) no luciferase activity was induced by the bispecific CD40xCD137 antibodies (lower panels, second and fourth panel).

Example 5: Non-Antigen-Specific T-Cell Proliferation Assay to Measure Trans-Activation by Bispecific Antibodies Binding to CD40 and CD137

To measure non-antigen-specific proliferation, T cells in a peripheral blood mononuclear cell (PBMC) population were incubated with a sub-optimal concentration of anti-CD3 antibody (clone UCHT1), combined with CD40xCD137 bispecific or control antibodies. Within this PBMC population, antigen-presenting cells expressing CD40 can be bound by the CD40-specific arm of the bispecific antibody, whereas the T cells in the population can be bound by the CD137-specific arm. Trans-activation of the T cells induced by cross-linking to the antigen-presenting cells via the bispecific antibody is measured as T-cell proliferation.

PBMCs were obtained from buffy coats of healthy donors (Transfusionszentrale, University Hospital, Mainz, Germany) using a Ficoll gradient (VWR, cat. no. 17-5446-02). PBMCs were labeled using 1.6 μM carboxyfluorescein succinimidyl ester (CFSE) (Thermo Fisher, cat. no. C34564) in PBS, according to the manufacturer's instructions. 75,000 CFSE-labeled PBMCs were seeded per well in a 96-well round-bottom plate (Sigma Aldrich, CLS3799-50EA) and incubated with a sub-optimal concentration of anti-CD3 antibody (R&D Systems, clone UCHT1, cat. no. MAB100; 0.01-0.1 μg/mL final concentration) that was pre-determined for each donor, and bispecific or control antibodies, in 150 μL IMDM GlutaMAX supplemented with 5% human AB serum, at 37° C., 5% $CO_2$, for four days. Proliferation of $CD4^+$ and $CD8^+$ T cells was analyzed by flow cytometry, essentially as described supra. 30 μL containing PE-labeled CD4 antibody (BD Biosciences, cat. no. 555347; 1:80 final dilution), PE-Cy7-labeled CD8a antibody (clone RPA-T8, eBioscience, cat. no. 25-0088-41; 1:80 final dilution) APC-labeled CD56 antibody (eBiosciences, cat. no. 17-0567; 1:80 final dilution) and 7-AAD (Beckman Coulter, cat. no. A07704; 1:80 final dilution) in FACS buffer was used to stain the cells and exclude natural killer (NK) cells (CD56) and dead cells (7-AAD) from the analysis. Samples were measured on a FACSCanto II (BD Biosciences). Detailed analyses of T-cell proliferation based on CFSE-peaks indicating cell divisions were made by FlowJo 7.6.5 software. Mean percentages of T cells that went into division (% divided cells) and the average number of divisions of cells that went into division (proliferation index) were calculated.

Figure 8:
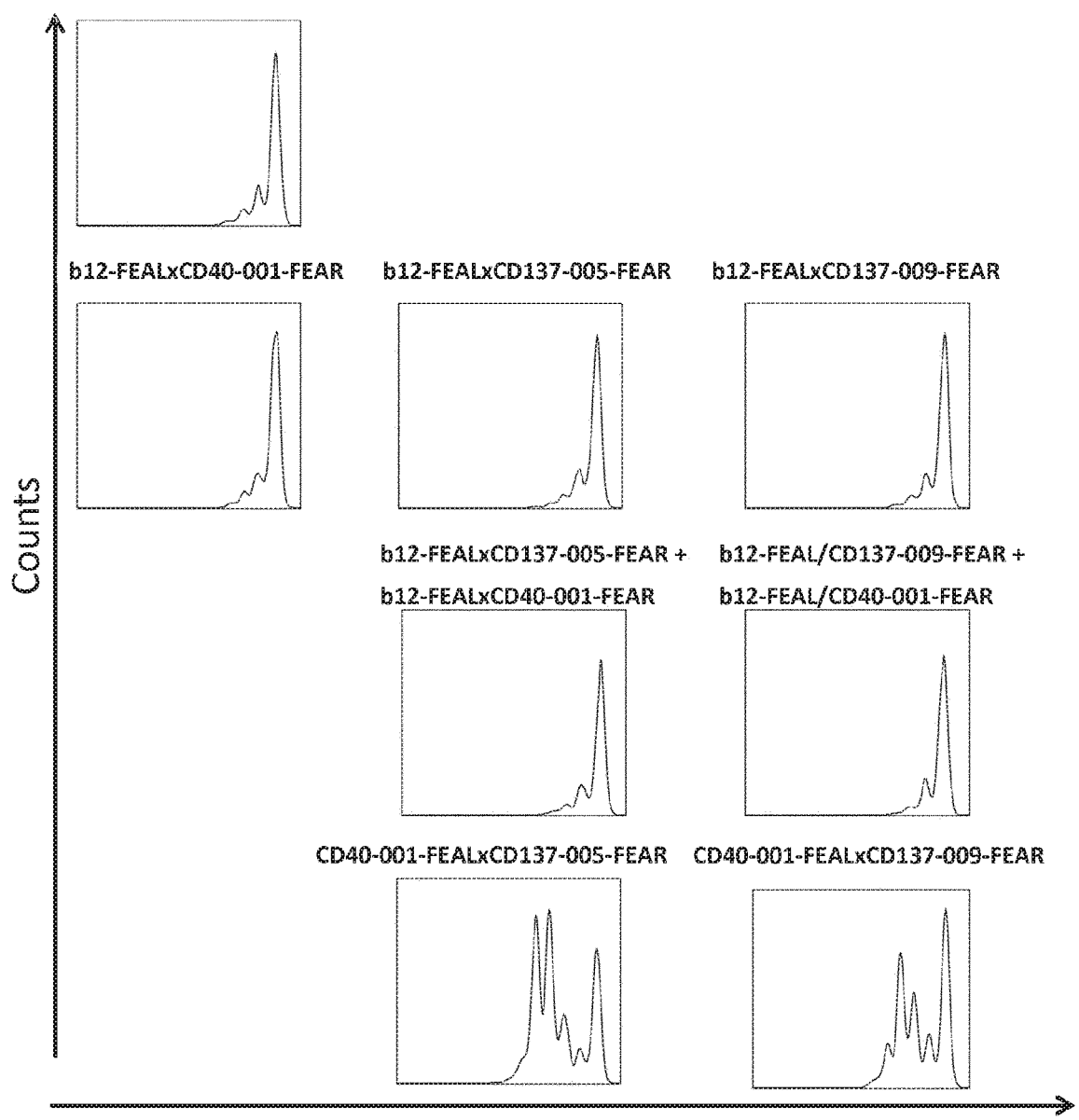
FIG. 8: Induction of CD8+ T-cell proliferation by CD40xCD137 bispecific antibodies in a non-antigen-specific T cell assay. CFSE-labeled PBMCs were incubated with CD40xCD137 bispecific antibodies or monospecific, monovalent control antibodies, for four days. Proliferation of CD8+ cells was measured by flow cytometry. Data shown are CFSE plots showing CD8+ T-cell proliferation induced by the indicated bispecific and control antibodies at 0.02 µg/mL (A), percentages of divided cells and proliferation indices for CD40-001-FEALxCD137-005-FEAR (B), CD40-001-FEALxCD137-009-FEAR (C), CD40-001-FEALxCD137-003-FEAR (D) and CD40-001-FEALxCD137-011-FEAR (E), as calculated using FlowJo software.
Figure 8:
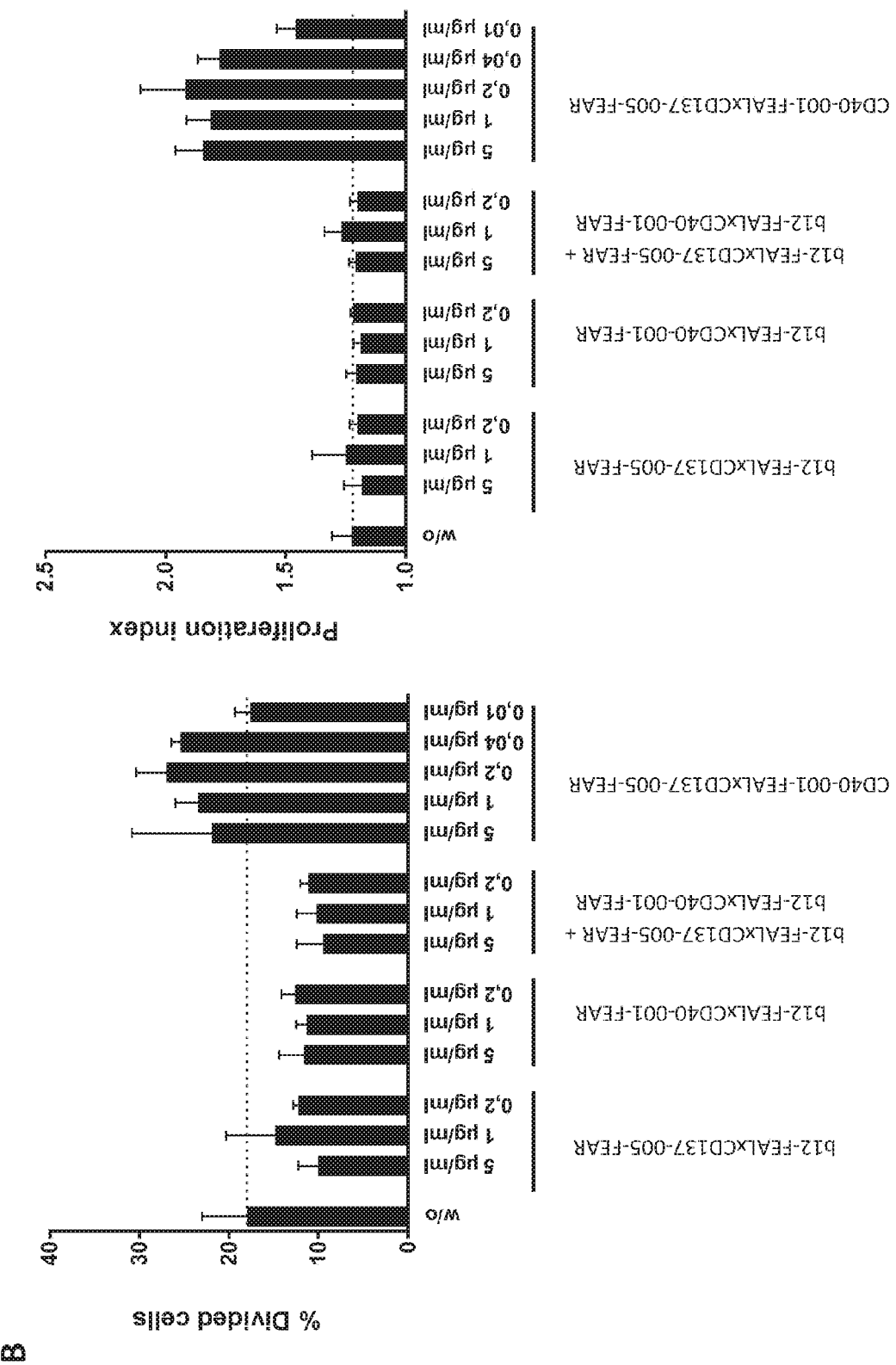
Figure 8:
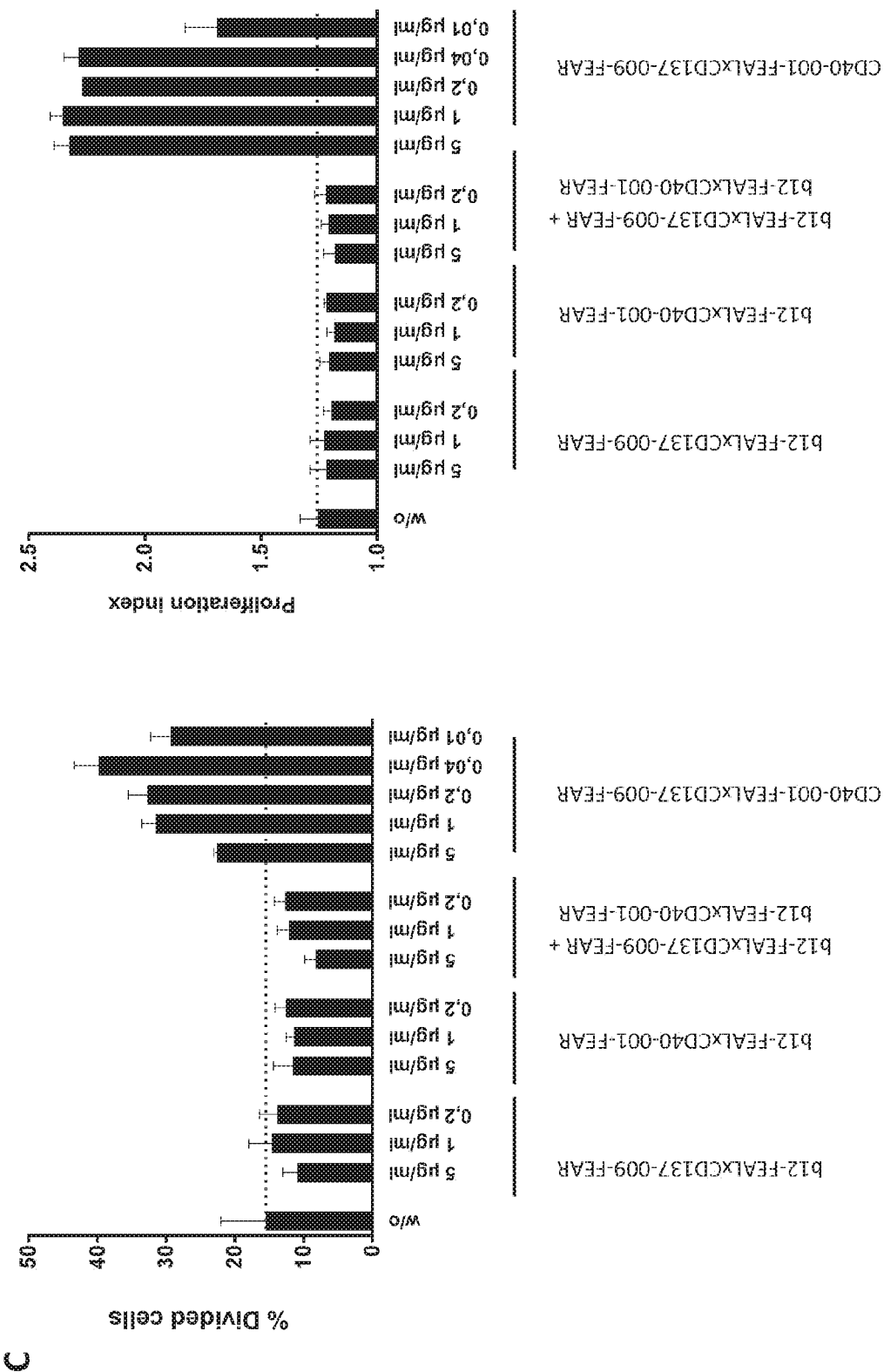
Figure 8:
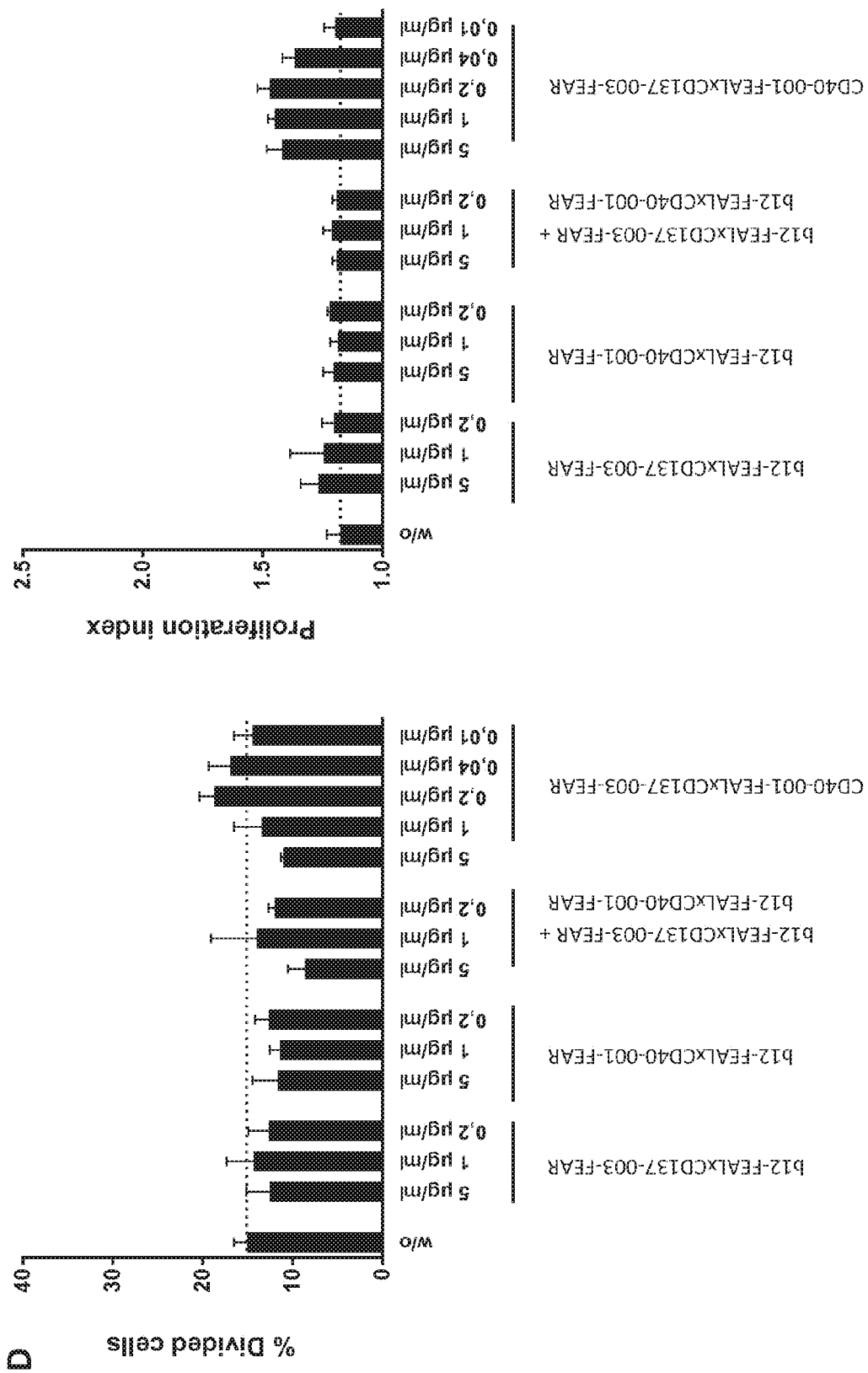
Figure 8:
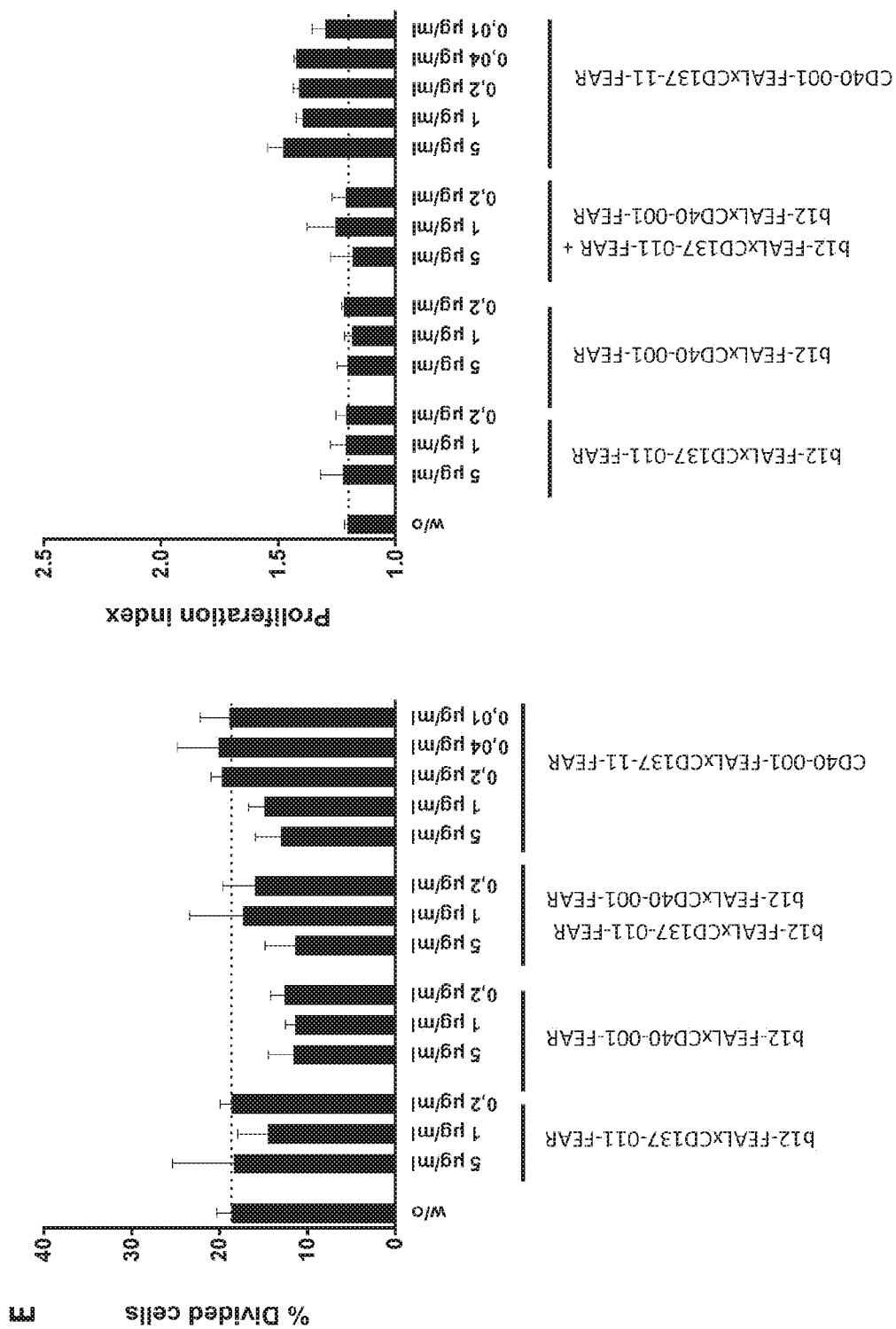

FIG. 8A shows that only the CD40xCD137 bispecific antibodies efficiently enhanced proliferation of $CD8^+$ T cells. The control monospecific, monovalent antibodies (b12xCD40; b12xCD137) and the combination of monospecific, monovalent CD40 with monospecific, monovalent CD137 antibodies (b12xCD40+b12xCD137) did not induce more proliferation than observed in the control (only the weakly activated PBMCs, ctrl, w/o). The flow cytometry histograms, for the different antibodies at different concentrations, were quantified to indicate percentage of divided cells (FIG. 8B) and proliferation index (FIG. 8C), as described supra. These figures show that only the bispecific antibodies were capable of inducing proliferation of $CD8^+$ cells, with an optimum between 0.04 and 0.2 μg/mL.

Example 6: Antigen-Specific $CD8^+$ T Cell Proliferation Assay to Measure Trans-Activation by Bispecific Antibodies Binding to CD40 and CD137

To measure induction of proliferation by the bispecific antibodies in an antigen-specific assay, dendritic cells (DCs) were transfected with claudin 6 in vitro-transcribed RNA (IVT-RNA,) to express the claudin 6 antigen. T cells were transfected with the claudin-6-specific, HLA-A2-restricted T cell receptor (TCR). This TCR can recognize the claudin-6-derived epitope presented in HLA-A2 on the DC. The CD40xCD137 bispecific antibody can cross-link CD40 on the dendritic cell and CD137 on the T cell, leading to activation of the DC and a co-stimulatory signal to the T cell, resulting in T-cell proliferation.

$HLA-A2^+$ PBMCs were obtained from healthy donors (Transfusionszentrale, University Hospital, Mainz, Germany). Monocytes were isolated from PBMCs by magnetic-activated cell sorting (MACS) technology using anti-CD14 MicroBeads (Miltenyi; cat. no. 130-050-201), according to the manufacturer's instructions. The peripheral blood lymphocytes (PBLs, CD14-negative fraction) were frozen for future T-cell isolation. For differentiation into immature DCs (iDCs), $1 \times 10^6$ monocytes/mL were cultured in RPMI GlutaMAX (Life technologies GmbH, cat. no. 61870-044) containing 5% human AB serum (Sigma-Aldrich Chemie GmbH, cat. no. H4522-100ML), sodium pyruvate (Life technologies GmbH, cat. no. 11360-039), non-essential amino acids (Life technologies GmbH, cat. no. 11140-035), 100 IU/mL penicillin-streptomycin (Life technologies GmbH, cat. no. 15140-122), 1000 IU/mL granulocyte-macrophage colony-stimulating factor (GM-CSF; Miltenyi, cat. no. 130-093-868) and 1000 IU/mL interleukin 4 (IL-4; Miltenyi, cat. no. 130-093-924), for five days. Once during these five days, half of the medium was replaced with fresh medium. iDCs were harvested by collecting non-adherent cells; adherent cells were detached by incubation with PBS containing 2 mM EDTA for 10 min at 37°. After washing, iDCs were frozen in RPMI GlutaMAX containing 10% v/v DMSO (AppliChem GmbH, cat. no A3672,0050) and 50% v/v human AB serum for future antigen-specific T cell assays.

One day before T-cell assays were started, frozen PBLs and iDCs, from the same donor, were thawed. PBLs were used for isolation of $CD8^+$ T cells by MACS technology using anti-CD8 MicroBeads (Miltenyi, cat. no. 130-045-201), according to the manufacturer's instructions. About $10-15 \times 10^6$ $CD8^+$ T cells were electroporated with 10 μg IVT-RNA encoding the alpha-chain plus 10 μg of IVT-RNA encoding the beta-chain of a claudin-6-specific murine TCR (HLA-A2-restricted; described in WO 2015150327 A1) in 250 μL X-Vivo15 (Biozym Scientific GmbH, cat. no. 881026) in a 4-mm electroporation cuvette (VWR International GmbH, cat. no. 732-0023) using the BTX ECM® 830 Electroporation System device (BTX; 500 V, 1×3 ms pulse). Immediately after electroporation, cells were transferred into fresh IMDM medium (Life Technologies GmbH, cat.

no. 12440-061) supplemented with 5% human AB serum and rested at 37° C., 5% $CO_2$ for at least 1 hour. T cells were labeled using 1.6 µM carboxyfluorescein succinimidyl ester (CFSE; Invitrogen, cat. no. C34564) in PBS, according to the manufacturer's instructions, and incubated in IMDM medium supplemented with 5% human AB serum, O/N.

Up to $5 \times 10^6$ thawed iDCs were electroporated with 0.4-5 µg IVT-RNA encoding full length claudin-6 (Uniprot P56747), in 250 µL X-Vivo15 medium, using the electroporation system as described above (300 V, 1×12 ms pulse) and incubated in IMDM medium supplemented with 5% human AB serum, O/N.

The next day, cells were harvested. Cell surface expression of claudin-6 on DCs and TCR on T cells were checked by flow cytometry. Therefore, DCs were stained with an Alexa647-conjugated CLDN6-specific antibody (not commercially available; in-house production) and T cells were stained with an anti-mouse TCR B Chain antibody (Becton Dickinson GmbH, cat. no. 553174). 5,000 electroporated DCs were incubated with 50,000 electroporated, CFSE-labeled T cells in the presence of bispecific or control antibodies in IMDM GlutaMAX (Life Technologies, cat. no. 12440-061) supplemented with 5% human AB serum in a 96-well round-bottom plate. T-cell proliferation was measured after 5 days by flow cytometry. Detailed analyses of T-cell proliferation based on CFSE-peaks indicating cell divisions were made by FlowJo 7.6.5 software. Mean percentages of T cells that went into division (% divided cells) and the average number of divisions of cells that went into division (proliferation index) were calculated.

Figure 9:
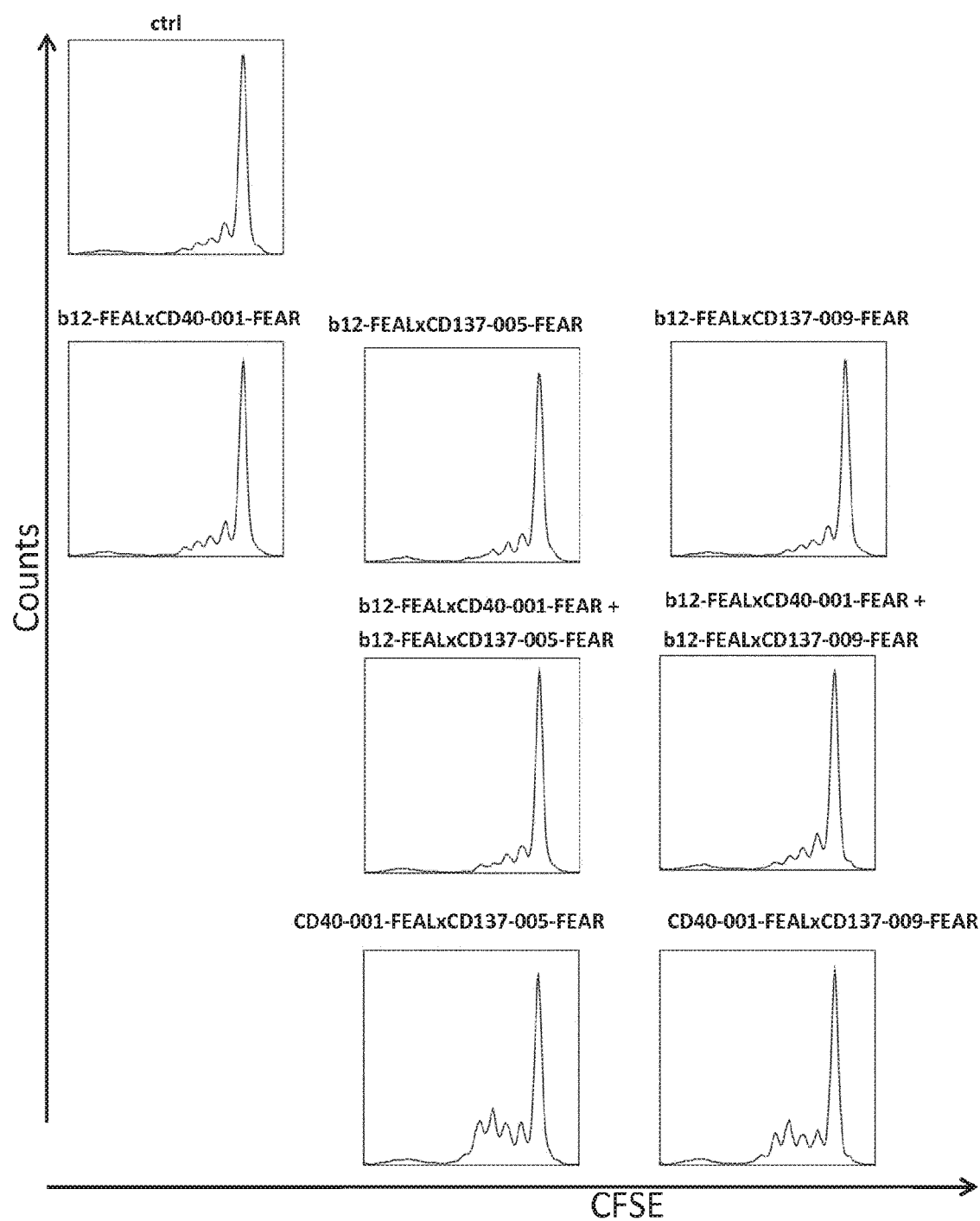
FIG. 9: Enhancement of CD8+ T-cell proliferation by CD40xCD137 bispecific antibodies in an antigen-specific T-cell assay. T cells transfected with a claudin-6-specific TCR and labeled with CFSE were incubated with claudin-6 IVT-RNA-electroporated immature DCs in the presence or absence of CD40xCD137 bispecific antibodies or control antibodies for five days. CD8+ T-cell proliferation was measured by flow cytometry. Data shown are CFSE plots showing CD8+ T-cell proliferation induced by the indicated bispecific antibodies and controls at 0.02 µg/mL (A), percentages divided cells and proliferation indices for the indicated bispecific antibodies (B) and for CD40-001-FEALxCD137-005-FEAR and control antibodies (C) and CD40-001-FEALxCD137-009-FEAR and control antibodies (D) at the indicated concentrations, as calculated using FlowJo software. Proliferation index curves for the indicated bispecific antibodies at serial dilutions ranging from 6.4× $10^{-5}$ to 5 µg/mL are also shown (E). Curves were analyzed by non-linear regression (sigmoidal dose-response with variable slope) using GraphPad Prism 5 software (GraphPad Software, San Diego, Calif., USA). The EC50 values for induction of T-cell proliferation for CD40-001-FEALxCD137-005-FEAR and CD40-001-FEALxCD137-009-FEAR were 0.005 and 0.030 µg/mL, respectively.
Figure 9:
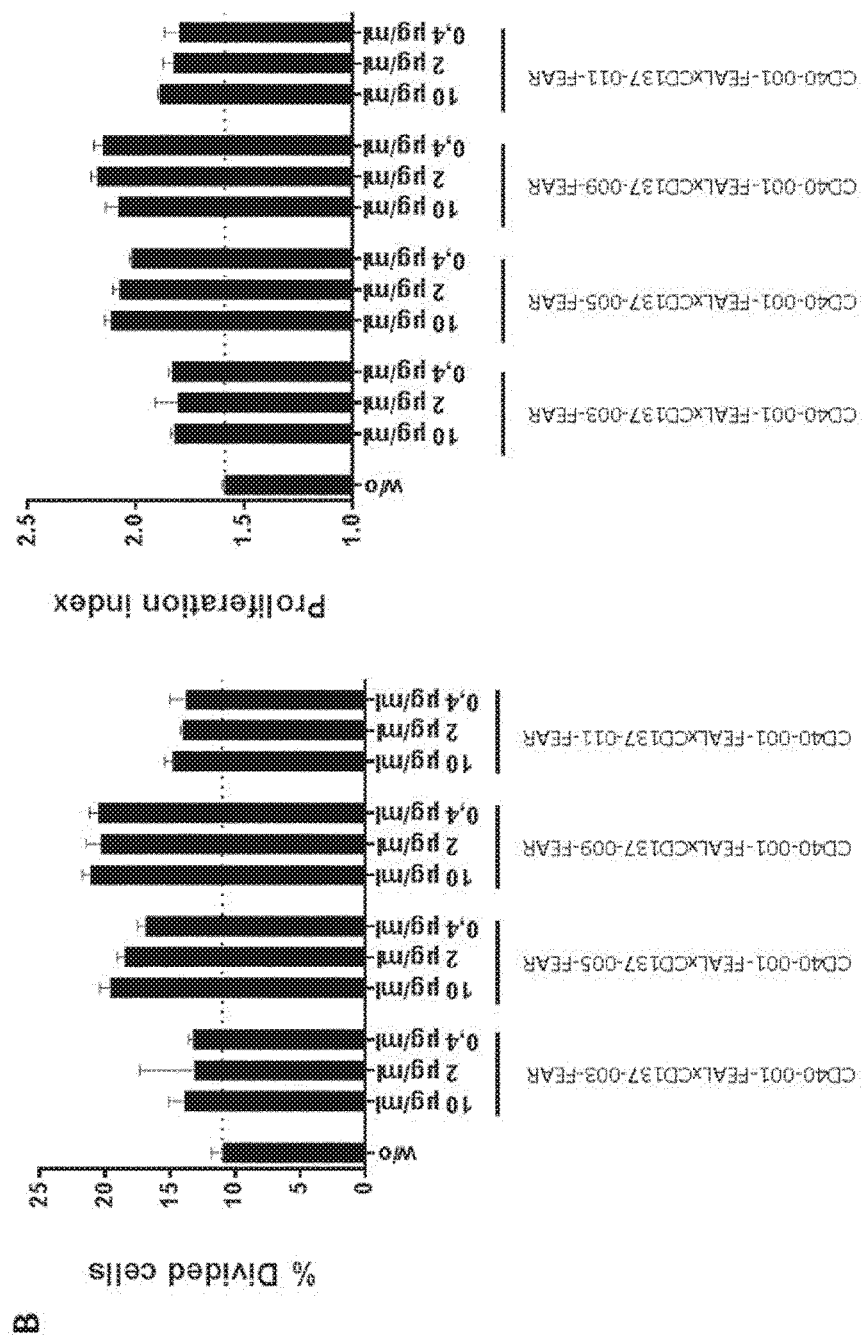
Figure 9:
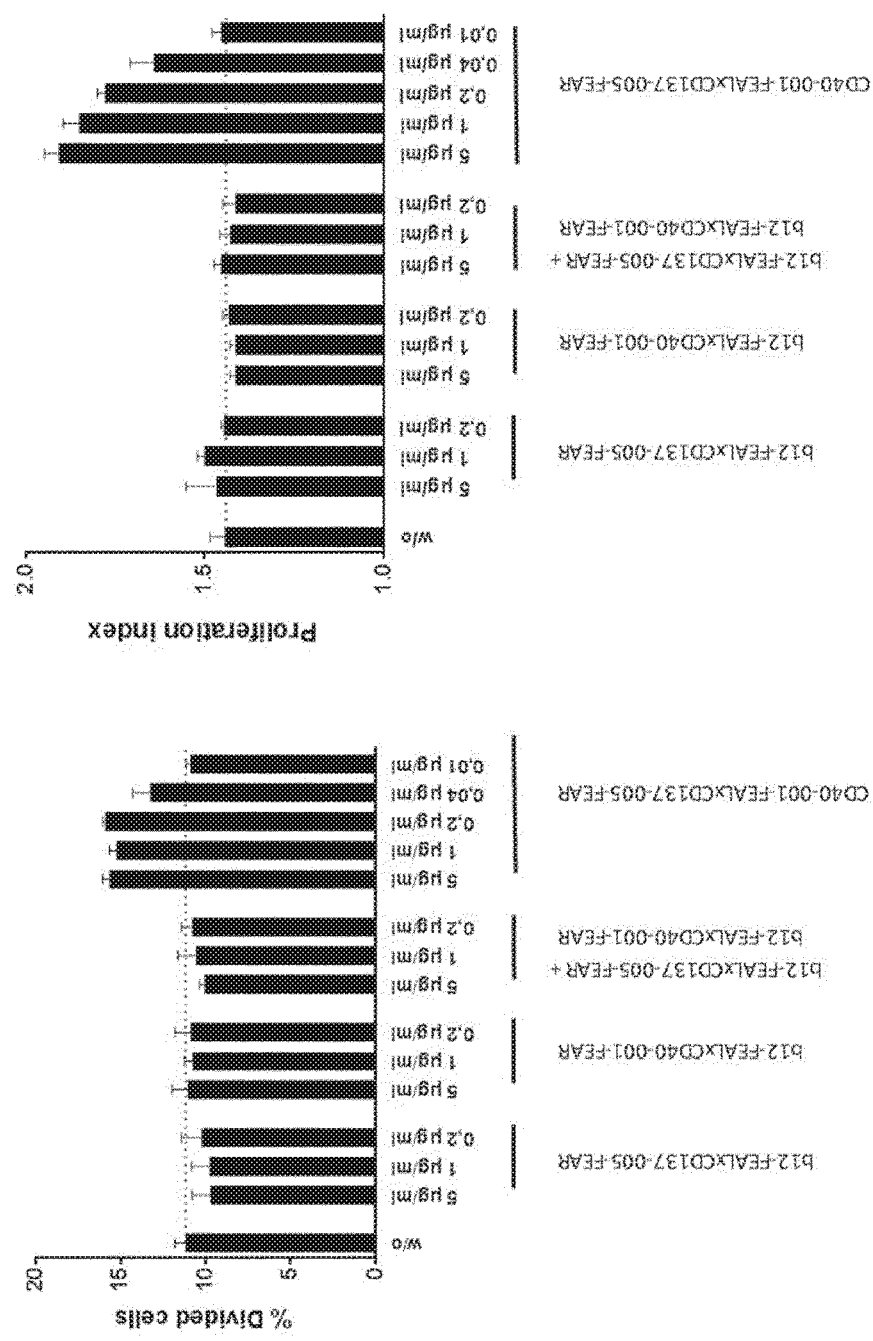
Figure 9:
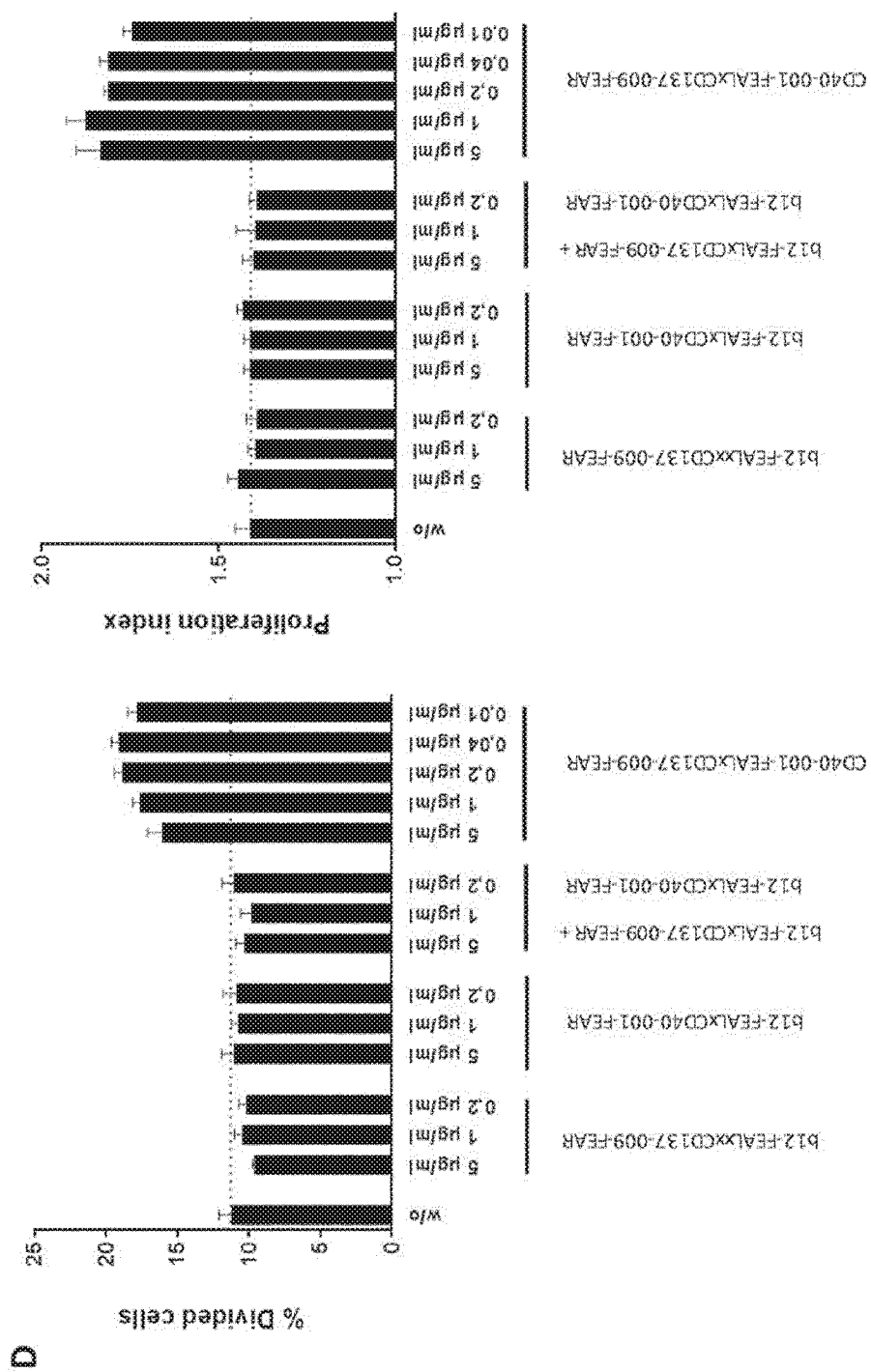
Figure 9:
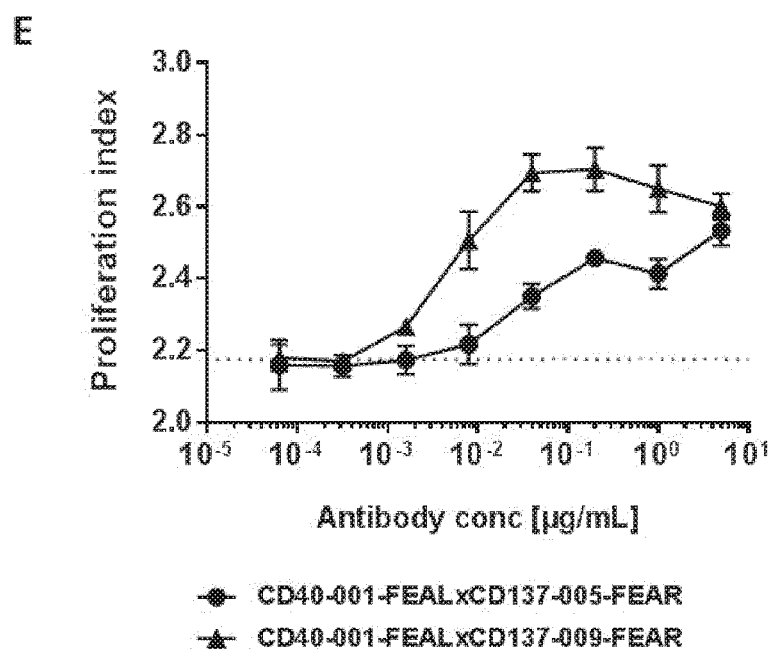

FIG. 9A shows that only the CD40xCD137 bispecific antibodies efficiently enhanced proliferation of $CD8^+$ T cells. The control monospecific, monovalent antibodies (b12xCD40; b12xCD137) and the combination of monospecific, monovalent CD40 with monospecific, monovalent CD137 antibodies (b12xCD40+b12xCD137) did not induce more proliferation than observed in the control (only the weakly activated PBMCs, ctrl, w/o). The same is also reflected in the percentage of divided cells (FIG. 9B) and is very clear from the proliferation index (FIG. 9C). FIG. 9D shows that the induction of antigen-specific proliferation by the CD40xCD137 bispecific antibodies was concentration dependent, with an optimum around 0.1 µg/mL in this assay.

Example 7: Humanization of Murine and Rabbit Antibodies

Humanized antibody sequences from the antibodies mouse anti-CD40-001 and rabbit anti-CD137-009 were generated at Antitope (Cambridge, UK). Humanized antibody sequences were generated using germline humanization (CDR-grafting) technology. Humanized V region genes were designed based upon human germline sequences with closest homology to the VH and Vκ amino acid sequences of the murine and rabbit antibodies. A series of four to six VH and four or five Vκ (VL) germline humanized V-region genes were designed for each of the non-human parental antibodies. Structural models of the non-human parental antibody V regions were produced using Swiss PDB and analyzed in order to identify amino acids in the V region frameworks that may be important for the binding properties of the antibody. These amino acids were noted for incorporation into one or more variant CDR-grafted antibodies. The closest matching germline sequences used as the basis for the humanized designs are shown in Table 3.

TABLE 3

Closest matching human germline V segment and J segment sequences.

| Antibody | Heavy chain | | Light chain (K) | |
|---|---|---|---|---|
| | Human V region germline segment | Human J region germline segment | Human V region germline segment | Human J region germline segment |
| Mouse anti-CD40-001 | hIGHV1-46*01 | hIGHJ4 | hIGKV1-33*01 | IGKJ4 |
| Rabbit anti-CD137-009 | hIGHV3-49*04 | hIGHJ4 | hIGKV1-33*01 | IGKJ4 |

Variant sequences with the lowest incidence of potential T cell epitopes were then selected using Antitope's proprietary in silico technologies, iTope™ and TCED™_ (T Cell Epitope Database) (Perry, L. C. A, Jones, T. D. and Baker, M. P. New Approaches to Prediction of Immune Responses to Therapeutic Proteins during Preclinical Development (2008). Drugs in R&D 9 (6): 385-396; 20; Bryson, C. J., Jones, T. D. and Baker, M. P. Prediction of Immunogenicity of Therapeutic Proteins (2010). Biodrugs 24 (1):1-8). Finally, the nucleotide sequences of the designed variants were codon-optimized for expression in human cells.

The variable region sequences of the humanized CD40 and CD137 antibodies are shown in the Sequence Listing and in Table 1 above.

Example 8: Expression Constructs for Antibodies, Transient Expression and Purification For antibody expression the VH and VL sequences were cloned in expression vectors (pcDNA3.3) containing, in case of the VH, the relevant constant heavy chain (HC), in certain cases containing a F405L or K409R mutation, and/or L234F, L235E and D265A, and, in case of the VL, light chain (LC) regions. Antibodies were expressed as IgG1,κ. Plasmid DNA mixtures encoding both heavy and light chains of antibodies were transiently transfected in Expi293F cells (Life technologies, USA) using 293fectin (Life technologies) essentially as described by Vink et al. (Vink et al., Methods, 65 (1), 5-10 2014). Next, antibodies were purified by immobilized protein G chromatography.

Example 9: Non-Specific T-Cell Proliferation Assay to Test the Functionality of a Humanized Bispecific Antibody Binding to CD40 and CD137

To measure the functionality of a humanized bispecific antibody binding to CD40 and CD137, a non-antigen-specific T-cell proliferation assay was performed as described supra. In short, PBMCs of one donor were CFSE-labeled and incubated with a sub-optimal concentration of anti-CD3 antibody (clone UCHT1; 0.01 µg/mL as determined for this donor) and 0.008, 0.04, 0.2 or 1 µg/mL humanized CD40xCD137 bispecific antibody, the parental bispecific antibody or IgG1 control antibody.

Proliferation of $CD8^+$ T cells was analyzed by flow cytometry, essentially as described supra. Detailed analyses of T-cell proliferation based on CFSE-peaks indicating cell divisions were made by FlowJo 7.6.5 software. Mean percentages of T cells that went into division (% divided cells) and the average number of divisions of cells that went into division (proliferation index) were calculated.

Figure 10:
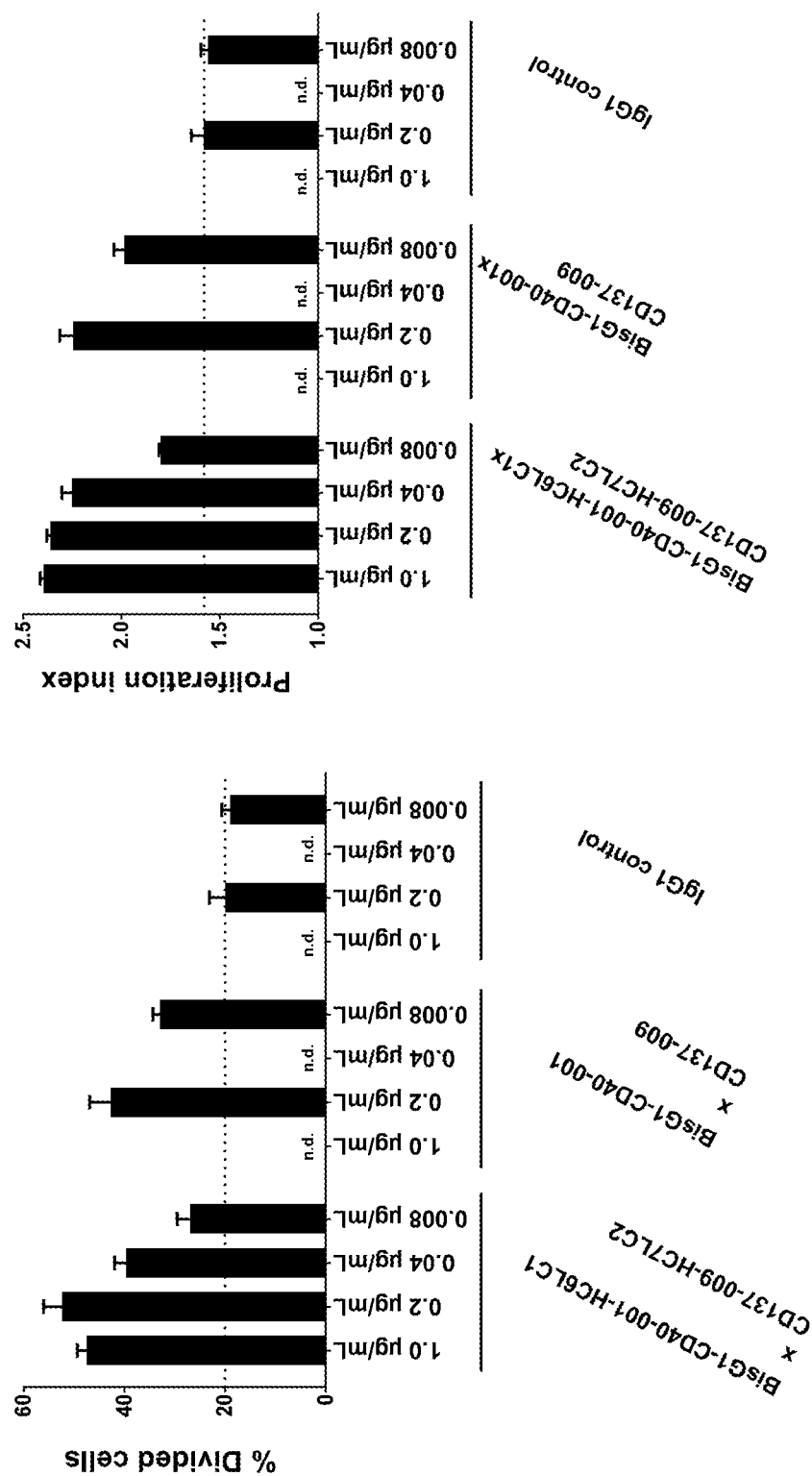
FIG. 10: Induction of CD8+ T-cell proliferation by the humanized CD40xCD137 bispecific antibody in a non-antigen-specific T cell assay. CFSE-labeled PBMCs were incubated with humanized CD40xCD137 bispecific antibody, the parental bispecific antibody or IgG1 control antibody for four days. Proliferation of CD8+ T cells was measured by flow cytometry. Data shown are percentages of divided cells and proliferation index, as calculated by FlowJo software. (n.d.=not determined)

FIG. 10 shows that the humanized CD40xCD137 bispecific antibody (BisG1-CD40-001-HC6LC1-FEALxCD137-

009-HC7LC2-FEAR) efficiently enhanced proliferation of CD8+ T cells. The humanized bispecific antibody enhanced both the percentage of divided cells and the average number of divisions of CD8+ cells. Efficacy of the humanized bispecific antibody was comparable to that of the parental bispecific antibody (CD40-001xCD137-009).

Example 10: Antigen-Specific CD8+ T-Cell Proliferation Assay to Test the Functionality of the Humanized Bispecific Antibody Binding to CD40 and CD137

To measure the functionality of the humanized bispecific antibody binding to CD40 and CD137, an antigen-specific CD8+ T-cell proliferation assay was performed as described supra. In short, CFSE-labeled, CLDN6-TCR transfected CD8+ T-cells were incubated with CLDN6 RNA-electroporated DCs in the presence of humanized CD40xCD137 bispecific antibody, the parental antibody or IgG1 control antibody. T-cell proliferation was measured by flow cytometry after 4 days. Detailed analyses of T-cell proliferation based on CFSE-peaks indicating cell divisions were made by FlowJo 7.6.5 software. Mean percentages of T cells that went into division (% divided cells) and the average number of divisions of cells that went into division (proliferation index) were calculated.

Figure 11:
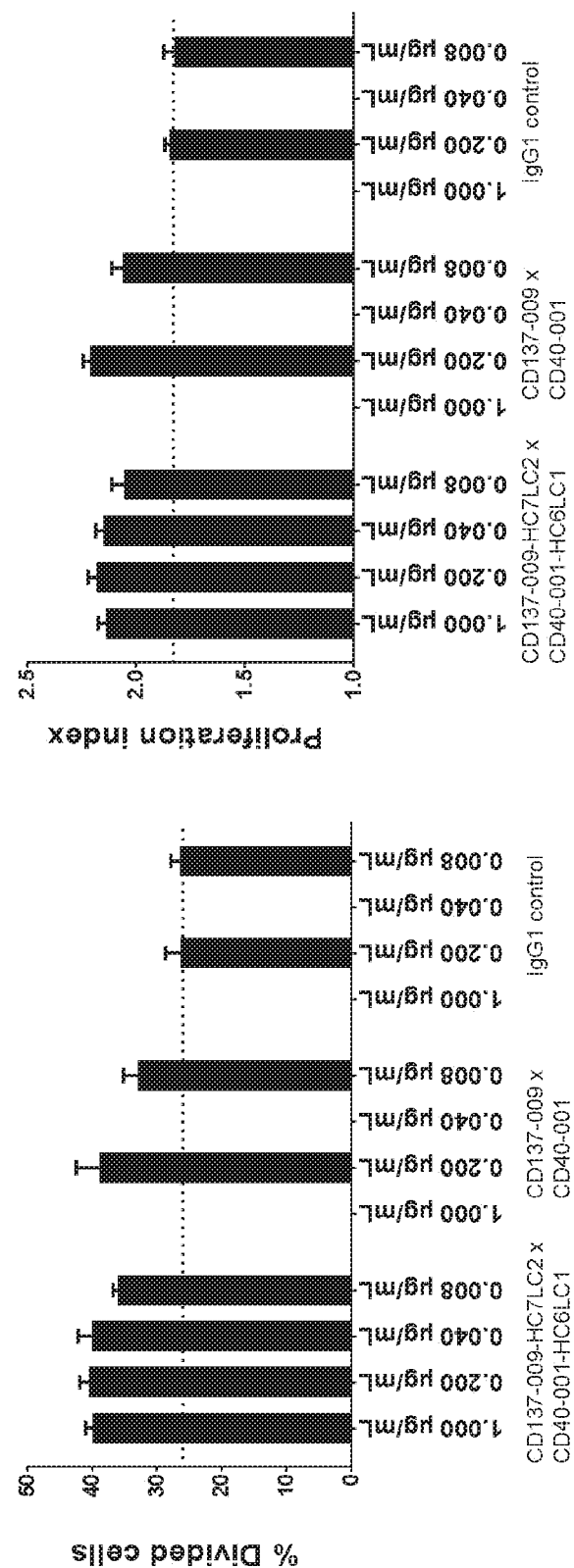
FIG. 11: Enhancement of CD8+ T-cell proliferation by a humanized CD40xCD137 bispecific antibody in an antigen-specific T-cell assay. T cells transfected with a claudin-6-specific TCR and labeled with CFSE were incubated with claudin-6 IVT-RNA-electroporated immature DCs in the presence or absence of a humanized CD40xCD137 bispecific antibody (BisG1-CD40-001-H6LC1-FEALxCD137-009-HC7LC2-FEAR), the parental bispecific antibody or an IgG1 control antibody for four days. CD8+ T-cell proliferation was measured by flow cytometry. Data shown are percentages divided cells and proliferation indices for the indicated antibodies, as calculated using FlowJo software. (n.d.=not determined)

FIG. 11 shows that the humanized CD40xCD137 bispecific antibody (BisG1-CD40-001-H6LC1-FEALxCD137-009-HC7LC2-FEAR) efficiently enhanced proliferation of CD8+ T cells. Efficacy of the humanized bispecific antibody was comparable to that of the parental bispecific antibody (CD40-001xCD137-009). Both the humanized and the parental bispecific antibody enhanced the percentage of divided cells as well as the proliferation index of the CD8+ cells in this assay.

Example 11: Ex Vivo TIL Expansion Assay to Evaluate the Effects of CD40xCD137 Bispecific Antibodies on Tumor Infiltrating Lymphocytes To evaluate the effects of CD40xCD137 bispecific antibody (BisG1-CD40-001-FEAL/CD137-009-FEAR) on tumor infiltrating lymphocytes (TIL), ex vivo culture of human tumor tissue was performed as follows. Freshly human tumor tissue resections were washed three times by transferring the isolated tumor chunks from one wash medium-containing well of a six-well plate (Fisher Scientific cat. no. 10110151) to the next using a spatula or serological pipette. Wash medium was composed of X-VIVO 15 (Biozym, cat. no. 881024) supplemented with 1% Pen/Strep (Thermo Fisher, cat. no. 15140-122) and 1% Fungizone (Thermo Fisher, cat. no. 15290-026). Next, the tumor was dissected with a surgical knife (Braun/Roth, cat. no. 5518091 BA223) and cut into tumor pieces with a diameter of about 1-2 mm. Two pieces each were put into one well of a 24-well plate (VWR international, cat. no. 701605) containing 1 mL TIL medium (X-VIVO 15, 10% Human Serum Albumin (HSA, CSL Behring, cat. no. PZN-6446518), 1% Pen/Strep, 1% Fungizone and IL-2 (Proleukin®S, Novartis Pharma, cat. no. 02238131) at the indicated concentration. Bispecific antibody binding to CD40 and CD137 was added at the indicated final concentrations. Culture plates were incubated at 37° C. and 5% $CO_2$ for 72 hours and 1 mL fresh TIL medium containing the indicated IL-2 concentration and the indicated concentration of bispecific antibody was added to each well. Wells were monitored for the occurrence of TIL clusters using a Leica DMi1 microscope equipped with a 5.0 megapixel camera, every other day. Wells were split on an individual basis, when more than 25 TIL microclusters were detected. To split TIL cultures, cells were re-suspended and transferred to a well of a 6-well plate and supplemented with another 2 mL of TIL medium.

After a total culture period of 10-14 days, TILs were harvested and analyzed by flow cytometry. To allow for quantitative comparison of the different treatment groups, cell pellets were re-suspended after the last washing step with FACS-buffer supplemented with BD™ CompBeads (BD biosciences, cat. no. 51-90-9001291). Flow cytometric analysis was performed on a BD FACSCanto™ II flow cytometer (Becton Dickinson) and acquired data was analyzed using FlowJo 7.6.5 software. The relative viable TIL count (7-AAD-negative cells) per 1,000 beads was calculated for each well.

Figure 12:
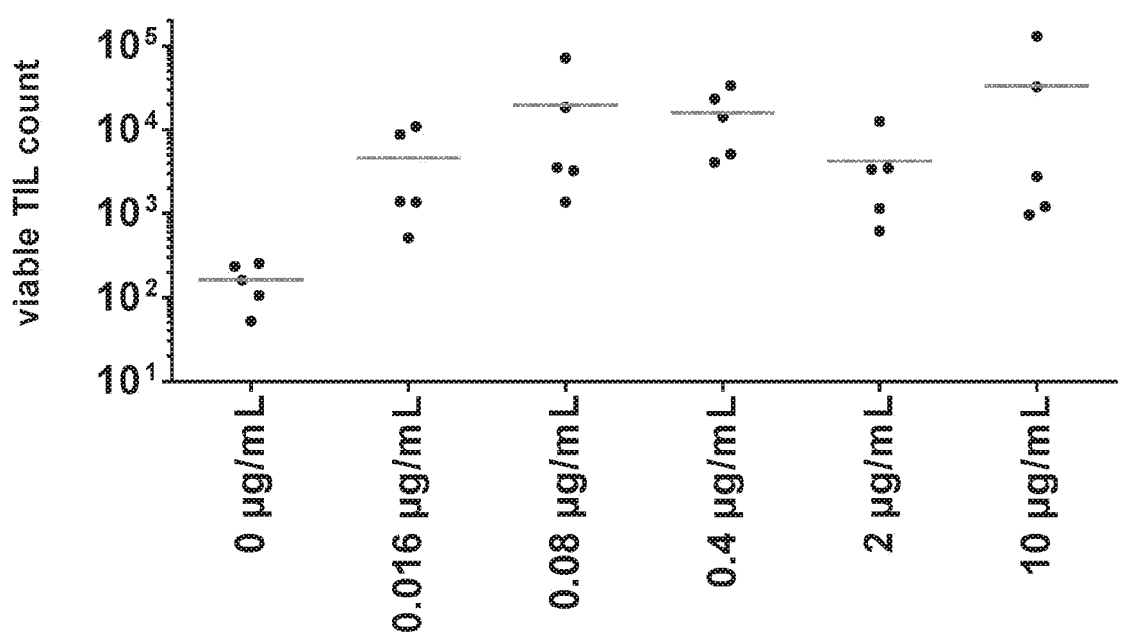
FIG. 12: Ex vivo expansion of TILs from a human melanoma tissue resection by a CD40xCD137 bispecific antibody. Tumor pieces from the resected tissue were cultured with 100 U/mL IL-2 and the indicated concentration of a CD40xCD137 bispecific antibody (BisG1-CD40-001-FEALxCD137-009-FEAR). After 14 days of culture, cells were harvested and analyzed by flow cytometry. Relative viable TIL count per sample (normalized to 1,000 measured counting beads) is shown. Each data point refers to a single well, representing the expansion of TILs out of two tumor pieces analyzed in one FACS tube. The line indicates the mean of five measured samples.

FIG. 12 shows the analysis of a TIL expansion from a human melanoma tissue. Here, 100 U/mL IL-2 was used as supplement for the TIL medium. Moreover, the following concentrations of the bispecific antibody binding to CD40 and CD137 (BisG1-CD40-001-FEAL/CD137-009-FEAR) were added: 0.016, 0.08, 0.4, 2.0 and 10.0 µg/mL; wells without antibody addition served as negative control. After 14 days of culture, TILs were harvested and analyzed by flow cytometry. Five samples for each antibody concentration, derived from different wells of the 24-well plate, were measured. In all samples cultured with the bispecific antibody binding to CD40 and CD137 the viable count of TIL was substantially increased in comparison to the control samples without antibody. Overall, about a 100-fold increase of the mean relative viable TIL count was observed (FIG. 12).

Figure 13:
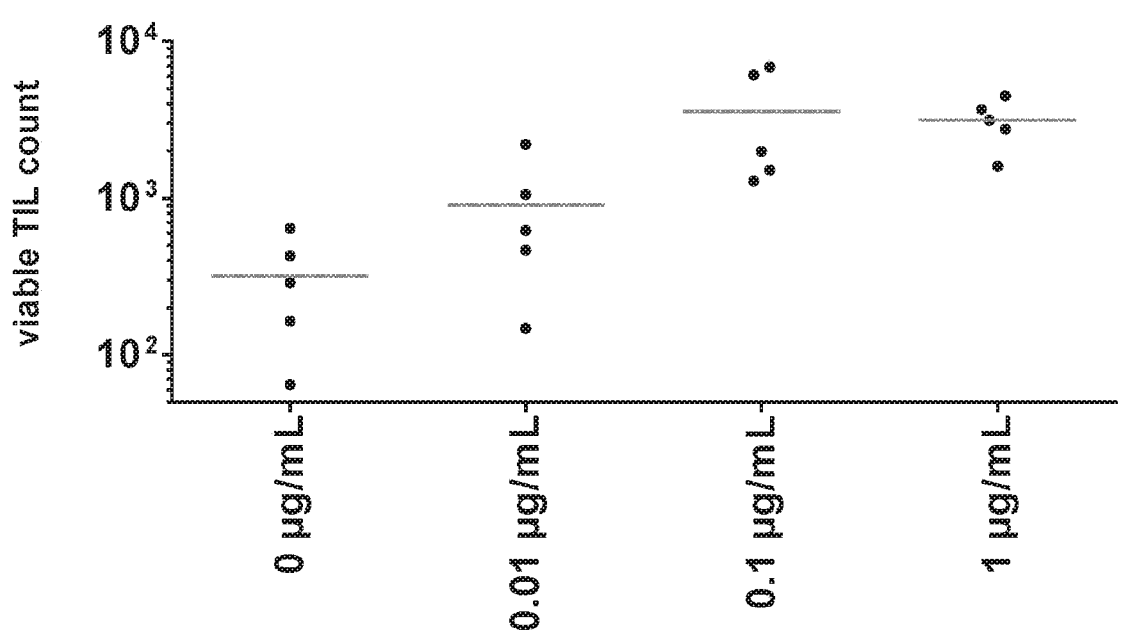
FIG. 13: Ex vivo expansion of TILs from a human non-small cell lung cancer (NSCLC) tissue resection by a CD40xCD137 bispecific antibody. Tumor pieces from resected NSCLC tissue were cultured with 10 U/mL IL-2 and the indicated concentration of CD40xCD137 bispecific antibody (BisG1-CD40-001-FEALxCD137-009-FEAR). After 10 days of culture, cells were harvested and analyzed by flow cytometry. Relative viable TIL count per sample (normalized to 1,000 measured counting beads) is shown. Each data point refers to a single well, representing the expansion of TILs out of two tumor pieces analyzed in one FACS tube. The line indicates the mean of five measured samples.

FIG. 13 shows the analysis of a TIL expansion from a non-small cell lung cancer (NSCLC) tissue. Here, 10 U/mL IL-2 was used as supplement for the TIL medium. In addition, the following final concentrations of the bispecific antibody binding to CD40 and CD137 (BisG1-CD40-001-FEAL/CD137-009-FEAR) were administered: 0.01, 0.1, and 1.0 µg/mL; wells without antibody addition served as negative control. After 10 days of culture, TILs were harvested and analyzed by flow cytometry. Five samples for each antibody concentration, derived from different wells of the 24-well plate, were measured. In all samples cultured with the bispecific antibody binding to CD40 and CD137, the viable count of TIL was substantially increased in comparison to the control samples without antibody. Overall, an up to 10-fold increase of the mean relative viable TIL count was observed at 0.1 or 1 µg/mL (FIG. 13).

The invention claimed is:

1. A method of producing a multispecific antibody, comprising:
   a) providing a first antibody comprising two first antigen-binding regions and a first Fc region,
      wherein each first antigen-binding region is capable of binding to CD40 and comprises three heavy chain CDRs comprising amino acid sequences of SEQ ID NO:1 (HCDR1), SEQ ID NO:2 (HCDR2), and SEQ ID NO:3 (HCDR3); and three light chain CDRs comprising amino acid sequences of SEQ ID NO:4 (LCDR1), YTS (LCDR2), and SEQ ID NO:5 (LCDR3); and
      wherein the first Fc region comprises a first CH3 region;
   b) providing a second antibody comprising two second antigen-binding regions and a second Fc region,
      wherein each second antigen-binding region is capable of binding to CD137 and comprises:
      i) three heavy chain CDRs comprising amino acid sequences of SEQ ID NO:64 (HCDR1), SEQ ID NO:65 (HCDR2), and SEQ ID NO:66 (HCDR3); and three light chain CDRs comprising amino acid sequences of SEQ ID NO:67 (LCDR1), GAS (LCDR2), and SEQ ID NO:68 (LCDR3); or
      ii) three heavy chain CDRs comprising amino acid sequences of SEQ ID NO:36 (HCDR1), SEQ ID NO:37 (HCDR2), and SEQ ID NO:38 (HCDR3); and three light chain CDRs comprising amino acid sequences of SEQ ID NO:39 (LCDR1), SAS (LCDR2), and SEQ ID NO:40 (LCDR3); and
      wherein the second Fc region comprises a second CH3 region; and wherein the amino acid sequences of the first and second CH3 regions are different, and wherein the heterodimeric interaction between the first and second CH3 regions has a lower dissociation equilibrium constant ($K_D$) than each of the homodimeric interactions of the first and second CH3 regions;
   c) incubating the first antibody together with the second antibody under reducing conditions; and
   d) isolating a CD40xCD137 antibody.

2. The method of claim 1, wherein each of the first antigen-binding regions comprises: (i) a heavy chain variable region (VH) comprising an amino acid sequence having at least 90% identity to SEQ ID NO:117 or SEQ ID NO:6; and/or (ii) a light chain variable region (VL) comprising an amino acid sequence having at least 90% identity to SEQ ID NO:121 or SEQ ID NO:7.

3. The method of claim 1, wherein each of the first antigen-binding regions comprises a VH comprising an amino acid sequence of SEQ ID NO:117; and a VL comprising an amino acid sequence of SEQ ID NO:121.

4. The method of claim 1, wherein each of the second antigen-binding regions comprises three heavy chain CDRs comprising amino acid sequences of SEQ ID NO:64 (HCDR1), SEQ ID NO:65 (HCDR2), and SEQ ID NO:66 (HCDR3); and three light chain CDRs comprising amino acid sequences of SEQ ID NO:67 (LCDR1), GAS (LCDR2), and SEQ ID NO:68 (LCDR3).

5. The method of claim 1, wherein each of the second antigen-binding regions comprises a VH comprising an amino acid sequence having at least 90% identity to SEQ ID NO:123 or SEQ ID NO:69.

6. The method of claim 1, wherein each of the second antigen-binding regions comprises a VL comprising an amino acid sequence having at least 90% identity to SEQ ID NO:127 or SEQ ID NO:70.

7. The method of claim 1, wherein each of the second antigen-binding regions comprises a VH comprising an amino acid sequence of SEQ ID NO:123; and a VL comprising an amino acid sequence of SEQ ID NO:127.

8. The method of claim 1, wherein each of the second antigen-binding regions comprises three heavy chain CDRs comprising amino acid sequences of SEQ ID NO:36 (HCDR1), SEQ ID NO:37 (HCDR2), and SEQ ID NO:38 (HCDR3); and three light chain CDRs comprising amino acid sequences of SEQ ID NO:39 (LCDR1), SAS (LCDR2), and SEQ ID NO:40 (LCDR3).

9. The method of claim 1, wherein each of the second antigen-binding regions comprises a VH comprising an amino acid sequence having at least 90% identity to SEQ ID NO:41.

10. The method of claim 1, wherein each of the second antigen binding regions comprises a VL comprising an amino acid sequence having at least 90% identity to SEQ ID NO:42.

11. The method of claim 1, wherein each of the second antigen-binding regions comprises a VH comprising an amino acid sequence of SEQ ID NO:41; and a VL comprising an amino acid sequence of SEQ ID NO:42.

12. The method of claim 1, wherein the first and second Fc regions each comprise at least a hinge region, a CH2 region, and a CH3 region.

13. The method of claim 1, wherein the first and second CH3 regions each comprise one or more asymmetrical amino acid mutations.

14. The method of claim 1, wherein the first and second CH3 regions each comprise an amino acid substitution at one or more positions corresponding to EU index positions T366, L368, K370, D399, F405, Y407, and/or K409 in a human IgG1 heavy chain; and wherein the first and second heavy chains comprise amino acid substitutions at non-identical positions.

15. The method of claim 1, wherein the first CH3 region comprises a leucine (L) at the position corresponding to EU index position F405 in a human IgG1 heavy chain, and the second CH3 region comprises an arginine (R) at the position corresponding to EU index position K409 in a human IgG1 heavy chain.

16. The method of claim 1, wherein the first CH3 region comprises an arginine (R) at the position corresponding to EU index position K409 in a human IgG1 heavy chain, and the second CH3 region comprises a leucine (L) at the position corresponding to EU index position F405 in a human IgG1 heavy chain.

17. The method of claim 1, wherein the first and second Fc regions each comprise a phenylalanine (F) and a glutamic acid (E) at positions corresponding to EU index positions L234 and L235 in a human IgG1 heavy chain, respectively.

18. The method of claim 1, wherein the first and second Fc regions each comprise a phenylalanine (F), a glutamic acid (E), and an alanine (A) at positions corresponding to EU index positions L234, L235, and D265 in a human IgG1 heavy chain, respectively.

19. The method of claim 18, wherein the first Fc region comprises a leucine (L) at the position corresponding to EU index position F405 in a human IgG1 heavy chain and the second Fc region comprises an arginine (R) at the position corresponding to EU index position K409 in a human IgG1 heavy chain.

20. The method of claim 18, wherein the second Fc region comprises a leucine (L) at the position corresponding to EU index position F405 in a human IgG1 heavy chain and the first Fc region comprises an arginine (R) at the position corresponding to EU index position K409 in a human IgG1 heavy chain.

* * * * *

UNITED STATES PATENT AND TRADEMARK OFFICE
CERTIFICATE OF CORRECTION

| | |
|---|---|
| PATENT NO. | : 11,091,557 B2 |
| APPLICATION NO. | : 16/316534 |
| DATED | : August 17, 2021 |
| INVENTOR(S) | : Altintas et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 246 days.

Signed and Sealed this
Thirty-first Day of January, 2023

Katherine Kelly Vidal
*Director of the United States Patent and Trademark Office*

SEQUENCE LISTING

<160> NUMBER OF SEQ ID NOS: 136

<210> SEQ ID NO 1
<211> LENGTH: 8
<212> TYPE: PRT

```
<213> ORGANISM: Mus Musculus

<400> SEQUENCE: 1

Gly Tyr Thr Phe Thr Glu Tyr Ile
1               5

<210> SEQ ID NO 2
<211> LENGTH: 8
<212> TYPE: PRT
<213> ORGANISM: Mus Musculus

<400> SEQUENCE: 2

Ile Ile Pro Asn Asn Gly Gly Thr
1               5

<210> SEQ ID NO 3
<211> LENGTH: 15
<212> TYPE: PRT
<213> ORGANISM: Mus Musculus

<400> SEQUENCE: 3

Thr Arg Arg Glu Val Tyr Gly Arg Asn Tyr Tyr Ala Leu Asp Tyr
1               5                   10                  15

<210> SEQ ID NO 4
<211> LENGTH: 6
<212> TYPE: PRT
<213> ORGANISM: Mus Musculus

<400> SEQUENCE: 4

Gln Gly Ile Asn Asn Tyr
1               5

<210> SEQ ID NO 5
<211> LENGTH: 9
<212> TYPE: PRT
<213> ORGANISM: Mus Musculus

<400> SEQUENCE: 5

Gln Gln Tyr Ser Asn Leu Pro Tyr Thr
1               5

<210> SEQ ID NO 6
<211> LENGTH: 122
<212> TYPE: PRT
<213> ORGANISM: Mus Musculus

<400> SEQUENCE: 6

Glu Val Gln Leu Gln Gln Ser Gly Pro Asp Leu Val Lys Pro Gly Ala
1               5                   10                  15

Ser Val Lys Ile Ser Cys Lys Thr Ser Gly Tyr Thr Phe Thr Glu Tyr
            20                  25                  30

Ile Met His Trp Val Lys Gln Ser His Gly Lys Ser Leu Glu Trp Ile
        35                  40                  45

Gly Gly Ile Ile Pro Asn Asn Gly Gly Thr Ser Tyr Asn Gln Lys Phe
    50                  55                  60

Lys Asp Lys Ala Thr Met Thr Val Asp Lys Ser Ser Ser Thr Gly Tyr
65                  70                  75                  80

Met Glu Leu Arg Ser Leu Thr Ser Glu Asp Ser Ala Val Tyr Tyr Cys
                85                  90                  95

Thr Arg Arg Glu Val Tyr Gly Arg Asn Tyr Tyr Ala Leu Asp Tyr Trp
            100                 105                 110
```

```
Gly Gln Gly Thr Leu Val Thr Val Ser Ser
        115                 120
```

<210> SEQ ID NO 7
<211> LENGTH: 107
<212> TYPE: PRT
<213> ORGANISM: Mus Musculus

<400> SEQUENCE: 7

```
Asp Ile Gln Met Thr Gln Thr Thr Ser Ser Leu Ser Ala Ser Leu Gly
1               5                   10                  15
Asp Arg Val Thr Ile Thr Cys Ser Ala Ser Gln Gly Ile Asn Asn Tyr
            20                  25                  30
Leu Asn Trp Tyr Gln Gln Lys Pro Asp Gly Thr Val Lys Leu Leu Ile
        35                  40                  45
Tyr Tyr Thr Ser Ser Leu His Ser Gly Val Pro Ser Arg Phe Ser Gly
    50                  55                  60
Ser Gly Ser Gly Thr Asp Tyr Ser Leu Thr Ile Ser Asn Leu Glu Pro
65                  70                  75                  80
Glu Asp Ile Ala Thr Tyr Tyr Cys Gln Gln Tyr Ser Asn Leu Pro Tyr
                85                  90                  95
Thr Phe Gly Gly Gly Thr Lys Leu Glu Ile Lys
            100                 105
```

<210> SEQ ID NO 8
<211> LENGTH: 8
<212> TYPE: PRT
<213> ORGANISM: Oryctolagus cuniculus

<400> SEQUENCE: 8

```
Gly Phe Ser Leu Ser Ser Tyr Ala
1               5
```

<210> SEQ ID NO 9
<211> LENGTH: 7
<212> TYPE: PRT
<213> ORGANISM: Oryctolagus cuniculus

<400> SEQUENCE: 9

```
Ile Trp Asn Asn Gly Ala Thr
1               5
```

<210> SEQ ID NO 10
<211> LENGTH: 14
<212> TYPE: PRT
<213> ORGANISM: Oryctolagus cuniculus

<400> SEQUENCE: 10

```
Ala Arg Ser Ala Asn Asp Ala Trp Ser Thr Tyr Ser Asp Leu
1               5                   10
```

<210> SEQ ID NO 11
<211> LENGTH: 6
<212> TYPE: PRT
<213> ORGANISM: Oryctolagus cuniculus

<400> SEQUENCE: 11

```
Gln Thr Ile Thr Asn Tyr
1               5
```

<210> SEQ ID NO 12

```
<211> LENGTH: 14
<212> TYPE: PRT
<213> ORGANISM: Oryctolagus cuniculus

<400> SEQUENCE: 12

Gln Asn Tyr Tyr Tyr Gly Ser Ser Ser Gly Tyr Gly Phe Val
1               5                   10

<210> SEQ ID NO 13
<211> LENGTH: 117
<212> TYPE: PRT
<213> ORGANISM: Oryctolagus cuniculus

<400> SEQUENCE: 13

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Tyr Ala
            20                  25                  30

Val Ser Trp Val Arg Gln Ala Pro Gly Lys Gly Leu Glu Trp Ile Gly
        35                  40                  45

Val Ile Trp Asn Asn Gly Ala Thr His Tyr Ala Thr Trp Ala Lys Gly
    50                  55                  60

Arg Phe Thr Ile Ser Lys Ala Ser Thr Thr Val Asp Leu Lys Val Thr
65                  70                  75                  80

Ser Pro Thr Thr Glu Asp Thr Ala Thr Tyr Phe Cys Ala Arg Ser Ala
                85                  90                  95

Asn Asp Ala Trp Ser Thr Tyr Ser Asp Leu Trp Gly Gln Gly Thr Leu
            100                 105                 110

Val Thr Val Ser Ser
        115

<210> SEQ ID NO 14
<211> LENGTH: 112
<212> TYPE: PRT
<213> ORGANISM: Oryctolagus cuniculus

<400> SEQUENCE: 14

Asp Ile Val Met Thr Gln Thr Pro Ala Ser Val Glu Ala Ala Val Gly
1               5                   10                  15

Gly Thr Val Thr Ile Lys Cys Gln Ala Ser Gln Thr Ile Thr Asn Tyr
            20                  25                  30

Leu Ser Trp Tyr Gln Gln Lys Pro Gly Gln Pro Pro Lys Leu Leu Ile
        35                  40                  45

Tyr Lys Ala Ser Thr Leu Thr Ser Gly Val Ser Ser Arg Phe Lys Gly
    50                  55                  60

Ser Gly Ser Gly Thr Glu Phe Thr Leu Thr Ile Ser Asp Leu Glu Ser
65                  70                  75                  80

Asp Asp Ala Ala Thr Tyr Tyr Cys Gln Asn Tyr Tyr Tyr Gly Ser Ser
                85                  90                  95

Ser Gly Tyr Gly Phe Val Phe Gly Gly Gly Thr Glu Val Val Val Lys
            100                 105                 110

<210> SEQ ID NO 15
<211> LENGTH: 8
<212> TYPE: PRT
<213> ORGANISM: Oryctolagus cuniculus

<400> SEQUENCE: 15

Gly Phe Ser Leu Thr Tyr Tyr Ala
```

```
1               5

<210> SEQ ID NO 16
<211> LENGTH: 7
<212> TYPE: PRT
<213> ORGANISM: Oryctolagus cuniculus

<400> SEQUENCE: 16

Ile Tyr Asp Asn Gly Ala Thr
1               5

<210> SEQ ID NO 17
<211> LENGTH: 14
<212> TYPE: PRT
<213> ORGANISM: Oryctolagus cuniculus

<400> SEQUENCE: 17

Ala Arg Ser Ala Asn Asn Ala Trp Ser Thr Tyr Ser Asn Leu
1               5                   10

<210> SEQ ID NO 18
<211> LENGTH: 6
<212> TYPE: PRT
<213> ORGANISM: Oryctolagus cuniculus

<400> SEQUENCE: 18

Glu Asp Ile Ser Ser Tyr
1               5

<210> SEQ ID NO 19
<211> LENGTH: 14
<212> TYPE: PRT
<213> ORGANISM: Oryctolagus cuniculus

<400> SEQUENCE: 19

Gln Ser Tyr Tyr Ser Gly Ser Ile Ser Gly Tyr Gly Phe Val
1               5                   10

<210> SEQ ID NO 20
<211> LENGTH: 117
<212> TYPE: PRT
<213> ORGANISM: Oryctolagus cuniculus

<400> SEQUENCE: 20

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Thr Tyr Tyr Ala
            20                  25                  30

Val Thr Trp Val Arg Gln Pro Pro Gly Lys Gly Leu Glu Trp Ile Gly
        35                  40                  45

Val Ile Tyr Asp Asn Gly Ala Thr Ala Phe Ala Thr Trp Ala Lys Gly
    50                  55                  60

Arg Phe Thr Met Ser Lys Asn Ser Thr Thr Val Ala Leu Lys Val Thr
65                  70                  75                  80

Ser Pro Thr Thr Glu Asp Thr Ala Thr Tyr Phe Cys Ala Arg Ser Ala
                85                  90                  95

Asn Asn Ala Trp Ser Thr Tyr Ser Asn Leu Trp Gly Gln Gly Thr Leu
                100                 105                 110

Val Thr Val Ser Ser
            115
```

<210> SEQ ID NO 21
<211> LENGTH: 112
<212> TYPE: PRT
<213> ORGANISM: Oryctolagus cuniculus

<400> SEQUENCE: 21

Asp Ile Val Met Thr Gln Thr Pro Ser Ser Val Ser Ala Ala Val Gly
1               5                   10                  15

Gly Thr Val Thr Ile Asn Cys Gln Ala Ser Glu Asp Ile Ser Ser Tyr
            20                  25                  30

Leu Ser Trp Tyr Gln Gln Lys Leu Gly Gln Pro Pro Lys Leu Leu Ile
        35                  40                  45

Tyr Lys Ala Ser Thr Leu Glu Ser Gly Val Pro Ser Arg Phe Lys Gly
50                  55                  60

Ser Gly Ser Gly Thr Glu Tyr Thr Leu Thr Ile Ser Asp Leu Glu Ser
65                  70                  75                  80

Asp Asp Ala Ala Thr Tyr Tyr Cys Gln Ser Tyr Tyr Ser Gly Ser Ile
                85                  90                  95

Ser Gly Tyr Gly Phe Val Phe Gly Gly Gly Thr Gly Val Val Val Lys
            100                 105                 110

<210> SEQ ID NO 22
<211> LENGTH: 8
<212> TYPE: PRT
<213> ORGANISM: Oryctolagus cuniculus

<400> SEQUENCE: 22

Gly Phe Thr Ile Ser Ser Tyr His
1               5

<210> SEQ ID NO 23
<211> LENGTH: 8
<212> TYPE: PRT
<213> ORGANISM: Oryctolagus cuniculus

<400> SEQUENCE: 23

Ile Tyr Gly Gly Thr Ala Thr Thr
1               5

<210> SEQ ID NO 24
<211> LENGTH: 17
<212> TYPE: PRT
<213> ORGANISM: Oryctolagus cuniculus

<400> SEQUENCE: 24

Ala Arg Ala Arg Tyr Ser Gly Gly Ser Tyr Ala Asn Tyr Val Phe Asn
1               5                   10                  15

Leu

<210> SEQ ID NO 25
<211> LENGTH: 6
<212> TYPE: PRT
<213> ORGANISM: Oryctolagus cuniculus

<400> SEQUENCE: 25

Gln Ser Ile Ser Ser Tyr
1               5

<210> SEQ ID NO 26
<211> LENGTH: 14
<212> TYPE: PRT
<213> ORGANISM: Oryctolagus cuniculus

<400> SEQUENCE: 26

Gln Gly Tyr Asp Trp Ser Ser Ser Asn Arg Tyr Asp Asn Thr
1               5                   10

<210> SEQ ID NO 27
<211> LENGTH: 121
<212> TYPE: PRT
<213> ORGANISM: Oryctolagus cuniculus

<400> SEQUENCE: 27

Gln Ser Val Glu Glu Ser Gly Gly Arg Leu Val Thr Pro Gly Thr Pro
1               5                   10                  15

Leu Thr Leu Thr Cys Thr Ala Ser Gly Phe Thr Ile Ser Ser Tyr His
            20                  25                  30

Met Ile Trp Val Arg Gln Ala Pro Gly Glu Gly Leu Glu Trp Ile Gly
        35                  40                  45

Asp Ile Tyr Gly Gly Thr Ala Thr Thr Asp Tyr Ala Ser Trp Ala Lys
    50                  55                  60

Gly Arg Phe Thr Ile Ser Lys Thr Ser Thr Thr Val Asp Leu Lys Met
65                  70                  75                  80

Thr Ser Leu Thr Thr Glu Asp Thr Ala Thr Tyr Phe Cys Ala Arg Ala
                85                  90                  95

Arg Tyr Ser Gly Gly Ser Tyr Ala Asn Tyr Val Phe Asn Leu Trp Gly
            100                 105                 110

Gln Gly Thr Leu Val Thr Val Ser Ser
        115                 120

<210> SEQ ID NO 28
<211> LENGTH: 112
<212> TYPE: PRT
<213> ORGANISM: Oryctolagus cuniculus

<400> SEQUENCE: 28

Asp Ile Val Met Thr Gln Thr Pro Ala Ser Val Glu Ala Ala Val Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly Gln Pro Pro Lys Leu Leu Ile
        35                  40                  45

Tyr Arg Thr Ser Thr Leu Glu Ser Gly Val Pro Ser Arg Phe Lys Gly
    50                  55                  60

Ser Gly Ser Gly Thr Glu Phe Thr Leu Thr Ile Ser Asp Leu Glu Ser
65                  70                  75                  80

Ala Asp Ala Ala Thr Tyr Tyr Cys Gln Gly Tyr Asp Trp Ser Ser Ser
                85                  90                  95

Asn Arg Tyr Asp Asn Thr Phe Gly Gly Gly Thr Glu Val Val Val Lys
            100                 105                 110

<210> SEQ ID NO 29
<211> LENGTH: 8
<212> TYPE: PRT
<213> ORGANISM: Oryctolagus cuniculus

<400> SEQUENCE: 29

Gly Phe Ser Leu Ser Arg Tyr Asp
1               5

<210> SEQ ID NO 30
<211> LENGTH: 7
<212> TYPE: PRT
<213> ORGANISM: Oryctolagus cuniculus

<400> SEQUENCE: 30

Ile Ser Ser Ser Gly Gly Thr
1               5

<210> SEQ ID NO 31
<211> LENGTH: 11
<212> TYPE: PRT
<213> ORGANISM: Oryctolagus cuniculus

<400> SEQUENCE: 31

Ala Arg Glu Gly Asp Tyr Trp Asp Phe Asn Leu
1               5                   10

<210> SEQ ID NO 32
<211> LENGTH: 6
<212> TYPE: PRT
<213> ORGANISM: Oryctolagus cuniculus

<400> SEQUENCE: 32

Gln Ser Ile Ser Asn Leu
1               5

<210> SEQ ID NO 33
<211> LENGTH: 12
<212> TYPE: PRT
<213> ORGANISM: Oryctolagus cuniculus

<400> SEQUENCE: 33

Ala Gly Gly Phe Pro Gly Leu Asp Thr Val Ala Ala
1               5                   10

<210> SEQ ID NO 34
<211> LENGTH: 114
<212> TYPE: PRT
<213> ORGANISM: Oryctolagus cuniculus

<400> SEQUENCE: 34

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Arg Tyr Asp
            20                  25                  30

Met Ser Trp Val Arg Gln Ala Pro Gly Lys Gly Leu Glu Tyr Ile Gly
        35                  40                  45

Val Ile Ser Ser Ser Gly Gly Thr Asn Tyr Ala Asn Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Glu Gly
                85                  90                  95

Asp Tyr Trp Asp Phe Asn Leu Trp Gly Pro Gly Thr Leu Val Thr Val
            100                 105                 110

Ser Ser

<210> SEQ ID NO 35
<211> LENGTH: 110
<212> TYPE: PRT
<213> ORGANISM: Oryctolagus cuniculus

<400> SEQUENCE: 35

Ala Gln Val Leu Thr Gln Thr Pro Ser Ser Val Ser Ala Ala Val Gly
1               5                   10                  15

Gly Thr Val Thr Ile Asn Cys Gln Ala Ser Gln Ser Ile Ser Asn Leu
            20                  25                  30

Leu Ala Trp Tyr Gln Gln Lys Pro Gly Gln Pro Pro Lys Leu Leu Ile
        35                  40                  45

Tyr Gly Ala Ser Thr Leu Ala Ser Gly Val Pro Ser Arg Phe Ser Gly
    50                  55                  60

Ser Gly Ser Gly Thr Glu Phe Thr Leu Thr Ile Ser Asp Leu Glu Ser
65                  70                  75                  80

Asp Asp Ala Ala Thr Tyr Tyr Cys Ala Gly Gly Phe Pro Gly Leu Asp
                85                  90                  95

Thr Val Ala Ala Phe Gly Gly Gly Thr Glu Ala Val Val Thr
            100                 105                 110

<210> SEQ ID NO 36
<211> LENGTH: 8
<212> TYPE: PRT
<213> ORGANISM: Oryctolagus cuniculus

<400> SEQUENCE: 36

Gly Phe Thr Ile Ser Asp Phe His
1               5

<210> SEQ ID NO 37
<211> LENGTH: 8
<212> TYPE: PRT
<213> ORGANISM: Oryctolagus cuniculus

<400> SEQUENCE: 37

Ile Ile Thr Ser Ala Ser Thr Thr
1               5

<210> SEQ ID NO 38
<211> LENGTH: 15
<212> TYPE: PRT
<213> ORGANISM: Oryctolagus cuniculus

<400> SEQUENCE: 38

Ala Arg Ser Thr Tyr Thr Asp Thr Ser Gly Tyr Tyr Phe Asp Phe
1               5                   10                  15

<210> SEQ ID NO 39
<211> LENGTH: 8
<212> TYPE: PRT
<213> ORGANISM: Oryctolagus cuniculus

<400> SEQUENCE: 39

Gln Ser Ile Tyr Asn Gly Asn Arg
1               5

<210> SEQ ID NO 40
<211> LENGTH: 13
<212> TYPE: PRT
<213> ORGANISM: Oryctolagus cuniculus

<400> SEQUENCE: 40

Leu Gly Ser Tyr Asp Cys Asp Ser Ala Asp Cys Phe Ala
1               5                   10

```
<210> SEQ ID NO 41
<211> LENGTH: 119
<212> TYPE: PRT
<213> ORGANISM: Oryctolagus cuniculus

<400> SEQUENCE: 41

Gln Ser Val Glu Glu Ser Gly Gly Arg Leu Val Thr Pro Gly Thr Pro
1               5                   10                  15

Leu Thr Leu Thr Cys Thr Ala Ser Gly Phe Thr Ile Ser Asp Phe His
            20                  25                  30

Val Thr Trp Val Arg Gln Ala Pro Gly Lys Gly Leu Glu Trp Ile Gly
        35                  40                  45

Thr Ile Ile Thr Ser Ala Ser Thr Thr Ala Tyr Ala Thr Trp Ala Arg
    50                  55                  60

Gly Arg Phe Thr Ile Ser Lys Ser Ser Thr Thr Val Asn Leu Lys Ile
65                  70                  75                  80

Val Ser Pro Thr Thr Glu Asp Thr Ala Thr Tyr Phe Cys Ala Arg Ser
                85                  90                  95

Thr Tyr Thr Asp Thr Ser Gly Tyr Tyr Phe Asp Phe Trp Gly Gln Gly
            100                 105                 110

Thr Leu Val Thr Val Ser Ser
        115

<210> SEQ ID NO 42
<211> LENGTH: 113
<212> TYPE: PRT
<213> ORGANISM: Oryctolagus cuniculus

<400> SEQUENCE: 42

Ala Gln Val Leu Thr Gln Thr Ala Ser Pro Val Ser Ala Ala Val Gly
1               5                   10                  15

Gly Thr Val Ile Ile Asn Cys Gln Ser Ser Gln Ser Ile Tyr Asn Gly
            20                  25                  30

Asn Arg Leu Ser Trp Tyr Gln Gln Lys Pro Gly Gln Pro Pro Lys Leu
        35                  40                  45

Leu Ile Tyr Ser Ala Ser Thr Leu Ala Ser Gly Val Ser Ser Arg Phe
    50                  55                  60

Lys Gly Ser Gly Ser Gly Thr Gln Phe Thr Leu Ala Ile Ser Asp Val
65                  70                  75                  80

Gln Ser Asp Asp Ala Ala Thr Tyr Tyr Cys Leu Gly Ser Tyr Asp Cys
                85                  90                  95

Asp Ser Ala Asp Cys Phe Ala Phe Gly Gly Gly Thr Glu Val Val Val
            100                 105                 110

Glu

<210> SEQ ID NO 43
<211> LENGTH: 8
<212> TYPE: PRT
<213> ORGANISM: Oryctolagus cuniculus

<400> SEQUENCE: 43

Gly Phe Ser Leu Ser Ser Tyr Ala
1               5

<210> SEQ ID NO 44
<211> LENGTH: 7
<212> TYPE: PRT
<213> ORGANISM: Oryctolagus cuniculus
```

<400> SEQUENCE: 44

Ile Ser Thr Ser Gly Ile Thr
1               5

<210> SEQ ID NO 45
<211> LENGTH: 15
<212> TYPE: PRT
<213> ORGANISM: Oryctolagus cuniculus

<400> SEQUENCE: 45

Ala Arg Leu Asn Gly Phe Asp Asp Tyr Val Arg Tyr Phe Asp Phe
1               5                   10                  15

<210> SEQ ID NO 46
<211> LENGTH: 6
<212> TYPE: PRT
<213> ORGANISM: Oryctolagus cuniculus

<400> SEQUENCE: 46

Glu Ser Ile Ala Ser Asn
1               5

<210> SEQ ID NO 47
<211> LENGTH: 12
<212> TYPE: PRT
<213> ORGANISM: Oryctolagus cuniculus

<400> SEQUENCE: 47

Gln Ser Ala Phe Tyr Val Ser Ser Ser Asp Asn Ala
1               5                   10

<210> SEQ ID NO 48
<211> LENGTH: 118
<212> TYPE: PRT
<213> ORGANISM: Oryctolagus cuniculus

<400> SEQUENCE: 48

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Val Arg Gln Ala Pro Gly Lys Gly Leu Glu Trp Ile Gly
        35                  40                  45

Ile Ile Ser Thr Ser Gly Ile Thr Tyr Tyr Ala Ser Trp Ala Lys Gly
    50                  55                  60

Arg Phe Thr Ile Ser Lys Thr Ser Thr Met Val Asp Leu Lys Ile Thr
65                  70                  75                  80

Ser Pro Thr Thr Glu Asp Thr Ala Thr Tyr Phe Cys Ala Arg Leu Asn
                85                  90                  95

Gly Phe Asp Asp Tyr Val Arg Tyr Phe Asp Phe Trp Gly Leu Gly Thr
            100                 105                 110

Leu Val Thr Val Ser Ser
        115

<210> SEQ ID NO 49
<211> LENGTH: 110
<212> TYPE: PRT
<213> ORGANISM: Oryctolagus cuniculus

<400> SEQUENCE: 49

```
Ala Ile Glu Leu Thr Gln Thr Pro Ser Ser Val Ser Ala Ala Val Gly
1               5                   10                  15

Gly Thr Val Thr Ile Asn Cys Gln Ala Ser Glu Ser Ile Ala Ser Asn
            20                  25                  30

Leu Ala Trp Tyr Gln Gln Lys Pro Gly Gln Pro Pro Lys Leu Leu Ile
        35                  40                  45

Tyr Ala Ala Ser Tyr Leu Ala Ser Gly Val Pro Ser Arg Phe Lys Gly
    50                  55                  60

Ser Gly Ser Gly Thr Glu Tyr Thr Leu Thr Ile Ser Gly Val Gln Ser
65                  70                  75                  80

Ala Asp Ala Ala Thr Tyr Tyr Cys Gln Ser Ala Phe Tyr Val Ser Ser
                85                  90                  95

Ser Asp Asn Ala Phe Gly Gly Gly Thr Glu Val Val Val Lys
            100                 105                 110
```

```
<210> SEQ ID NO 50
<211> LENGTH: 8
<212> TYPE: PRT
<213> ORGANISM: Oryctolagus cuniculus

<400> SEQUENCE: 50

Gly Phe Ser Leu Ser Ser Tyr Asp
1               5
```

```
<210> SEQ ID NO 51
<211> LENGTH: 7
<212> TYPE: PRT
<213> ORGANISM: Oryctolagus cuniculus

<400> SEQUENCE: 51

Ile Gly Ser Asp Gly Ser Ala
1               5
```

```
<210> SEQ ID NO 52
<211> LENGTH: 12
<212> TYPE: PRT
<213> ORGANISM: Oryctolagus cuniculus

<400> SEQUENCE: 52

Ala Arg Asp Trp Asn Asp Tyr Trp Ala His Asp Leu
1               5                   10
```

```
<210> SEQ ID NO 53
<211> LENGTH: 8
<212> TYPE: PRT
<213> ORGANISM: Oryctolagus cuniculus

<400> SEQUENCE: 53

Gln Ile Val Thr Ser Lys Ser Ala
1               5
```

```
<210> SEQ ID NO 54
<211> LENGTH: 12
<212> TYPE: PRT
<213> ORGANISM: Oryctolagus cuniculus

<400> SEQUENCE: 54

Ala Gly Gly Tyr Tyr Asn Ser Gly Asp Leu Asn Pro
1               5                   10
```

```
<210> SEQ ID NO 55
<211> LENGTH: 115
```

<212> TYPE: PRT
<213> ORGANISM: Oryctolagus cuniculus

<400> SEQUENCE: 55

Gln Ser Leu Glu Glu Ser Gly Gly Arg Leu Val Thr Pro Gly Thr Pro
1               5                   10                  15
Leu Thr Leu Thr Cys Thr Ala Ser Gly Phe Ser Leu Ser Ser Tyr Asp
                20                  25                  30
Val Ser Trp Val Arg Gln Ala Pro Gly Lys Gly Leu Glu Tyr Ile Gly
            35                  40                  45
Phe Ile Gly Ser Asp Gly Ser Ala His Tyr Ala Thr Trp Val Lys Gly
        50                  55                  60
Arg Phe Thr Ile Ser Lys Thr Ser Thr Thr Val Asp Leu Lys Ile Thr
65                  70                  75                  80
Ser Pro Thr Thr Glu Asp Thr Ala Thr Tyr Phe Cys Ala Arg Asp Trp
                85                  90                  95
Asn Asp Tyr Trp Ala His Asp Leu Trp Gly Pro Gly Thr Leu Val Thr
                100                 105                 110
Val Ser Ser
        115

<210> SEQ ID NO 56
<211> LENGTH: 112
<212> TYPE: PRT
<213> ORGANISM: Oryctolagus cuniculus

<400> SEQUENCE: 56

Ala Gln Val Leu Thr Gln Thr Thr Ser Pro Val Ser Ala Ala Val Gly
1               5                   10                  15
Gly Thr Val Thr Ile Asn Cys Gln Ala Ser Gln Ile Val Thr Ser Lys
                20                  25                  30
Ser Ala Leu Ser Trp Tyr Gln Gln Lys Pro Gly Gln Pro Pro Arg Leu
            35                  40                  45
Leu Ile Tyr Lys Ala Ser Thr Leu Ala Ser Gly Val Pro Ser Arg Phe
        50                  55                  60
Ser Gly Ser Gly Ser Gly Thr Gln Phe Thr Leu Thr Ile Ser Asp Leu
65                  70                  75                  80
Glu Ser Asp Asp Ala Ala Thr Tyr Tyr Cys Ala Gly Gly Tyr Tyr Asn
                85                  90                  95
Ser Gly Asp Leu Asn Pro Phe Gly Gly Gly Thr Glu Val Val Val Lys
                100                 105                 110

<210> SEQ ID NO 57
<211> LENGTH: 8
<212> TYPE: PRT
<213> ORGANISM: Oryctolagus cuniculus

<400> SEQUENCE: 57

Gly Phe Ser Leu Ser Ser Tyr Asp
1               5

<210> SEQ ID NO 58
<211> LENGTH: 7
<212> TYPE: PRT
<213> ORGANISM: Oryctolagus cuniculus

<400> SEQUENCE: 58

Ile Ser Ser Ser Gly Asn Thr
1               5

<210> SEQ ID NO 59
<211> LENGTH: 11
<212> TYPE: PRT
<213> ORGANISM: Oryctolagus cuniculus

<400> SEQUENCE: 59

Ala Arg Glu Gly Asp Tyr Trp Asp Phe Asn Leu
1               5                   10

<210> SEQ ID NO 60
<211> LENGTH: 6
<212> TYPE: PRT
<213> ORGANISM: Oryctolagus cuniculus

<400> SEQUENCE: 60

Gln Ser Ile Ser Asn Leu
1               5

<210> SEQ ID NO 61
<211> LENGTH: 12
<212> TYPE: PRT
<213> ORGANISM: Oryctolagus cuniculus

<400> SEQUENCE: 61

Ala Gly Gly Phe Pro Gly Leu Asp Thr Gly Ala Thr
1               5                   10

<210> SEQ ID NO 62
<211> LENGTH: 114
<212> TYPE: PRT
<213> ORGANISM: Oryctolagus cuniculus

<400> SEQUENCE: 62

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Asp
            20                  25                  30

Met Ser Trp Val Arg Gln Ala Pro Gly Lys Gly Leu Glu Tyr Ile Gly
        35                  40                  45

Tyr Ile Ser Ser Ser Gly Asn Thr Tyr Tyr Ala Ser Trp Ala Lys Ser
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Glu Gly
                85                  90                  95

Asp Tyr Trp Asp Phe Asn Leu Trp Gly Pro Gly Thr Leu Val Thr Val
            100                 105                 110

Ser Ser

<210> SEQ ID NO 63
<211> LENGTH: 110
<212> TYPE: PRT
<213> ORGANISM: Oryctolagus cuniculus

<400> SEQUENCE: 63

Ala Gln Val Leu Thr Gln Thr Pro Ser Ser Val Ser Ala Ala Val Gly
1               5                   10                  15

Gly Thr Val Thr Ile Asn Cys Gln Ala Ser Gln Ser Ile Ser Asn Leu
            20                  25                  30

-continued

```
Leu Ala Trp Tyr Gln Gln Lys Pro Gly Gln Arg Pro Arg Leu Leu Ile
             35                  40                  45

Tyr Arg Ala Ser Thr Leu Ala Ser Gly Val Pro Ser Arg Phe Lys Gly
 50                  55                  60

Ser Gly Ser Gly Thr Glu Phe Thr Leu Thr Ile Ser Asp Leu Glu Ser
 65                  70                  75                  80

Glu Asp Ala Ala Thr Tyr Tyr Cys Ala Gly Phe Pro Gly Leu Asp
                 85                  90                  95

Thr Gly Ala Thr Phe Gly Gly Gly Thr Glu Ala Val Val Thr
            100                 105                 110
```

<210> SEQ ID NO 64
<211> LENGTH: 8
<212> TYPE: PRT
<213> ORGANISM: Oryctolagus cuniculus

<400> SEQUENCE: 64

```
Gly Phe Ser Leu Asn Asp Tyr Trp
 1               5
```

<210> SEQ ID NO 65
<211> LENGTH: 7
<212> TYPE: PRT
<213> ORGANISM: Oryctolagus cuniculus

<400> SEQUENCE: 65

```
Ile Asp Val Gly Gly Ser Leu
 1               5
```

<210> SEQ ID NO 66
<211> LENGTH: 11
<212> TYPE: PRT
<213> ORGANISM: Oryctolagus cuniculus

<400> SEQUENCE: 66

```
Ala Arg Gly Gly Leu Thr Tyr Gly Phe Asp Leu
 1               5                  10
```

<210> SEQ ID NO 67
<211> LENGTH: 6
<212> TYPE: PRT
<213> ORGANISM: Oryctolagus cuniculus

<400> SEQUENCE: 67

```
Glu Asp Ile Ser Ser Tyr
 1               5
```

<210> SEQ ID NO 68
<211> LENGTH: 12
<212> TYPE: PRT
<213> ORGANISM: Oryctolagus cuniculus

<400> SEQUENCE: 68

```
His Tyr Tyr Ala Thr Ile Ser Gly Leu Gly Val Ala
 1               5                  10
```

<210> SEQ ID NO 69
<211> LENGTH: 114
<212> TYPE: PRT
<213> ORGANISM: Oryctolagus cuniculus

<400> SEQUENCE: 69

```
Gln Ser Leu Glu Glu Ser Gly Gly Arg Leu Val Thr Pro Gly Thr Pro
```

```
            1               5                  10                 15
Leu Thr Leu Thr Cys Thr Val Ser Gly Phe Ser Leu Asn Asp Tyr Trp
            20                 25                 30

Met Ser Trp Val Arg Gln Ala Pro Gly Lys Gly Leu Glu Trp Ile Gly
        35                 40                 45

Tyr Ile Asp Val Gly Gly Ser Leu Tyr Tyr Ala Ser Trp Ala Lys Gly
        50                 55                 60

Arg Phe Thr Ile Ser Arg Thr Ser Thr Thr Val Asp Leu Lys Met Thr
65                  70                 75                 80

Ser Leu Thr Thr Glu Asp Thr Ala Thr Tyr Phe Cys Ala Arg Gly Gly
                85                 90                 95

Leu Thr Tyr Gly Phe Asp Leu Trp Gly Pro Gly Thr Leu Val Thr Val
            100                105                110

Ser Ser

<210> SEQ ID NO 70
<211> LENGTH: 110
<212> TYPE: PRT
<213> ORGANISM: Oryctolagus cuniculus

<400> SEQUENCE: 70

Asp Ile Val Met Thr Gln Thr Pro Ala Ser Val Ser Glu Pro Val Gly
1               5                  10                 15

Gly Thr Val Thr Ile Asn Cys Gln Ala Ser Glu Asp Ile Ser Ser Tyr
            20                 25                 30

Leu Ala Trp Tyr Gln Gln Lys Pro Gly Gln Arg Pro Lys Arg Leu Ile
        35                 40                 45

Tyr Gly Ala Ser Asp Leu Ala Ser Gly Val Pro Ser Arg Phe Ser Ala
        50                 55                 60

Ser Gly Ser Gly Thr Glu Tyr Ala Leu Thr Ile Ser Asp Leu Glu Ser
65                  70                 75                 80

Ala Asp Ala Ala Thr Tyr Tyr Cys His Tyr Tyr Ala Thr Ile Ser Gly
                85                 90                 95

Leu Gly Val Ala Phe Gly Gly Gly Thr Glu Val Val Val Lys
            100                105                110

<210> SEQ ID NO 71
<211> LENGTH: 8
<212> TYPE: PRT
<213> ORGANISM: Oryctolagus cuniculus

<400> SEQUENCE: 71

Gly Phe Ser Leu Ser Thr Tyr Ala
1               5

<210> SEQ ID NO 72
<211> LENGTH: 7
<212> TYPE: PRT
<213> ORGANISM: Oryctolagus cuniculus

<400> SEQUENCE: 72

Val Tyr Asp Asn Gly Tyr Ile
1               5

<210> SEQ ID NO 73
<211> LENGTH: 14
<212> TYPE: PRT
<213> ORGANISM: Oryctolagus cuniculus
```

<400> SEQUENCE: 73

Ala Arg Ser Ala Asp Gly Ser Trp Ser Thr Tyr Phe Asn Leu
1               5                   10

<210> SEQ ID NO 74
<211> LENGTH: 6
<212> TYPE: PRT
<213> ORGANISM: Oryctolagus cuniculus

<400> SEQUENCE: 74

Glu Ser Ile Ser Asn Tyr
1               5

<210> SEQ ID NO 75
<211> LENGTH: 14
<212> TYPE: PRT
<213> ORGANISM: Oryctolagus cuniculus

<400> SEQUENCE: 75

Gln Thr Asn Tyr Cys Cys Ser Ser Ser Asp Asn Gly Phe Ala
1               5                   10

<210> SEQ ID NO 76
<211> LENGTH: 117
<212> TYPE: PRT
<213> ORGANISM: Oryctolagus cuniculus

<400> SEQUENCE: 76

Gln Ser Val Glu Glu Ser Gly Gly Arg Leu Val Thr Pro Thr Pro
1               5                   10                  15

Leu Thr Leu Thr Cys Thr Val Ser Gly Phe Ser Leu Ser Thr Tyr Ala
                20                  25                  30

Met Ile Trp Val Arg Gln Ala Pro Gly Lys Gly Leu Glu Trp Ile Gly
            35                  40                  45

Val Val Tyr Asp Asn Gly Tyr Ile Ser His Ala Thr Trp Val Lys Gly
        50                  55                  60

Arg Phe Thr Ile Ser Lys Thr Ser Thr Thr Val Gly Leu Glu Ile Thr
65                  70                  75                  80

Ser Pro Thr Thr Glu Asp Thr Ala Thr Tyr Phe Cys Ala Arg Ser Ala
                85                  90                  95

Asp Gly Ser Trp Ser Thr Tyr Phe Asn Leu Trp Gly Gln Gly Thr Leu
            100                 105                 110

Val Thr Val Ser Ser
        115

<210> SEQ ID NO 77
<211> LENGTH: 112
<212> TYPE: PRT
<213> ORGANISM: Oryctolagus cuniculus

<400> SEQUENCE: 77

Asp Ile Val Met Thr Gln Thr Pro Ala Ser Val Glu Ala Ala Val Gly
1               5                   10                  15

Gly Thr Val Thr Ile Lys Cys Gln Ala Ser Glu Ser Ile Ser Asn Tyr
                20                  25                  30

Leu Ala Trp Tyr Gln Gln Lys Pro Gly Gln Pro Pro Lys Leu Leu Ile
            35                  40                  45

Tyr Lys Ala Ser Thr Leu Ala Ser Gly Val Ser Ser Arg Phe Lys Gly
        50                  55                  60

-continued

```
Ser Gly Ser Gly Thr Glu Phe Thr Leu Thr Ile Ser Asp Leu Glu Ser
 65                  70                  75                  80

Ala Asp Ala Ala Thr Tyr Tyr Cys Gln Thr Asn Tyr Cys Ser Ser
                 85                  90                  95

Ser Asp Asn Gly Phe Ala Phe Gly Gly Gly Thr Glu Val Val Val Lys
            100                 105                 110
```

<210> SEQ ID NO 78
<211> LENGTH: 8
<212> TYPE: PRT
<213> ORGANISM: Oryctolagus cuniculus

<400> SEQUENCE: 78

```
Gly Ile Asp Leu Ser Ser Tyr His
 1               5
```

<210> SEQ ID NO 79
<211> LENGTH: 7
<212> TYPE: PRT
<213> ORGANISM: Oryctolagus cuniculus

<400> SEQUENCE: 79

```
Ile Ala Tyr Gly Gly Asn Thr
 1               5
```

<210> SEQ ID NO 80
<211> LENGTH: 12
<212> TYPE: PRT
<213> ORGANISM: Oryctolagus cuniculus

<400> SEQUENCE: 80

```
Ala Arg Gly Tyr Ser Glu Asp Ser Tyr Trp Gly Leu
 1               5                   10
```

<210> SEQ ID NO 81
<211> LENGTH: 6
<212> TYPE: PRT
<213> ORGANISM: Oryctolagus cuniculus

<400> SEQUENCE: 81

```
Gln Asn Ile Glu Asn Tyr
 1               5
```

<210> SEQ ID NO 82
<211> LENGTH: 12
<212> TYPE: PRT
<213> ORGANISM: Oryctolagus cuniculus

<400> SEQUENCE: 82

```
Gln Gln Asp Tyr Gly Ile Ile Phe Val Asp Asn Ile
 1               5                   10
```

<210> SEQ ID NO 83
<211> LENGTH: 115
<212> TYPE: PRT
<213> ORGANISM: Oryctolagus cuniculus

<400> SEQUENCE: 83

```
Gln Ser Leu Glu Glu Ser Gly Gly Arg Leu Val Thr Pro Gly Thr Pro
 1               5                   10                  15

Leu Thr Leu Thr Cys Thr Val Ser Gly Ile Asp Leu Ser Ser Tyr His
                20                  25                  30

Met Cys Trp Val Arg Gln Ala Pro Gly Lys Gly Leu Glu Tyr Ile Gly
```

```
            35                  40                  45
Tyr Ile Ala Tyr Gly Gly Asn Thr Tyr Ala Asn Trp Ala Lys Gly
 50                  55                  60

Arg Phe Thr Ile Ser Lys Thr Ser Thr Val Asp Leu Arg Ile Thr
65                  70                  75                  80

Ser Pro Thr Thr Glu Asp Thr Ala Thr Tyr Phe Cys Ala Arg Gly Tyr
                85                  90                  95

Ser Glu Asp Ser Tyr Trp Gly Leu Trp Gly Pro Gly Thr Leu Val Thr
            100                 105                 110

Val Ser Ser
        115

<210> SEQ ID NO 84
<211> LENGTH: 110
<212> TYPE: PRT
<213> ORGANISM: Oryctolagus cuniculus

<400> SEQUENCE: 84

Ala Tyr Asp Met Thr Gln Thr Pro Ala Ser Val Glu Ala Ala Val Gly
 1               5                  10                  15

Gly Thr Val Thr Ile Lys Cys Gln Ala Ser Gln Asn Ile Glu Asn Tyr
                20                  25                  30

Leu Ala Trp Tyr Gln Gln Lys Pro Gly Gln Pro Pro Lys Leu Leu Ile
            35                  40                  45

Tyr Asp Thr Ser Lys Leu Thr Ser Gly Val Pro Ser Arg Phe Ser Gly
 50                  55                  60

Ser Gly Ser Gly Thr Asp Phe Thr Leu Thr Ile Ser Gly Val Gln Ser
65                  70                  75                  80

Asp Asp Ala Ala Thr Tyr Tyr Cys Gln Gln Asp Tyr Gly Ile Ile Phe
                85                  90                  95

Val Asp Asn Ile Phe Gly Gly Gly Thr Glu Val Val Val Lys
            100                 105                 110

<210> SEQ ID NO 85
<211> LENGTH: 8
<212> TYPE: PRT
<213> ORGANISM: Oryctolagus cuniculus

<400> SEQUENCE: 85

Gly Phe Ser Leu Ser Asp Tyr Tyr
 1               5

<210> SEQ ID NO 86
<211> LENGTH: 7
<212> TYPE: PRT
<213> ORGANISM: Oryctolagus cuniculus

<400> SEQUENCE: 86

Met Ser Gly Ser Gly Ser Thr
 1               5

<210> SEQ ID NO 87
<211> LENGTH: 18
<212> TYPE: PRT
<213> ORGANISM: Oryctolagus cuniculus

<400> SEQUENCE: 87

Ala Arg Asp Gly Asp Tyr Ala Gly Trp Gly Tyr Ala Thr Gly Ala Phe
 1               5                  10                  15
```

Asp Pro

<210> SEQ ID NO 88
<211> LENGTH: 8
<212> TYPE: PRT
<213> ORGANISM: Oryctolagus cuniculus

<400> SEQUENCE: 88

Gln Ser Val Val Gly Asn Ser Leu
1               5

<210> SEQ ID NO 89
<211> LENGTH: 12
<212> TYPE: PRT
<213> ORGANISM: Oryctolagus cuniculus

<400> SEQUENCE: 89

Thr Gly Arg Tyr Asn Ser Asp Thr Asp Thr Phe Val
1               5                   10

<210> SEQ ID NO 90
<211> LENGTH: 122
<212> TYPE: PRT
<213> ORGANISM: Oryctolagus cuniculus

<400> SEQUENCE: 90

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asp Tyr Tyr
            20                  25                  30

Met Thr Trp Val Arg Gln Ala Pro Gly Lys Gly Leu Glu Tyr Ile Gly
        35                  40                  45

Ile Met Ser Gly Ser Gly Ser Thr Tyr Tyr Ala Ser Trp Ala Lys Gly
    50                  55                  60

Arg Phe Thr Ile Ser Lys Thr Ser Ser Thr Thr Leu Glu Leu Lys Ile
65                  70                  75                  80

Thr Ser Pro Thr Thr Glu Asp Thr Ala Ile Tyr Phe Cys Ala Arg Asp
                85                  90                  95

Gly Asp Tyr Ala Gly Trp Gly Tyr Ala Thr Gly Ala Phe Asp Pro Trp
                100                 105                 110

Gly Pro Gly Thr Leu Val Thr Val Ser Ser
            115                 120

<210> SEQ ID NO 91
<211> LENGTH: 112
<212> TYPE: PRT
<213> ORGANISM: Oryctolagus cuniculus

<400> SEQUENCE: 91

Ala Ala Val Leu Thr Gln Thr Pro Ser Pro Val Ser Ala Ala Val Gly
1               5                   10                  15

Gly Thr Val Thr Ile Ser Cys Gln Ala Ser Gln Ser Val Val Gly Asn
            20                  25                  30

Ser Leu Leu Ser Trp Phe Gln Lys Lys Pro Gly Gln Pro Pro Lys Leu
        35                  40                  45

Leu Ile Tyr Ser Ala Ser Ser Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Ser Asp Asp Ala Ala Thr Tyr Tyr Cys Thr Gly Arg Tyr Asn Ser
                85                  90                  95

Asp Thr Asp Thr Phe Val Phe Gly Gly Gly Thr Glu Val Val Val Lys
            100                 105                 110

<210> SEQ ID NO 92
<211> LENGTH: 255
<212> TYPE: PRT
<213> ORGANISM: homo sapiens

<400> SEQUENCE: 92

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu
                245                 250                 255

<210> SEQ ID NO 93
<211> LENGTH: 205
<212> TYPE: PRT
<213> ORGANISM: Artificial sequence
<220> FEATURE:
<223> OTHER INFORMATION: Homo Sapiens; Sus scrofa recombinant protein

<400> SEQUENCE: 93

Met Gly Asn Ser Cys Tyr Asn Ile Val Ala Thr Leu Leu Leu Val Leu
1               5                   10                  15

Asn Phe Glu Arg Thr Arg Ser Val Pro Asp Pro Cys Ser Asn Cys Ser
            20                  25                  30

Ala Gly Thr Phe Cys Gly Lys Asn Ile Gln Glu Leu Cys Met Pro Cys

```
            35                  40                  45
Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
                100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
            130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
                180                 185                 190

Ala Leu Thr Ser Thr Ala Leu Leu Gly Gly Cys Glu Leu
            195                 200                 205

<210> SEQ ID NO 94
<211> LENGTH: 255
<212> TYPE: PRT
<213> ORGANISM: artificial sequence
<220> FEATURE:
<223> OTHER INFORMATION: Homo Sapiens; Loxodonta recombinant protein

<400> SEQUENCE: 94

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Leu Asn Ser Phe Ser Ser Thr Gly Gly Gln Met Asn Cys Asp Met
    50                  55                  60

Cys Arg Lys Cys Glu Gly Val Phe Lys Thr Lys Arg Ala Cys Ser Pro
65                  70                  75                  80

Thr Arg Asp Ala Glu Cys Glu Cys Thr Pro Gly Phe His Cys Leu Gly
                85                  90                  95

Ala Gly Cys Ser Met Cys Glu Gln Asp Cys Lys Gln Gly Gln Glu Leu
                100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
            130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
                180                 185                 190

Ala Leu Thr Ser Thr Ala Leu Leu Phe Leu Leu Phe Phe Leu Thr Leu
```

```
                    195                 200                 205
Arg Phe Ser Val Val Lys Arg Gly Arg Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                    245                 250                 255

<210> SEQ ID NO 95
<211> LENGTH: 255
<212> TYPE: PRT
<213> ORGANISM: artificial sequence
<220> FEATURE:
<223> OTHER INFORMATION: Homo Sapiens; Sus scrofa recombinant protein

<400> SEQUENCE: 95

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Val Pro Gly Phe Arg Cys Leu Gly
                85                  90                  95

Ala Gly Cys Ala Met Cys Glu Glu Tyr Cys Gln Gln Gly Gln Glu Leu
            100                 105                 110

Thr Gln Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 96
<211> LENGTH: 255
<212> TYPE: PRT
<213> ORGANISM: artificial sequence
<220> FEATURE:
<223> OTHER INFORMATION: Homo Sapiens; Sus scrofa recombinant protein

<400> SEQUENCE: 96
```

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
                100                 105                 110

Thr Lys Glu Gly Cys Lys Asp Cys Ser Phe Gly Thr Phe Asn Asp Glu
            115                 120                 125

Glu His Gly Val Cys Arg Pro Trp Thr Asp Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 97
<211> LENGTH: 255
<212> TYPE: PRT
<213> ORGANISM: artificial sequence
<220> FEATURE:
<223> OTHER INFORMATION: Homo Sapiens; Sus scrofa recombinant protein

<400> SEQUENCE: 97

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
                100                 105                 110
```

```
Thr Lys Lys Gly Cys Lys Asp Cys Phe Gly Thr Phe Asn Asp Gln
        115                 120                 125

Lys Arg Gly Ile Cys Arg Pro Trp Thr Asn Cys Ser Leu Ala Gly Lys
130                 135                 140

Pro Val Leu Met Asn Gly Thr Lys Ala Arg Asp Val Val Cys Gly Pro
145                 150                 155                 160

Arg Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 98
<211> LENGTH: 255
<212> TYPE: PRT
<213> ORGANISM: artificial sequence
<220> FEATURE:
<223> OTHER INFORMATION: Homo Sapiens; Sus scrofa recombinant protein

<400> SEQUENCE: 98

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Phe Gly Thr Phe Asn Asp Gln
        115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Thr Asp Phe Ser Pro Gly Thr Pro Ser Thr Thr Met Pro Val
                165                 170                 175

Pro Gly Gly Glu Pro Gly His Thr Ser His Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220
```

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu
                245                 250                 255

<210> SEQ ID NO 99
<211> LENGTH: 8
<212> TYPE: PRT
<213> ORGANISM: homo sapiens

<400> SEQUENCE: 99

Gly Tyr Arg Phe Ser Asn Phe Val
1               5

<210> SEQ ID NO 100
<211> LENGTH: 8
<212> TYPE: PRT
<213> ORGANISM: homo sapiens

<400> SEQUENCE: 100

Ile Asn Pro Tyr Asn Gly Asn Lys
1               5

<210> SEQ ID NO 101
<211> LENGTH: 20
<212> TYPE: PRT
<213> ORGANISM: homo sapiens

<400> SEQUENCE: 101

Ala Arg Val Gly Pro Tyr Ser Trp Asp Asp Pro Gln Asp Asn Tyr
1               5                   10                  15

Tyr Met Asp Val
            20

<210> SEQ ID NO 102
<211> LENGTH: 7
<212> TYPE: PRT
<213> ORGANISM: homo sapiens

<400> SEQUENCE: 102

His Ser Ile Arg Ser Arg Arg
1               5

<210> SEQ ID NO 103
<211> LENGTH: 9
<212> TYPE: PRT
<213> ORGANISM: homo sapiens

<400> SEQUENCE: 103

Gln Val Tyr Gly Ala Ser Ser Tyr Thr
1               5

<210> SEQ ID NO 104
<211> LENGTH: 127
<212> TYPE: PRT
<213> ORGANISM: homo sapiens

<400> SEQUENCE: 104

Gln Val Gln Leu Val Gln Ser Gly Ala Glu Val Lys Lys Pro Gly Ala
1               5                   10                  15

Ser Val Lys Val Ser Cys Gln Ala Ser Gly Tyr Arg Phe Ser Asn Phe
            20                  25                  30

Val Ile His Trp Val Arg Gln Ala Pro Gly Gln Arg Phe Glu Trp Met

```
            35                  40                  45

Gly Trp Ile Asn Pro Tyr Asn Gly Asn Lys Glu Phe Ser Ala Lys Phe
 50                  55                  60

Gln Asp Arg Val Thr Phe Thr Ala Asp Thr Ser Ala Asn Thr Ala Tyr
 65                  70                  75                  80

Met Glu Leu Arg Ser Leu Arg Ser Ala Asp Thr Ala Val Tyr Tyr Cys
                 85                  90                  95

Ala Arg Val Gly Pro Tyr Ser Trp Asp Ser Pro Gln Asp Asn Tyr
                100                 105                 110

Tyr Met Asp Val Trp Gly Lys Gly Thr Thr Val Ile Val Ser Ser
                115                 120                 125

<210> SEQ ID NO 105
<211> LENGTH: 108
<212> TYPE: PRT
<213> ORGANISM: homo sapiens

<400> SEQUENCE: 105

Glu Ile Val Leu Thr Gln Ser Pro Gly Thr Leu Ser Leu Ser Pro Gly
 1               5                  10                  15

Glu Arg Ala Thr Phe Ser Cys Arg Ser Ser His Ser Ile Arg Ser Arg
                20                  25                  30

Arg Val Ala Trp Tyr Gln His Lys Pro Gly Gln Ala Pro Arg Leu Val
            35                  40                  45

Ile His Gly Val Ser Asn Arg Ala Ser Gly Ile Ser Asp Arg Phe Ser
 50                  55                  60

Gly Ser Gly Ser Gly Thr Asp Phe Thr Leu Thr Ile Thr Arg Val Glu
 65                  70                  75                  80

Pro Glu Asp Phe Ala Leu Tyr Tyr Cys Gln Val Tyr Gly Ala Ser Ser
                 85                  90                  95

Tyr Thr Phe Gly Gln Gly Thr Lys Leu Glu Arg Lys
                100                 105

<210> SEQ ID NO 106
<211> LENGTH: 107
<212> TYPE: PRT
<213> ORGANISM: homo sapiens

<400> SEQUENCE: 106

Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
                100                 105

<210> SEQ ID NO 107
<211> LENGTH: 107
<212> TYPE: PRT
```

<213> ORGANISM: homo sapiens

<400> SEQUENCE: 107

Gly Gln Pro Arg Glu Pro Gln Val Tyr Thr Leu Pro Pro Ser Arg Glu
1               5                   10                  15
Glu Met Thr Lys Asn Gln Val Ser Leu Thr Cys Leu Val Lys Gly Phe
            20                  25                  30
Tyr Pro Ser Asp Ile Ala Val Glu Trp Glu Ser Asn Gly Gln Pro Glu
        35                  40                  45
Asn Asn Tyr Lys Thr Thr Pro Pro Val Leu Asp Ser Asp Gly Ser Phe
    50                  55                  60
Phe Leu Tyr Ser Lys Leu Thr Val Asp Lys Ser Arg Trp Gln Gln Gly
65                  70                  75                  80
Asn Val Phe Ser Cys Ser Val Met His Glu Ala Leu His Asn His Tyr
                85                  90                  95
Thr Gln Lys Ser Leu Ser Leu Ser Pro Gly Lys
            100                 105

<210> SEQ ID NO 108
<211> LENGTH: 107
<212> TYPE: PRT
<213> ORGANISM: homo sapiens

<400> SEQUENCE: 108

Gly Gln Pro Arg Glu Pro Gln Val Tyr Thr Leu Pro Pro Ser Arg Asp
1               5                   10                  15
Glu Leu Thr Lys Asn Gln Val Ser Leu Thr Cys Leu Val Lys Gly Phe
            20                  25                  30
Tyr Pro Ser Asp Ile Ala Val Glu Trp Glu Ser Asn Gly Gln Pro Glu
        35                  40                  45
Asn Asn Tyr Lys Thr Thr Pro Pro Val Leu Asp Ser Asp Gly Ser Phe
    50                  55                  60
Phe Leu Tyr Ser Lys Leu Thr Val Asp Lys Ser Arg Trp Gln Gln Gly
65                  70                  75                  80
Asn Val Phe Ser Cys Ser Val Met His Glu Gly Leu His Asn His Tyr
                85                  90                  95
Thr Gln Lys Ser Leu Ser Leu Ser Pro Gly Lys
            100                 105

<210> SEQ ID NO 109
<211> LENGTH: 330
<212> TYPE: PRT
<213> ORGANISM: homo sapiens

<400> SEQUENCE: 109

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95

```
Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 110
<211> LENGTH: 330
<212> TYPE: PRT
<213> ORGANISM: Artificial Sequence
<220> FEATURE:
<223> OTHER INFORMATION: IgG1 heavy chain constant region with amino
      acid substitution

<400> SEQUENCE: 110

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
            115                 120                 125
Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 111
<211> LENGTH: 330
<212> TYPE: PRT
<213> ORGANISM: Artificial Sequence
<220> FEATURE:
<223> OTHER INFORMATION: IgG1 heavy chain constant region with amino
      acid substitution

<400> SEQUENCE: 111

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 112
<211> LENGTH: 330
<212> TYPE: PRT
<213> ORGANISM: Artificial Sequence
<220> FEATURE:
<223> OTHER INFORMATION: IgG1 heavy chain constant region with amino
      acid substitutions

<400> SEQUENCE: 112

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 113
<211> LENGTH: 330
<212> TYPE: PRT
<213> ORGANISM: Artificial Sequence
<220> FEATURE:
<223> OTHER INFORMATION: IgG1 heavy chain constant region with amino
      acid substitutions

<400> SEQUENCE: 113

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
```

```
                195                 200                 205
Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Leu
                275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 114
<211> LENGTH: 107
<212> TYPE: PRT
<213> ORGANISM: Homo Sapiens

<400> SEQUENCE: 114

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 115
<211> LENGTH: 277
<212> TYPE: PRT
<213> ORGANISM: Homo Sapiens

<400> SEQUENCE: 115

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
                20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
        50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
```

```
            85                  90                  95
Ser Glu Thr Asp Thr Ile Cys Thr Cys Glu Glu Gly Trp His Cys Thr
                100                 105                 110

Ser Glu Ala Cys Glu Ser Cys Val Leu His Arg Ser Cys Ser Pro Gly
                115                 120                 125

Phe Gly Val Lys Gln Ile Ala Thr Gly Val Ser Asp Thr Ile Cys Glu
130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
                180                 185                 190

Arg Ala Leu Val Val Ile Pro Ile Ile Phe Gly Ile Leu Phe Ala Ile
                195                 200                 205

Leu Leu Val Leu Val Phe Ile Lys Lys Val Ala Lys Lys Pro Thr Asn
                210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
                260                 265                 270

Val Gln Glu Arg Gln
                275

<210> SEQ ID NO 116
<211> LENGTH: 330
<212> TYPE: PRT
<213> ORGANISM: Artificial sequence
<220> FEATURE:
<223> OTHER INFORMATION: IgG1 heavy chain constant region with amino
      acid substitutions

<400> SEQUENCE: 116

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Phe Glu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Ala Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 117
<211> LENGTH: 122
<212> TYPE: PRT
<213> ORGANISM: Artificial Sequence
<220> FEATURE:
<223> OTHER INFORMATION: Synthesized; humanized antibody variable region

<400> SEQUENCE: 117

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
            20                  25                  30

Ile Met His Trp Val Arg Gln Ala Pro Gly Gln Gly Leu Glu Trp Met
        35                  40                  45

Gly Gly Ile Ile Pro Asn Asn Gly Gly Thr Ser Tyr Asn Gln Lys Phe
    50                  55                  60

Gln Gly Arg Val Thr Met Thr Val Asp Lys Ser Thr Ser Thr Gly Tyr
65                  70                  75                  80

Met Glu Leu Ser Ser Leu Arg Ser Glu Asp Thr Ala Val Tyr Tyr Cys
                85                  90                  95

Thr Arg Arg Glu Val Tyr Gly Arg Asn Tyr Tyr Ala Leu Asp Tyr Trp
            100                 105                 110

Gly Gln Gly Thr Leu Val Thr Val Ser Ser
        115                 120

<210> SEQ ID NO 118
<211> LENGTH: 452
<212> TYPE: PRT
<213> ORGANISM: Artificial Sequence
<220> FEATURE:
<223> OTHER INFORMATION: Synthesized; antibody heavy chain

<400> SEQUENCE: 118

Glu Val Gln Leu Val Gln Ser Gly Ala Glu Val Lys Lys Pro Gly Ala
1               5                   10                  15
```

```
Ser Val Lys Val Ser Cys Lys Thr Ser Gly Tyr Thr Phe Thr Glu Tyr
            20                  25                  30
Ile Met His Trp Val Arg Gln Ala Pro Gly Gln Gly Leu Glu Trp Met
            35                  40                  45
Gly Gly Ile Ile Pro Asn Asn Gly Gly Thr Ser Tyr Asn Gln Lys Phe
 50                  55                  60
Gln Gly Arg Val Thr Met Thr Val Asp Lys Ser Thr Ser Thr Gly Tyr
 65                  70                  75                  80
Met Glu Leu Ser Ser Leu Arg Ser Glu Asp Thr Ala Val Tyr Tyr Cys
            85                  90                  95
Thr Arg Arg Glu Val Tyr Gly Arg Asn Tyr Tyr Ala Leu Asp Tyr Trp
            100                 105                 110
Gly Gln Gly Thr Leu Val Thr Val Ser Ser Ala Ser Thr Lys Gly Pro
            115                 120                 125
Ser Val Phe Pro Leu Ala Pro Ser Ser Lys Ser Thr Ser Gly Gly Thr
 130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
            165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
            195                 200                 205
His Lys Pro Ser Asn Thr Lys Val Asp Lys Arg Val Glu Pro Lys Ser
            210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
            245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
            275                 280                 285
Val His Asn Ala Lys Thr Lys Pro Arg Glu Glu Gln Tyr Asn Ser Thr
            290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
            325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Glu Glu Met Thr Lys Asn Gln Val
            355                 360                 365
Ser Leu Thr Cys Leu Val Lys Gly Phe Tyr Pro Ser Asp Ile Ala Val
            370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
            405                 410                 415
Val Asp Lys Ser Arg Trp Gln Gln Gly Asn Val Phe Ser Cys Ser Val
            420                 425                 430
```

Met His Glu Ala Leu His Asn His Tyr Thr Gln Lys Ser Leu Ser Leu
            435                 440                 445

Ser Pro Gly Lys
        450

<210> SEQ ID NO 119
<211> LENGTH: 452
<212> TYPE: PRT
<213> ORGANISM: Artificial Sequence
<220> FEATURE:
<223> OTHER INFORMATION: Synthesized; antibody heavy chain

<400> SEQUENCE: 119

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
            20                  25                  30

Ile Met His Trp Val Arg Gln Ala Pro Gly Gln Gly Leu Glu Trp Met
        35                  40                  45

Gly Gly Ile Ile Pro Asn Asn Gly Gly Thr Ser Tyr Asn Gln Lys Phe
    50                  55                  60

Gln Gly Arg Val Thr Met Thr Val Asp Lys Ser Thr Ser Thr Gly Tyr
65                  70                  75                  80

Met Glu Leu Ser Ser Leu Arg Ser Glu Asp Thr Ala Val Tyr Tyr Cys
                85                  90                  95

Thr Arg Arg Glu Val Tyr Gly Arg Asn Tyr Tyr Ala Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ala Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

-continued

```
Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Leu Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
        450

<210> SEQ ID NO 120
<211> LENGTH: 452
<212> TYPE: PRT
<213> ORGANISM: Artificial Sequence
<220> FEATURE:
<223> OTHER INFORMATION: Synthesized; antibody heavy chain

<400> SEQUENCE: 120

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
            20                  25                  30

Ile Met His Trp Val Arg Gln Ala Pro Gly Gln Gly Leu Glu Trp Met
        35                  40                  45

Gly Gly Ile Ile Pro Asn Asn Gly Gly Thr Ser Tyr Asn Gln Lys Phe
    50                  55                  60

Gln Gly Arg Val Thr Met Thr Val Asp Lys Ser Thr Ser Thr Gly Tyr
65                  70                  75                  80

Met Glu Leu Ser Ser Leu Arg Ser Glu Asp Thr Ala Val Tyr Tyr Cys
                85                  90                  95

Thr Arg Arg Glu Val Tyr Gly Arg Asn Tyr Tyr Ala Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Phe Glu
225                 230                 235                 240
```

```
Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Ala Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 121
<211> LENGTH: 107
<212> TYPE: PRT
<213> ORGANISM: Artificial Sequence
<220> FEATURE:
<223> OTHER INFORMATION: Synthesized: Humanized IgG1 light chain
      variable region

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Asn Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Ser Asn Leu Pro Tyr
                85                  90                  95

Thr Phe Gly Gly Gly Thr Lys Val Glu Ile Lys
            100                 105

<210> SEQ ID NO 122
<211> LENGTH: 214
<212> TYPE: PRT
<213> ORGANISM: Artificial Sequence
```

<220> FEATURE:
<223> OTHER INFORMATION: Synthesized; antibody light chain constant
      region

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Asn Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Ser Asn Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 123
<211> LENGTH: 117
<212> TYPE: PRT
<213> ORGANISM: Artificial Sequence
<220> FEATURE:
<223> OTHER INFORMATION: Synthesized; IgG1 heavy chain variable region

<400> SEQUENCE: 123

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Leu Asn Asp Tyr
            20                  25                  30

Trp Met Ser Trp Val Arg Gln Ala Pro Gly Lys Gly Leu Glu Trp Val
        35                  40                  45

Gly Tyr Ile Asp Val Gly Gly Ser Leu Tyr Tyr Ala Ala Ser Val Lys
50                  55                  60

Gly Arg Phe Thr Ile Ser Arg Asp Asp Ser Lys Ser Ile Ala Tyr Leu
65                  70                  75                  80

Gln Met Asn Ser Leu Lys Thr Glu Asp Thr Ala Val Tyr Tyr Cys Ala
                85                  90                  95

Arg Gly Gly Leu Thr Tyr Gly Phe Asp Leu Trp Gly Gln Gly Thr Leu
            100                 105                 110

Val Thr Val Ser Ser
         115

<210> SEQ ID NO 124
<211> LENGTH: 447
<212> TYPE: PRT
<213> ORGANISM: Artificial Sequence
<220> FEATURE:
<223> OTHER INFORMATION: Synthesized; antibody heavy chain constant
      region

<400> SEQUENCE: 124

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Leu Asn Asp Tyr
            20                  25                  30

Trp Met Ser Trp Val Arg Gln Ala Pro Gly Lys Gly Leu Glu Trp Val
        35                  40                  45

Gly Tyr Ile Asp Val Gly Gly Ser Leu Tyr Tyr Ala Ala Ser Val Lys
    50                  55                  60

Gly Arg Phe Thr Ile Ser Arg Asp Asp Ser Lys Ser Ile Ala Tyr Leu
65                  70                  75                  80

Gln Met Asn Ser Leu Lys Thr Glu Asp Thr Ala Val Tyr Tyr Cys Ala
                85                  90                  95

Arg Gly Gly Leu Thr Tyr Gly Phe Asp Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

```
Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 125
<211> LENGTH: 447
<212> TYPE: PRT
<213> ORGANISM: Artificial Sequence
<220> FEATURE:
<223> OTHER INFORMATION: Synthesized; antibody heavy chain constant
      region with substitutions

<400> SEQUENCE: 125

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Leu Asn Asp Tyr
                20                  25                  30

Trp Met Ser Trp Val Arg Gln Ala Pro Gly Lys Gly Leu Glu Trp Val
            35                  40                  45

Gly Tyr Ile Asp Val Gly Gly Ser Leu Tyr Tyr Ala Ala Ser Val Lys
    50                  55                  60

Gly Arg Phe Thr Ile Ser Arg Asp Asp Ser Lys Ser Ile Ala Tyr Leu
65                  70                  75                  80

Gln Met Asn Ser Leu Lys Thr Glu Asp Thr Ala Val Tyr Tyr Cys Ala
                85                  90                  95

Arg Gly Gly Leu Thr Tyr Gly Phe Asp Leu Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Ala Val Ser His Glu Asp Pro Glu
```

```
                260                 265                 270
Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 126
<211> LENGTH: 447
<212> TYPE: PRT
<213> ORGANISM: Artificial Sequence
<220> FEATURE:
<223> OTHER INFORMATION: Synthesized; antibody heavy chain with
      substitutions

<400> SEQUENCE: 126

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Leu Asn Asp Tyr
            20                  25                  30

Trp Met Ser Trp Val Arg Gln Ala Pro Gly Lys Gly Leu Glu Trp Val
        35                  40                  45

Gly Tyr Ile Asp Val Gly Gly Ser Leu Tyr Tyr Ala Ala Ser Val Lys
    50                  55                  60

Gly Arg Phe Thr Ile Ser Arg Asp Asp Ser Lys Ser Ile Ala Tyr Leu
65                  70                  75                  80

Gln Met Asn Ser Leu Lys Thr Glu Asp Thr Ala Val Tyr Tyr Cys Ala
                85                  90                  95

Arg Gly Gly Leu Thr Tyr Gly Phe Asp Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

```
Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
        210                 215                 220

Thr Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Ala Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Leu Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 127
<211> LENGTH: 110
<212> TYPE: PRT
<213> ORGANISM: Artificial Sequence
<220> FEATURE:
<223> OTHER INFORMATION: Synthesized: Humanized IgG1 light chain
      variable region

<400> SEQUENCE: 127

Asp Ile Val Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Ser Tyr
            20                  25                  30

Leu Ala Trp Tyr Gln Gln Lys Pro Gly Lys Ala Pro Lys Arg Leu Ile
        35                  40                  45

Tyr Gly Ala Ser Asp Leu Ala Ser Gly Val Pro Ser Arg Phe Ser Ala
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys His Tyr Tyr Ala Thr Ile Ser Gly
                85                  90                  95
```

```
Leu Gly Val Ala Phe Gly Gly Gly Thr Lys Val Glu Ile Lys
            100                 105                 110

<210> SEQ ID NO 128
<211> LENGTH: 217
<212> TYPE: PRT
<213> ORGANISM: Artificial Sequence
<220> FEATURE:
<223> OTHER INFORMATION: Synthesized; antibody light chain constant
      region

<400> SEQUENCE: 128

Asp Ile Val Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Ser Tyr
            20                  25                  30

Leu Ala Trp Tyr Gln Gln Lys Pro Gly Lys Ala Pro Lys Arg Leu Ile
        35                  40                  45

Tyr Gly Ala Ser Asp Leu Ala Ser Gly Val Pro Ser Arg Phe Ser Ala
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys His Tyr Ala Thr Ile Ser Gly
                85                  90                  95

Leu Gly Val Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 129
<211> LENGTH: 24
<212> TYPE: PRT
<213> ORGANISM: Homo Sapiens

<400> SEQUENCE: 129

Leu Gln Asp Pro Cys Ser Asn Cys Pro Ala Gly Thr Phe Cys Asp Asn
1               5                   10                  15

Asn Arg Asn Gln Ile Cys Ser Pro
            20

<210> SEQ ID NO 130
<211> LENGTH: 41
<212> TYPE: PRT
<213> ORGANISM: Homo Sapiens

<400> SEQUENCE: 130
```

Cys Pro Pro Asn Ser Phe Ser Ala Gly Gly Gln Arg Thr Cys Asp
1               5                   10                  15

Ile Cys Arg Gln Cys Lys Gly Val Phe Arg Thr Arg Lys Glu Cys Ser
            20                  25                  30

Ser Thr Ser Asn Ala Glu Cys Asp Cys
        35                  40

<210> SEQ ID NO 131
<211> LENGTH: 26
<212> TYPE: PRT
<213> ORGANISM: Homo Sapiens

<400> SEQUENCE: 131

Thr Pro Gly Phe His Cys Leu Gly Ala Gly Cys Ser Met Cys Glu Gln
1               5                   10                  15

Asp Cys Lys Gln Gly Gln Glu Leu Thr Lys
            20                  25

<210> SEQ ID NO 132
<211> LENGTH: 24
<212> TYPE: PRT
<213> ORGANISM: Homo Sapiens

<400> SEQUENCE: 132

Lys Gly Cys Lys Asp Cys Cys Phe Gly Thr Phe Asn Asp Gln Lys Arg
1               5                   10                  15

Gly Ile Cys Arg Pro Trp Thr Asn
            20

<210> SEQ ID NO 133
<211> LENGTH: 23
<212> TYPE: PRT
<213> ORGANISM: Homo Sapiens

<400> SEQUENCE: 133

Cys Ser Leu Asp Gly Lys Ser Val Leu Val Asn Gly Thr Lys Glu Arg
1               5                   10                  15

Asp Val Val Cys Gly Pro Ser
            20

<210> SEQ ID NO 134
<211> LENGTH: 25
<212> TYPE: PRT
<213> ORGANISM: Homo Sapiens

<400> SEQUENCE: 134

Pro Ala Asp Leu Ser Pro Gly Ala Ser Ser Val Thr Pro Pro Ala Pro
1               5                   10                  15

Ala Arg Glu Pro Gly His Ser Pro Gln
            20                  25

<210> SEQ ID NO 135
<211> LENGTH: 255
<212> TYPE: PRT
<213> ORGANISM: sus scrofa

<400> SEQUENCE: 135

Met Gly Asn Gly Tyr Tyr Asn Ile Val Ala Thr Val Leu Leu Val Met
1               5                   10                  15

Asn Phe Glu Arg Thr Arg Ser Val Pro Asp Pro Cys Ser Asn Cys Ser
            20                  25                  30

```
Ala Gly Thr Phe Cys Gly Lys Asn Ile Gln Glu Leu Cys Met Pro Cys
        35                  40                  45

Pro Ser Asn Ser Phe Ser Ser Thr Ser Gly Lys Ala Cys Asn Val
50                  55                  60

Cys Arg Lys Cys Glu Gly Val Phe Arg Thr Lys Lys Glu Cys Ser Ser
65                  70                  75                  80

Thr Ser Asn Ala Val Cys Glu Cys Val Pro Gly Phe Arg Cys Leu Gly
                85                  90                  95

Ala Gly Cys Ala Met Cys Glu Glu Tyr Cys Gln Gln Gly Gln Glu Leu
            100                 105                 110

Thr Gln Glu Gly Cys Lys Asp Cys Ser Phe Gly Thr Phe Asn Asp Glu
            115                 120                 125

Glu His Gly Val Cys Arg Pro Trp Thr Asp Cys Ser Leu Ala Gly Lys
        130                 135                 140

Pro Val Leu Met Asn Gly Thr Lys Ala Arg Asp Val Val Cys Gly Pro
145                 150                 155                 160

Arg Pro Thr Asp Phe Ser Pro Gly Thr Pro Ser Thr Thr Met Pro Val
                165                 170                 175

Pro Gly Gly Glu Pro Gly His Thr Ser His Val Ile Ile Phe Phe Leu
            180                 185                 190

Ala Leu Met Ser Thr Ala Val Phe Val Leu Val Ser Tyr Leu Ala Leu
            195                 200                 205

Arg Phe Ser Val Val Gln Gln Gly Arg Lys Lys Leu Leu Tyr Ile Val
        210                 215                 220

Lys Gln Pro Phe Leu Lys Pro Ala Gln Thr Val Gln Glu Glu Asp Ala
225                 230                 235                 240

Cys Ser Cys Arg Phe Pro Glu Glu Glu Glu Gly Glu Cys Glu Leu
                245                 250                 255

<210> SEQ ID NO 136
<211> LENGTH: 255
<212> TYPE: PRT
<213> ORGANISM: loxodonta africana

<400> SEQUENCE: 136

Met Gly Asn Gly Tyr Tyr Asn Met Val Ala Thr Val Leu Leu Val Met
1               5                   10                  15

Asn Phe Glu Arg Thr Gly Ala Val Gln Asp Ser Cys Arg Asp Cys Leu
                20                  25                  30

Ala Gly Thr Tyr Cys Val Lys Asn Glu Ser Gln Ile Cys Ser Pro Cys
        35                  40                  45

Pro Leu Asn Ser Phe Ser Ser Thr Gly Gly Gln Met Asn Cys Asp Met
50                  55                  60

Cys Arg Lys Cys Glu Gly Val Phe Lys Thr Lys Arg Ala Cys Ser Pro
65                  70                  75                  80

Thr Arg Asp Ala Glu Cys Glu Cys Val Ser Gly Phe His Cys Leu Gly
                85                  90                  95

Ala Gly Cys Thr Met Cys Gln Gln Asp Cys Lys Gln Gly Gln Glu Leu
            100                 105                 110

Thr Lys Glu Gly Cys Lys Asp Cys Cys Leu Gly Thr Phe Asn Asp Gln
            115                 120                 125

Lys Asn Gly Ile Cys Arg Pro Trp Thr Asn Cys Ser Leu Glu Gly Lys
        130                 135                 140

Ser Val Leu Ala Asn Gly Thr Lys Lys Arg Asp Val Val Cys Gly Pro
145                 150                 155                 160
```

```
Pro Ala Ala Asp Ser Phe Pro Asp Thr Ser Ser Val Thr Val Pro Ala
            165             170             175

Pro Glu Arg Lys Pro Asp His His Pro Gln Ile Ile Thr Phe Phe Leu
            180             185             190

Ala Leu Ile Ser Ala Ala Leu Leu Phe Leu Val Phe Phe Leu Val Val
        195             200             205

Arg Phe Ser Val Ala Lys Trp Gly Arg Lys Lys Leu Leu Tyr Ile Phe
        210             215             220

Lys Gln Pro Phe Ile Lys Pro Val Gln Thr Ala Gln Glu Glu Asp Gly
225             230             235             240

Cys Ser Cys Arg Phe Pro Glu Glu Glu Glu Gly Asp Cys Glu Leu
            245             250             255
```